US012742166B2

(12) United States Patent
Mikkelsen et al.

(10) Patent No.: US 12,742,166 B2
(45) Date of Patent: Sep. 22, 2026

(54) METHODS AND SYSTEMS FOR PROCESSING POLYNUCLEOTIDES

(71) Applicant: 10x Genomics, Inc., Pleasanton, CA (US)

(72) Inventors: Tarjei Sigurd Mikkelsen, Dublin, CA (US); Phillip Belgrader, Livermore, CA (US); Xinying Zheng, San Jose, CA (US)

(73) Assignee: 10x Genomics, Inc., Pleasonton, CA (US)

( * ) Notice: Subject to any disclaimer, the term of this patent is extended or adjusted under 35 U.S.C. 154(b) by 0 days.

(21) Appl. No.: 17/692,758

(22) Filed: Mar. 11, 2022

(65) Prior Publication Data

US 2022/0389503 A1 Dec. 8, 2022

Related U.S. Application Data

(63) Continuation of application No. 17/131,494, filed on Dec. 22, 2020, now abandoned, which is a continuation of application No. 15/825,740, filed on Nov. 29, 2017, now abandoned, which is a continuation of application No. PCT/US2017/057269, filed on Oct. 18, 2017.

(60) Provisional application No. 62/490,546, filed on Apr. 26, 2017, provisional application No. 62/410,326, filed on Oct. 19, 2016.

(51) Int. Cl.

| | |
|---|---|
| ***C12Q 1/6806*** | (2018.01) |
| ***C12N 5/071*** | (2010.01) |
| ***C12N 15/10*** | (2006.01) |
| ***C12Q 1/6804*** | (2018.01) |
| ***C12Q 1/6816*** | (2018.01) |
| ***C12Q 1/6834*** | (2018.01) |
| ***C12Q 1/6853*** | (2018.01) |
| ***C12Q 1/686*** | (2018.01) |
| ***C12Q 1/6869*** | (2018.01) |
| ***C12Q 1/6874*** | (2018.01) |
| *C12Q 1/6855* | (2018.01) |

(52) U.S. Cl.

CPC ....... *C12N 15/1003* (2013.01); *C12N 5/0602* (2013.01); *C12N 15/1062* (2013.01); *C12N 15/1065* (2013.01); *C12N 15/1075* (2013.01); *C12N 15/1096* (2013.01); *C12Q 1/6804* (2013.01); *C12Q 1/6806* (2013.01); *C12Q 1/6816* (2013.01); *C12Q 1/6834* (2013.01); *C12Q 1/6853* (2013.01); *C12Q 1/686* (2013.01); *C12Q 1/6869* (2013.01); *C12Q 1/6874* (2013.01); *C12Q 1/6855* (2013.01)

(58) Field of Classification Search

None

See application file for complete search history.

(56) References Cited

U.S. PATENT DOCUMENTS

| | | | |
|---|---|---|---|
| 2,797,149 | A | 6/1957 | Skeggs |
| 3,047,367 | A | 7/1962 | Kessler |
| 3,479,141 | A | 11/1969 | William et al. |
| 4,124,638 | A | 11/1978 | Hansen |
| 4,253,846 | A | 3/1981 | Smythe et al. |
| 4,582,802 | A | 4/1986 | Zimmerman et al. |
| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |
| 5,002,882 | A | 3/1991 | Lunnen |
| 5,130,238 | A | 7/1992 | Malek |
| 5,137,829 | A | 8/1992 | Nag et al. |
| 5,149,625 | A | 9/1992 | Church et al. |
| 5,185,099 | A | 2/1993 | Delpuech et al. |
| 5,202,231 | A | 4/1993 | Drmanac et al. |
| 5,270,183 | A | 12/1993 | Corbett et al. |
| 5,308,751 | A | 5/1994 | Ohkawa |
| 5,321,130 | A | 6/1994 | Yue |
| 5,410,030 | A | 4/1995 | Yue |
| 5,413,924 | A | 5/1995 | Kosak et al. |

(Continued)

FOREIGN PATENT DOCUMENTS

| | | |
|---|---|---|
| CN | 1680604 | 10/2005 |
| CN | 102292455 | 12/2011 |

(Continued)

OTHER PUBLICATIONS

Eastburn, Microfluidic droplet enrichment for targeted sequencing, Nucleic Acids Research, 43(13): 1-8, 2015. (Year: 2015).*

(Continued)

*Primary Examiner* — Carolyn L Greene

(74) *Attorney, Agent, or Firm* — Seed Intellectual Property Law Group LLP

(57) ABSTRACT

The present disclosure provides methods, compositions and systems for analyzing individual cells or cell populations through a partitioned analysis of contents of individual cells or cell populations, such as cancer cells and cells of the immune system. Individual cells or cell populations may be co-partitioned with processing reagents for accessing cellular contents, and for uniquely identifying the content of a given cell or cell population, and subsequently analyzing the content of the cell and characterizing it as having derived from an individual cell or cell population, including analysis and characterization of nucleic acid(s) from the cell through sequencing.

22 Claims, 46 Drawing Sheets

Specification includes a Sequence Listing.

(56) References Cited

U.S. PATENT DOCUMENTS

| | | | |
|---|---|---|---|
| 5,418,149 | A | 5/1995 | Gelfand et al. |
| 5,436,130 | A | 7/1995 | Mathies et al. |
| 5,436,134 | A | 7/1995 | Haugland |
| 5,455,166 | A | 10/1995 | Walker |
| 5,478,893 | A | 12/1995 | Ghosh et al. |
| 5,489,523 | A | 2/1996 | Mathur |
| 5,494,810 | A | 2/1996 | Barany et al. |
| 5,503,980 | A | 4/1996 | Cantor |
| 5,512,131 | A | 4/1996 | Kumar et al. |
| 5,512,439 | A | 4/1996 | Hornes |
| 5,512,462 | A | 4/1996 | Cheng |
| 5,558,071 | A | 9/1996 | Ward et al. |
| 5,582,977 | A | 12/1996 | Yue |
| 5,585,069 | A | 12/1996 | Zanzucchi et al. |
| 5,587,128 | A | 12/1996 | Wilding et al. |
| 5,599,675 | A | 2/1997 | Brenner |
| 5,605,793 | A | 2/1997 | Stemmer |
| 5,618,711 | A | 4/1997 | Gelfand et al. |
| 5,641,658 | A | 6/1997 | Adams |
| 5,648,245 | A | 7/1997 | Fire et al. |
| 5,658,751 | A | 8/1997 | Yue |
| 5,695,940 | A | 12/1997 | Drmanac et al. |
| 5,700,642 | A | 12/1997 | Monforte et al. |
| 5,705,628 | A | 1/1998 | Hawkins |
| 5,708,153 | A | 1/1998 | Dower et al. |
| 5,736,330 | A | 4/1998 | Fulton |
| 5,739,036 | A | 4/1998 | Parris |
| 5,744,311 | A | 4/1998 | Fraiser et al. |
| 5,750,341 | A | 5/1998 | Macevicz |
| 5,756,334 | A | 5/1998 | Perler et al. |
| 5,763,175 | A | 6/1998 | Brenner |
| 5,830,663 | A | 11/1998 | Embleton et al. |
| 5,830,711 | A | 11/1998 | Barany et al. |
| 5,834,197 | A | 11/1998 | Parton |
| 5,837,832 | A | 11/1998 | Chee et al. |
| 5,842,787 | A | 12/1998 | Kopf-Sill et al. |
| 5,846,719 | A | 12/1998 | Brenner et al. |
| 5,846,727 | A | 12/1998 | Soper et al. |
| 5,851,769 | A | 12/1998 | Gray et al. |
| 5,854,033 | A | 12/1998 | Lizardi |
| 5,856,174 | A | 1/1999 | Lipshutz et al. |
| 5,863,753 | A | 1/1999 | Haugland |
| 5,871,921 | A | 2/1999 | Landegren et al. |
| 5,872,010 | A | 2/1999 | Karger et al. |
| 5,897,783 | A | 4/1999 | Howe et al. |
| 5,900,481 | A | 5/1999 | Lough et al. |
| 5,912,148 | A | 6/1999 | Eggerding |
| 5,942,609 | A | 8/1999 | Hunkapiller et al. |
| 5,958,703 | A | 9/1999 | Dower et al. |
| 5,965,443 | A | 10/1999 | Reznikoff et al. |
| 5,994,056 | A | 11/1999 | Higuchi |
| 5,997,636 | A | 12/1999 | Gamarnik et al. |
| 6,013,440 | A | 1/2000 | Lipshutz |
| 6,027,889 | A | 2/2000 | Barany et al. |
| 6,033,880 | A | 3/2000 | Haff et al. |
| 6,046,003 | A | 4/2000 | Mandecki |
| 6,051,377 | A | 4/2000 | Mandecki |
| 6,057,107 | A | 5/2000 | Fulton |
| 6,057,149 | A | 5/2000 | Burns et al. |
| 6,060,240 | A | 5/2000 | Kamb et al. |
| 6,103,537 | A | 8/2000 | Ullman et al. |
| 6,110,678 | A | 8/2000 | Weisburg et al. |
| 6,123,798 | A | 9/2000 | Gandhi et al. |
| 6,130,073 | A | 10/2000 | Eggerding |
| 6,133,436 | A | 10/2000 | Koester et al. |
| 6,143,496 | A | 11/2000 | Brown et al. |
| 6,153,389 | A | 11/2000 | Haarer |
| 6,159,717 | A | 12/2000 | Savakis et al. |
| 6,165,714 | A | 12/2000 | Lane et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,207,384 | B1 | 3/2001 | Mekalanos et al. |
| 6,210,891 | B1 | 4/2001 | Nyren |
| 6,210,894 | B1 | 4/2001 | Brennan |
| 6,214,587 | B1 | 4/2001 | Dattagupta |
| 6,258,568 | B1 | 7/2001 | Nyren |
| 6,258,571 | B1 | 7/2001 | Chumakov et al. |
| 6,265,552 | B1 | 7/2001 | Schatz |
| 6,266,459 | B1 | 7/2001 | Walt |
| 6,274,320 | B1 | 8/2001 | Rothberg |
| 6,291,243 | B1 | 9/2001 | Fogarty et al. |
| 6,294,385 | B1 | 9/2001 | Goryshin et al. |
| 6,296,020 | B1 | 10/2001 | Mcneely et al. |
| 6,297,006 | B1 | 10/2001 | Drmanac et al. |
| 6,297,017 | B1 | 10/2001 | Schmidt et al. |
| 6,300,063 | B1 | 10/2001 | Lipshutz et al. |
| 6,303,343 | B1 | 10/2001 | Kopf-Sill |
| 6,306,590 | B1 | 10/2001 | Mehta et al. |
| 6,309,824 | B1 | 10/2001 | Drmanac |
| 6,327,410 | B1 | 12/2001 | Walt et al. |
| 6,344,316 | B1 | 2/2002 | Lockhart |
| 6,355,198 | B1 | 3/2002 | Kim et al. |
| 6,355,431 | B1 | 3/2002 | Chee |
| 6,361,950 | B1 | 3/2002 | Mandecki |
| 6,368,801 | B1 | 4/2002 | Faruqi |
| 6,372,813 | B1 | 4/2002 | Johnson et al. |
| 6,379,929 | B1 | 4/2002 | Burns et al. |
| 6,401,267 | B1 | 6/2002 | Drmanac |
| 6,404,907 | B1 | 6/2002 | Gilchrist |
| 6,406,848 | B1 | 6/2002 | Bridgham et al. |
| 6,409,832 | B2 | 6/2002 | Weigl et al. |
| 6,410,246 | B1 | 6/2002 | Zhu et al. |
| 6,432,290 | B1 | 8/2002 | Harrison et al. |
| 6,432,360 | B1 | 8/2002 | Church |
| 6,485,944 | B1 | 11/2002 | Church et al. |
| 6,492,118 | B1 | 12/2002 | Abrams et al. |
| 6,503,713 | B1 | 1/2003 | Rana |
| 6,506,561 | B1 | 1/2003 | Cheval et al. |
| 6,511,803 | B1 | 1/2003 | Church et al. |
| 6,524,456 | B1 | 2/2003 | Ramsey et al. |
| 6,544,732 | B1 | 4/2003 | Chee |
| 6,569,631 | B1 | 5/2003 | Pantoliano et al. |
| 6,579,851 | B2 | 6/2003 | Goeke et al. |
| 6,586,176 | B1 | 7/2003 | Trnovsky et al. |
| 6,593,113 | B1 | 7/2003 | Tenkanen et al. |
| 6,613,752 | B2 | 9/2003 | Kay et al. |
| 6,620,584 | B1 | 9/2003 | Chee |
| 6,632,606 | B1 | 10/2003 | Ullman et al. |
| 6,632,641 | B1 | 10/2003 | Brennan |
| 6,632,655 | B1 | 10/2003 | Mehta et al. |
| 6,670,133 | B2 | 12/2003 | Knapp et al. |
| 6,723,513 | B2 | 4/2004 | Lexow |
| 6,737,236 | B1 | 5/2004 | Pieken et al. |
| 6,767,731 | B2 | 7/2004 | Hannah |
| 6,770,441 | B2 | 8/2004 | Dickinson |
| 6,773,886 | B2 | 8/2004 | Kaufman |
| 6,787,308 | B2 | 9/2004 | Balasubramanian |
| 6,800,298 | B1 | 10/2004 | Burdick et al. |
| 6,800,453 | B2 | 10/2004 | Labaer |
| 6,806,052 | B2 | 10/2004 | Bridgham et al. |
| 6,806,058 | B2 | 10/2004 | Jesperson et al. |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,859,570 | B2 | 2/2005 | Walt et al. |
| 6,864,052 | B1 | 3/2005 | Drmanac |
| 6,880,576 | B2 | 4/2005 | Karp et al. |
| 6,884,788 | B2 | 4/2005 | Bulpitt et al. |
| 6,897,023 | B2 | 5/2005 | Fu |
| 6,913,935 | B1 | 7/2005 | Thomas |
| 6,915,679 | B2 | 7/2005 | Chien et al. |
| 6,929,859 | B2 | 8/2005 | Chandler et al. |
| 6,942,968 | B1 | 9/2005 | Dickinson et al. |
| 6,969,488 | B2 | 11/2005 | Bridgham et al. |
| 6,974,669 | B2 | 12/2005 | Mirkin et al. |
| 7,041,481 | B2 | 5/2006 | Anderson et al. |
| 7,057,026 | B2 | 6/2006 | Barnes |
| 7,115,400 | B1 | 10/2006 | Adessi et al. |
| 7,118,883 | B2 | 10/2006 | Inoue |
| 7,129,091 | B2 | 10/2006 | Ismagilov et al. |
| 7,138,267 | B1 | 11/2006 | Jendrisak et al. |
| 7,166,431 | B2 | 1/2007 | Chee et al. |
| 7,211,414 | B2 | 5/2007 | Hardin |

(56) References Cited

U.S. PATENT DOCUMENTS 7,211,654 B2 5/2007 Gao et al.
7,255,994 B2 8/2007 Lao
7,258,976 B2 8/2007 Mitsuhashi
7,262,056 B2 8/2007 Wooddell et al.
7,268,167 B2 9/2007 Higuchi et al.
7,282,370 B2 10/2007 Bridgham et al.
7,294,503 B2 11/2007 Quake et al.
7,297,485 B2 11/2007 Bornarth et al.
7,297,518 B2 11/2007 Quake
7,316,903 B2 1/2008 Yanagihara et al.
7,323,305 B2 1/2008 Leamon et al.
7,329,492 B2 2/2008 Hardin
7,329,493 B2 2/2008 Chou et al.
7,361,488 B2 4/2008 Fan et al.
7,378,242 B2 5/2008 Hurt
7,393,665 B2 7/2008 Brenner
7,405,281 B2 7/2008 Xu
7,407,757 B2 8/2008 Brenner
7,425,431 B2 9/2008 Church et al.
7,536,928 B2 5/2009 Kazuno
7,537,897 B2 5/2009 Brenner
7,544,473 B2 6/2009 Brenner
7,563,576 B2 7/2009 Chee
7,582,420 B2 9/2009 Oliphant et al.
7,595,060 B2 9/2009 Duke et al.
7,601,498 B2 10/2009 Mao
7,604,938 B2 10/2009 Takahashi et al.
7,608,434 B2 10/2009 Reznikoff et al.
7,608,451 B2 10/2009 Cooper et al.
7,622,076 B2 11/2009 Davies et al.
7,622,280 B2 11/2009 Holliger et al.
7,635,566 B2 12/2009 Brenner
7,638,276 B2 12/2009 Griffiths et al.
7,645,596 B2 1/2010 Williams et al.
7,666,664 B2 2/2010 Sarofim et al.
7,674,752 B2 3/2010 He
7,700,325 B2 4/2010 Cantor et al.
7,708,949 B2 5/2010 Stone et al.
7,709,197 B2 5/2010 Drmanac
7,745,178 B2 6/2010 Dong
7,745,218 B2 6/2010 Kim et al.
7,772,287 B2 8/2010 Higuchi et al.
7,776,547 B2 8/2010 Roth
7,776,567 B2 8/2010 Mao
7,776,927 B2 8/2010 Chu et al.
RE41,780 E 9/2010 Anderson et al.
7,799,553 B2 9/2010 Mathies et al.
7,803,943 B2 9/2010 Mao
7,842,457 B2 11/2010 Berka et al.
7,901,891 B2 3/2011 Drmanac
7,910,304 B2 3/2011 Drmanac
7,910,354 B2 3/2011 Drmanac et al.
7,927,797 B2 4/2011 Nobile et al.
7,947,477 B2 5/2011 Schroeder et al.
7,955,794 B2 6/2011 Shen et al.
7,960,104 B2 6/2011 Drmanac et al.
7,960,119 B2 6/2011 Chee
7,968,287 B2 6/2011 Griffiths et al.
7,972,778 B2 7/2011 Brown et al.
8,003,312 B2 8/2011 Krutzik et al.
8,003,354 B2 8/2011 Shen et al.
8,008,018 B2 8/2011 Quake et al.
8,053,192 B2 11/2011 Bignell et al.
8,067,159 B2 11/2011 Brown et al.
8,101,346 B2 1/2012 Takahama
8,124,404 B2 2/2012 Alphey
8,133,719 B2 3/2012 Drmanac et al.
8,137,563 B2 3/2012 Ma et al.
8,148,068 B2 4/2012 Brenner
8,168,385 B2 5/2012 Brenner
8,206,917 B2 6/2012 Chee
8,252,539 B2 8/2012 Quake et al.
8,268,564 B2 9/2012 Roth et al.
8,273,573 B2 9/2012 Ismagilov et al.
8,278,071 B2 10/2012 Brown et al.
8,288,103 B2 10/2012 Oliphant
8,298,767 B2 10/2012 Brenner et al.
8,304,193 B2 11/2012 Ismagilov et al.
8,318,433 B2 11/2012 Brenner
8,318,460 B2 11/2012 Cantor et al.
8,329,407 B2 12/2012 Ismagilov et al.
8,337,778 B2 12/2012 Stone et al.
8,343,500 B2 1/2013 Wraith
8,361,299 B2 1/2013 Sabin et al.
8,394,590 B2 3/2013 Kwong et al.
8,420,386 B2 4/2013 Ivics et al.
8,460,865 B2 6/2013 Chee
8,461,129 B2 6/2013 Bolduc et al.
8,481,257 B2 7/2013 Van Eijk
8,563,274 B2 10/2013 Brenner et al.
8,592,150 B2 11/2013 Drmanac et al.
8,598,328 B2 12/2013 Koga et al.
8,603,743 B2 12/2013 Liu et al.
8,603,749 B2 12/2013 Gillevet
8,658,430 B2 2/2014 Miller et al.
8,679,756 B1 3/2014 Brenner et al.
8,691,510 B2 4/2014 Faham et al.
8,748,094 B2 6/2014 Weitz et al.
8,748,102 B2 6/2014 Berka et al.
8,765,380 B2 7/2014 Berka et al.
8,815,512 B2 8/2014 Van Eijk
8,822,148 B2 9/2014 Ismagliov et al.
8,829,171 B2 9/2014 Steemers et al.
8,835,358 B2 9/2014 Fodor et al.
8,871,444 B2 10/2014 Griffiths et al.
8,889,083 B2 11/2014 Ismagilov et al.
8,911,945 B2 12/2014 Van Eijk
8,927,218 B2 1/2015 Forsyth
8,975,302 B2 3/2015 Light et al.
8,986,286 B2 3/2015 Tanghoj et al.
8,986,628 B2 3/2015 Stone et al.
9,005,935 B2 4/2015 Belyaev
9,012,390 B2 4/2015 Holtze et al.
9,017,948 B2 4/2015 Agresti et al.
9,029,083 B2 5/2015 Griffiths et al.
9,029,085 B2 5/2015 Agresti et al.
9,034,601 B2 5/2015 Hufton et al.
9,040,256 B2 5/2015 Grunenwald et al.
9,062,348 B1 6/2015 Van Eijk
9,068,210 B2 6/2015 Agresti et al.
9,074,251 B2 7/2015 Steemers et al.
9,080,211 B2 7/2015 Grunenwald et al.
9,085,798 B2 7/2015 Chee
9,089,844 B2 7/2015 Hiddessen et al.
9,102,980 B2 8/2015 Brenner et al.
9,126,160 B2 9/2015 Ness et al.
9,150,916 B2 10/2015 Christen et al.
9,151,757 B2 10/2015 Reker-Hadrup et al.
9,156,010 B2 10/2015 Colston, Jr. et al.
9,175,295 B2 11/2015 Kaminaka et al.
9,194,001 B2 11/2015 Brenner
9,194,861 B2 11/2015 Hindson et al.
9,216,392 B2 12/2015 Hindson et al.
9,217,176 B2 12/2015 Faham et al.
9,238,671 B2 1/2016 Goryshin et al.
9,249,460 B2 2/2016 Pushkarev et al.
9,266,104 B2 2/2016 Link
9,273,349 B2 3/2016 Nguyen et al.
9,290,808 B2 3/2016 Fodor et al.
9,290,809 B2 3/2016 Fodor
9,328,382 B2 5/2016 Drmanac et al.
9,328,383 B2 5/2016 Van Eijk
9,334,536 B2 5/2016 Van Eijk
9,347,059 B2 5/2016 Saxonov
9,365,901 B2 6/2016 Pepin et al.
9,371,598 B2 6/2016 Chee
9,388,465 B2 7/2016 Hindson et al.
9,404,156 B2 8/2016 Hicks
9,410,201 B2 8/2016 Hindson et al.
9,417,190 B2 8/2016 Hindson et al.
9,436,088 B2 9/2016 Seul et al.
9,486,757 B2 11/2016 Romanowsky et al.
9,499,865 B2 11/2016 Faham et al.
9,500,664 B2 11/2016 Ness et al.

(56) References Cited

U.S. PATENT DOCUMENTS 9,506,061 B2 11/2016 Brown et al.
9,506,119 B2 11/2016 Faham et al.
9,512,487 B2 12/2016 Faham et al.
9,567,631 B2 2/2017 Hindson et al.
9,574,226 B2 2/2017 Gormley et al.
9,593,365 B2 3/2017 Frisen et al.
9,623,384 B2 4/2017 Hindson et al.
9,637,799 B2 5/2017 Fan et al.
9,644,204 B2 5/2017 Hindson et al.
9,689,024 B2 6/2017 Hindson et al.
9,694,361 B2 7/2017 Bharadwaj et al.
9,695,468 B2 7/2017 Hindson et al.
9,701,998 B2 7/2017 Hindson et al.
9,702,004 B2 7/2017 Van Eijk
9,708,657 B2 7/2017 Asbury et al.
9,727,810 B2 8/2017 Fodor et al.
9,764,322 B2 9/2017 Hiddessen et al.
9,777,324 B2 10/2017 Van Eijk
9,834,814 B2 12/2017 Peter et al.
9,850,536 B2 12/2017 Oliphant et al.
9,856,530 B2 1/2018 Hindson et al.
9,868,979 B2 1/2018 Chee et al.
9,879,313 B2 1/2018 Chee et al.
9,902,950 B2 2/2018 Church et al.
9,951,386 B2 4/2018 Hindson et al.
9,957,558 B2 5/2018 Leamon et al.
10,002,316 B2 6/2018 Fodor et al.
10,011,872 B1 7/2018 Belgrader et al.
10,017,759 B2 7/2018 Kaper et al.
10,023,907 B2 7/2018 Van Eijk
10,030,261 B2 7/2018 Frisen et al.
10,030,267 B2 7/2018 Hindson et al.
10,041,116 B2 8/2018 Hindson et al.
10,053,723 B2 8/2018 Hindson et al.
10,059,989 B2 8/2018 Giresi et al.
10,071,377 B2 9/2018 Bharadwaj et al.
10,119,167 B2 11/2018 Srinivasan et al.
10,137,449 B2 11/2018 Bharadwaj et al.
10,144,950 B2 12/2018 Nolan
10,150,117 B2 12/2018 Bharadwaj et al.
10,150,963 B2 12/2018 Hindson et al.
10,150,964 B2 12/2018 Hindson et al.
10,150,995 B1 12/2018 Giresi et al.
10,174,310 B2 1/2019 Nolan
10,208,343 B2 2/2019 Hindson et al.
10,208,982 B2 2/2019 Bannish et al.
10,221,436 B2 3/2019 Hardenbol et al.
10,221,442 B2 3/2019 Hindson et al.
10,227,648 B2 3/2019 Hindson et al.
10,253,364 B2 4/2019 Hindson et al.
10,266,876 B2 4/2019 Cai et al.
10,267,808 B2 4/2019 Cai
10,273,541 B2 4/2019 Hindson et al.
10,357,771 B2 7/2019 Bharadwaj
10,472,669 B2 11/2019 Chee
10,480,022 B2 11/2019 Chee
10,480,029 B2 11/2019 Bent et al.
10,494,667 B2 12/2019 Chee
10,550,429 B2 2/2020 Harada et al.
10,590,244 B2 3/2020 Delaney et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,858,702 B2 12/2020 Lucero et al.
10,872,679 B2 12/2020 Cai et al.
10,913,975 B2 2/2021 So et al.
10,914,730 B2 2/2021 Chee et al.
10,927,403 B2 2/2021 Chee et al.
10,961,566 B2 3/2021 Chee
11,008,607 B2 5/2021 Chee
11,008,608 B2 5/2021 Samusik et al.
11,046,996 B1 6/2021 Chee et al.
11,067,567 B2 7/2021 Chee
11,156,603 B2 10/2021 Chee
11,162,132 B2 11/2021 Frisen et al.
11,208,684 B2 12/2021 Chee
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,479,809 B2 10/2022 Frisen et al.
11,479,810 B1 10/2022 Chee
11,492,612 B1 11/2022 Dadhwal
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.
11,753,675 B2 9/2023 Ramachandran Iyer
11,761,030 B2 9/2023 Chee
11,761,038 B1 9/2023 Stoeckius
11,767,550 B2 9/2023 Chee
11,768,175 B1 9/2023 Kim et al.
11,773,433 B2 10/2023 Gallant et al.
11,781,130 B2 10/2023 Dadhwal
11,788,122 B2 10/2023 Frisen et al.
11,795,498 B2 10/2023 Frisen et al.
11,795,507 B2 10/2023 Chell et al.
11,808,769 B2 11/2023 Uytingco et al.
11,821,024 B2 11/2023 Chee et al.
11,821,035 B1 11/2023 Bent et al.
11,827,935 B1 11/2023 Ramachandran Iyer et al.
11,835,462 B2 12/2023 Bava
11,840,687 B2 12/2023 Gallant et al.
11,840,724 B2 12/2023 Chew et al.
11,845,979 B2 12/2023 Engblom et al.
11,859,178 B2 1/2024 Gallant et al.
11,866,767 B2 1/2024 Uytingco et al.
11,866,770 B2 1/2024 Chee
11,873,482 B2 1/2024 Kim et al.
11,891,654 B2 2/2024 Alvarado Martinez et al.

(56) References Cited

U.S. PATENT DOCUMENTS 11,898,205 B2 2/2024 Bava
2001/0020588 A1 9/2001 Adourian et al.
2001/0036669 A1 11/2001 Jedrzejewski et al.
2001/0041357 A1 11/2001 Fouillet et al.
2001/0044109 A1 11/2001 Mandecki
2001/0048900 A1 12/2001 Bardell et al.
2001/0053519 A1 12/2001 Fodor et al.
2002/0001856 A1 1/2002 Chow et al.
2002/0005354 A1 1/2002 Spence et al.
2002/0034737 A1 3/2002 Drmanac
2002/0040275 A1 4/2002 Cravatt
2002/0043463 A1 4/2002 Shenderov
2002/0051971 A1 5/2002 Stuelpnagel et al.
2002/0051992 A1 5/2002 Bridgham et al.
2002/0058332 A1 5/2002 Quake et al.
2002/0065609 A1 5/2002 Ashby et al.
2002/0068278 A1 6/2002 Giese et al.
2002/0089100 A1 7/2002 Kawasaki
2002/0092767 A1 7/2002 Bjornson et al.
2002/0113009 A1 8/2002 O'Connor et al.
2002/0119455 A1 8/2002 Chan et al.
2002/0119536 A1 8/2002 Stern
2002/0127736 A1 9/2002 Chou et al.
2002/0131147 A1 9/2002 Paolini et al.
2002/0160518 A1 10/2002 Hayenga et al.
2002/0164611 A1 11/2002 Bamdad
2002/0164820 A1 11/2002 Brown
2002/0166582 A1 11/2002 O'Connor et al.
2002/0172965 A1 11/2002 Kamb et al.
2002/0175079 A1 11/2002 Christel et al.
2002/0179849 A1 12/2002 Maher et al.
2003/0005967 A1 1/2003 Karp
2003/0007898 A1 1/2003 Bohm et al.
2003/0008285 A1 1/2003 Fischer
2003/0008323 A1 1/2003 Ravkin et al.
2003/0017451 A1 1/2003 Wang et al.
2003/0022207 A1 1/2003 Balasubramanian
2003/0022231 A1 1/2003 Wangh et al.
2003/0027214 A1 2/2003 Kamb
2003/0027221 A1 2/2003 Scott et al.
2003/0028981 A1 2/2003 Chandler et al.
2003/0032141 A1 2/2003 Nguyen et al.
2003/0036206 A1 2/2003 Chien et al.
2003/0039978 A1 2/2003 Hannah
2003/0044777 A1 3/2003 Beattie
2003/0044836 A1 3/2003 Levine et al.
2003/0075446 A1 4/2003 Culbertson et al.
2003/0082587 A1 5/2003 Seul et al.
2003/0087232 A1 5/2003 Christians
2003/0089605 A1 5/2003 Timperman
2003/0104466 A1 6/2003 Knapp et al.
2003/0108897 A1 6/2003 Drmanac
2003/0124509 A1 7/2003 Kenis et al.
2003/0148335 A1 8/2003 Shen et al.
2003/0149307 A1 8/2003 Hai et al.
2003/0162216 A1 8/2003 Gold
2003/0170698 A1 9/2003 Gascoyne et al.
2003/0182068 A1 9/2003 Battersby et al.
2003/0207260 A1 11/2003 Trnovsky et al.
2003/0211489 A1 11/2003 Shen et al.
2003/0215862 A1 11/2003 Parce et al.
2003/0224419 A1 12/2003 Corcoran
2003/0232348 A1 12/2003 Jones et al.
2003/0232382 A1 12/2003 Brennan
2004/0033499 A1 2/2004 Ilsley et al.
2004/0063138 A1 4/2004 Mcginnis et al.
2004/0067492 A1 4/2004 Peng et al.
2004/0081962 A1 4/2004 Chen et al.
2004/0096853 A1 5/2004 Mayer
2004/0101680 A1 5/2004 Barber et al.
2004/0101880 A1 5/2004 Rozwadowski et al.
2004/0106110 A1 6/2004 Balasubramanian
2004/0132122 A1 7/2004 Banerjee et al.
2004/0224331 A1 11/2004 Cantor et al.
2004/0258701 A1 12/2004 Dominowski et al.
2005/0019839 A1 1/2005 Jespersen et al.
2005/0037393 A1 2/2005 Gunderson et al.
2005/0042625 A1 2/2005 Schmidt et al.
2005/0048580 A1 3/2005 Labaer
2005/0079510 A1 4/2005 Berka et al.
2005/0100900 A1 5/2005 Kawashima et al.
2005/0130173 A1 6/2005 Leamon et al.
2005/0130188 A1 6/2005 Walt et al.
2005/0136414 A1 6/2005 Gunderson et al.
2005/0172476 A1 8/2005 Stone et al.
2005/0181379 A1 8/2005 Su et al.
2005/0191656 A1 9/2005 Drmanac et al.
2005/0191698 A1 9/2005 Chee et al.
2005/0202429 A1 9/2005 Trau et al.
2005/0202433 A1 9/2005 Van Beuningen
2005/0202489 A1 9/2005 Cho et al.
2005/0221339 A1 10/2005 Griffiths et al.
2005/0227271 A1 10/2005 Kwon
2005/0244850 A1 11/2005 Huang et al.
2005/0250147 A1 11/2005 Macevicz
2005/0260653 A1 11/2005 LaBaer
2005/0266582 A1 12/2005 Modlin et al.
2005/0272159 A1 12/2005 Ismagilov et al.
2005/0287572 A1 12/2005 Mathies et al.
2006/0002890 A1 1/2006 Hersel et al.
2006/0008799 A1 1/2006 Cai et al.
2006/0020371 A1 1/2006 Ham et al.
2006/0040382 A1 2/2006 Heffron et al.
2006/0046313 A1 3/2006 Roth
2006/0073487 A1 4/2006 Oliver et al.
2006/0078888 A1 4/2006 Griffiths et al.
2006/0153924 A1 7/2006 Griffiths et al.
2006/0163385 A1 7/2006 Link et al.
2006/0177832 A1 8/2006 Brenner
2006/0177833 A1 8/2006 Brenner
2006/0199193 A1 9/2006 Koo et al.
2006/0211001 A1 9/2006 Yu et al.
2006/0216775 A1 9/2006 Burkart et al.
2006/0240506 A1 10/2006 Kushmaro et al.
2006/0257893 A1 11/2006 Takahashi et al.
2006/0263789 A1 11/2006 Kincaid
2006/0263888 A1 11/2006 Fritz et al.
2006/0275782 A1 12/2006 Gunderson et al.
2006/0286570 A1 12/2006 Rowlen et al.
2006/0292583 A1 12/2006 Schneider et al.
2007/0003442 A1 1/2007 Link et al.
2007/0020617 A1 1/2007 Trnovsky et al.
2007/0020640 A1 1/2007 Mccloskey et al.
2007/0026401 A1 2/2007 Hofmann et al.
2007/0031829 A1 2/2007 Yasuno et al.
2007/0042400 A1 2/2007 Choi et al.
2007/0042419 A1 2/2007 Barany et al.
2007/0054119 A1 3/2007 Garstecki et al.
2007/0054288 A1 3/2007 Su et al.
2007/0072208 A1 3/2007 Drmanac
2007/0077572 A1 4/2007 Tawfik et al.
2007/0092914 A1 4/2007 Griffiths et al.
2007/0099208 A1 5/2007 Drmanac et al.
2007/0128624 A1 6/2007 Gormley et al.
2007/0128656 A1 6/2007 Agrawal
2007/0134277 A1 6/2007 Chen et al.
2007/0141584 A1 6/2007 Roberts et al.
2007/0154903 A1 7/2007 Marla et al.
2007/0160503 A1 7/2007 Sethu et al.
2007/0172873 A1 7/2007 Brenner et al.
2007/0190543 A1 8/2007 Livak
2007/0195127 A1 8/2007 Ahn et al.
2007/0196397 A1 8/2007 Torii et al.
2007/0207060 A1 9/2007 Zou et al.
2007/0207482 A1 9/2007 Church et al.
2007/0228588 A1 10/2007 Noritomi et al.
2007/0231823 A1 10/2007 Mckernan et al.
2007/0238113 A1 10/2007 Kanda et al.
2007/0254305 A1 11/2007 Paik et al.
2007/0259357 A1 11/2007 Brenner
2007/0264320 A1 11/2007 Lee et al.
2007/0269805 A1 11/2007 Hogers
2008/0003142 A1 1/2008 Link et al.
2008/0004436 A1 1/2008 Tawfik et al.

(56) References Cited

U.S. PATENT DOCUMENTS

2008/0009420 A1 1/2008 Schroth et al.
2008/0014589 A1 1/2008 Link et al.
2008/0056948 A1 3/2008 Dale et al.
2008/0108804 A1 5/2008 Hayashizaki et al.
2008/0124726 A1 5/2008 Monforte
2008/0138878 A1 6/2008 Kubu et al.
2008/0160580 A1 7/2008 Adessi et al.
2008/0166720 A1 7/2008 Hsieh et al.
2008/0213766 A1 9/2008 Brown et al.
2008/0220434 A1 9/2008 Thomas
2008/0228268 A1 9/2008 Shannon et al.
2008/0241820 A1 10/2008 Krutzik et al.
2008/0242560 A1 10/2008 Gunderson et al.
2008/0261204 A1 10/2008 Lexow
2008/0268450 A1 10/2008 Nam et al.
2008/0268507 A1 10/2008 Xu et al.
2008/0286795 A1 11/2008 Kawashima et al.
2009/0005252 A1 1/2009 Drmanac et al.
2009/0006002 A1 1/2009 Honisch et al.
2009/0011943 A1 1/2009 Drmanac et al.
2009/0012187 A1 1/2009 Chu et al.
2009/0018024 A1 1/2009 Church et al.
2009/0025277 A1 1/2009 Takanashi
2009/0026082 A1 1/2009 Rothberg et al.
2009/0035770 A1 2/2009 Mathies et al.
2009/0047713 A1 2/2009 Handique
2009/0048124 A1 2/2009 Leamon et al.
2009/0053169 A1 2/2009 Castillo et al.
2009/0062129 A1 3/2009 Mckernan et al.
2009/0068170 A1 3/2009 Weitz et al.
2009/0082212 A1 3/2009 Williams
2009/0098555 A1 4/2009 Roth et al.
2009/0099041 A1 4/2009 Church et al.
2009/0105959 A1 4/2009 Braverman et al.
2009/0117573 A1 5/2009 Fu et al.
2009/0118488 A1 5/2009 Drmanac et al.
2009/0127589 A1 5/2009 Rothberg et al.
2009/0131543 A1 5/2009 Weitz et al.
2009/0134027 A1 5/2009 Jary
2009/0137404 A1 5/2009 Drmanac et al.
2009/0137414 A1 5/2009 Drmanac et al.
2009/0143244 A1 6/2009 Bridgham et al.
2009/0148961 A1 6/2009 Luchini et al.
2009/0155563 A1 6/2009 Petsev et al.
2009/0155780 A1 6/2009 Xiao et al.
2009/0155781 A1 6/2009 Drmanac et al.
2009/0197248 A1 8/2009 Griffiths et al.
2009/0197772 A1 8/2009 Griffiths et al.
2009/0202984 A1 8/2009 Cantor
2009/0203531 A1 8/2009 Kurn
2009/0233802 A1 9/2009 Bignell et al.
2009/0235990 A1 9/2009 Beer
2009/0253581 A1 10/2009 van Eijk et al.
2009/0264299 A1 10/2009 Drmanac et al.
2009/0269248 A1 10/2009 Falb et al.
2009/0286687 A1 11/2009 Dressman et al.
2009/0289184 A1 11/2009 Deininger
2009/0291854 A1 11/2009 Weisinger-Mayr et al.
2009/0312193 A1 12/2009 Kim et al.
2009/0325260 A1 12/2009 Otto et al.
2010/0021973 A1 1/2010 Makarov et al.
2010/0021984 A1 1/2010 Edd et al.
2010/0022414 A1 1/2010 Link et al.
2010/0035249 A1 2/2010 Hayashizaki et al.
2010/0035254 A1 2/2010 Williams
2010/0062494 A1 3/2010 Church et al.
2010/0069263 A1 3/2010 Shendure et al.
2010/0086914 A1 4/2010 Bentley et al.
2010/0105112 A1 4/2010 Holtze et al.
2010/0105866 A1 4/2010 Fraden et al.
2010/0113296 A1 5/2010 Myerson
2010/0120097 A1 5/2010 Matz et al.
2010/0120098 A1 5/2010 Grunenwald et al.
2010/0130369 A1 5/2010 Shenderov et al.
2010/0136544 A1 6/2010 Agresti et al.
2010/0137163 A1 6/2010 Link et al.
2010/0145037 A1 6/2010 Brive et al.
2010/0173394 A1 7/2010 Colston, Jr. et al.
2010/0184928 A1 7/2010 Kumacheva
2010/0187705 A1 7/2010 Lee et al.
2010/0210479 A1 8/2010 Griffiths et al.
2010/0216153 A1 8/2010 Lapidus et al.
2010/0248237 A1 9/2010 Froehlich et al.
2010/0248991 A1 9/2010 Roesler et al.
2010/0304982 A1 12/2010 Hinz et al.
2011/0000560 A1 1/2011 Miller et al.
2011/0008775 A1 1/2011 Gao et al.
2011/0028412 A1 2/2011 Cappello et al.
2011/0028685 A1 2/2011 Purkayastha et al.
2011/0033548 A1 2/2011 Lai et al.
2011/0033854 A1 2/2011 Drmanac et al.
2011/0053798 A1 3/2011 Hindson et al.
2011/0059436 A1 3/2011 Hardin et al.
2011/0059556 A1 3/2011 Strey et al.
2011/0071053 A1 3/2011 Drmanac et al.
2011/0086780 A1 4/2011 Colston, Jr. et al.
2011/0092376 A1 4/2011 Colston, Jr. et al.
2011/0092392 A1 4/2011 Colston, Jr. et al.
2011/0160078 A1 6/2011 Fodor et al.
2011/0166034 A1 7/2011 Kwong et al.
2011/0195496 A1 8/2011 Muraguchi et al.
2011/0201526 A1 8/2011 Berka et al.
2011/0212090 A1 9/2011 Pedersen et al.
2011/0217736 A1 9/2011 Hindson
2011/0218123 A1 9/2011 Weitz et al.
2011/0223613 A1 9/2011 Gut
2011/0245111 A1 10/2011 Chee
2011/0263457 A1 10/2011 Krutzik et al.
2011/0267457 A1 11/2011 Weitz et al.
2011/0281736 A1 11/2011 Drmanac et al.
2011/0281738 A1 11/2011 Drmanac et al.
2011/0287435 A1 11/2011 Grunenwald et al.
2011/0305761 A1 12/2011 Shum et al.
2011/0306141 A1 12/2011 Bronchetti et al.
2011/0319281 A1 12/2011 Drmanac
2012/0000777 A1 1/2012 Garrell et al.
2012/0003657 A1 1/2012 Myllykangas et al.
2012/0010091 A1 1/2012 Linnarson et al.
2012/0010098 A1 1/2012 Griffiths et al.
2012/0010107 A1 1/2012 Griffiths et al.
2012/0014977 A1 1/2012 Furihata et al.
2012/0015382 A1 1/2012 Weitz et al.
2012/0015822 A1 1/2012 Weitz et al.
2012/0071331 A1 3/2012 Casbon et al.
2012/0121481 A1 5/2012 Romanowsky et al.
2012/0132288 A1 5/2012 Weitz et al.
2012/0135871 A1 5/2012 van Eijk et al.
2012/0135893 A1 5/2012 Drmanac et al.
2012/0165219 A1 6/2012 Van Der Zaag et al.
2012/0172259 A1 7/2012 Rigatti et al.
2012/0184449 A1 7/2012 Hixson et al.
2012/0190032 A1 7/2012 Ness et al.
2012/0190037 A1 7/2012 Durin et al.
2012/0196288 A1 8/2012 Beer et al.
2012/0202698 A1 8/2012 van Eijk et al.
2012/0208705 A1 8/2012 Steemers et al.
2012/0208724 A1 8/2012 Steemers et al.
2012/0211084 A1 8/2012 Weitz et al.
2012/0219947 A1 8/2012 Yurkovetsky et al.
2012/0220494 A1 8/2012 Samuels et al.
2012/0220497 A1 8/2012 Jacobson et al.
2012/0222748 A1 9/2012 Weitz et al.
2012/0231972 A1 9/2012 Golyshin et al.
2012/0252012 A1 10/2012 Armougom et al.
2012/0253689 A1 10/2012 Rogan et al.
2012/0289428 A1 11/2012 Duffy et al.
2012/0297493 A1 11/2012 Cooper et al.
2012/0309002 A1 12/2012 Link
2012/0316074 A1 12/2012 Saxonov
2013/0017978 A1 1/2013 Kavanagh et al.
2013/0018970 A1 1/2013 Woundy et al.
2013/0022682 A1 1/2013 Lee et al.
2013/0028812 A1 1/2013 Prieto et al.
2013/0041004 A1 2/2013 Drager et al.

(56) References Cited

U.S. PATENT DOCUMENTS

2013/0046030 A1 2/2013 Rotem et al.
2013/0059310 A1 3/2013 Brenner et al.
2013/0078638 A1 3/2013 Berka et al.
2013/0079231 A1 3/2013 Pushkarev et al.
2013/0079251 A1 3/2013 Boles
2013/0084243 A1 4/2013 Goetsch et al.
2013/0096073 A1 4/2013 Sidelman
2013/0109575 A1 5/2013 Kleinschmidt et al.
2013/0109576 A1 5/2013 Shuber et al.
2013/0109596 A1 5/2013 Peterson et al.
2013/0121893 A1 5/2013 Delamarche et al.
2013/0130919 A1 5/2013 Chen et al.
2013/0157870 A1 6/2013 Pushkarev et al.
2013/0157899 A1 6/2013 Adler, Jr. et al.
2013/0178368 A1 7/2013 Griffiths et al.
2013/0189700 A1 7/2013 So et al.
2013/0203605 A1 8/2013 Shendure et al.
2013/0203675 A1 8/2013 Desimone et al.
2013/0210639 A1 8/2013 Link et al.
2013/0210991 A1 8/2013 Fonnum et al.
2013/0211055 A1 8/2013 Raines et al.
2013/0225418 A1 8/2013 Watson
2013/0225623 A1 8/2013 Buxbaum et al.
2013/0273640 A1 10/2013 Krishnan et al.
2013/0274117 A1 10/2013 Church et al.
2013/0296173 A1 11/2013 Callow et al.
2013/0343317 A1 12/2013 Etemad et al.
2013/0344508 A1 12/2013 Schwartz et al.
2014/0030350 A1 1/2014 Ashrafi et al.
2014/0038178 A1 2/2014 Otto et al.
2014/0057799 A1 2/2014 Johnson et al.
2014/0065234 A1 3/2014 Shum et al.
2014/0065609 A1 3/2014 Hicks et al.
2014/0066318 A1 3/2014 Frisen et al.
2014/0080717 A1 3/2014 Li et al.
2014/0093916 A1 4/2014 Belyaev et al.
2014/0120529 A1 5/2014 Andersen et al.
2014/0155274 A1 6/2014 Xie et al.
2014/0155295 A1 6/2014 Hindson et al.
2014/0194323 A1 7/2014 Gillevet
2014/0199730 A1 7/2014 Agresti et al.
2014/0199731 A1 7/2014 Agresti et al.
2014/0206554 A1 7/2014 Hindson et al.
2014/0221239 A1 8/2014 Carman et al.
2014/0227684 A1 8/2014 Hindson et al.
2014/0227706 A1 8/2014 Kato et al.
2014/0228255 A1 8/2014 Hindson et al.
2014/0235506 A1 8/2014 Hindson et al.
2014/0242664 A1 8/2014 Zhang et al.
2014/0270435 A1 9/2014 Dunn
2014/0272996 A1 9/2014 Bemis
2014/0274731 A1 9/2014 Raymond et al.
2014/0274740 A1 9/2014 Srinivasan et al.
2014/0287963 A1 9/2014 Hindson et al.
2014/0302503 A1 10/2014 Lowe et al.
2014/0315725 A1 10/2014 Faham et al.
2014/0315755 A1 10/2014 Chen et al.
2014/0323330 A1 10/2014 Glezer et al.
2014/0338753 A1 11/2014 Sperling et al.
2014/0357500 A1 12/2014 Vigneault et al.
2014/0378322 A1 12/2014 Hindson et al.
2014/0378345 A1 12/2014 Hindson et al.
2014/0378349 A1 12/2014 Hindson et al.
2014/0378350 A1 12/2014 Hindson et al.
2015/0005188 A1 1/2015 Levner et al.
2015/0005199 A1 1/2015 Hindson et al.
2015/0005200 A1 1/2015 Hindson et al.
2015/0011430 A1 1/2015 Saxonov
2015/0011432 A1 1/2015 Saxonov
2015/0031037 A1 1/2015 Li et al.
2015/0057163 A1 2/2015 Rotem et al.
2015/0072899 A1 3/2015 Ward et al.
2015/0111256 A1 4/2015 Church et al.
2015/0111788 A1 4/2015 Fernandez et al.
2015/0119280 A1 4/2015 Srinivas et al.
2015/0211056 A1 7/2015 Um et al.
2015/0218633 A1 8/2015 Hindson et al.
2015/0224466 A1 8/2015 Hindson et al.
2015/0225777 A1 8/2015 Hindson et al.
2015/0225786 A1 8/2015 Litterst et al.
2015/0247182 A1 9/2015 Faham et al.
2015/0259736 A1 9/2015 Steemers et al.
2015/0267191 A1 9/2015 Steelman et al.
2015/0291942 A1 10/2015 Gloeckner et al.
2015/0292988 A1 10/2015 Bharadwaj et al.
2015/0298091 A1 10/2015 Weitz et al.
2015/0299772 A1 10/2015 Zhang
2015/0299784 A1 10/2015 Fan et al.
2015/0329617 A1 11/2015 Winther et al.
2015/0329852 A1 11/2015 Nolan et al.
2015/0329891 A1 11/2015 Tan et al.
2015/0337298 A1 11/2015 Xi et al.
2015/0344942 A1 12/2015 Frisen et al.
2015/0353999 A1 12/2015 Agresti et al.
2015/0361418 A1 12/2015 Reed et al.
2015/0368638 A1 12/2015 Steemers et al.
2015/0368694 A1 12/2015 Pan et al.
2015/0376605 A1 12/2015 Jarosz et al.
2015/0376608 A1 12/2015 Kaper et al.
2015/0376609 A1 12/2015 Hindson et al.
2015/0376700 A1 12/2015 Schnall-Levin et al.
2015/0379196 A1 12/2015 Schnall-Levin et al.
2016/0024493 A1 1/2016 Robins
2016/0024558 A1 1/2016 Hardenbol
2016/0024572 A1 1/2016 Shishkin et al.
2016/0025726 A1 1/2016 Altin et al.
2016/0032282 A1 2/2016 Vigneault et al.
2016/0053253 A1 2/2016 Salathia et al.
2016/0059204 A1 3/2016 Hindson et al.
2016/0060621 A1 3/2016 Agresti et al.
2016/0060691 A1 3/2016 Giresi et al.
2016/0115474 A1 4/2016 Jelinek et al.
2016/0122753 A1 5/2016 Mikkelsen et al.
2016/0122817 A1 5/2016 Jarosz et al.
2016/0138091 A1 5/2016 Chee et al.
2016/0145677 A1 5/2016 Chee et al.
2016/0145683 A1 5/2016 Fan et al.
2016/0153005 A1 6/2016 Zhang et al.
2016/0160235 A1 6/2016 Solodushko et al.
2016/0177359 A1 6/2016 Ukanis et al.
2016/0201125 A1 7/2016 Samuels et al.
2016/0208323 A1 7/2016 Bernstein et al.
2016/0231324 A1 8/2016 Zhao et al.
2016/0244742 A1 8/2016 Linnarsson et al.
2016/0244809 A1 8/2016 Belgrader et al.
2016/0244811 A1 8/2016 Edwards
2016/0244825 A1 8/2016 Vigneault et al.
2016/0251697 A1 9/2016 Nolan et al.
2016/0253584 A1 9/2016 Fodor et al.
2016/0257984 A1 9/2016 Hardenbol et al.
2016/0257993 A1 9/2016 Fu et al.
2016/0281160 A1 9/2016 Jarosz et al.
2016/0289669 A1 10/2016 Fan et al.
2016/0289740 A1 10/2016 Fu et al.
2016/0289769 A1 10/2016 Schwartz et al.
2016/0298180 A1 10/2016 Chee
2016/0304860 A1 10/2016 Hindson et al.
2016/0304956 A1 10/2016 Robins
2016/0326583 A1 11/2016 Johnson et al.
2016/0348093 A1 12/2016 Price et al.
2016/0376663 A1 12/2016 Brown
2017/0009274 A1 1/2017 Abate et al.
2017/0016041 A1 1/2017 Greenfield et al.
2017/0114390 A1 4/2017 Hindson et al.
2017/0128937 A1 5/2017 Hung et al.
2017/0144161 A1 5/2017 Hindson et al.
2017/0145476 A1 5/2017 Ryvkin et al.
2017/0159109 A1 6/2017 Zheng et al.
2017/0183701 A1 6/2017 Agresti et al.
2017/0211127 A1 7/2017 Mikkelsen et al.
2017/0220733 A1 8/2017 Zhuang et al.
2017/0242020 A1 8/2017 Yamauchi et al.
2017/0247757 A1 8/2017 Hindson et al.
2017/0260584 A1 9/2017 Zheng et al.

(56) References Cited

U.S. PATENT DOCUMENTS

2017/0268056 A1 9/2017 Vigneault et al.
2017/0321252 A1 11/2017 Hindson et al.
2017/0335385 A1 11/2017 Hindson et al.
2017/0342404 A1 11/2017 Hindson et al.
2017/0342405 A1 11/2017 Fu et al.
2017/0343545 A1 11/2017 Hadrup et al.
2017/0348691 A1 12/2017 Bharadwaj et al.
2017/0356027 A1 12/2017 Hindson et al.
2017/0362587 A1 12/2017 Hindson et al.
2018/0008984 A1 1/2018 Bharadwaj et al.
2018/0015472 A1 1/2018 Bharadwaj et al.
2018/0015473 A1 1/2018 Bharadwaj et al.
2018/0016634 A1 1/2018 Hindson et al.
2018/0030512 A1 2/2018 Hindson et al.
2018/0030515 A1 2/2018 Regev et al.
2018/0057868 A1 3/2018 Walder et al.
2018/0057873 A1 3/2018 Zhou et al.
2018/0080019 A1 3/2018 Blainey et al.
2018/0080021 A1 3/2018 Reuter et al.
2018/0087050 A1 3/2018 Zheng et al.
2018/0088112 A1 3/2018 Fan et al.
2018/0105808 A1 4/2018 Mikkelsen et al.
2018/0112253 A1 4/2018 Hindson et al.
2018/0112261 A1 4/2018 Van Driel et al.
2018/0114316 A1 4/2018 Lele et al.
2018/0179580 A1 6/2018 Hindson et al.
2018/0179591 A1 6/2018 Belgrader et al.
2018/0180601 A1 6/2018 Pedersen et al.
2018/0195060 A1 7/2018 Wang et al.
2018/0195112 A1 7/2018 Lebofsky et al.
2018/0201980 A1 7/2018 Chee et al.
2018/0216162 A1 8/2018 Belhocine et al.
2018/0237951 A1 8/2018 Bock et al.
2018/0245142 A1 8/2018 So et al.
2018/0251825 A1 9/2018 Stoeckius et al.
2018/0258466 A1 9/2018 Hindson et al.
2018/0258482 A1 9/2018 Hindson et al.
2018/0265928 A1 9/2018 Schnall-Levin et al.
2018/0267036 A1 9/2018 Fan et al.
2018/0273933 A1 9/2018 Gunderson et al.
2018/0274027 A1 9/2018 Hindson et al.
2018/0282803 A1 10/2018 Belgrader et al.
2018/0282804 A1 10/2018 Hindson et al.
2018/0291427 A1 10/2018 Edelman
2018/0291439 A1 10/2018 van Eijk et al.
2018/0305681 A1 10/2018 Jovanovich et al.
2018/0305685 A1 10/2018 Li et al.
2018/0327839 A1 11/2018 Hindson et al.
2018/0335424 A1 11/2018 Chen et al.
2018/0340169 A1 11/2018 Belhocine et al.
2018/0340170 A1 11/2018 Belhocine et al.
2018/0340171 A1 11/2018 Belhocine et al.
2018/0340172 A1 11/2018 Belhocine et al.
2018/0340939 A1 11/2018 Gaublomme et al.
2018/0346970 A1 12/2018 Chang
2018/0346979 A1 12/2018 Hindson et al.
2018/0363029 A1 12/2018 Hindson et al.
2018/0371538 A1 12/2018 Blauwkamp et al.
2018/0371540 A1 12/2018 Hindson et al.
2018/0376609 A1 12/2018 Ju et al.
2019/0002967 A1 1/2019 Chen et al.
2019/0024166 A1 1/2019 Hindson et al.
2019/0032129 A1 1/2019 Hindson et al.
2019/0032130 A1 1/2019 Giresi et al.
2019/0040382 A1 2/2019 Steemers et al.
2019/0040464 A1 2/2019 Giresi et al.
2019/0064173 A1 2/2019 Bharadwaj et al.
2019/0071656 A1 3/2019 Chang et al.
2019/0078150 A1 3/2019 Chen et al.
2019/0085324 A1 3/2019 Rerey et al.
2019/0085391 A1 3/2019 Hindson et al.
2019/0127731 A1 5/2019 Mcdermott
2019/0136316 A1 5/2019 Hindson et al.
2019/0136317 A1 5/2019 Hindson et al.
2019/0136319 A1 5/2019 Hindson et al.
2019/0144936 A1 5/2019 Gierahn et al.
2019/0153436 A1 5/2019 Belhocine et al.
2019/0153532 A1 5/2019 Bharadwaj et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0203275 A1 7/2019 Frisen et al.
2019/0233878 A1 8/2019 Delaney et al.
2019/0249226 A1 8/2019 Bent et al.
2019/0262831 A1 8/2019 West et al.
2019/0264268 A1 8/2019 Frisen et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0338353 A1 11/2019 Belgrader et al.
2019/0352708 A1 11/2019 Gaige et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0002764 A1 1/2020 Belgrader et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0109443 A1 4/2020 Chee
2020/0173985 A1 6/2020 Dong et al.
2020/0256867 A1 8/2020 Hennek et al.
2020/0277663 A1 9/2020 Iyer
2020/0277664 A1 9/2020 Frenz
2020/0299757 A1 9/2020 Chee et al.
2020/0325531 A1 10/2020 Chee
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0095331 A1 4/2021 Fan et al.
2021/0123040 A1 4/2021 Macosko et al.
2021/0140982 A1 5/2021 Uytingco et al.
2021/0155982 A1 5/2021 Yin et al.
2021/0158522 A1 5/2021 Weisenfeld et al.
2021/0172007 A1 6/2021 Chee et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee
2021/0214785 A1 7/2021 Stoeckius
2021/0222235 A1 7/2021 Chee
2021/0222241 A1 7/2021 Bharadwaj
2021/0222242 A1 7/2021 Ramachandran Iyer
2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee

(56) References Cited

U.S. PATENT DOCUMENTS

2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0317524 A1 10/2021 Lucero et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0064630 A1 3/2022 Bent et al.
2022/0081728 A1 3/2022 Williams
2022/0090058 A1 3/2022 Frisen et al.
2022/0090175 A1 3/2022 Uytingco et al.
2022/0098576 A1 3/2022 Dadhwal
2022/0098661 A1 3/2022 Chew et al.
2022/0106632 A1 4/2022 Galonska et al.
2022/0106633 A1 4/2022 Engblom et al.
2022/0112486 A1 4/2022 Ramachandran Iyer et al.
2022/0112545 A1 4/2022 Chee
2022/0119869 A1 4/2022 Ramachandran Iyer et al.
2022/0127659 A1 4/2022 Frisen et al.
2022/0127666 A1 4/2022 Katiraee et al.
2022/0127672 A1 4/2022 Stoeckius
2022/0145361 A1 5/2022 Frenz et al.
2022/0154255 A1 5/2022 Chee et al.
2022/0170083 A1 6/2022 Khaled et al.
2022/0195422 A1 6/2022 Gallant et al.
2022/0195505 A1 6/2022 Frisen et al.
2022/0196644 A1 6/2022 Chee
2022/0213526 A1 7/2022 Frisen et al.
2022/0241780 A1 8/2022 Tentori et al.
2022/0267844 A1 8/2022 Ramachandran Iyer et al.
2022/0282329 A1 9/2022 Chell et al.
2022/0290217 A1 9/2022 Frenz et al.
2022/0290219 A1 9/2022 Chee
2022/0298560 A1 9/2022 Frisen et al.
2022/0315984 A1 10/2022 Edelman et al.
2022/0325325 A1 10/2022 Chee et al.
2022/0326251 A1 10/2022 Uytingco et al.
2022/0333171 A1 10/2022 Chee
2022/0333191 A1 10/2022 Mikkelsen et al.
2022/0333192 A1 10/2022 Uytingco
2022/0333195 A1 10/2022 Schnall-Levin et al.
2022/0334031 A1 10/2022 Delaney et al.
2022/0348905 A1 11/2022 Dadhwal
2022/0348992 A1 11/2022 Stoeckius et al.
2022/0356464 A1 11/2022 Kim et al.
2022/0364163 A1 11/2022 Stahl et al.
2022/0389491 A1 12/2022 Chee
2022/0389504 A1 12/2022 Chew et al.
2022/0403374 A1 12/2022 Soumillon
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0033960 A1 2/2023 Gallant et al.
2023/0034039 A1 2/2023 Shahjamali
2023/0034216 A1 2/2023 Bava
2023/0040363 A1 2/2023 Chee
2023/0042088 A1 2/2023 Chee
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0107023 A1 4/2023 Chee
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0151412 A1 5/2023 Chee
2023/0159994 A1 5/2023 Chee
2023/0159995 A1 5/2023 Iyer et al.
2023/0160008 A1 5/2023 Chell et al.
2023/0175045 A1 6/2023 Katsori et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0212655 A1 7/2023 Chee
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323436 A1 10/2023 Chee
2023/0323447 A1 10/2023 Schnall-Levin et al.
2023/0323453 A1 10/2023 Stoeckius
2023/0332138 A1 10/2023 Kim et al.
2023/0332211 A1 10/2023 Chee
2023/0332212 A1 10/2023 Chew et al.
2023/0332227 A1 10/2023 Ramachandran Iyer
2023/0332247 A1 10/2023 Singh et al.
2023/0358733 A1 11/2023 Chee
2023/0366008 A1 11/2023 Chew et al.
2023/0383285 A1 11/2023 Kim et al.
2023/0383344 A1 11/2023 Stoeckius
2023/0392204 A1 12/2023 Chell et al.
2023/0393071 A1 12/2023 Bava
2023/0407404 A1 12/2023 Baumgartner et al.
2023/0416807 A1 12/2023 Chee
2023/0416808 A1 12/2023 Sukovich et al.
2023/0416850 A1 12/2023 Singh et al.
2024/0002931 A1 1/2024 Bava
2024/0011081 A1 1/2024 Chee
2024/0011090 A1 1/2024 Chew et al.
2024/0018572 A1 1/2024 Mignardi
2024/0018575 A1 1/2024 Gallant et al.
2024/0018589 A1 1/2024 Schnall-Levin et al.
2024/0026445 A1 1/2024 Ramachandran Iyer et al.

(56) References Cited

U.S. PATENT DOCUMENTS

| | | | |
|---|---|---|---|
| 2024/0035937 A1 | 2/2024 | Cox et al. |
| 2024/0043908 A1 | 2/2024 | Chew et al. |
| 2024/0043925 A1 | 2/2024 | Bent et al. |

FOREIGN PATENT DOCUMENTS

| | | | |
|---|---|---|---|
| CN | 102292455 A | 12/2011 |
| CN | 103202812 A | 7/2013 |
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1923471 | 5/2008 |
| EP | 1944368 A1 | 7/2008 |
| EP | 2002017 | 12/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| EP | 2881465 | 6/2015 |
| EP | 3013984 | 5/2016 |
| EP | 2635679 B1 | 4/2017 |
| EP | 3511423 | 7/2019 |
| EP | 3541956 | 9/2019 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 | 4/2009 |
| JP | 2009513948 A | 4/2009 |
| JP | 2009208074 A | 9/2009 |
| JP | 2012131798 A | 7/2012 |
| JP | 2012522517 A | 9/2012 |
| RU | 2270254 | 2/2006 |
| WO | WO-84/002000 A1 | 5/1984 |
| WO | WO-8402000 A1 | 5/1984 |
| WO | WO 1989/010977 | 11/1989 |
| WO | WO 1991/006678 | 5/1991 |
| WO | WO-93/001498 A1 | 1/1993 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO 1995/025116 | 9/1995 |
| WO | WO-9530782 A1 | 11/1995 |
| WO | WO 1995/035505 | 12/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-99/042597 A1 | 8/1999 |
| WO | WO-9942597 A1 | 8/1999 |
| WO | WO-9952708 A1 | 10/1999 |
| WO | WO-00/008212 A1 | 2/2000 |
| WO | WO-0008212 A1 | 2/2000 |
| WO | WO 2000/017390 | 3/2000 |
| WO | WO-0023181 A1 | 4/2000 |
| WO | WO 2000/024940 | 5/2000 |
| WO | WO-0026412 A1 | 5/2000 |
| WO | WO-0034527 A2 | 6/2000 |
| WO | WO-0043766 A1 | 7/2000 |
| WO | WO 2000/063437 | 10/2000 |
| WO | WO-0070095 A2 | 11/2000 |
| WO | WO-01/002850 A1 | 1/2001 |
| WO | WO-0102850 A1 | 1/2001 |
| WO | WO-01/014589 A2 | 3/2001 |
| WO | WO-0114589 A2 | 3/2001 |
| WO | WO-0189787 A2 | 11/2001 |
| WO | WO-0190418 A1 | 11/2001 |
| WO | WO 2002/024952 | 3/2002 |
| WO | WO-0127610 A3 | 3/2002 |
| WO | WO-0231203 A2 | 4/2002 |
| WO | WO 2002/059355 | 8/2002 |
| WO | WO-02/072631 A2 | 9/2002 |
| WO | WO-02/072631 A3 | 9/2002 |
| WO | WO 2002/077283 | 10/2002 |
| WO | WO-02086148 A1 | 10/2002 |
| WO | WO 2003/002979 | 1/2003 |
| WO | WO-0218949 A3 | 1/2003 |
| WO | WO 2003/010176 | 2/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO 2005/007814 | 1/2005 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006/040551 A2 | 4/2006 |
| WO | WO-2006071770 A2 | 7/2006 |
| WO | WO-2006078841 A1 | 7/2006 |
| WO | WO-2006086210 A2 | 8/2006 |
| WO | WO-2006096571 A2 | 9/2006 |
| WO | WO 2006/117541 | 11/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007/044091 A2 | 4/2007 |
| WO | WO 2007/073171 | 6/2007 |
| WO | WO 2007/076726 | 7/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO 2007/145612 | 12/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008135512 A2 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO 2009/032167 | 3/2009 |

(56) References Cited

FOREIGN PATENT DOCUMENTS

WO WO-2009048532 A2 4/2009
WO WO-2009061372 A1 5/2009
WO WO-2009085215 A1 7/2009
WO WO-2009/152928 A2 12/2009
WO WO-2009147386 A1 12/2009
WO WO-2010004018 A2 1/2010
WO WO-2010009735 A2 1/2010
WO WO-2010033200 A2 3/2010
WO WO-2010048605 A1 4/2010
WO WO-2010104604 A1 9/2010
WO WO-2010/117620 A2 10/2010
WO WO-2010115154 A1 10/2010
WO WO 2010/126614 11/2010
WO WO-2010148039 A2 12/2010
WO WO-2010151776 A2 12/2010
WO WO 2011/008502 1/2011
WO WO-2010117620 A3 2/2011
WO WO-2011028539 A1 3/2011
WO WO-2011047870 A1 4/2011
WO WO-2011056546 A1 5/2011
WO WO 2011/068088 6/2011
WO WO-2011066476 A1 6/2011
WO WO-2011074960 A1 6/2011
WO WO 2011/094669 8/2011
WO WO-2011106314 A2 9/2011
WO WO-2011140627 A1 11/2011
WO WO-2011156529 A2 12/2011
WO WO-2012012037 A1 1/2012
WO WO-2011140510 A3 3/2012
WO WO-2012047889 A2 4/2012
WO WO-2012048340 A2 4/2012
WO WO-2012048341 A1 4/2012
WO WO-2012061832 A1 5/2012
WO WO-2012083225 A2 6/2012
WO WO-2012087736 A1 6/2012
WO WO-2012/116331 A2 8/2012
WO WO-2012106546 A2 8/2012
WO WO-2012112804 A1 8/2012
WO WO-2012112970 A2 8/2012
WO WO-2012/142531 A2 10/2012
WO WO-2012136734 A1 10/2012
WO WO-2012142611 A2 10/2012
WO WO 2012/159089 11/2012
WO WO-2012148497 A2 11/2012
WO WO-2012149042 A2 11/2012
WO WO-2012150317 A1 11/2012
WO WO-2012/167142 A2 12/2012
WO WO-2012166425 A2 12/2012
WO WO-2013019751 A1 2/2013
WO WO-2013036929 A1 3/2013
WO WO-2013055955 A1 4/2013
WO WO-2013096643 A1 6/2013
WO WO 2013/123442 8/2013
WO WO-2013122996 A1 8/2013
WO WO-2013123125 A1 8/2013
WO WO-2013126741 A1 8/2013
WO WO 2013/131962 9/2013
WO WO 2013/138510 9/2013
WO WO-2013134261 A1 9/2013
WO WO 2013/150082 10/2013
WO WO-2013150083 A1 10/2013
WO WO-2013177220 A1 11/2013
WO WO-2013188872 A1 12/2013
WO WO-2014018460 A1 1/2014
WO WO-2014/028378 A2 2/2014
WO WO-2014028537 A1 2/2014
WO WO 2014/060483 4/2014
WO WO-2014053854 A1 4/2014
WO WO-2014071361 A1 5/2014
WO WO-2014072703 A1 5/2014
WO WO-2014074611 A1 5/2014
WO WO-2014093676 A1 6/2014
WO WO-2014108810 A2 7/2014
WO WO-2014140309 A1 9/2014
WO WO-2014144495 A1 9/2014
WO WO 2014144822 A2 9/2014
WO WO-2014145047 A1 9/2014
WO WO-2014150931 A1 9/2014
WO WO-2014/165559 A2 10/2014
WO WO-2014182835 A1 11/2014
WO WO-2014189957 A2 11/2014
WO WO 2014/210223 12/2014
WO WO-2014200767 A1 12/2014
WO WO-2014210353 A2 12/2014
WO WO-2015/015199 A2 2/2015
WO WO-2015/035087 A1 3/2015
WO WO-2015031691 A1 3/2015
WO WO-2015044428 A1 4/2015
WO WO-2015/103339 A1 7/2015
WO WO-2015164212 A1 10/2015
WO WO-2015185067 A1 12/2015
WO WO-2015188839 A2 12/2015
WO WO-2015200893 A2 12/2015
WO WO-2016040476 A1 3/2016
WO WO 2016/057552 4/2016
WO WO-2016033251 A3 4/2016
WO WO-2016061517 A2 4/2016
WO WO-2016100976 A2 6/2016
WO WO-2016126871 A2 8/2016
WO WO 2016/138500 9/2016
WO WO-2016/145409 A1 9/2016
WO WO-2016138496 A1 9/2016
WO WO-2016149661 A1 9/2016
WO WO 2016/162309 10/2016
WO WO 2016/166128 10/2016
WO WO 2016/168825 10/2016
WO WO-2016168584 A1 10/2016
WO WO-2016176322 A1 11/2016
WO WO-2016187256 A2 11/2016
WO WO-2016187717 A1 12/2016
WO WO-2016191618 A1 12/2016
WO WO-2016207647 A1 12/2016
WO WO-2016207653 A1 12/2016
WO WO-2016207661 A1 12/2016
WO WO 2017/013170 1/2017
WO WO-2017015075 A1 1/2017
WO WO 2017/019456 2/2017
WO WO-2017025594 A1 2/2017
WO WO-2017034970 A1 3/2017
WO WO-2017053902 A1 3/2017
WO WO-2017053903 A1 3/2017
WO WO-2017053905 A1 3/2017
WO WO 2017/075293 5/2017
WO WO-2017075265 A1 5/2017
WO WO-2017075294 A1 5/2017
WO WO-2017079593 A1 5/2017
WO WO-2017096158 A1 6/2017
WO WO-2017117358 A1 7/2017
WO WO 2017/147483 8/2017
WO WO-2017151828 A1 9/2017
WO WO-2017156336 A1 9/2017
WO WO-2017180420 A1 10/2017
WO WO-2018031631 A1 2/2018
WO WO-2018039969 A1 3/2018
WO WO-2018045186 A1 3/2018
WO WO-2018058073 A2 3/2018
WO WO 2018/064640 4/2018
WO WO 2018/075693 4/2018
WO WO 2018/091676 5/2018
WO WO-2018103025 A1 6/2018
WO WO-2018119301 A1 6/2018
WO WO-2018119447 A2 6/2018
WO WO-2018125982 A1 7/2018
WO WO-2018129368 A2 7/2018
WO WO-2018132635 A1 7/2018
WO WO 2018/175779 9/2018
WO WO-2018172726 A1 9/2018
WO WO-2018174827 A1 9/2018
WO WO-2018191701 A1 10/2018
WO WO-2019028166 A1 2/2019
WO WO 2019/104337 5/2019
WO WO-2019084328 A1 5/2019
WO WO-2019099751 A1 5/2019
WO WO 2019/113457 6/2019

(56) References Cited

FOREIGN PATENT DOCUMENTS

| | | |
|---|---|---|
| WO | WO 2019/113533 | 6/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047010 | 3/2020 |
| WO | WO 2020/076979 | 4/2020 |
| WO | WO 2020/077236 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/227309 | 11/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |

OTHER PUBLICATIONS

Brown, Profiling tissue-resident T cell repertoires by RNA sequencing, Genome Medicine, 7:125, 1-8, 2015. (Year: 2015).*
AH006633.3 (*Homo sapiens* clone P1 and PAC max interactor 1 (MXI1) gene, complete cds, NCBI Reference Sequence, priority to Jun. 10, 2016, 5 pages) (Year:2016).
Ahern, H. The Scientist, vol. 20, pp. 20 and 22. July (Year: 1995).
Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).
Australian Office Action issued Dec. 17, 2013 for Application No. AU 2010315580.
Bentolila, et al. Single-step multicolor fluorescence in situ hybridization using semiconductor quantum dot-DNA conjugates. Cell Biochem Biophys. 2006;45(1):59-70.
Bystrykh, et al. Generalized DNA barcode design based on Hamming codes. PLoS One. 2012;7(5):e36852. doi: 10.1371/journal.pone.0036852. Epub May 17, 2012.
Co-pending U.S. Appl. No. 16/395,090, filed Apr. 25, 2019.
Co-pending U.S. Appl. No. 16/419,428, filed May 22, 2019.
Co-pending U.S. Appl. No. 16/419,461, filed May 22, 2019.
Co-pending U.S. Appl. No. 16/419,555, filed May 22, 2019.
Co-pending U.S. Appl. No. 16/419,630, filed May 22, 2019.
Co-pending U.S. Appl. No. 16/419,820, filed May 22, 2019.
Co-pending U.S. Appl. No. 16/435,362, filed Jun. 7, 2019.
Co-pending U.S. Appl. No. 16/435,417, filed Jun. 7, 2019.
Dhingra, et al. A complete solution for high throughput single cell targeted multiomic DNA and RNA sequencing for cancer research. Poster. AACR 2019.
Epicenter, EZ-Tn5 Transposase, Epicenter, 2012, 1-5. (Year: 2012).
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bentley, et al. 2008. Supplementary Information. pp 1-55 Nature. Nov. 6, 2008; 456(7218):53-9.
Cejas, P. et al. "Chromatin immunoprecipitation from fixed clinical tissues reveals tumor-specific enhancer profiles" Nature Med (2016) 22(6):685-691.
Co-pending U.S. Appl. No. 16/294,769, filed Mar. 6, 2019.
Fanielli, M. et al. "Pathology tissue-chromatin immunoprecipitation, coupled with high-throughput sequencing, allows the epigenetic profiling of patient samples" PNAS (2010) 107(50):21535-21540.
Hebenstreit. Methods, Challenges and Potentials of Single Cell RNA-seq. Biology (Basel). Nov. 16, 2012;1(3):658-67. doi: 10.3390/biology1030658.
Mali, et al. Barcoding cells using cell-surface programmable DNA-binding domains. Nat Methods. May 2013;10(5):403-6. doi: 10.1038/nmeth.2407. Epub Mar. 17, 2013.
Mignardi, M. et al. "Oligonucleotide gap-fill ligation for mutation detection and sequencing in situ" Nucl Acids Res (2015) 43(22):e151.

(56) References Cited

OTHER PUBLICATIONS

Pfeifer, et al. Bivalent cholesterol-based coupling of oligonucleotides to lipid membrane assemblies. J Am Chem Soc. Aug. 25, 2004;126(33):10224-5.
Anonymous: "Three Ways to Get Intimate with Epigenetic Marks". Oct. 24, 2012. Retrieved from Internet: https://epigenie.com/three-ways-to-get-intimate-with-epigenetic-marks/.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,142, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/249,688, filed Jan. 16, 2019.
Meyer, et al. Targeted high-throughput sequencing of tagged nucleic acid samples. Nucleic Acids Res. 2007;35(15):e97.
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.
Co-pending U.S. Appl. No. 16/033,065, filed Jul. 11, 2018.
Co-pending U.S. Appl. No. 16/043,874, filed Jul. 24, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/206,168, filed Nov. 30, 2018.
Co-pending U.S. Appl. No. 16/212,441, filed Dec. 6, 2018.
Delehanty, et al. Peptides for specific intracellular delivery and targeting of nanoparticles: implications for developing nanoparticle-mediated drug delivery. Ther Deliv. Sep. 2010;1(3):411-33.
Epicentre., "EZ-Tn5TM Custom Transposome Construction Kits", http://www.epicentre.com, pp. 1-17, 2012.
"How many species of bacteria are there" (wisegeek.com; accessed Jan. 21, 2014).
"List of sequenced bacterial genomes" (Wikipedia.com; accessed Jan. 24, 2014).
Margulies 2005 Supplementary methods (Year: 2005).
Margulies et al. "Genome sequencing in microfabricated high-density picoliter reactors", Nature (2005) 437:376-380.
"Meyer, et al., From micrograms to picograms: quantitative PCR reduces the material demands of high-throughput sequencing, Nucleic Acids Research, 2008, vol. 36, No. 1, 6 pages".
Thaxton, C.S. et al. "A Bio-Bar-Code Assay Based Upon Dithiothreitol Oligonucleotide Release" Anal Chem (2005) 77:8174-8178.
Ullal et al. Cancer Cell Profiling by Barcoding Allows Multiplexed Protein Analysis in Fine-Needle Aspirates. Sci Transl Med. Jan. 15, 2014; 6(219): 219ra9.
Zhang, et al. Reconstruction of DNA sequencing by hybridization. Bioinformatics. Jan. 2003;19(1):14-21.
Co-pending U.S. Appl. No. 16/196,684, filed Nov. 20, 2018.
Jin, et al. Genome-wide detection of DNase I hypersensitive sites in single cells and FFPE tissue samples. Nature. Dec. 3, 2015;528(7580):142-6. doi: 10.1038/nature15740.
Adey, et al., "Ultra-low-input, tagmentation-based whole-genome bisulfite sequencing", Genome Research, 2012, 22 ;6): 1139-1143.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Ason et al. DNA sequence bias during Tn5 transposition. Journal of molecular biology 335.5 (2004): 1213-1225.
Bjornsson et al., Intra-individual change over time in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.
Buenrostro, et al., "Tranposition of native chromatin for fast and sensitive epigenomic profiling of open chromatin, DNA-binding proteins and nucleosome position", Nature Methods, 2013, 10(12): 1213-1218.
Caruccio, et al. Nextera Technology for NGS DNA Library Preparation: Simultaneous Fragmentation and Tagging by in Vitro Transposition, Nextera Technology, 2009, 16-3, 1-3. (Year: 2009).
Co-pending U.S. Appl. No. 16/045,474, filed Jul. 25, 2018.
Co-pending U.S. Appl. No. 16/138,448, filed Sep. 21, 2018.
Co-pending U.S. Appl. No. 16/144,832, filed Sep. 27, 2018.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Haring, et al. Chromatin immunoprecipitation: optimization, quantitative analysis and data normalization. Plant Methods. 2007; 3: 11.
Hu et al., Shape Controllable Microgel Particles Prepared by Microfluidic Combining External Crosslinking, Biomicrofluidics 6:26502 (May 18, 2012).
Lebedev, A. et al. "Hot Start PCR with heat-activatable primers: a novel approach for improved PCR performance" NAR (2008) 36(20):E131-1.
Mcginnis, et al. MULTI-seq: Scalable sample multiplexing for single-cell RNA sequencing using lipid-tagged indices. bioRxiv 387241; doi: https://doi.org/10.1101/387241. . . .
PARK. ChIP-seq: advantages and challenges of a maturing technology. Nature Reviews Genetics vol. 10, pp. 669-680 (2009).
Savva, et al. The structural basis of specific base-excision repair by uracil-DNA glycosylase. Nature. Feb. 9, 1995;373(6514):487-93.
Simon, et al., "Using formaldehyde-assisted isolation of regulatory elements (FAIRE) to isolate active regulatory DNA", Nature Protocols, 2012, 7(2): 256-267.
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Zentner, et al. Surveying the epigenomic landscape, one base at a time. Genome Biol. Oct. 22, 2012;13(10):250. doi: 10.1186/gb4051.
Zhang, et al. One-step fabrication of supramolecular microcapsules from microfluidic droplets. Science. Feb. 10, 2012;335(6069):690-4. doi: 10.1126/science.1215416.
Co-pending U.S. Appl. No. 16/052,431, filed Aug. 1, 2018.
Co-pending U.S. Appl. No. 16/052,486, filed Aug. 1, 2018.
Co-pending U.S. Appl. No. 16/056,231, filed Aug. 6, 2018.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
"U.S. Appl. No. 61/982,001, filed Apr. 21, 2014 (Year:2014)".
Co-pending U.S. Appl. No. 15/588,519, filed May 5, 2017.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Depristo et al. A framework for variation discovery and genotyping using next-generation DNA sequencing data. Nature Genet 43:491-498 (2011).
Han, Sw et al. "Targeted Sequencing of Cancer-Related Genes in Colorectal Cancer Using Next-Generation Sequencing" PLOS One (2013) 8(5):e64271.
Knapp, et al. Generating barcoded libraries for multiplex high-throughput sequencing. Methods Mol Biol. 2012;840:155-70. doi: 10.1007/978-1-61779-516-9_19.

(56) References Cited

OTHER PUBLICATIONS

Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Lander, et al. Initial sequencing and analysis of the human genome. Nature, 409 (Feb. 15, 2001): 860-921.
Shaikh, et al. A modular microfluidic architecture for integrated biochemical analysis. Proc Natl Acad Sci U S A. Jul. 12, 2005;102(28):9745-50. Epub Jun. 28, 2005.
Smith, et al. Highly-multiplexed barcode sequencing: an efficient method for parallel analysis of pooled samples. Nucleic Acids Research, 38(13): e142 (2010).
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Wong, et al. Multiplexed Barcoded CRISPR-Cas9 Screening Enabled By CombiGEM. PNAS. Mar. 1, 2016, vol. 113, pp. 2544-2549.
Adamson et al., "Production of arrays of chemically distinct nanolitre plugs via repeated splitting in microfluidic devices", Lab Chip 6(9): 1178-1186 (Sep. 2006).
Fu, et al. A Microfabricated Fluorescence-Activated Cell Sorter. Nature Biotechnology.1999; 17:1109-1111.
Kolodeziejczyk et al., "The technology and biology of single-cell RNA sequencing", Molecular Cell, vol. 58 (May 21, 2015).
Xia and Whitesides, Soft Lithography, Angew. Chem. Int. Ed. 37:550-575 (1998).
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.
Adamson, et al. A Multiplexed Single-Cell CRISPR Screening Platform Enables Systematic Dissection of the Unfolded Protein Response. Cell. Dec. 15, 2016;167(7):1867-1882.e21. doi:10.1016/j.cell.2016.11.048.
Brenner, et al. In vitro cloning of complex mixtures of DNA on microbeads: physical separation of differentially expressed cDNAs. Proc Natl Acad Sci U S A. Feb. 15, 2000;97(4):1665-70.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. Transposition of native chromatin for fast and sensitive epigenomic profiling of open chromatin, DNA-binding proteins and nucleosome position. Nat Methods. Dec. 2013;10(12):1213-8. doi: 10.1038/nmeth.2688. Epub Oct. 6, 2013.
Chang et al. Droplet-based microfluidic platform for heterogeneous enzymatic assays, 2013, Lab Chip, 13, 1817-1822 (Year: 2013).
Clark, et al. Single-cell epigenomics: powerful new methods for understanding gene regulation and cell identity. Genome Biol. Apr. 18, 2016;17:72. doi: 10.1186/s13059-016-0944-x.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.
Cusanovich, et al. Multiplex single-cell profiling of chromatin accessibility by combinatorial cellular indexing. Sciencexpress, May 7, 2014, p. 1-9.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Dey, et al. Integrated genome and transcriptome sequencing of the same cell. Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi:10.1016/j.cell.2016.11.038.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Lake, et al. Integrative Single-Cell Analysis By Transcriptional and Epigenetic States in Human Adult Brain. Apr. 19, 2017. doi: https://doi.org/10.1101/128520.
Lasken, et al. Archaebacterial DNA Polymerases Tightly Bind Uracil-containing DNA. The Journal of Biological Chemistry 1996, 271(30):17692-17696.
Lee et al. Alginate: Properties and biomedical applications. Prog Polym Sci 37(1):106-126 (2012).
Macaulay, et al., G&T-seq: parallel sequencing of single-cell genomes and transcriptomes. Nature Methods, 2015, p. 1-7.
Macaulay, et al. Single-Cell Multiomics: Multiple Measurements from Single Cells. Trends in Genetics 33.2: 155-168. PMC. Web. Dec. 18, 2017.
Miller-Stephenson Chemicals 157 FS Series catalog, www.miller-stephenon.com.
Morimoto, et al. Monodisperse semi-permeable microcapsules for continuous observation of cells. 2009. Lab Chip 9(15):2217-2223.
Narayanan, J. et al. Determination of agarose gel pore size: Absorbance measurements vis a vis other techniques. Journal of Physics: Conference Series 28 (2006) 83-86.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Sakaguchi, et al. Cautionary Note on the Use of dUMP-Containing PCR Primers with Pfu and VentR. Biotechniques 1996, 21(3): 369-370.
Spormann Laboratory, Polymerase Chain Reaction (PCR), Alfred Spormann Laboratory, 2009, 1-3.
ThermoFisher, Protocols, M-270 Streptavidin, ThermoFisherScientific, 2007, 1-5.
Zhou, Y. et al. Development of an enzyme activity screening system for p-glucosidase-displaying yeasts using calcium alginate micro-beads and flow sorting. Appl Microbiol Biotechnol (2009) 84:375-382.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adey, et al. Rapid, low-input, low-bias construction of shotgun fragment libraries by high-density in vitro transposition. Genome Biology 11:R119 (2010).

(56) References Cited

OTHER PUBLICATIONS

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna, S.L., et al., "Formation of dispersions using "flow focusing" in microchannels," Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/Ihtc/shared/import/migration/2 VISCOSITY.pdf.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi:10.1016/j.ajhg.2007.08.001.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio N., Preparation of Next-Generation Sequencing Libraries Using Nextera Technology: Simultaneous DNA Fragmentation and Adaptor Tagging by in Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 20117.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics. 2010;186:757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clausell-Tormos et al., "Droplet-based microfluidic platforms for the encapsulation and screening of mammalian cells and multicellular organisms", Chem. Biol. 15:427-437 (2008).

(56) References Cited

OTHER PUBLICATIONS

Cong, et al. Multiplex genome engineering using CRISPR/Cas systems. Science. Feb. 15, 2013;339(6121):819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/596,754, filed May 16, 2017.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/693,374, filed Aug. 31, 2017.
Co-pending U.S. Appl. No. 15/717,840, filed Sep. 27, 2017.
Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/719,459, filed Sep. 28, 2017.
Co-pending U.S. Appl. No. 15/720,085, filed Sep. 29, 2017.
Co-pending U.S. Appl. No. 15/831,726, filed Dec. 5, 2017.
Co-pending U.S. Appl. No. 15/831,847, filed Dec. 5, 2017.
Co-pending U.S. Appl. No. 15/832,183, filed Dec. 5, 2017.
Co-pending U.S. Appl. No. 15/832,547, filed Dec. 5, 2017.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):1306-11.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. doi:10.1073/pnas.0808319105. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, et al. A scalable, fully automated process for construction of sequence-ready human exome targeted capture libraries. Genome Biol. 2011;12(1):R1. doi: 10.1186/GB-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fulton et al., Advanced multiplexed analysis with the FlowMetrix system. Clin Chem. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, X. et al. "CRISPR-Cas9 delivery to hard-to-transfect cells via membrane deformation" Science Advances (2015) 1(7): E1500454 (8 pages).
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.

(56) References Cited

OTHER PUBLICATIONS

Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
Huebner, "Quantitative detection of protein expression in single cells using droplet microfluidics", Chem. Commun. 1218-1220 (2007).
Hug, et al. Measurement of the No. of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to the University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. Jul. 2, 1999;285(5424):83-5.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly( ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioj, et al., "Counting Absolute Numbers of Molecules Using Unique Molecular Identifiers", Nature Methods 9, 72-74 (2012).
Klein, et al. Droplet barcoding for single-cell transcriptomics applied to embryonic stem cells. Cell. May 21, 2015;161(5):1187-201. doi: 10.1016/j.cell.2015.04.044.
Knight, et al. Subtle chromosomal rearrangements in children with unexplained mental retardation. Lancet. Nov. 13, 1999;354(9191):1676-81.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip the Royal Soc. of Chern. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al., "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Laird et al, Hairpin-bisulfite PCR: Assessing epigenetic methylation patterns on complementary strands of individual DNA molecules, 2004, PNAS, 101, 204-209.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee, et al., "Highly multiplexed subcellular RNA sequencing in situ. Science. Mar. 21, 2014;343(6177):1360-3. doi: 10.1126/science.1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
Lennon; et al., "Lennon et al. A scalable, fully automated process for construction of sequence-ready barcoded libraries for 454. Genome Biology 11:R15 (2010)."
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
Liu, et al. Preparation of uniform-sized PLA microcapsules by combining Shirasu porous glass membrane emulsification technique

(56) References Cited

OTHER PUBLICATIONS and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015; 161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Man. Monolithic Structures for Integrated Microfluidic Analysis. PhD Thesis. 2001.
Marcus. Gene method offers diagnostic hope. The Wall Street Journal. Jul. 11, 2012.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller Jc, et al. An improved zinc-finger nuclease architecture for highly specific genome editing. Nat. Biotechnol. 2007;25:778-785.
miRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation By Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. pp. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al.,. "Controlled Production ofMonodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics. ,13:1, 2012.
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, et al. Accurate whole-genome sequencing and haplotyping from 10 to 20 human cells. Nature. Jul. 11, 2012;487(7406):190-5. doi: 10.1038/Nature11236.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Rakszewska, A. et al. "One drop at a time: toward droplet microfluidics as a versatile tool for single-cell analysis" NPG Asia Materials (2014) 6(10):e133 (12 pages).

(56) References Cited

OTHER PUBLICATIONS

Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran, et al., Genome Engineering Using the CRISPR-Cas9 System, Nature Protocol, (2013), 8(11):2281-2308.
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 UsingMultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexldentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sander JD, et al. Selection-free zinc-finger-nuclease engineering by context-dependent assembly (CoDA). Nat. Methods. 2011;8:67-69.
Schirinzi et al. Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Skerra A. Phosphorothioate primers improve the amplification of DNA sequences by DNA polymerases with proofreading activity. Nucleic Acids Res. Jul. 25, 1992; 20(14):3551-4.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.

(56) References Cited

OTHER PUBLICATIONS

Thorsen, et al. Dynamic pattern formation in a vesicle-generating microfluidic device. Physical Review Letters. American Physical Society. 2001; 86(18):4163-4166.
Tomer, et al. Advanced Clarity for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams et al., Amplification of complex gene libraries by emulsion PCR, Nature Methods 3(7):545-550 (2006).
Wiseman, R.W. et al. "Major histocompatibility complex genotyping with massively parallel pyrosequencing" Nature Medicine (Oct. 11, 2009) 15(11):1322-1326.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum. Antibodies Hybridomas. Jan. 1992;3(1 ): 14-8.
Zong, et al. Genome-wide detection of single-nucleotide and copy-number variations of a single human cell. Science. Dec. 21, 2012;338(6114):1622-6. doi: 10.1126/science.1229164.
Bakker, A.H. et al. (Mar. 11, 2008, e-published Feb. 28, 2008). "Conditional MHC class I ligands and peptide exchange technology for the human MHC gene products HLA-A1, -A3, -A11, and -B7," *Proc Natl Acad Sci U S A*. 105(10):3825-3830.
Bentzen, A.K. et al. (Oct. 2016, e-published Aug. 29, 2016). Large-scale detection of antigen-specific T cells using peptide-MHC-I multimers labeled with DNA barcodes. *Nat Biotechnol*. 34(10):1037-1045.
Briggs, A.W. et al. (May 5, 2017). "Tumor-infiltrating immune repertoires captures by single-cell barcoding in emulsion" with Supplementary material. *bioRxiv* 134841.
Chokkalingam, V. et al., (Dec. 21, 2013). "Probing cellular heterogeneity in cytokine-secreting immune cells using droplet-based microfluidics," *Lab Chip* 13(24):4740-4744.
Han, A. et al. (Jul. 2014, e-published Jun. 22, 2014). Linking T-cell receptor sequence to functional phenotype at the single-cell level. *Nat Biotechnol*. 32(7):684-92. (Author Manuscript Version; 23 pgs.).
Kondo, A. et al. (Mar. 2004, e-published Jan. 10, 2004). "Yeast cell-surface display—applications of molecular display," *Appl Microbiol Biotechnol* 64(1):28-40.
Mcdaniel, J.R. et al. (Mar. 2016, e-published Feb. 4, 2016). "Ultra-high-throughput sequencing of the immune receptor repertoire from millions of lymphocytes," *Nat Protoc*. 11(3):429-442.

(56) References Cited

OTHER PUBLICATIONS

Morozov, G.I et al. (Feb. 23, 2016, e-published Feb. 11, 2016). "Interaction of TAPBPR, a tapasin homolog, with MHC-I molecules promotes peptide editing," *Proc Natl Acad Sci U S A* 113(8):E1006-15.
Neal, L.R. et al. (2017, e-published Jun. 26, 2017). "The Basics of Artificial Antigen Presenting Cells in T Cell-Based Cancer Immunotherapies," *J Immunol Res Ther*. 2(1):68-79. (Author Manuscript Version; 19 pgs.).
Newell, E.W. et al. (Jul. 2009, e-published Jun. 21, 2009). "Simultaneous detection of many T-cell specificities using combinatorial tetramer staining," *Nat Methods* 6(7)497-499.
Omidfar, K. et al. (Jun. 2015, e-published Apr. 24, 2015). "Advances in phage display technology for drug discovery," *Expert Opin Drug Discov*. 10(6):651-669.
Toebes, M. et al. (Feb. 2006, e-published Feb. 5, 2006). "Design and use of conditional MHC class I ligands," *Nat Med*. 12(2):246-251.
Toebes, M. et al. (Nov. 2009). "Generation of peptide MHC class I monomers and multimers through ligand exchange," *Curr Protoc Immunol*. Chapter 18:Unit 18.16.
Vandormael, P. et al. (Feb. 2017). "cDNA phage display for the discovery of theranostic autoantibodies in rheumatoid arthritis," Immunol Res. 65(1):307-325.
Wiseman, R.W. et al. (Nov. 2009, e-published Oct. 11, 2009). "Major histocompatibility complex genotyping with massively parallel pyrosequencing" *Nature Medicine* 15(11):1322-1326.
10X Genomics, Inc. CG00026. Chromium Single Cell 3' Reagent Kit User Guide. 2016.
10X Genomics, Inc. LIT00003.Rev B Chromium Genome Solution Application Note 2017.
Abate, A.R. et al. "Beating Poisson encapsulation statistics using close-packed ordering" Lab on a Chip (Sep. 21, 2009) 9(18):2628-2631.
Agasti, S.S. et al. "Photocleavable DNA barcode-antibody conjugates allow sensitive and multiplexed protein analysis in single cell" J Am Chem Soc (2012) 134(45):18499-18502.
Anna et al., "Formation of dispersions using 'flow focusing' in microchannels", Appl. Phys. Letts. 82:3 364 (2003).
Baret, "Surfactants in droplet-based microfluidics" Lab Chip (12(3):422-433 (2012).
Beer et al., On-Chip, Real-Time, Single-Copy Polymerase Chain Reaction in Picoliter Droplets, Anal. Chem., 2007, v. 79, pp. 8471-8475.
Burns, J.R. et al. "The intensification of rapid reactions in multiphase systems using slug flow in capillaries" Lab Chip. (Sep. 2001) 1(1):10-15.
Burns, M.A. et al. "An Integrated Nanoliter DNA Analysis Device" Science (1998) 282:484-487.
Burns, M.A. et al. "Microfabricated structures for integrated DNA analysis" PNAS (1996) 93(11):5556-5561.
Chen, F. et al. "Chemical transfection of cells in picoliter aqueous droplets in fluorocarbon oil" Anal Chem (2011) 83(22):8816-8820.
Chien et al. "Multiport flow-control system for lab-on-a-chip microfluidic devices", Fresenius J. Anal Chem, 371:106-111 (Jul. 27, 2001).
Chu, L-Y. et al., "Controllable monodisperse multiple emulsions" Angew. Chem. Int. Ed. (2007) 46:8970-8974.
Damean, N. et al. "Simultaneous measurement of reactions in microdroplets filled by concentration gradients" Lab Chip (Jun. 21, 2009) 9(12):1707-1713.
Duffy et al., Rapid Protyping of Microfluidic Systems and Polydimethylsiloxane, Anal Chem 70:4974-4984 (1998).
Eastburn, D.J. et al., "Ultrahigh-throughput mammalian single-cell reverse-transcriptase polymerase chain reaction in microfluidic droplets" Anal. Chem. (2013) 85:8016-8021.
Gericke, M. et al. "Functional Cellulose Beads: Preparation, Characterization, and Applications" Chem Rev (2013) 113(7):4812-4836.
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Hug, H. et al. "Measurement of the number of molecules of a single mRNA species in a complex mRNA preparation" J Theor Biol. Apr. 21, 2003;221(4):615-24.
Islam et al. Highly multiplexed and strand-specific single-cell RNA 5' end sequencing. Nat Protoc. Apr. 5, 2012;7(5):813-28. doi: 10.1038/nprot.2012.022.
Jaitin et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Kaper, F. et al. "Whole-genome haplotyping by dilution, amplification, and sequencing" PNAS (Apr. 2013) 110:5552-5557.
Kenis, P.J. et al. "Microfabrication inside capillaries using multiphase laminar flow patterning" Science (Jul. 2, 1999);285(5424):83-85.
Kivioj, A. et al., "Counting Absolute Numbers of Molecules Using Unique Molecular Identifiers", Nature Methods 9, 72-74 (2012).
Klein, et al. Droplet barcoding for single-cell transcriptomics applied to embryonic stem cells. Cell. May 21, 2015; 161:1187-1201.
Lagally, E.T. et al. "Single-Molecule DNA Amplification and Analysis in an Integrated Microfluidic Device" Anal. Chem. (2001) 73(3):565-570.
Lennon et al. "A scalable, fully automated process for construction of sequence-ready barcoded libraries for 454." Genome Biology 11:R15 (2010).
Mair, D.A. et al., "Injection molded microfluidic chips featuring integrated interconnects" Lab Chip (2006) 6:1346-1354.
Mccoy, R. et al. "Illumina TruSeq Synthetic Long-Reads Empower De Novo Assembly and Resolve Complex, Highly-Repetitive Transposable Elements" PLOS (2014) 9(9):e1016689.
Navin, N.E. "The first five years of single-cell cancer genomics and beyond" Genome Res. (2015) 25:1499-1507.
Nisisako et al. "Droplet formation in a microchannel on PMMA plate" Micro Total Analysis Systems 2001. Ramsey, J.M. , van den Berg, A. 137-138 (2001).
Nisisako, T. et al. "Droplet formation in a microchannel network" Lab on a Chip (2002) 2:24-26.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914 (Year: 2012).
Peters et al., "Accurate whole-genome sequencing and haplotyping from 10 to 20 human cells," Nature, Jul. 12, 2012, vol. 487, pp. 190-195.
Priest, "Generation of monodisperse gel emulsions in a microfluidic device", Apl Phys Lett. 88:024106 (2006).
Pushkarev et al. "Single-molecule sequencing of an individual human genome," Nature Biotech (2009) 17:847-850.
Ramskold et al. "Full-length mRNA-Seq from single-cell levels of RNA and individual circulating tumor cells" Nature Biotech (2012) 30(8):777-782.
Rotem, A. et al., "High-throughput single-cell labeling (Hi-SCL) for RNA-Seq using drop-based microfluidics" PLOS One (Mapy 22, 2015) 0116328 (14 pages).
Schubert, et al. "Microemulsifying fluorinated oils with mixtures of fluorinated an hydrogenated surfactants" Colloids and Surfaces A: Physicochemical and Engineering Aspects (1994) 84:97-106.

(56) References Cited

OTHER PUBLICATIONS

Seiffert, S. et al., "Smart microgel capsules from macromolecular precursors" J. Am. Chem. Soc. (2010) 132:6606-6609.
Seiffert, et al. (Nov. 2010). "Microfluidic fabrication of smart microgels from macromolecular precursors," Polymer 51(25):5883-5889.
Shendure et al. "Accurate Multiplex Polony Sequencing of an Evolved bacterial Genome" Science (2005) 309:1728-1732.
Smith, A.M. et al. "Highly-multiplexed barcode sequencing: an efficient method for parallel analysis of pooled samples" Nucl Acids Res (2010) 38(13):e142 Epub May 11, 2010.
Song, H. et al. "Reactions in Droplets in Microfluidic Channels" Angew. Chem. Int. Ed. (2006) 45:7336-7356.
Theberge, A.B, et al. Microdropelts in microfluidics: an evolving platform for discoveries in chemistry and biology. Angew Chem Int Ed Engl. Aug. 9, 2010;49(34):5846-68. doi: 10.1002/anie.200906653.
Thorsen, T. et al. "Dynamic Pattern Formation in a Vesicle-Generating Microfluidic Device" Phys Rev Letts (Apr. 30, 2001) 86(18):4163-4166.
Tonelli, C. et al., "Perfluoropolyether functional oligomers: unusual reactivity in organic chemistry" J. Fluorine Chem. (2002) 118:107-121.
Turchinovich et al. Capture and Amplification by Tailing and Switching (CATS). An ultrasensitive ligation-independent method for generation of DNA libraries for deep sequencing from picogram amounts of DNA and RNA. RNA Biol. 2014;11(7):817-28. doi: 10.4161/rna.29304. Epub Jun. 12, 2014.
Uttamapinant et al., "Fast, Cell-compatible Click Chemistry with Copper-chelating Azides for Biomolecular Labeling," Angew Chem Int Ed Engl. Jun. 11, 2012; 51(24): 5852-5856; doi:10.1002/anie.201108181.
Wagner, O et al., "Biocompatible fluorinated polyglycerols for droplet microfluidics as an alternative to PEG-based copolymer surfactants" Lab Chip DOI:10.1039/C5LC00823A. (2015).
Weigl, B.H. et al. "Microfluidic Diffusion-Based Separation and Detection" Science (Jan. 15, 1999) 283(5400):346-347.
Williams, R. et al. "Amplification of complex gene libraries by emulsion PCR" Nature Methods (Jul. 2006) 3(7):545-550.
Zheng, X.Y. et al. "Haplotyping germline and cancer genomes with high-throughput linked-read sequencing" Nature Biotech (Feb. 1, 2016) 34(3):303-311 and Supplemental Material.
Zhu, YY et al. "Reverse transcriptase template switching: a SMART approach for full-length cDNA library construction" Biotechniques (2001) 30(4):892-897.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrNOCH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adam et al., "Psychrophilic proteases dramatically reduce single-cell RNA-seq artifacts: a molecular atlas of kidney development," Development, Oct. 1, 2017, 144(19):3625-3632.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Armani et al, "2D-PCR: a method of mapping DNA in tissue sections," Lab Chip, 2009, 9(24):3526-34.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micro-patterning," Lab Chip, Jun. 2009, 9(11):1640-1642.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

(56) References Cited

OTHER PUBLICATIONS

Bergenstråhle et al., "Seamless integration of image and molecular analysis for spatial transcriptomics workflows," BMC Genomics, Jul. 2020, 21(1):482, 7 pages.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the Encode pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "ATAC-see reveals the accessible genome by transposase-mediated imaging and sequencing," Nature Methods, Dec. 2016, 13(12):1013-1020.
Chen et al., "Geometric control of cell life and death," Science, May 1997, 276(5317):1425-1428.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Codeluppi et al., "Spatial organization of the somatosensory cortex revealed by osmFISH," Nature Methods, Nov. 2018, 15:932-935.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring," Life Science News, Amersham Life Science, 1998, pp. 11-14.
Corces et al., "Lineage-specific and single-cell chromatin accessibility charts human hematopoiesis and leukemia evolution," Nature Genetics, Oct. 2016, 48(10):1193-1203.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Definition of "corresponding", Merriam-Webster Online, downloaded from www.merriam-webster.com/dictionary/corresponding (Year: 2019).
DePasquale et al., "DoubletDecon: Deconvoluting Doublets from Single-Cell RNA-Sequencing Data," Cell Rep., Nov. 5, 2019, 29(6):1718-1727.e8, 19 pages.
Ding et al., "On-chip manipulation of single microparticles, cells, and organisms using surface acoustic waves," PNAS, Jul. 2012, 109(28):11105-11109.
Duncan et al., "Affinity chromatography of a sequence-specific DNA binding protein using Teflon-linked oligonucleotides," Anal. Biochem., 1988, 169(1):104-108.
Eastburn et al., "Identification of Genetic Analysis of Cancer Cells with PCT-activated Cell Sorting," Nucleic Acids Research, Jul. 16, 2014, 42(16):e128, 10 pages.
Eberwine et al., "Analysis of gene expression in single live neurons," Proc. Natl. Acad. Sci., USA 89, 3010-3014, 1992.
Edsgard et al., "Identification of spatial expression trends in single-cell gene expression data," Nature Methods, Mar. 19, 2018, 15: 339-342, 16 pages.

(56) References Cited

OTHER PUBLICATIONS

Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Falconnet et al., "Surface engineering approaches to micropattern surfaces for cell-based assays," Biomaterials, Jun. 2006, 27(16):3044-3063.
Fire et al., "Rolling replication of short DNA circles," Proc. Natl. Acad. Sci., 1995, 92(10):4641-4645.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging in Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gross et al., "Technologies for Single-Cell Isolation," Int. J Mol. Sci., Jul. 2015, 16(8):16897-16919.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Ha et al, "Self-assembly hollow nanosphere for enzyme encapsulation," Soft Matter, Feb. 11, 2010, 6, 1405-1408, 10 pages.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS ONE, 2012, 7(7):e40405, 9 pages.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing," PLoS One, 5(7): e11345, 2010.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hu et al., "A thermo-degradable hydrogel with light-tunable degradation and drug release," Biomaterials, Jan. 2017, 112:133-140.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hughes et al., "Highly Efficient, Massively-Parallel Single-Cell RNA-Seq Reveals Cellular States and Molecular Features of Human Skin Pathology," bioRxiv, Jul. 2019, 51 pages.
Jabara et al., Accurate sampling and deep sequencing of the HIV-1 protease gene using a Primer ID. PNAS 108(50);20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jones et al., "Comparative lesion sequencing provides insights into tumor evolution," Proc. Natl. Acad. Sci. USA, 105(11): 4283-4288, 2008.
Ju et al, "Supramolecular dendrimer capsules by cooperative binding," Chem. Commun., Jan. 7, 2011, 47(1):268-270, 8 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kaya-Okur et al., "CUT&Tag for efficient epigenomic profiling of small samples and single cells," Apr. 2019, 10(1):1930, 10 pages.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.
Kozlov et al., "A highly scalable peptide-based assay system for proteomics," PLoS ONE, 2012, 7(6):e37441, 10 pages.
Kristensen et al., "High-Throughput Methods for Detection of Genetic Variation," BioTechniques, Feb. 2001, 30(2):318-332.
Kuiper et al, "Enzymes containing porous polymersomes as nano reaction vessels for cascade reactions," Org. Biomol, Chem, Oct. 15, 2008, 6(23):4315-4318.

(56) References Cited

OTHER PUBLICATIONS

Kurz et al., “cDNA—protein fusions: covalent protein—gene conjugates for the in vitro selection of peptides and proteins,” ChemBioChem., 2001, 2(9):666-72.
Kwok, “High-throughput genotyping assay approaches,” Pharmocogenomics, Feb. 2000, 1(1):95-100.
Lacar et al., “Nuclear RNA-seq of single neurons reveals molecular signatures of activation,” Nat Commun., Apr. 2016, 7:11022, 12 pages.
Lage et al., “Whole genome analysis of genetic alterations in small DNA samples using hyperbranched strand displacement amplification and array-CGH,” Genome Research, 2003, 13(2):294-307.
Lake et al., “Neuronal subtypes and diversity revealed by single-nucleus RNA sequencing of the human brain,” Science, Jun. 2016, 352(6293):1586-90.
Landegren et al., “Reading bits of genetic information: methods for single-nucleotide polymorphism analysis,” Genome Res., Aug. 1998, 8(8):769-76.
Langdale et al., “A rapid method of gene detection using DNA bound to Sephacryl,” Gene, 1985, 36(3):201-210.
Laurell et al., “Chip integrated strategies for acoustic separation and manipulation of cells and particles,” Chem. Soc. Rev., Mar. 2007, 36(3):492-506.
Lee et al., “XYZeq: Spatially resolved single-cell RNA sequencing reveals expression heterogeneity in the tumor microenvironment,” Science Advances, 2021, 7:eabg4755, 1-14.
Leriche et al., “Cleavable linkers in chemical biology,” Bioorganic & Medicinal Chemistry, 2012, 20:571-582.
Liberali et al., “Single-cell and multivariate approaches in genetic perturbation screens,” Nat Rev Genet., Jan. 2015, 16(1):18-32.
Lin et al., “Microfluidic cell trap array for controlled positioning of single cells on adhesive micropatterns,” Lab Chip, Feb. 2013, 13(4):714-721.
Linnarsson, “Recent advances in DNA sequencing methods—general principles of sample preparation,” Experimental Cell Research, 2010, 316(8):1339-1343.
Liu et al., “High-Spatial-Resolution Multi-Omics Atlas Sequencing of Mouse Embryos via Deterministic Barcoding in Tissue,” BioRxiv, 2019, 55 pages.
Liu et al., “High-Spatial-Resolution Multi-Omics Sequencing via Deterministic Barcoding in Tissue,” Cell, Nov. 13, 2020, 183(6):1665-1681, 36 pages.
Liu et al., “Preparation and Characterization of Temperature-Sensitive Poly(N-isopropylacrylamide)-b-poly(d,1-lactide) Microspheres for Protein Delivery,” Biomacromolecules, 2003, 4(6):1784-1793.
Liu et al., “Spatial transcriptome sequencing of FFPE tissues at cellular level,” bioRxiv 788992, Oct. 14, 2020, 39 pages.
Lizardi et al., “Mutation detection and single-molecule counting using isothermal rolling-circle amplification,” Nat. Genet., 1998, 19(3):225-232.
Lubeck et al., “Single cell systems biology by super-resolution imaging and combinatorial labeling,” Nature Methods, Jan. 2013, 9(7):743-748, 18 pages.
Lubeck et al., “Single-cell in situ RNA profiling by sequential hybridization,” Nature Methods, Apr. 2014, 11(4):360-361, 2 pages (Supplemental Materials).
Lundberg et al., “Multiplexed homogeneous proximity ligation assays for high-throughput protein biomarker research in serological material,” Mol Cell Proteomics, 2011, 10(4):M110.004978, 11 pages.
Luo et al., “Probing infectious disease by single-cell RNA sequencing: Progresses and perspectives,” Computational and Structural Biotechnology Journal, Oct. 21, 2020, 18:2962-2971.
Lyu et al., “One-Pot Synthesis of Protein-Embedded Metal-Organic Frameworks with Enhanced Biological Activities,” Nano Lett., Sep. 11, 2014, 14:5761-5765.
MacBeath et al., “Printing proteins as microarrays for high-throughput function determination,” Science, Sep. 2000, 289(5485):1760-1763.
Madissoon et al., “scRNA-seq assessment of the human lung, spleen, and esophagus tissue stability after cold preservation,” Genome Biol., Dec. 2019, 21(1):1, 16 pages.
Mamedov et al., “Preparing unbiased T-cell receptor and antibody cDNA libraries for the deep next generation sequencing profiling,” Frontiers in Immunol., Dec. 23, 2013, 4(456):1-10.
Marx, “Method of the Year: spatially resolved transcriptomics,” Nature Methods, 2021, 18(1):9-14.
Massoni-Badosa et al, “Sampling artifacts in single-cell genomics cohort studies,” bioRxiv, Jan. 15, 2020, 32 pages.
McGinnis et al., “MULTI-seq: sample multiplexing for single-cell RNA sequencing using lipid-tagged indices,” Nat Methods, Jul. 2019, 16(7): 619-626, 14 pages.
Meers et al., “Improved CUT&RUN chromatin profiling tools,” Elife, Jun. 2019, 8:e46314, 16 pages.
Merritt et al., “Multiplex digital spatial profiling of proteins and RNA in fixed tissue,” Nat Biotechnol, May 2020, 38(5):586-599.
Metzker, “Sequencing technologies—the next generation,” Nature Reviews Genetics, 2010, 11(1):31-46.
Miller et al., “Basic concepts of microarrays and potential applications in clinical microbiology,” Clinical Microbiology Reviews, 2009, 22(4):611-633.
Miller et al., “Chapter 11—Solid and Suspension Microarrays for Microbial Diagnostics,” Methods in Microbiology, 2015, 42:395-431.
Miller et al., “Rapid and Efficient Enzyme Encapsulation in a Dendrimer Silica Nanocomposite,” Macromolecular Bioscience, Oct. 25, 2006, 6(10):839-845.
Mishra et al., “Three-dimensional genome architecture and emerging technologies: looping in disease,” Genome Medicine, 2017, 9(1):87, 14 pages.
Mitra et al., “Digital genotyping and haplotyping with polymerase colonies,” Proc. Natl. Acad. Sci. USA, May 2003, 100(10):5926-5931.
Mizusawa et al., “A bacteriophage lambda vector for cloning with BamHI and Sau3A,” Gene, 1982, 20(3):317-322.
Mortazavi et al., “Mapping and quantifying mammalian transcriptomes by RNA-Seq,” Nature Methods, 5(7): 621-8, 2008.
Nakamura et al., “Biocompatible inkjet printing technique for designed seeding of individual living cells,” Tissue Eng, Nov. 2005, 11(11-12):1658-1666.
Nam et al., “Somatic mutations and cell identity linked by Genotyping of Transcriptomes,” Nature, Jul. 2019, 571(7765):355-360.
Ncbi.nlm.nih.gov, [online], “Molecular Inversion Probe Assay,” available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nikiforov et al., “The use of 96-well polystyrene plates for DNA hybridization-based assays: an evaluation of different approaches to oligonucleotide immobilization,” Anal Biochem, May 1995, 227(1):201-9.
Nowak et al., “Entering the Postgenome Era,” Science, 1995, 270(5235):368-71.
O’Huallachain et al., “Ultra-high throughput single-cell analysis of proteins and RNAs by split-pool synthesis,” Communications Biology, 2020, 3:213, 19 pages.
O’Flanagan et al, “Dissociation of solid tumor tissues with cold active protease for single-cell RNA-seq minimizes conserved collagenase-associated stress responses,” Genome Biology, Oct. 17, 2019, 20:210, 13 pages.
Ostuni et al., “Patterning Mammalian Cells Using Elastomeric Membranes,” Langmuir, Aug. 2000, 16(20):7811-7819.
PCT International Search Report and Written Opinion in International Appln. No. PCT/US2017/057269, dated Mar. 5, 2018, 20 pages.
Pellegrino et al, “High-throughput Single-cell DNA Sequencing of Acut Myeloid Leukemia Tumors with Droplet Microfluidics,” Genome Research, Aug. 7, 2018, 28(9):1345-1352.
Pemov et al., “DNA analysis with multiplex microarray-enhanced PCR,” Nucl. Acids Res., Jan. 2005, 33(2):e11, 9 pages.

(56) References Cited

OTHER PUBLICATIONS

Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
Rahimi et al., "Synthesis and Characterization of Thermo-Sensitive Nanoparticles for Drug Delivery Applications," J. Biomed. Nanotechnol. Dec. 2008, 4(4):482-490, 19 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Rodriques et al., "Slide-seq: A scalable technology for measuring genome-wide expression at high spatial resolution," Science, 2019, 363(6434):1463-1467.
Rohland et al., "Partial uracil-DNA-glycosylase treatment for screening of ancient DNA," Phil. Trans. R. Soc. B, Jan. 19, 2015, 370(1660): Jun. 24, 2013, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Salmén et al., "Barcoded solid-phase RNA capture for Spatial Transcriptomics profiling in mammalian tissue sections," Nature Protocols, Oct. 2018, 13(11):2501-2534.
Satija et al., "Spatial reconstruction of single-cell gene expression data," Nature, Apr. 13, 2015, 33(5):495-402, 14 pages.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Setliff et al., High-Throughput Mapping of B Cell Receptor Sequences to Antigen Specificity, Cell, 2019, 179:1636-1646.
Shalon et al., "A DNA microarray system for analyzing complex DNA samples using two-color fluorescent probe hybridization," Genome Res., Jul. 1996, 6(7):639-45.
Shieh, et al., "Imparting Functionality to Biocatalysts via Embedding Enzymes into Nanoporous Materials by a de Novo Approach: Size-Selective Sheltering of Catalase in Metal—Organic Framework Microcrystals," J Am Chem Soc., Apr. 8, 2015, 137(13):4276-4279, 4 pages.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Soderberg, "Droplet Microfluidics Reverse Transcription and PCR Towards Single Cell and Exosome Analysis," Doctoral Thesis, KTH School of Biotechnology Science for Life Laboratory, 2017, 69 pages.
Sountoulidis et al., "Scrinshot, a spatial method for single-cell resolution mapping of cell states in tissue sections," PLoS Biol., Nov. 2020, 18(11):e3000675, 32 pages.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoeckius et al., "Cell Hashing with barcoded antibodies enables multiplexing and doublet detection for single cell genomics," Genome Biology, Dec. 19, 2018, 19: 224, 12 pages.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stuart et al., "Comprehensive Integration of Single-Cell Data," Cell, Jun. 2019, 177(7):1888-1902.
Stubbington et al., "T cell fate and clonality inference from single cell transcriptomes," Nature Methods, Apr. 2016, 13(4):329-332.
Suh et al., "A simple soft lithographic route to fabrication of poly(ethylene glycol) microstructures for protein and cell patterning," Biomaterials, Feb. 2004, 25(3):557-563.
Sun et al., "Statistical Analysis of Spanal Expression Pattern for Spatially Resolved Transcriptome Studies," Nature Methods, Jan. 27, 2020, 17(2): 193-200.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Tentori et al., "Detection of Isoforms Differing by a Single Charge Unit in Individual Cells," Chem. Int. Ed., 2016, 55(40):12431-5.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vermesh et al., "High-density, multiplexed patterning of cells at single-cell resolution for tissue engineering and other applications," Angew Chem Int Ed Engl, Aug. 2011, 50(32):7378-7380.

(56) References Cited

OTHER PUBLICATIONS

Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nat. Commun. Oct. 14, 2016, 7:13182, 9 pages.
Vickovic et al., "Massive and parallel expression profiling using microarrayed single-cell sequencing," Nature Communications, 2016, 7(13182):1-9.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics,'" Trends Biotechnol., 28: 281-90, 2010.
Wheeler et al., "Microfluidic device for single-cell analysis," Analytical Chemistry, Jul. 2003, 75(14):3581-3586.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning," J Biomed Mater Res A., May 2008, 85(2):530-538.
Xia et al., "Spatial transcriptome profiling by Merfish reveals subcellular RNA compartmentalization and cell cycle-dependent gene expression", Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yershov et al., "DNA analysis and diagnostics on oligonucleotide microchips," Proc. Natl. Acad. Sci. USA, May 1996, 93(10):4913-4918.
Yusof et al., "Inkjet-like printing of single-cells," Lab Chip, Jul. 2011, 11(14):2447-2454.
Zhang et al., "Block-Cell-Printing for live single-cell printing," PNAS, Feb. 2014, 111(8):2948-2953.
Zheng et al., "Massively parallel digital transcriptional profiling of single cells," Nat Commun., Jan. 16, 2017, 8:14049, 12 pages.
Bentzen, A.K. et al. (May 2017, e-published Mar. 17, 2017). "Evolution of MHC-based technologies used for detection of antigen-responsive T cells," *Cancer Immunol Immunother* 66(5):657-666.
Hashimshony, T. et al. (Apr. 28, 2016). "CEL-Seq2: sensitive highly-multiplexed single-cell RNA-Seq," Genome Biology 17:77.
Lu Wen et al. (2014). "Recent progress in single-cell RNA-Seq analysis," *Hereditas* 36(11):1069-1976. (English Abstract provided).
Chao-ping Zhou et al. (Dec. 27, 2013). "Research Progress in Analyzing Transcriptome at the Level of Single Cells," *Progress in Biochemistry and Biophysics* 40(12):1193-1200. (English Abstract provided).
International Preliminary Report on Patentability mailed on May 21, 2018, for PCT Application No. PCT/US2017068320, filed Dec. 22, 2017, 12 pages.
Proprietor's reply of Jul. 16, 2021 to a Communication from the Examining Division of the EPO, European Patent Application No. EP 17 885 003.8, 3 pages.
Proprietor's response of Jan. 11, 2021 to the European Search Opinion, European Patent Application No. EP 17 885 003.8, 4 pages.
European Search Opinion of EP 17 885 003.8, dated May 29, 2020, 3 pages.
Lu et al., "Highly multiplexed profiling of single-cell effector functions reveals deep functional heterogeneity in response to pathogenic ligands," PNAS, Feb. 2, 2015, E607-E615.
Lu et al., "Highly multiplexed profiling of single-cell effector functions reveals deep functional heterogeneity in response to pathogenic ligands," PNAS, Feb. 2, 2015, E607-E615 (Supplementary Information), 94 pages.
Pittcon, "Single Molecule Detection of Proteins in Single Cells," News-Medical, Feb. 3, 2017, retreived on Nov. 1, 2023, retrieved from URL <https://www.news-medical.net/news/20170203/Single-molecule-detection-of-proteins-in-single-cells.aspx>, 13 pages.
Redmond et al., "Single-cell TCRseq: paired recovery of entire T-cell alpha and beta chain transcripts in T-cell receptors from single-cell RNAseq," Genome Med, 2016, 8:80, 12 pages.
Tang et al., "mRNA-Seq whole-transcriptome analysis of a single cell," Nat Methods, 2009, 6:377-382.

* cited by examiner

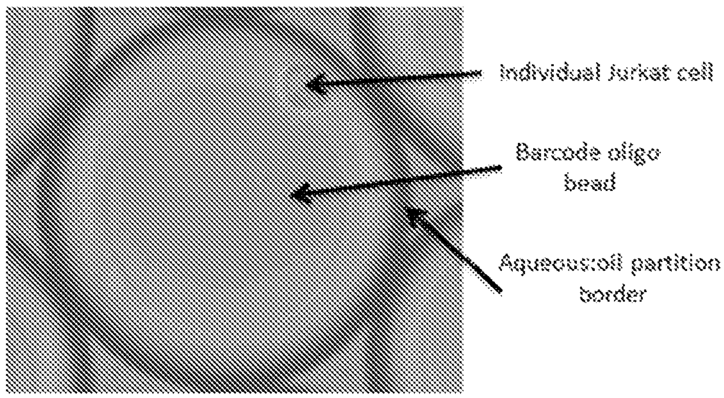
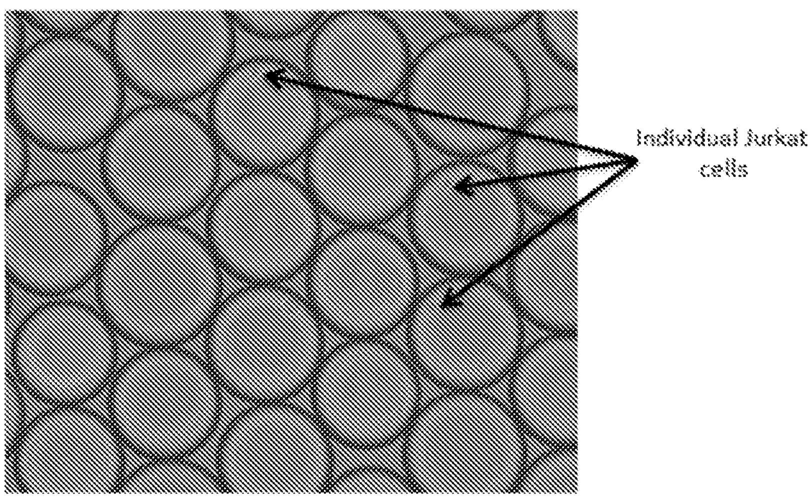
Figure 8

| Sample | Number of Cells | Mean Reads per Cell | Valid Barcodes | Reads Mapped Confidently to Transcriptome | Number of Reads | Reads Mapped Confidently to Exonic Regions | Reads Mapped Confidently to Intronic Regions | Reads Mapped Confidently to Intergenic Regions | Q30 Bases in Barcode | Q30 Bases in Read 1 | Q30 Bases in Sample Index | Fraction reads unmapped |
|---|---|---|---|---|---|---|---|---|---|---|---|---|
| unenriched | 0 | 0 | 96.00% | 58.30% | 95,373 | 69.90% | 12.50% | 3.50% | 92.20% | 92.80% | 89.60% | 8.90% |
| TRAC | 0 | 0 | 61.60% | 16.30% | 671,224 | 30.50% | 3.60% | 4.90% | 61.40% | 93.40% | 89.20% | 49.30% |
| TRBC | 0 | 0 | 64.90% | 21.80% | 780,871 | 33.60% | 4.30% | 4.10% | 64.30% | 93.20% | 89.60% | 45.70% |
| TRAC/TRBC | 0 | 0 | 73.50% | 24.10% | 1,522,739 | 43.50% | 3.60% | 4.30% | 71.50% | 93.20% | 89.60% | 39.50% |

Figure 23A

| Sample | Reads with polyA sequence | Reads with switch oligo sequence | Fraction reads with R1 sequence | Fraction reads with R2 sequence | Fraction reads with P7 sequence | Fraction reads with P5 sequence | Fraction reads with primer or homopolymer sequence | Number of detected cells CV | Relative difference of detected cells from expected cells | Barcodes detected | Fraction fragments mapped to VDJ |
|---|---|---|---|---|---|---|---|---|---|---|---|
| unenriched | 1.60% | 0.00% | 0.00% | 2.00% | 0.30% | 0.00% | 4.40% | 0.00% | -100.00% | 14,921 | 0.30% |
| TRAC | 0.20% | 0.00% | 0.00% | 4.70% | 3.10% | 0.00% | 6.80% | 0.00% | -100.00% | 33,520 | 15.50% |
| TRBC | 0.20% | 0.00% | 0.00% | 6.40% | 3.90% | 0.00% | 8.80% | 0.00% | -100.00% | 34,978 | 19.70% |
| TRAC/TRBC | 0.20% | 0.00% | 0.00% | 8.00% | 4.40% | 0.00% | 10.30% | 0.00% | -100.00% | 39,921 | 29.50% |

Figure 23B

METHODS AND SYSTEMS FOR PROCESSING POLYNUCLEOTIDES

SEQUENCE LISTING

The instant application contains a Sequence Listing which has been submitted electronically in ASCII format and is hereby incorporated by reference in its entirety. Said ASCII copy, created on Feb. 25, 2022, is named 057862_574_SL.txt and is 44,022 bytes in size.

BACKGROUND

Significant advances in analyzing and characterizing biological and biochemical materials and systems have led to unprecedented advances in understanding the mechanisms of life, health, disease and treatment. Among these advances, technologies that target and characterize the genomic make up of biological systems have yielded some of the most groundbreaking results, including advances in the use and exploitation of genetic amplification technologies, and nucleic acid sequencing technologies.

Nucleic acid sequencing can be used to obtain information in a wide variety of biomedical contexts, including diagnostics, prognostics, biotechnology, and forensic biology. Sequencing may involve methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others. Nucleic acid sequencing technologies, including next-generation DNA sequencing, have been useful for genomic and proteomic analysis of cell populations.

SUMMARY

Recognized herein is the need for methods, compositions and systems for analyzing genomic and proteomic information from individual cells or a small population of cells. Such cells include, but are not limited to, cancer cells, fetal cells, and immune cells involved in immune responses. Provided herein are methods, compositions and systems for analyzing individual cells or a small population of cells, including the analysis and attribution of nucleic acids from and to these individual cells or cell populations.

In an aspect, the present disclosure provides a method for nucleic acid sequencing, comprising (a) providing a plurality of droplets, wherein a droplet of the plurality of droplets comprises (i) a ribonucleic acid (RNA) molecule comprising a nucleic acid sequence, and (ii) a bead comprising a nucleic acid barcode molecule coupled thereto, wherein the nucleic acid barcode molecule comprises a barcode sequence; (b) using the RNA molecule and the nucleic acid barcode molecule to generate a barcoded nucleic acid molecule comprising, from a 5'end to a 3'end, a sequence corresponding to the nucleic acid sequence of the RNA molecule and a complement of the barcode sequence; and (c) sequencing the barcoded nucleic acid molecule or a derivative thereof.

In some embodiments, the RNA molecule is from a cell. In some embodiments, the droplet comprises the cell. In some embodiments, the method further comprises releasing the RNA molecule from the cell prior to (b).

In some embodiments, the bead comprises a plurality of nucleic acid molecules coupled thereto, wherein the plurality of nucleic acid molecules comprises the nucleic acid barcode molecule.

In some embodiments, each of the plurality of nucleic acid molecules comprises the barcode sequence. In some embodiments, each of the plurality of nucleic acid molecules comprises an additional barcode sequence that varies across the plurality of nucleic acid molecules.

In some embodiments, the nucleic acid barcode molecule comprises a template switching sequence.

In some embodiments, the method further comprises, prior to (c), subjecting the barcoded nucleic acid molecule or derivative thereof to nucleic acid amplification. In some embodiments, the nucleic acid amplification is performed subsequent to releasing the barcoded nucleic acid molecule or derivative thereof from the droplet. In some embodiments, the nucleic acid amplification is polymerase chain reaction. In some embodiments, the RNA molecule is a messenger ribonucleic acid (mRNA) molecule.

In some embodiments, in (a) the droplet comprises (i) an additional nucleic acid molecule comprising an additional nucleic acid sequence, and (ii) an additional nucleic acid barcode molecule comprising an additional barcode sequence, and wherein in (b) the additional nucleic acid molecule and the additional nucleic acid barcode molecule are used to generate an additional barcoded nucleic acid molecule comprising, from a 5'end to a 3'end, the additional barcode sequence and an additional sequence corresponding to the additional nucleic acid sequence. In some embodiments, the additional nucleic acid barcode molecule is coupled to the bead. In some embodiments, the additional nucleic acid barcode molecule is coupled to an additional bead.

In some embodiments, (b) is performed in the droplet.

In some embodiments, the method further comprises releasing the barcoded nucleic acid molecule or a derivative thereof from the droplet.

In some embodiments, the barcoded nucleic acid molecule further comprises, towards a 3' end, a functional sequence for permitting the barcoded nucleic acid molecule or a derivative thereof to couple to a flow cell of a sequencer.

In some embodiments, the sequence is a reverse complement of the nucleic acid sequence.

In some embodiments, the method further comprises, prior to (c), using the barcoded nucleic acid molecule or a derivative thereof and a pair of primers to generate a subset of nucleic acids having a target nucleic acid sequence. In some embodiments, the target nucleic acid sequence comprises a T cell receptor variable region sequence, a B cell receptor variable region sequence, or an immunoglobulin variable region sequence. In some embodiments, the at least one of the pair of primers hybridizes to a constant region of a T cell receptor nucleic acid sequence, a constant region of a B cell receptor nucleic acid sequence, or a constant region of an immunoglobulin nucleic acid sequence. In some embodiments, the subset of nucleic acids or derivatives thereof are sequenced in (c).

In some embodiments, the method further comprises releasing the nucleic acid barcode molecule from the bead. In some embodiments, the nucleic acid barcode molecule is released from the bead before the barcoded nucleic acid molecule is generated. In some embodiments, the nucleic acid barcode molecule is released from the bead while the barcoded nucleic acid molecule is generated. In some embodiments, the nucleic acid barcode molecule is released from the bead after the barcoded nucleic acid molecule is generated. In some embodiments, the bead is a gel bead.

In some embodiments, the barcode sequence is a combinatorial assembly of a plurality of barcode segments. In some embodiments, the plurality of barcode segments comprises at least three segments.

In an aspect, the present disclosure provides a method for generating a labeled polynucleotide. The method comprises (a) subjecting a reaction mixture to a first amplification reaction under conditions sufficient to generate a first amplification product, wherein the reaction mixture comprises a template polynucleotide and (i) a primer having a sequence towards a 3' end that hybridizes to the template polynucleotide, and (ii) a template switching oligonucleotide that comprises a first predefined sequence towards a 5' end; and (b) subjecting the first amplification product to a second amplification reaction in the presence of a barcoded oligonucleotide under conditions sufficient to generate a second amplification product, wherein the barcoded oligonucleotide comprises a sequence of at least a segment of the template switching oligonucleotide and at least a second predefined sequence, wherein (i) the second amplification reaction uses the first amplification product as a template and the barcoded oligonucleotide as a primer, or (ii) the second amplification reaction uses the barcoded oligonucleotide as a template and at least a portion of the first amplification product as a primer, to generate the second amplification product, wherein the first amplification reaction and the second amplification reaction are performed within a same reaction volume. In some embodiments, the second amplification reaction uses the first amplification product as a template and the barcoded oligonucleotide as a primer. In some embodiments, the second amplification reaction uses the barcoded oligonucleotide as a template and at least a portion of the first amplification product as a primer.

In an aspect, the present disclosure provides a method for generating a labeled polynucleotide comprising (a) providing a reaction mixture in a reaction volume, wherein the reaction mixture comprises (i) a template polynucleotide, (ii) a primer comprising a sequence towards a 3' end of the primer that hybridizes to the template polynucleotide, and (iii) a template switching oligonucleotide; (b) in the reaction volume, subjecting the reaction mixture to a first reaction under conditions sufficient to generate a first nucleic acid product comprising the primer, a reverse complement of a sequence of the template polynucleotide, and a sequence complementary to at least a portion of the template switch oligonucleotide; and (c) subjecting the first nucleic acid product to a second reaction in the reaction volume, which second reaction comprises using (i) the first nucleic acid product as a template and a barcoded oligonucleotide as a primer, which barcoded oligonucleotide comprises a sequence of at least a segment of the template switching oligonucleotide, or (ii) the barcoded oligonucleotide as a template and at least a portion of the first nucleic acid as a primer, to generate a second nucleic acid product.

In some embodiments, the template polynucleotide is obtained from a single cell. In some embodiments, the single cell is an immune cell. In some embodiments, the immune cell is a T-cell. In some embodiments, the immune cell is a B-cell. In some embodiments, the method further comprises lysing the single cell in the same reaction volume to obtain the template polynucleotide prior to generating the first amplification product in the first amplification reaction.

In some embodiments, the template polynucleotide comprises a T-cell receptor gene or gene product. In some embodiments, the template polynucleotide comprises a B-cell receptor gene or gene product. In some embodiments, the template polynucleotide is among a plurality of template polynucleotides.

In some embodiments, a concentration of the template switching oligonucleotide in the same reaction volume is at least two times that of a concentration of the barcoded oligonucleotide in the same reaction volume. In some embodiments, a concentration of the template switching oligonucleotide in the same reaction volume is at least five times that of a concentration of the barcoded oligonucleotide in the same reaction volume. In some embodiments, a concentration of the template switching oligonucleotide in the same reaction volume is at least ten times that of a concentration of the barcoded oligonucleotide in the same reaction volume. In some embodiments, a concentration of the template switching oligonucleotide in the same reaction volume is at least twenty times that of a concentration of the barcoded oligonucleotide in the same reaction volume. In some embodiments, a concentration of the template switching oligonucleotide in the same reaction volume is at least fifty times that of a concentration of the barcoded oligonucleotide in the same reaction volume. In some embodiments, a concentration of the template switching oligonucleotide in the same reaction volume is at least one hundred times that of a concentration of the barcoded oligonucleotide in the same reaction volume. In some embodiments, a concentration of the template switching oligonucleotide in the same reaction volume is at least two hundred times that of a concentration of the barcoded oligonucleotide in the same reaction volume.

In some embodiments, the primer comprises a sequence towards a 5' end that does not specifically hybridize to the template polynucleotide.

In some embodiments, the first amplification reaction is facilitated using an enzyme comprising polymerase activity. In some embodiments, the enzyme is a DNA-dependent polymerase. In some embodiments, the enzyme is a reverse transcriptase.

In some embodiments, the second amplification reaction is facilitated using an enzyme comprising polymerase activity. In some embodiments, the enzyme is a DNA-dependent polymerase.

In some embodiments, the first amplification reaction comprises polymerase chain reaction. In some embodiments, the first amplification reaction comprises reverse transcription. In some embodiments, the second amplification reaction comprises polymerase chain reaction.

In some embodiments, the first amplification reaction and the second amplification reaction are performed sequentially in the absence of an intervening purification step.

In some embodiments, the template switching oligonucleotide is not available for primer extension during the second amplification reaction.

In some embodiments, the method further comprises degrading the template switching oligonucleotide prior to the second amplification reaction. In some embodiments, the template switching oligonucleotide comprises ribonucleic acids (RNA). In some embodiments, the template switching oligonucleotide comprises at least 10% ribonucleic acids (RNA).

In some embodiments, the method further comprises degrading the template switching oligonucleotide during the second amplification reaction. In some embodiments, the template switching oligonucleotide comprises ribonucleic acids (RNA). In some embodiments, the template switching oligonucleotide comprises at least 10% ribonucleic acids (RNA).

In some embodiments, a first reaction rate of the second amplification reaction using the barcoded oligonucleotide is greater than a second reaction rate of the second amplification using the template switching oligonucleotide.

In some embodiments, the first amplification product and the barcoded oligonucleotide has a higher melting temperature as compared to a melting temperature of the first amplification product and the template switching oligonucleotide. In some embodiments, a primer annealing temperature of the second amplification reaction is at least 0.5° C. greater than a primer annealing temperature of the first amplification reaction.

In some embodiments, the template switching oligonucleotide comprises modified nucleotides. In some embodiments, the template switching oligonucleotide comprises at least 10% modified nucleotides. In some embodiments, the template switching oligonucleotide comprises modified nucleotides selected from unlocked nucleic acids (UNAs), locked nucleic acids (LNAs), and 5-hydroxybutynl-2'-deoxyuridine.

In some embodiments, the barcoded oligonucleotide comprises modified nucleotides. In some embodiments, the barcoded oligonucleotide comprises at least 10% modified nucleotides. In some embodiments, the barcoded oligonucleotide comprises modified nucleotides selected from locked nucleic acids (LNAs), unlocked nucleic acids (UNAs), and 5-hydroxybutynl-2'-deoxyuridine.

In some embodiments, the same reaction volume comprises an emulsion, a droplet, or a microwell.

In some embodiments, the first defined sequence comprises at least one of an adaptor sequence, a barcode sequence, a unique molecular identifier sequence, a primer binding site, and a sequencing primer binding site. In some embodiments, the second defined sequence comprises at least one of an adaptor sequence, a barcode sequence, a unique molecular identifier sequence, a primer binding site, and a sequencing primer binding site.

In some embodiments, the primer is among a plurality of primers. In some embodiments, the sequence towards the 3' end of the primer comprises a random sequence. In some embodiments, the sequence towards the 3' end of the primer comprises a gene specific sequence. In some embodiments, the sequence towards the 3' end of the primer comprises a polyA sequence.

In some embodiments, the template switching oligonucleotide is among a plurality of template switching oligonucleotides. In some embodiments, the barcoded oligonucleotide is among a plurality of barcoded oligonucleotides.

In some embodiments, the method further comprises subjecting the second amplification product to sequencing.

In some embodiments, the barcoded oligonucleotide is releasably coupled to a microcapsule. In some embodiments, the method further comprises releasing the barcoded oligonucleotide from the microcapsule. In some embodiments, the barcoded oligonucleotide is released from the microcapsule upon application of a stimulus. In some embodiments, the stimulus is at least one of a biological stimulus, a chemical stimulus, a thermal stimulus, an electrical stimulus, a magnetic stimulus, a photo stimulus, or any combination thereof. In some embodiments, the microcapsule is a degradable microcapsule and releasing the barcoded oligonucleotide comprises degrading the microcapsule. In some embodiments, the microcapsule comprises a polymer gel. In some embodiments, the polymer gel is a polyacrylamide. In some embodiments, the microcapsule comprises a bead. In some embodiments, the bead is a gel bead. In some embodiments, the microcapsule comprises a chemical cross-linker. In some embodiments, the chemical cross-linker is a disulfide bond.

In an aspect, the present disclosure provides a method comprising (a) providing a reaction volume comprising (i) a cell or cell derivative, and (ii) a bead comprising a barcoded oligonucleotide releasably coupled thereto, wherein the barcoded oligonucleotide is a template switching oligonucleotide; and (b) releasing the barcoded oligonucleotide from the bead to provide the barcoded oligonucleotide in the reaction volume at a concentration of at least about 0.20 μM; and (c) subjecting the reaction volume to an amplification reaction to generate an amplification product, wherein during the amplification reaction, the reaction volume comprises a template polynucleotide from the cell or cell derivative, the barcoded oligonucleotide and a primer having a sequence towards a 3' end that hybridizes to the template polynucleotide, and wherein the amplification product has sequence complementarity with the template polynucleotide and the barcoded oligonucleotide.

In an aspect, the present disclosure provides a method comprising (a) providing a reaction volume comprising a cell and a microcapsule comprising a barcoded oligonucleotide releasably coupled thereto, wherein the barcoded oligonucleotide is a template switching oligonucleotide; and (b) subjecting the reaction volume to dissociation conditions sufficient to release the barcoded oligonucleotide from the microcapsule, thereby providing the barcoded oligonucleotide in the reaction volume at a concentration of at least about 0.20 uM; and (c) subjecting the reaction volume to an amplification reaction to generate an amplification product, wherein during the amplification reaction, the reaction volume comprises a template polynucleotide from the cell, the barcoded oligonucleotide and a primer having a sequence towards a 3' end that hybridizes to the template polynucleotide, and wherein the amplification product has sequence complementarity with the template polynucleotide and the barcoded oligonucleotide.

In some embodiments, the method further comprises subjecting the amplification product to sequencing. In some embodiments, the barcoded oligonucleotide does not hybridize to the template polynucleotide. In some embodiments, the template polynucleotide is an mRNA molecule. In some embodiments, the method further comprises subjecting the reaction volume to a second amplification reaction to generate an additional amplification product using the amplification product as a template.

In some embodiments, the method further comprises subjecting the additional amplification product to sequencing.

In some embodiments, the cell is a mammalian cell. In some embodiments, the cell is an immune cell. In some embodiments, the immune cell is a B-cell. In some embodiments, the immune cell is a T-cell. In some embodiments, the cell is cancer cell. In some embodiments, the cancer cell is obtained from a tissue sample. In some embodiments, the cancer cell is obtained from a biological fluid. In some embodiments, the biological fluid comprises blood. In some embodiments, the biological fluid comprises lymph fluid.

In some embodiments, the template polynucleotide comprises a T cell receptor gene sequence, a B cell receptor gene sequence, or an immunoglobulin gene sequence. In some embodiments, the template polynucleotide is a T cell receptor mRNA molecule, a B cell receptor mRNA molecule, or an immunoglobulin mRNA molecule.

In some embodiments, the reaction volume further comprises an enzyme. In some embodiments, the enzyme is a DNA polymerase. In some embodiments, the enzyme is a reverse transcriptase.

In some embodiments, the reaction volume further comprises at least one reagent for nucleic acid amplification. In some embodiments, the at least one reagent comprises dNTPs. In some embodiments, the at least one reagent comprises oligonucleotide primers.

In some embodiments, the microcapsule comprises a polymer gel. In some embodiments, the polymer gel is a polyacrylamide. In some embodiments, the microcapsule comprises a bead. In some embodiments, the bead is a gel bead. In some embodiments, the microcapsule comprises a chemical cross-linker. In some embodiments, the chemical cross-linker is a disulfide bond. In some embodiments, the dissociation condition is at least one of a biological stimulus, a chemical stimulus, a thermal stimulus, an electrical stimulus, a magnetic stimulus, a photo stimulus, or any combination thereof.

In some embodiments, the barcoded oligonucleotide comprises at least one of an adaptor sequence, a barcode sequence, unique molecular identifier sequence, a primer binding site, and a sequencing primer binding site.

In some embodiments, the same reaction volume comprises an emulsion, a droplet, or a microwell.

In some embodiments, the method further comprises performing a third reaction, wherein the third reaction specifically amplifies variable region cDNAs, wherein the variable region cDNA are derived from a T cell receptor cDNA, a B cell receptor cDNA, or an immunoglobulin cDNA. In some embodiments, the third reaction comprises use of a primer that specifically binds in the constant region of the T cell receptor cDNA, B cell receptor cDNA, or immunoglobulin cDNA, and extends through the variable region of the T cell receptor cDNA, B cell receptor cDNA, or immunoglobulin cDNA. In some embodiments, the third reaction results in an enrichment product that comprises at (a) least one of a T cell receptor variable region sequence, a B cell receptor variable region sequence, and an immunoglobulin variable region sequence, and (b) at least one of an adaptor sequence, a barcode sequence, a unique molecular identifier sequence, a primer binding site, and a sequencing primer binding site. In some embodiments, greater than about 25% of reads in a subsequent short-read sequencing reaction map to a T cell receptor, a B cell receptor, or an immunoglobulin gene.

In an aspect, the present disclosure provides a non-transitory computer-readable medium comprising machine-executable code that, upon execution by one of more computer processors, implements a method for nucleic acid sequencing, comprising (a) providing a plurality of droplets, wherein a droplet of the plurality of droplets comprises (i) a ribonucleic acid (RNA) molecule comprising a nucleic acid sequence, and (ii) a bead comprising a nucleic acid barcode molecule coupled thereto, wherein the nucleic acid barcode molecule comprises a barcode sequence; (b) using the RNA molecule and the nucleic acid barcode molecule to generate a barcoded nucleic acid molecule comprising, from a 5'end to a 3'end, a sequence corresponding to the nucleic acid sequence of the RNA molecule and a complement of the barcode sequence; and (c) sequencing the barcoded nucleic acid molecule or a derivative thereof.

In an aspect, the present disclosure provides a non-transitory computer-readable medium comprising machine-executable code that, upon execution by one of more computer processors, implements a method for generating a labeled polynucleotide, the method comprising (a) subjecting a reaction mixture to a first reaction under conditions sufficient to generate a first nucleic acid product, wherein the reaction mixture comprises (i) a template polynucleotide, (ii) a primer having a sequence towards a 3' end that hybridizes to the template polynucleotide, and (iii) a template switching oligonucleotide, wherein the first nucleic acid product comprises the primer, a reverse complement of a sequence of the template polynucleotide, and a sequence complementary to at least a portion of the template switch oligonucleotide; and (b) subjecting the first nucleic acid product to a second reaction in the presence of a barcoded oligonucleotide under conditions sufficient to generate a second nucleic acid product, wherein the barcoded oligonucleotide comprises a sequence of at least a segment of the template switching oligonucleotide, wherein (i) the second reaction uses the first nucleic acid as a template and the barcoded oligonucleotide as a primer, or (ii) the second reaction uses the barcoded oligonucleotide as a template and at least a portion of the first nucleic acid as a primer, to generate the second nucleic acid product, wherein the first reaction and the second reaction are performed within a same reaction volume.

In an aspect, the present disclosure provides a non-transitory computer-readable medium comprising machine-executable code that, upon execution by one of more computer processors, implements a method for generating a labeled polynucleotide. The method comprises (a) subjecting a reaction mixture to a first amplification reaction under conditions sufficient to generate a first amplification product, wherein the reaction mixture comprises a template polynucleotide and (i) a primer having a sequence towards a 3' end that hybridizes to the template polynucleotide, and (ii) a template switching oligonucleotide that comprises a first predefined sequence towards a 5' end; and (b) subjecting the first amplification product to a second amplification reaction in the presence of a barcoded oligonucleotide under conditions sufficient to generate a second amplification product, wherein the barcoded oligonucleotide comprises a sequence of at least a segment of the template switching oligonucleotide and at least a second predefined sequence, wherein (i) the second amplification reaction uses the first amplification product as a template and the barcoded oligonucleotide as a primer, or (ii) the second amplification reaction uses the barcoded oligonucleotide as a template and at least a portion of the first amplification product as a primer, to generate the second amplification product, wherein the first amplification reaction and the second amplification reaction are performed within a same reaction volume.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 8 provides an image of individual cells co-partitioned along with individual barcode bearing beads.

FIG. 9A discloses SEQ ID NOS 167 and 167, respectively, in order of appearance. FIG. 9B discloses SEQ ID NOS 167, 167 and 167, respectively, in order of appearance. FIG. 9C discloses SEQ ID NOS 167 and 167, respectively, in order of appearance. FIG. 9D discloses SEQ ID NOS 167 and 167, respectively, in order of appearance. FIG. 9E discloses SEQ ID NOS 167 and 167, respectively, in order of appearance.

FIG. 10 discloses SEQ ID NOS 167 and 167, respectively, in order of appearance.

FIG. 11 discloses SEQ ID NOS 168-169 and 168-169, respectively, in order of appearance.

FIG. 19A discloses SEQ ID NOS 167, 167 and 167, respectively, in order of appearance. FIG. 19B discloses SEQ ID NOS 168-169, 168-169, 169, 169 and 169, respectively, in order of appearance.

FIG. 20 discloses SEQ ID NOS 167 and 167, respectively, in order of appearance.

FIG. 23A-23B shows sequencing results from cDNA that has been enriched using constant region primers compared to unenriched cDNA.

FIG. 29A discloses SEQ ID NOS, 170, 170, 170 and 170, respectively, in order of appearance.

DETAILED DESCRIPTION

Figure 1:
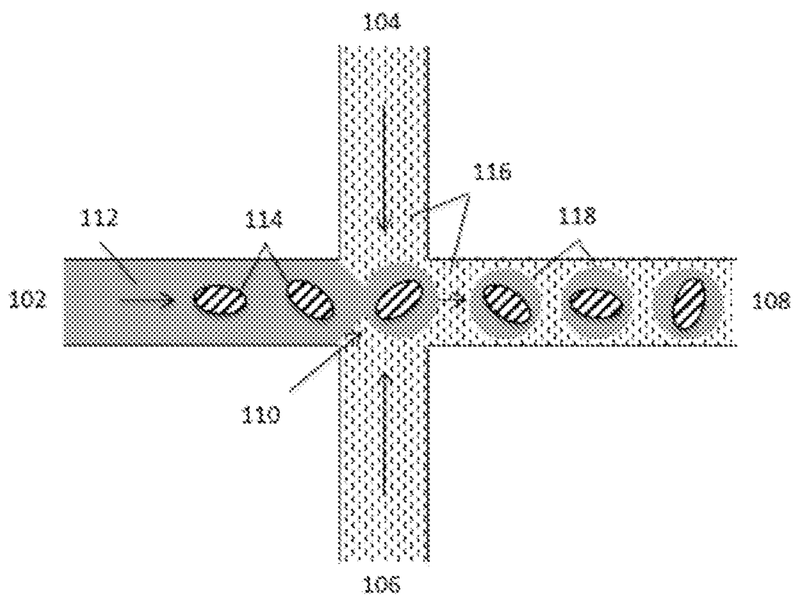
FIG. 1 schematically illustrates a microfluidic channel structure for partitioning individual or small groups of cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that can be part of an analyte to convey information about the analyte. A barcode can be a tag attached to an analyte (e.g., nucleic acid molecule) or a combination of the tag in addition to an endogenous characteristic of the analyte (e.g., size of the analyte or end sequence(s)). The barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. The barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time. In some examples, the barcode is generated in a combinatorial manner. Barcodes that may be used with methods, devices and systems of the present disclosure, including methods for forming such barcodes, are described in, for example, U.S. Patent Pub. No. 2014/0378350, which is entirely incorporated herein by reference.

The term "subject," as used herein, generally refers to an animal, such as a mammalian species (e.g., human) or avian (e.g., bird) species, or other organism, such as a plant. The subject can be a vertebrate, a mammal, a mouse, a primate, a simian or a human. Animals may include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome," as used herein, generally refers to an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, with limitation, a sequencing system by Illumina, Pacific Biosciences, Oxford Nanopore, or Life Technologies (Ion Torrent). Such devices may provide a plurality of raw genetic data corresponding to the genetic information of a subject (e.g., human), as generated by the device from a sample provided by the subject. In some situations, systems and methods provided herein may be used with proteomic information.

The term "variant," as used herein, generally refers to a genetic variant, such as a nucleic acid molecule comprising a polymorphism. A variant can be a structural variant or copy number variant, which can be genomic variants that are larger than single nucleotide variants or short indels. A variant can be an alteration or polymorphism in a nucleic acid sample or genome of a subject. Single nucleotide polymorphisms (SNPs) are a form of polymorphisms. Polymorphisms can include single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "bead," as used herein, generally refers to a particle. The bead may be a solid or semi-solid particle. The bead may be a gel. The bead may be formed of a polymeric material. The bead may be magnetic or non-magnetic.

The term "sample," as used herein, generally refers to a biological sample of a subject. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swap. The sample may be a plasma or serum sample. The sample may be a cell-free or cell free sample. A cell-free sample may include extracellular polynucleotides. Extracellular polynucleotides may be isolated from a bodily sample that may be selected from a group consisting of blood, plasma, serum, urine, saliva, mucosal excretions, sputum, stool and tears.

The term "primer," as used herein generally refers to a strand of RNA or DNA that serves as a starting point for nucleic acid (e.g., DNA) synthesis. A primer may be used in a primer extension reaction, which may be a nucleic acid amplification reaction, such as, for example, polymerase chain reaction (PCR) or reverse transcription PCR (RT-PCR). The primer may have a sequence that is capable of coupling to a nucleic acid molecule. Such sequence may be complementary to the nucleic acid molecule, such as a poly-T sequence or a predetermined sequence, or a sequence that is otherwise capable of coupling (e.g., hybridizing) to the nucleic acid molecule, such as a universal primer.

Nucleic acid sequencing technologies have yielded substantial results in sequencing biological materials, including providing substantial sequence information on individual organisms, and relatively pure biological samples. However, these systems have traditionally not been effective at being able to identify and characterize cells at the single cell level.

Many nucleic acid sequencing technologies derive the nucleic acids that they sequence from collections of cells obtained from tissue or other samples, such as biological fluids (e.g., blood, plasma, etc). The cells can be processed (e.g., all together) to extract the genetic material that represents an average of the population of cells, which can then be processed into sequencing ready DNA libraries that are configured for a given sequencing technology. Although often discussed in terms of DNA or nucleic acids, the nucleic acids derived from the cells may include DNA, or RNA, including, e.g., mRNA, total RNA, or the like, that may be processed to produce complementary DNA (cDNA) for sequencing. Following processing, absent a cell specific marker, attribution of genetic material as being contributed by a subset of cells or an individual cell may not be possible in such an ensemble approach.

In addition to the inability to attribute characteristics to particular subsets of cells or individual cells, such ensemble sample preparation methods can be, from the outset, predisposed to primarily identifying and characterizing the majority constituents in the sample of cells, and may not be designed to pick out the minority constituents, e.g., genetic material contributed by one cell, a few cells, or a small percentage of total cells in the sample. Likewise, where analyzing expression levels, e.g., of mRNA, an ensemble approach can be predisposed to presenting potentially inaccurate data from cell populations that are non-homogeneous in terms of expression levels. In some cases, where expression is high in a small minority of the cells in an analyzed population, and absent in the majority of the cells of the population, an ensemble method may indicate low level expression for the entire population.

These inaccuracies can be further magnified through processing operations used in generating the sequencing libraries from these samples. In particular, many next generation sequencing technologies (e.g., massively parallel sequencing) may rely upon the geometric amplification of nucleic acid fragments, such as via polymerase chain reaction, in order to produce sufficient DNA for the sequencing library. However, such amplification can be biased toward amplification of majority constituents in a sample, and may not preserve the starting ratios of such minority and majority components. While some of these difficulties may be addressed by utilizing different sequencing systems, such as single molecule systems that do not require amplification, the single molecule systems, as well as the ensemble sequencing methods of other next generation sequencing systems, can also have large input DNA requirements. Some single molecule sequencing systems, for example, can have sample input DNA requirements of from 500 nanograms (ng) to upwards of 10 micrograms (g), which may not be obtainable from individual cells or even small subpopulations of cells. Likewise, other NGS systems can be optimized for starting amounts of sample DNA in the sample of from approximately 50 ng to about 1 μg.

Disclosed herein are methods and systems for characterizing nucleic acids from small populations of cells, and in some cases, for characterizing nucleic acids from individual cells. The methods described herein may compartmentalize the analysis of individual cells or small populations of cells, including e.g., nucleic acids from individual cells or small groups of cells, and then allow that analysis to be attributed back to the individual cell or small group of cells from which the nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells from different tissue types of an individual or the same tissue type from different individuals, or biological organisms such as microorganisms from differing genera, species, strains, variants, or any combination of any or all of the foregoing. For example, differing cell types may include normal and tumor tissue from an individual, various cell types obtained from a human subject such as a variety of immune cells (e.g., B cells, T cells, and the like), multiple different bacterial species, strains and/or variants from environmental, forensic, microbiome or other samples, or any of a variety of other mixtures of cell types.

Methods and systems described herein may provide for the compartmentalization, depositing or partitioning of the nucleic acid contents of individual cells from a sample material containing cells, into discrete compartments or partitions (referred to interchangeably herein as partitions), where each partition maintains separation of its own contents from the contents of other partitions. In some examples, a partition is a droplet or well. Unique identifiers, e.g., barcodes, may be previously, subsequently or concurrently delivered to the partitions that hold the compartmentalized or partitioned cells or cellular derivatives, in order to allow for the later attribution of the characteristics of the individual cells to the particular compartment. Barcodes may be delivered, for example in an oligonucleotide to a partition via any suitable mechanism, such as using beads (e.g., gel beads). In some examples, cellular derivatives, such as cells or constituents of such cells in matrix (e.g., gel or polymeric matrix), are compartmentalized or partitioned in partitions (e.g., droplets or wells).

In some embodiments, barcoded oligonucleotides are delivered to a partition via a microcapsule. In some cases, barcoded oligonucleotides are initially associated with the microcapsule and then released from the microcapsule upon application of a stimulus which allows the oligonucleotides to dissociate or to be released from the microcapsule.

A microcapsule, in some embodiments, comprises a bead. In some embodiments, a bead may be porous, non-porous, solid, semi-solid, semi-fluidic, or fluidic. In some embodiments, a bead may be dissolvable, disruptable, or degradable. In some cases, a bead may not be degradable. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the beads are silica beads. In some cases, the beads are rigid. In some cases, the beads may be flexible and/or compressible.

In some embodiments, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor comprises one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials. For example, a polymer can be a natural polymer or a synthetic polymer. In some cases, a bead comprises both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads may also be formed from materials other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to attach oligonucleotides (e.g., barcoded oligonucleotides) to the bead. In some cases, polymers may be further polymerized with a cross-linker species or other type of monomer to generate a further polymeric network. Non-limiting examples of chemical cross-linkers (also referred to as a "crosslinker" or a "cross-linker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilane, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some embodiments, disulfide linkages can be formed between molecular precursor units (e.g., monomers, oligomers, or linear polymers) or precursors incorporated into a bead and oligonucleotides. Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some embodiments, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g., monomers, oligomers, linear polymers), oligonucleotides, primers, and other entities. In some cases, the covalent bonds comprise carbon-carbon bonds or thioether bonds.

In some cases, a bead may comprise an acrydite moiety, which in certain aspects may be used to attach one or more oligonucleotides (e.g., barcode sequence, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as an oligonucleotide (e.g., barcode sequence, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment is reversible, such that when the disulfide bond is broken (e.g., in the presence of a reducing agent), the attached species is released from the bead. In other cases, an acrydite moiety comprises a reactive hydroxyl group that may be used for attachment.

Functionalization of beads for attachment of oligonucleotides may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to an oligonucleotide, such as a primer (e.g., a primer for amplifying target nucleic acids, barcoded oligonucleotide, etc) that is desired to be incorporated into the bead. In some cases, the primer comprises a P5 sequence for attachment to a sequencing flow cell for Illumina sequencing. In some cases, the primer comprises a P7 sequence for attachment to a sequencing flow cell for Illumina sequencing. In some cases, the primer comprises a barcode sequence. In some cases, the primer further comprises a unique molecular identifier (UMI). In some cases, the primer comprises an R1 primer sequence for Illumina sequencing. In some cases, the primer comprises an R2 primer sequence for Illumina sequencing.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than about 10,000; 100,000; 1,000,000; 10,000,000; 100,000,000; 1,000,000,000; 10,000,000,000; or 100,000,000,000) of reducing agent may be used for reduction. Controlling the number of disulfide linkages that are reduced to free thiols may be useful in ensuring bead structural integrity during functionalization. In some cases, optically-active agents, such as fluorescent dyes may be may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

In some cases, an acrydite moiety linked to precursor, another species linked to a precursor, or a precursor itself comprises a labile bond, such as chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides, reagents for a nucleic acid amplification reaction (e.g., primers, polymerases, dNTPs, co-factors (e.g., ionic co-factors)) including those described herein, reagents for enzymatic reactions (e.g., enzymes, co-factors, substrates), or reagents for a nucleic acid modification reactions such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some cases, the diameter of a bead may be about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead may have a diameter of at least about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or more. In some cases, a bead may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads are provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, or even less than 5%.

Beads may be of any suitable shape. Examples of bead shapes include, but are not limited to, spherical, non-spherical, oval, oblong, amorphous, circular, cylindrical, and variations thereof.

In addition to, or as an alternative to the cleavable linkages between the beads and the associated molecules, e.g., barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead is degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., an oligonucleotide, e.g., barcoded oligonucleotide) may result in release of the species from the bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., an oligonucleotide, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be desirable to avoid exposing such beads to the stimulus or stimuli that cause such degradation prior to the desired time, in order to avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than 1/10th, less than 1/50th, and even less than 1/100th of the lower ranges for such materials used in degrading the beads. For example, for DTT, the reducing agent free preparation will typically have less than 0.01 mM, 0.005 mM, 0.001 mM DTT, 0.0005 mM DTT, or even less than 0.0001 mM DTT. In many cases, the amount of DTT will be undetectable.

In some cases, a stimulus may be used to trigger degradation of the bead, which may result in the release of contents from the bead. Generally, a stimulus may cause degradation of the bead structure, such as degradation of the covalent bonds or other types of physical interaction. These stimuli may be useful in inducing a bead to degrade and/or to release its contents. Examples of stimuli that may be used include chemical stimuli, thermal stimuli, optical stimuli (e.g., light) and any combination thereof, as described more fully below.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, or 10 mM. The reducing agent may be present at a concentration of at least about 0.1 mM, 0.5 mM, 1 mM, 5 mM, 10 mM, or greater. The reducing agent may be present at concentration of at most about 0.1 mM, 0.5 mM, 1 mM, 5 mM, or 10 mM.

Any suitable number of nucleic acid molecules (e.g., primer, e.g., barcoded oligonucleotide) can be associated with a bead such that, upon release from the bead, the nucleic acid molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer is limited by the process of producing oligonucleotide bearing beads.

In some aspects, the partitions refer to containers or vessels (such as wells, microwells, tubes, vials, through ports in nanoarray substrates, e.g., BioTrove nanoarrays, or other containers). In some aspects, the compartments or partitions comprise partitions that are flowable within fluid streams. These partitions may comprise, e.g., micro-vesicles that have an outer barrier surrounding an inner fluid center or core, or, in some cases, they may comprise a porous matrix that is capable of entraining and/or retaining materials within its matrix. In some aspects, partitions comprise droplets of aqueous fluid within a non-aqueous continuous phase, e.g., an oil phase. A variety of different vessels are described in, for example, U.S. Patent Application Publication No. 20140155295, the full disclosure of which is incorporated herein by reference in its entirety for all purposes. Emulsion systems for creating stable droplets in non-aqueous or oil continuous phases are described in detail in, e.g., U.S. Patent Application Publication No. 20100105112, the full disclosure of which is incorporated herein by reference in its entirety for all purposes.

In the case of droplets in an emulsion, allocating individual cells to discrete partitions may generally be accomplished by introducing a flowing stream of cells in an aqueous fluid into a flowing stream of a non-aqueous fluid, such that droplets are generated at the junction of the two streams. By providing the aqueous cell-containing stream at a certain concentration of cells, the occupancy of the resulting partitions (e.g., number of cells per partition) can be controlled. Where single cell partitions are desired, the relative flow rates of the fluids can be selected such that, on average, the partitions contain less than one cell per partition, in order to ensure that those partitions that are occupied, are primarily singly occupied. In some embodiments, the relative flow rates of the fluids can be selected such that a majority of partitions are occupied, e.g., allowing for only a small percentage of unoccupied partitions. In some aspects, the flows and channel architectures are controlled as to ensure a desired number of singly occupied partitions, less than a certain level of unoccupied partitions and less than a certain level of multiply occupied partitions.

The systems and methods described herein can be operated such that a majority of occupied partitions include no more than one cell per occupied partition. In some cases, the partitioning process is conducted such that fewer than 25% of the occupied partitions contain more than one cell, and in many cases, fewer than 20% of the occupied partitions have more than one cell. In some cases, fewer than 10% or even fewer than 5% of the occupied partitions include more than one cell per partition.

In some cases, it is desirable to avoid the creation of excessive numbers of empty partitions. For example, from a cost perspective and/or efficiency perspective, it may desirable to minimize the number of empty partitions. While this may be accomplished by providing sufficient numbers of cells into the partitioning zone, the Poissonian distribution may expectedly increase the number of partitions that may include multiple cells. As such, in accordance with aspects described herein, the flow of one or more of the cells, or other fluids directed into the partitioning zone are conducted such that, in many cases, no more than 50% of the generated partitions, no more than 25% of the generated partitions, or no more than 10% of the generated partitions are unoccupied. Further, in some aspects, these flows are controlled so as to present non-Poissonian distribution of single occupied partitions while providing lower levels of unoccupied partitions. Restated, in some aspects, the above noted ranges of unoccupied partitions can be achieved while still providing any of the single occupancy rates described above. For example, in many cases, the use of the systems and methods described herein creates resulting partitions that have multiple occupancy rates of less than 25%, less than 20%, less than 15%, less than 10%, and in many cases, less than 5%, while having unoccupied partitions of less than 50%, less than 40%, less than 30%, less than 20%, less than 10%, and in some cases, less than 5%.

As will be appreciated, the above-described occupancy rates are also applicable to partitions that include both cells and additional reagents, including, but not limited to, microcapsules carrying barcoded oligonucleotides. In some aspects, a substantial percentage of the overall occupied partitions can include both a microcapsule (e.g., bead) comprising barcoded oligonucleotides and a cell.

Although described in terms of providing substantially singly occupied partitions, above, in certain cases, it is desirable to provide multiply occupied partitions, e.g., containing two, three, four or more cells and/or microcapsules (e.g., beads) comprising barcoded oligonucleotides within a single partition. Accordingly, as noted above, the flow characteristics of the cell and/or bead containing fluids and partitioning fluids may be controlled to provide for such multiply occupied partitions. In particular, the flow parameters may be controlled to provide a desired occupancy rate at greater than 50% of the partitions, greater than 75%, and in some cases greater than 80%, 90%, 95%, or higher.

In some cases, additional microcapsules are used to deliver additional reagents to a partition. In such cases, it may be advantageous to introduce different beads into a common channel or droplet generation junction, from different bead sources, i.e., containing different associated reagents, through different channel inlets into such common channel or droplet generation junction. In such cases, the flow and frequency of the different beads into the channel or junction may be controlled to provide for the desired ratio of microcapsules from each source, while ensuring the desired pairing or combination of such beads into a partition with the desired number of cells.

The partitions described herein may comprise small volumes, e.g., less than 10 μL, less than 5 μL, less than 1 μL, less than 900 picoliters (pL), less than 800 pL, less than 700 pL, less than 600 pL, less than 500 pL, less than 400 pL, less than 300 pL, less than 200 pL, less than 100 pL, less than 50 pL, less than 20 pL, less than 10 pL, less than 1 pL, less than 500 nanoliters (nL), or even less than 100 nL, 50 nL, or even less.

For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with microcapsules, it will be appreciated that the sample fluid volume, e.g., including co-partitioned cells, within the partitions may be less than 90% of the above described volumes, less than 80%, less than 70%, less than 60%, less than 50%, less than 40%, less than 30%, less than 20%, or even less than 10% the above described volumes.

As is described elsewhere herein, partitioning species may generate a population or plurality of partitions. In such cases, any suitable number of partitions can be generated to generate the plurality of partitions. For example, in a method described herein, a plurality of partitions may be generated that comprises at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions or at least about 1,000,000,000 partitions. Moreover, the plurality of partitions may comprise both unoccupied partitions (e.g., empty partitions) and occupied partitions Microfluidic channel networks can be utilized to generate partitions as described herein. Alternative mechanisms may also be employed in the partitioning of individual cells, including porous membranes through which aqueous mixtures of cells are extruded into non-aqueous fluids.

An example of a simplified microfluidic channel structure for partitioning individual cells is illustrated in FIG. 1. As described elsewhere herein, in some cases, the majority of occupied partitions include no more than one cell per occupied partition and, in some cases, some of the generated partitions are unoccupied. In some cases, though, some of the occupied partitions may include more than one cell. In some cases, the partitioning process may be controlled such that fewer than 25% of the occupied partitions contain more than one cell, and in many cases, fewer than 20% of the occupied partitions have more than one cell, while in some cases, fewer than 10% or even fewer than 5% of the occupied partitions include more than one cell per partition. As shown, the channel structure can include channel segments 102, 104, 106 and 108 communicating at a channel junction 110. In operation, a first aqueous fluid 112 that includes suspended cells 114, may be transported along channel segment 102 into junction 110, while a second fluid 116 that is immiscible with the aqueous fluid 112 is delivered to the junction 110 from channel segments 104 and 106 to create discrete droplets 118 of the aqueous fluid including individual cells 114, flowing into channel segment 108.

In some aspects, this second fluid 116 comprises an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 20100105112, the full disclosure of which is hereby incorporated herein by reference in its entirety for all purposes.

In other aspects, in addition to or as an alternative to droplet based partitioning, cells may be encapsulated within a microcapsule that comprises an outer shell or layer or porous matrix in which is entrained one or more individual cells or small groups of cells, and may include other reagents. Encapsulation of cells may be carried out by a variety of processes. Such processes combine an aqueous fluid containing the cells to be analyzed with a polymeric precursor material that may be capable of being formed into a gel or other solid or semi-solid matrix upon application of a particular stimulus to the polymer precursor. Such stimuli include, e.g., thermal stimuli (either heating or cooling), photo-stimuli (e.g., through photo-curing), chemical stimuli (e.g., through crosslinking, polymerization initiation of the precursor (e.g., through added initiators), or the like.

Preparation of microcapsules comprising cells may be carried out by a variety of methods. For example, air knife droplet or aerosol generators may be used to dispense droplets of precursor fluids into gelling solutions in order to form microcapsules that include individual cells or small groups of cells. Likewise, membrane based encapsulation systems may be used to generate microcapsules comprising encapsulated cells as described herein. In some aspects, microfluidic systems like that shown in FIG. 1 may be readily used in encapsulating cells as described herein. In particular, and with reference to FIG. 1, the aqueous fluid comprising the cells and the polymer precursor material is flowed into channel junction 110, where it is partitioned into droplets 118 comprising the individual cells 114, through the flow of non-aqueous fluid 116. In the case of encapsulation methods, non-aqueous fluid 116 may also include an initiator to cause polymerization and/or crosslinking of the polymer precursor to form the microcapsule that includes the entrained cells. Examples of polymer precursor/initiator pairs include those described in U.S. Patent Application Publication No. 20140378345, the full disclosure of which are hereby incorporated herein by reference in their entireties for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams in channel segments 104 and 106, which initiates the copolymerization of the acrylamide and BAC into a cross-linked polymer network or, hydrogel.

Upon contact of the second fluid stream 116 with the first fluid stream 112 at junction 110 in the formation of droplets, the TEMED may diffuse from the second fluid 116 into the aqueous first fluid 112 comprising the linear polyacrylamide, which will activate the crosslinking of the polyacrylamide within the droplets, resulting in the formation of the gel, e.g., hydrogel, microcapsules 118, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions, e.g., Ca2+, can be used as an encapsulation process using the described processes. Likewise, agarose droplets may also be transformed into capsules through temperature based gelling, e.g., upon cooling, or the like. In some cases, encapsulated cells can be selectively releasable from the microcapsule, e.g., through passage of time, or upon application of a particular stimulus, that degrades the microcapsule sufficiently to allow the cell, or its contents to be released from the microcapsule, e.g., into a partition, such as a droplet. For example, in the case of the polyacrylamide polymer described above, degradation of the microcapsule may be accomplished through the introduction of an appropriate reducing agent, such as DTT or the like, to cleave disulfide bonds that cross link the polymer matrix (See, e.g., U.S. Patent Application Publication No. 20140378345, the full disclosures of which are hereby incorporated herein by reference in their entirety for all purposes.

Encapsulated cells or cell populations provide certain potential advantages of being storable, and more portable than droplet based partitioned cells. Furthermore, in some cases, it may be desirable to allow cells to be analyzed to incubate for a select period of time, in order to characterize changes in such cells over time, either in the presence or absence of different stimuli. In such cases, encapsulation of individual cells may allow for longer incubation than partitioning in emulsion droplets, although in some cases, droplet partitioned cells may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of cells may constitute the partitioning of the cells into which other reagents are co-partitioned. Alternatively, encapsulated cells may be readily deposited into other partitions, e.g., droplets, as described above.

In accordance with certain aspects, the cells may be partitioned along with lysis reagents in order to release the contents of the cells within the partition. In such cases, the lysis agents can be contacted with the cell suspension concurrently with, or immediately prior to the introduction of the cells into the partitioning junction/droplet generation zone, e.g., through an additional channel or channels upstream of channel junction 110. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the cells to cause the release of the cell's contents into the partitions. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of cells that may be in addition to or in place of droplet partitioning, where any pore size of the encapsulate is sufficiently small to retain nucleic acid fragments of a desired size, following cellular disruption.

In addition to the lysis agents co-partitioned with the cells described above, other reagents can also be co-partitioned with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cells, the cells may be exposed to an appropriate stimulus to release the cells or their contents from a co-partitioned microcapsule. For example, in some cases, a chemical stimulus may be co-partitioned along with an encapsulated cell to allow for the degradation of the microcapsule and release of the cell or its contents into the larger partition. In some cases, this stimulus may be the same as the stimulus described elsewhere herein for release of oligonucleotides from their respective microcapsule (e.g., bead). In alternative aspects, this may be a different and non-overlapping stimulus, in order to allow an encapsulated cell to be released into a partition at a different time from the release of oligonucleotides into the same partition.

Additional reagents may also be co-partitioned with the cells, such as endonucleases to fragment the cell's DNA, DNA polymerase enzymes and dNTPs used to amplify the cell's nucleic acid fragments and to attach the barcode oligonucleotides to the amplified fragments. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In one example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the nucleic acids contained therein may be further processed within the partitions. In accordance with the methods and systems described herein, the nucleic acid contents of individual cells can be provided with unique identifiers such that, upon characterization of those nucleic acids they may be attributed as having been derived from the same cell or cells. The ability to attribute characteristics to individual cells or groups of cells is provided by the assignment of unique identifiers specifically to an individual cell or groups of cells. Unique identifiers, e.g., in the form of nucleic acid barcodes can be assigned or associated with individual cells or populations of cells, in order to tag or label the cell's components (and as a result, its characteristics) with the unique identifiers. These unique identifiers can then be used to attribute the cell's components and characteristics to an individual cell or group of cells. In some aspects, this is carried out by co-partitioning the individual cells or groups of cells with the unique identifiers. In some aspects, the unique identifiers are provided in the form of oligonucleotides that comprise nucleic acid barcode sequences that may be attached to or otherwise associated with the nucleic acid contents of individual cells, or to other components of the cells, and particularly to fragments of those nucleic acids. The oligonucleotides are partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned cells. These sequences include, e.g., targeted or random/universal amplification primer sequences for amplifying the genomic DNA from the individual cells within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

Briefly, in one example, microcapsules, such as beads, are provided that each include large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the oligonucleotides into the partitions, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each bead can be provided with large numbers of oligonucleotide molecules attached. In particular, the number of molecules of oligonucleotides including the barcode sequence on an individual bead can be at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

Moreover, when the population of beads is partitioned, the resulting population of partitions can also include a diverse barcode library that includes at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each partition of the population can include at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

In some cases, it may be desirable to incorporate multiple different barcodes within a given partition, either attached to a single or multiple beads within the partition. For example, in some cases, a mixed, but known barcode sequences set may provide greater assurance of identification in the subsequent processing, e.g., by providing a stronger address or attribution of the barcodes to a given partition, as a duplicate or independent confirmation of the output from a given partition.

The oligonucleotides are releasable from the beads upon the application of a particular stimulus to the beads. In some cases, the stimulus may be a photo-stimulus, e.g., through cleavage of a photo-labile linkage that releases the oligonucleotides. In other cases, a thermal stimulus may be used, where elevation of the temperature of the beads environment will result in cleavage of a linkage or other release of the oligonucleotides form the beads. In still other cases, a chemical stimulus is used that cleaves a linkage of the oligonucleotides to the beads, or otherwise results in release of the oligonucleotides from the beads. In one case, such compositions include the polyacrylamide matrices described above for encapsulation of cells, and may be degraded for release of the attached oligonucleotides through exposure to a reducing agent, such as DTT.

Figure 2:
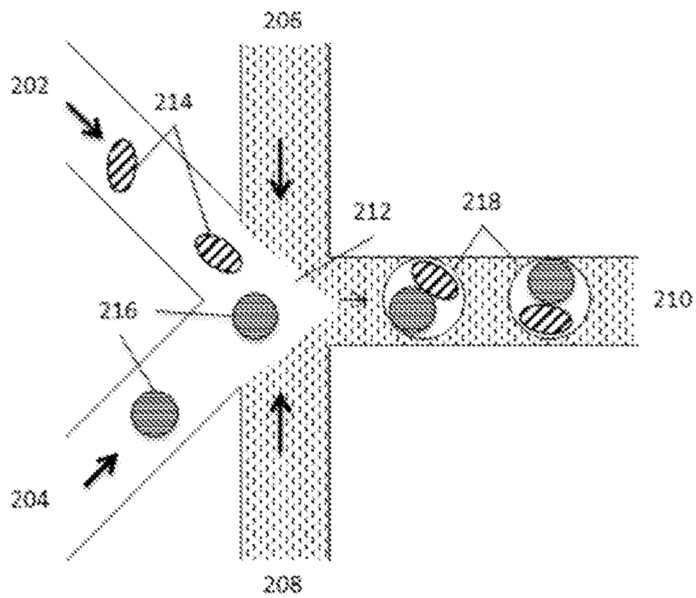
FIG. 2 schematically illustrates a microfluidic channel structure for co-partitioning cells and microcapsules (e.g., beads) comprising additional reagents.
Figure 3A:
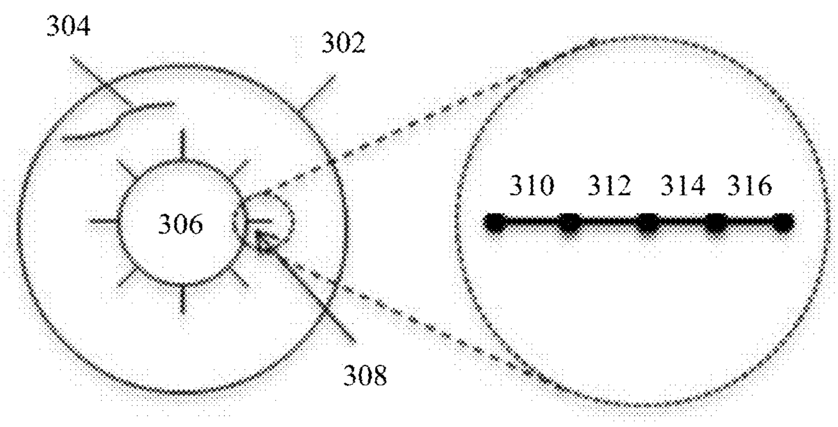
FIG. 3A-3F schematically illustrates an example process for amplification and barcoding of cell's nucleic acids.
Figure 3B:
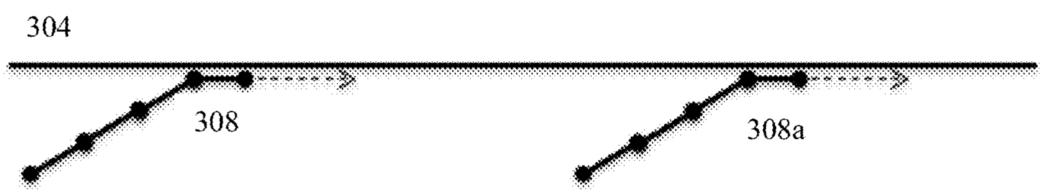
Figure 3C:
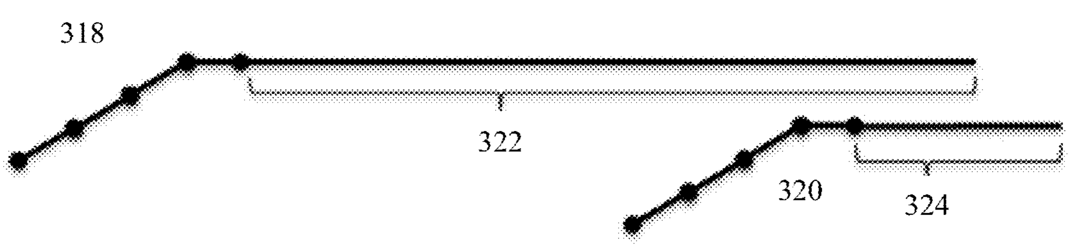
Figure 3D:
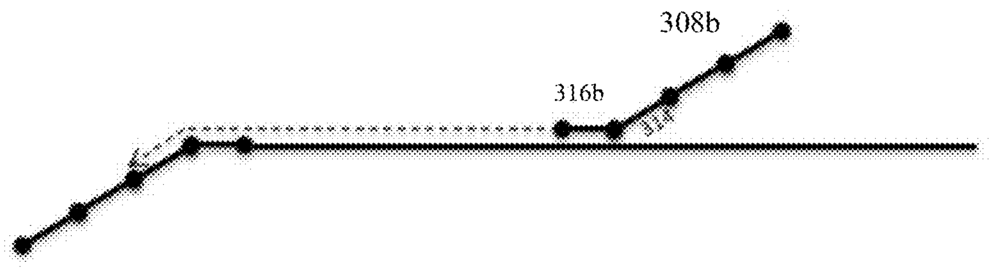
Figure 3E:
Figure 3F:
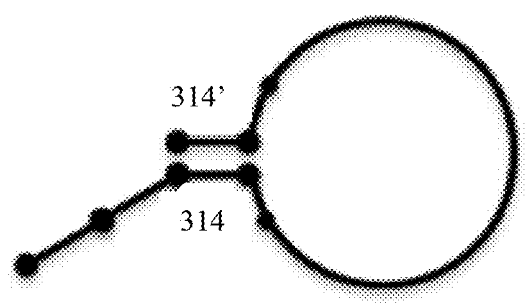

In accordance with the methods and systems described herein, the beads including the attached oligonucleotides are co-partitioned with the individual cells, such that a single bead and a single cell are contained within an individual partition. As noted above, while single cell/single bead occupancy is the most desired state, it will be appreciated that multiply occupied partitions (either in terms of cells, beads or both), or unoccupied partitions (either in terms of cells, beads or both) will often be present. An example of a microfluidic channel structure for co-partitioning cells and beads comprising barcode oligonucleotides is schematically illustrated in FIG. 2. As described elsewhere herein, in some aspects, a substantial percentage of the overall occupied partitions will include both a bead and a cell and, in some cases, some of the partitions that are generated will be unoccupied. In some cases, some of the partitions may have beads and cells that are not partitioned 1:1. In some cases, it may be desirable to provide multiply occupied partitions, e.g., containing two, three, four or more cells and/or beads within a single partition. As shown, channel segments 202, 204, 206, 208 and 210 are provided in fluid communication at channel junction 212. An aqueous stream comprising the individual cells 214, is flowed through channel segment 202 toward channel junction 212. As described above, these cells may be suspended within an aqueous fluid, or may have been pre-encapsulated, prior to the partitioning process.

Concurrently, an aqueous stream comprising the barcode carrying beads 216, is flowed through channel segment 204 toward channel junction 212. A non-aqueous partitioning fluid 216 is introduced into channel junction 212 from each of side channels 206 and 208, and the combined streams are flowed into outlet channel 210. Within channel junction 212, the two combined aqueous streams from channel segments 202 and 204 are combined, and partitioned into droplets 218, that include co-partitioned cells 214 and beads 216. As noted previously, by controlling the flow characteristics of each of the fluids combining at channel junction 212, as well as controlling the geometry of the channel junction, partitioning can be optimized to achieve a desired occupancy level of beads, cells or both, within the partitions 218 that are generated.

In some cases, lysis agents, e.g., cell lysis enzymes, may be introduced into the partition with the bead stream, e.g., flowing through channel segment 204, such that lysis of the cell only commences at or after the time of partitioning. Additional reagents may also be added to the partition in this configuration, such as endonucleases to fragment the cell's DNA, DNA polymerase enzyme and dNTPs used to amplify the cell's nucleic acid fragments and to attach the barcode oligonucleotides to the amplified fragments. As noted above, in many cases, a chemical stimulus, such as DTT, may be used to release the barcodes from their respective beads into the partition. In such cases, it may be particularly desirable to provide the chemical stimulus along with the cell-containing stream in channel segment 202, such that release of the barcodes only occurs after the two streams have been combined, e.g., within the partitions 218. Where the cells are encapsulated, however, introduction of a common chemical stimulus, e.g., that both releases the oligonucleotides form their beads, and releases cells from their microcapsules may generally be provided from a separate additional side channel (not shown) upstream of or connected to channel junction 212.

A number of other reagents may be co-partitioned along with the cells, beads, lysis agents and chemical stimuli, including, for example, protective reagents, like proteinase K, chelators, nucleic acid extension, replication, transcription or amplification reagents such as polymerases, reverse transcriptases, transposases which can be used for transposon based methods (e.g., Nextera), nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

The channel networks, e.g., as described herein, can be fluidly coupled to appropriate fluidic components. For example, the inlet channel segments, e.g., channel segments 202, 204, 206 and 208 are fluidly coupled to appropriate sources of the materials they are to deliver to channel junction 212. For example, channel segment 202 will be fluidly coupled to a source of an aqueous suspension of cells 214 to be analyzed, while channel segment 204 may be fluidly coupled to a source of an aqueous suspension of beads 216. Channel segments 206 and 208 may then be fluidly connected to one or more sources of the non-aqueous fluid. These sources may include any of a variety of different fluidic components, from simple reservoirs defined in or connected to a body structure of a microfluidic device, to fluid conduits that deliver fluids from off-device sources, manifolds, or the like. Likewise, the outlet channel segment 210 may be fluidly coupled to a receiving vessel or conduit for the partitioned cells. Again, this may be a reservoir defined in the body of a microfluidic device, or it may be a fluidic conduit for delivering the partitioned cells to a subsequent process operation, instrument or component.

FIG. 8 shows images of individual Jurkat cells co-partitioned along with barcode oligonucleotide containing beads in aqueous droplets in an aqueous in oil emulsion. As illustrated, individual cells may be readily co-partitioned with individual beads. As will be appreciated, optimization of individual cell loading may be carried out by a number of methods, including by providing dilutions of cell populations into the microfluidic system in order to achieve the desired cell loading per partition as described elsewhere herein.

In operation, once lysed, the nucleic acid contents of the individual cells are then available for further processing within the partitions, including, e.g., fragmentation, amplification and barcoding, as well as attachment of other functional sequences. As noted above, fragmentation may be accomplished through the co-partitioning of shearing enzymes, such as endonucleases, in order to fragment the nucleic acids into smaller fragments. These endonucleases may include restriction endonucleases, including type II and type IIs restriction endonucleases as well as other nucleic acid cleaving enzymes, such as nicking endonucleases, and the like. In some cases, fragmentation may not be desired, and full length nucleic acids may be retained within the partitions, or in the case of encapsulated cells or cell contents, fragmentation may be carried out prior to partitioning, e.g., through enzymatic methods, e.g., those described herein, or through mechanical methods, e.g., mechanical, acoustic or other shearing.

Once co-partitioned, and the cells are lysed to release their nucleic acids, the oligonucleotides disposed upon the bead may be used to barcode and amplify fragments of those nucleic acids. Briefly, in one aspect, the oligonucleotides present on the beads that are co-partitioned with the cells, are released from their beads into the partition with the cell's nucleic acids. The oligonucleotides can include, along with the barcode sequence, a primer sequence at its 5'end. This primer sequence may be a random oligonucleotide sequence intended to randomly prime numerous different regions on the cell's nucleic acids, or it may be a specific primer sequence targeted to prime upstream of a specific targeted region of the cell's genome.

Once released, the primer portion of the oligonucleotide can anneal to a complementary region of the cell's nucleic acid. Extension reaction reagents, e.g., DNA polymerase, nucleoside triphosphates, co-factors (e.g., $Mg2+$ or $Mn2+$), that are also co-partitioned with the cells and beads, then extend the primer sequence using the cell's nucleic acid as a template, to produce a complementary fragment to the strand of the cell's nucleic acid to which the primer annealed, which complementary fragment includes the oligonucleotide and its associated barcode sequence. Annealing and extension of multiple primers to different portions of the cell's nucleic acids will result in a large pool of overlapping complementary fragments of the nucleic acid, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow formation of a hairpin structure or partial hairpin structure, the reduces the ability of the molecule to be the basis for producing further iterative copies. As described herein, the cell's nucleic acids may include any desired nucleic acids within the cell including, for example, the cell's DNA, e.g., genomic DNA, RNA, e.g., messenger RNA, and the like. For example, in some cases, the methods and systems described herein are used in characterizing expressed mRNA, including, e.g., the presence and quantification of such mRNA, and may include RNA sequencing processes as the characterization process. Alternatively or additionally, the reagents partitioned along with the cells may include reagents for the conversion of mRNA into cDNA, e.g., reverse transcriptase enzymes and reagents, to facilitate sequencing processes where DNA sequencing is employed. In some cases, where the nucleic acids to be characterized comprise RNA, e.g., mRNA, schematic illustration of one example of this is shown in FIG. 3.

As shown, oligonucleotides that include a barcode sequence are co-partitioned in, e.g., a droplet 302 in an emulsion, along with a sample nucleic acid 304. As noted elsewhere herein, the oligonucleotides 308 may be provided on a bead 306 that is co-partitioned with the sample nucleic acid 304, which oligonucleotides are releasable from the bead 306, as shown in panel A. The oligonucleotides 308 include a barcode sequence 312, in addition to one or more functional sequences, e.g., sequences 310, 314 and 316. For example, oligonucleotide 308 is shown as comprising barcode sequence 312, as well as sequence 310 that may function as an attachment or immobilization sequence for a given sequencing system, e.g., a P5 sequence used for attachment in flow cells of an Illumina Hiseq® or Miseq® system. As shown, the oligonucleotides also include a primer sequence 316, which may include a random or targeted N-mer for priming replication of portions of the sample nucleic acid 304. Also included within oligonucleotide 308 is a sequence 314 which may provide a sequencing priming region, such as a "read1" or R1 priming region, that is used to prime polymerase mediated, template directed sequencing by synthesis reactions in sequencing systems. As will be appreciated, the functional sequences may be selected to be compatible with a variety of different sequencing systems, e.g., 454 Sequencing, Ion Torrent Proton or PGM, Illumina X10, etc., and the requirements thereof. In many cases, the barcode sequence 312, immobilization sequence 310 and R1 sequence 314 may be common to all of the oligonucleotides attached to a given bead. The primer sequence 316 may vary for random N-mer primers, or may be common to the oligonucleotides on a given bead for certain targeted applications.

As will be appreciated, in some cases, the functional sequences may include primer sequences useful for RNA-seq applications. For example, in some cases, the oligonucleotides may include poly-T primers for priming reverse transcription of RNA for RNA-seq. In still other cases, oligonucleotides in a given partition, e.g., included on an individual bead, may include multiple types of primer sequences in addition to the common barcode sequences, such as both DNA-sequencing and RNA sequencing primers, e.g., poly-T primer sequences included within the oligonucleotides coupled to the bead. In such cases, a single partitioned cell may be both subjected to DNA and RNA sequencing processes.

Based upon the presence of primer sequence 316, the oligonucleotides can prime the sample nucleic acid as shown in panel B, which allows for extension of the oligonucleotides 308 and 308*a* using polymerase enzymes and other extension reagents also co-partitioned with the bead 306 and sample nucleic acid 304. As shown in panel C, following extension of the oligonucleotides that, for random N-mer primers, may anneal to multiple different regions of the sample nucleic acid 304; multiple overlapping complements or fragments of the nucleic acid are created, e.g., fragments 318 and 320. Although including sequence portions that are complementary to portions of sample nucleic acid, e.g., sequences 322 and 324, these constructs are generally referred to herein as comprising fragments of the sample nucleic acid 304, having the attached barcode sequences.

The barcoded nucleic acid fragments may then be subjected to characterization, e.g., through sequence analysis, or they may be further amplified in the process, as shown in panel D. For example, additional oligonucleotides, e.g., oligonucleotide 308*b*, also released from bead 306, may prime the fragments 318 and 320. This shown for fragment 318. In particular, again, based upon the presence of the random N-mer primer 316*b* in oligonucleotide 308*b* (which in many cases can be different from other random N-mers in a given partition, e.g., primer sequence 316), the oligonucleotide anneals with the fragment 318, and is extended to create a complement 326 to at least a portion of fragment 318 which includes sequence 328, that comprises a duplicate of a portion of the sample nucleic acid sequence. Extension of the oligonucleotide 308*b* continues until it has replicated through the oligonucleotide portion 308 of fragment 318. As noted elsewhere herein, and as illustrated in panel D, the oligonucleotides may be configured to prompt a stop in the replication by the polymerase at a desired point, e.g., after replicating through sequences 316 and 314 of oligonucleotide 308 that is included within fragment 318. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 312 to prevent a non-uracil tolerant polymerase to cease replication of that region. As a result a fragment 326 is created that includes the full-length oligonucleotide 308*b* at one end, including the barcode sequence 312, the attachment sequence 310, the R1 primer region 314, and the random N-mer sequence 316*b*. At the other end of the sequence may be included the complement 316' to the random N-mer of the first oligonucleotide 308, as well as a complement to all or a portion of the R1 sequence, shown as sequence 314'. The R1 sequence 314 and its complement 314' are then able to hybridize together to form a partial hairpin structure 328. As will be appreciated because the random N-mers differ among different oligonucleotides, these sequences and their complements may not be expected to participate in hairpin formation, e.g., sequence 316', which is the complement to random N-mer 316, may not be expected to be complementary to random N-mer sequence 316*b*. This may not be the case for other applications, e.g., targeted primers, where the N-mers may be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 326.

In general, the amplification of the cell's nucleic acids is carried out until the barcoded overlapping fragments within the partition constitute at least 1× coverage of the particular portion or all of the cell's genome, at least 2×, at least 3×, at least 4×, at least 5×, at least 10×, at least 20×, at least 40× or more coverage of the genome or its relevant portion of interest. Once the barcoded fragments are produced, they may be directly sequenced on an appropriate sequencing system, e.g., an Illumina Hiseq®, Miseq® or X10 system, or they may be subjected to additional processing, such as further amplification, attachment of other functional sequences, e.g., second sequencing primers, for reverse reads, sample index sequences, and the like.

Figure 4:
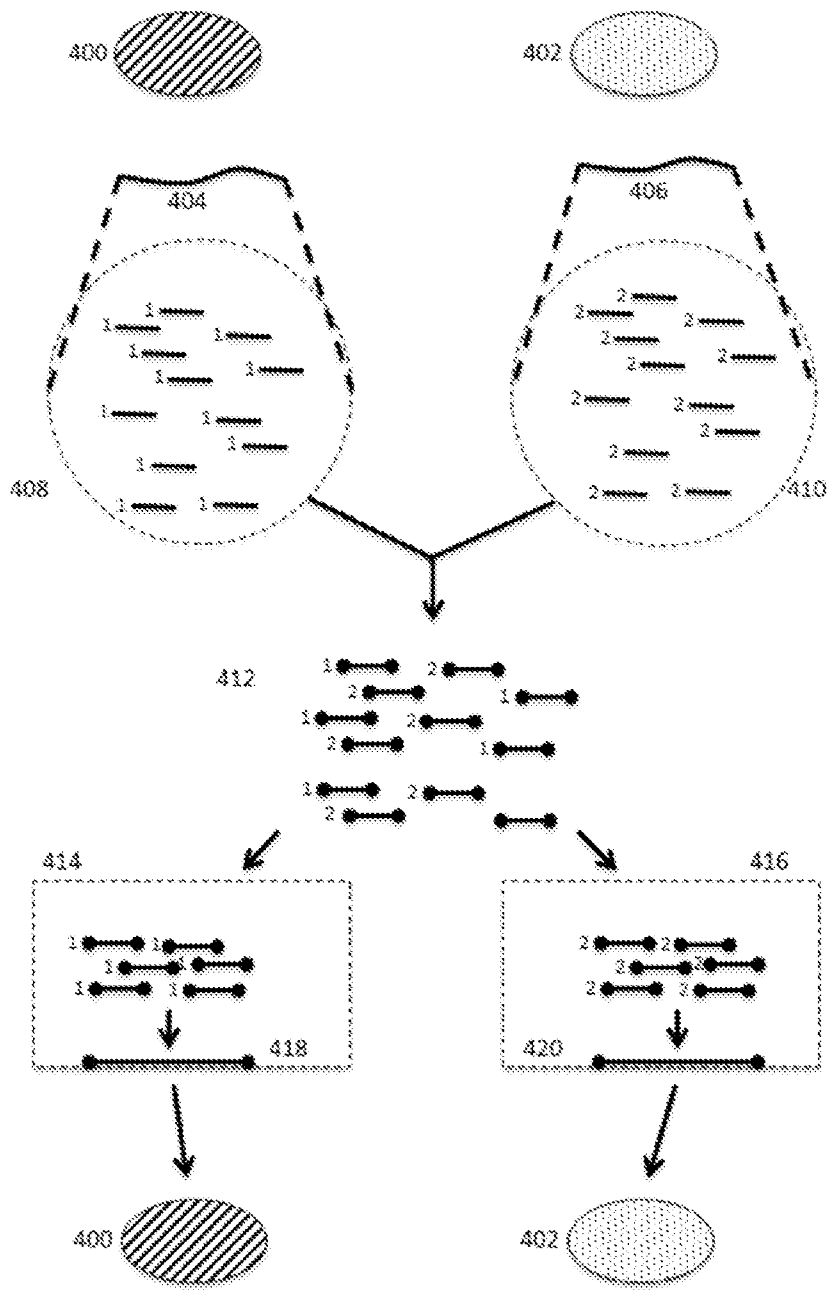
FIG. 4 provides a schematic illustration of use of barcoding of cell's nucleic acids in attributing sequence data to individual cells or groups of cells for use in their characterization.

All of the fragments from multiple different partitions may then be pooled for sequencing on high throughput sequencers as described herein, where the pooled fragments comprise a large number of fragments derived from the nucleic acids of different cells or small cell populations, but where the fragments from the nucleic acids of a given cell will share the same barcode sequence. In particular, because each fragment is coded as to its partition of origin, and consequently its single cell or small population of cells, the sequence of that fragment may be attributed back to that cell or those cells based upon the presence of the barcode, which will also aid in applying the various sequence fragments from multiple partitions to assembly of individual genomes for different cells. This is schematically illustrated in FIG. 4. As shown in one example, a first nucleic acid 404 from a first cell 400, and a second nucleic acid 406 from a second cell 402 are each partitioned along with their own sets of barcode oligonucleotides as described above. The nucleic acids may comprise a chromosome, entire genome or other large nucleic acid from the cells.

Within each partition, each cell's nucleic acids 404 and 406 is then processed to separately provide overlapping set of second fragments of the first fragment(s), e.g., second fragment sets 408 and 410. This processing also provides the second fragments with a barcode sequence that is the same for each of the second fragments derived from a particular first fragment. As shown, the barcode sequence for second fragment set 408 is denoted by "1" while the barcode sequence for fragment set 410 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 408 and 410, may then be pooled for sequencing using, for example, sequence by synthesis technologies available from Illumina or Ion Torrent division of Thermo-Fisher, Inc. Once sequenced, the sequence reads 412 can be attributed to their respective fragment set, e.g., as shown in aggregated reads 414 and 416, at least in part based upon the included barcodes, and in some cases, in part based upon the sequence of the fragment itself. The attributed sequence reads for each fragment set are then assembled to provide the assembled sequence for each cell's nucleic acids, e.g., sequences 418 and 420, which in turn, may be attributed to individual cells, e.g., cells 400 and 402.

While described in terms of analyzing the genetic material present within cells, the methods and systems described herein may have much broader applicability, including the ability to characterize other aspects of individual cells or cell populations, by allowing for the allocation of reagents to individual cells, and providing for the attributable analysis or characterization of those cells in response to those reagents. These methods and systems are particularly valuable in being able to characterize cells for, e.g., research, diagnostic, pathogen identification, and many other purposes. By way of example, a wide range of different cell surface features, e.g., cell surface proteins like cluster of differentiation or CD proteins, have significant diagnostic relevance in characterization of diseases like cancer.

In one particularly useful application, the methods and systems described herein may be used to characterize cell features, such as cell surface features, e.g., proteins, receptors, etc. In particular, the methods described herein may be used to attach reporter molecules to these cell features, that when partitioned as described above, may be barcoded and analyzed, e.g., using DNA sequencing technologies, to ascertain the presence, and in some cases, relative abundance or quantity of such cell features within an individual cell or population of cells.

In a particular example, a library of potential cell binding ligands, e.g., antibodies, antibody fragments, cell surface receptor binding molecules, or the like, maybe provided associated with a first set of nucleic acid reporter molecules, e.g., where a different reporter oligonucleotide sequence is associated with a specific ligand, and therefore capable of binding to a specific cell surface feature. In some aspects, different members of the library may be characterized by the presence of a different oligonucleotide sequence label, e.g., an antibody to a first type of cell surface protein or receptor may have associated with it a first known reporter oligonucleotide sequence, while an antibody to a second receptor protein may have a different known reporter oligonucleotide sequence associated with it. Prior to co-partitioning, the cells may be incubated with the library of ligands, that may represent antibodies to a broad panel of different cell surface features, e.g., receptors, proteins, etc., and which include their associated reporter oligonucleotides. Unbound ligands are washed from the cells, and the cells are then co-partitioned along with the barcode oligonucleotides described above. As a result, the partitions will include the cell or cells, as well as the bound ligands and their known, associated reporter oligonucleotides.

Without the need for lysing the cells within the partitions, one may then subject the reporter oligonucleotides to the barcoding operations described above for cellular nucleic acids, to produce barcoded, reporter oligonucleotides, where the presence of the reporter oligonucleotides can be indicative of the presence of the particular cell surface feature, and the barcode sequence will allow the attribution of the range of different cell surface features to a given individual cell or population of cells based upon the barcode sequence that was co-partitioned with that cell or population of cells. As a result, one may generate a cell-by-cell profile of the cell surface features within a broader population of cells. This aspect of the methods and systems described herein, is described in greater detail below.

Figure 5:
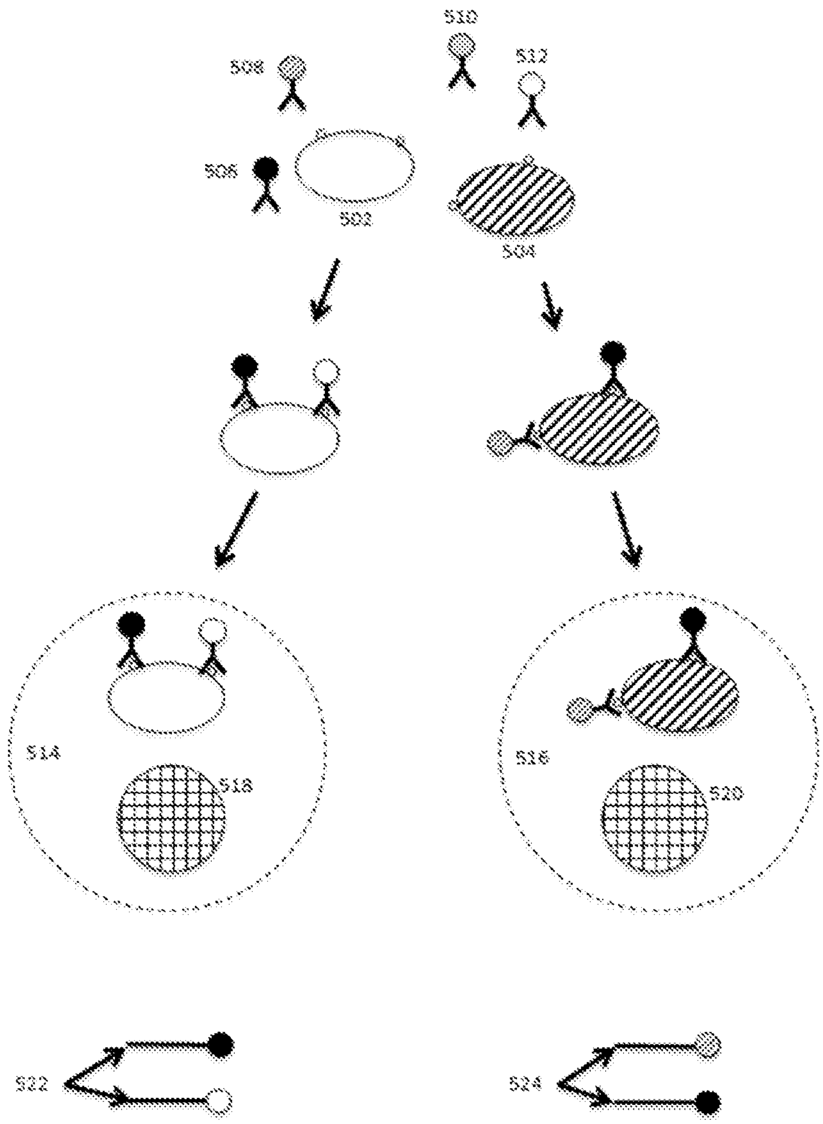
FIG. 5 provides a schematic illustration of cells associated with labeled cell-binding ligands.

This example is schematically illustrated in FIG. 5. As shown, a population of cells, represented by cells 502 and 504 are incubated with a library of cell surface associated reagents, e.g., antibodies, cell surface binding proteins, ligands or the like, where each different type of binding group includes an associated nucleic acid reporter molecule associated with it, shown as ligands and associated reporter molecules 506, 508, 510 and 512 (with the reporter molecules being indicated by the differently shaded circles). Where the cell expresses the surface features that are bound by the library, the ligands and their associated reporter molecules can become associated or coupled with the cell surface. Individual cells are then partitioned into separate partitions, e.g., droplets 514 and 516, along with their associated ligand/reporter molecules, as well as an individual barcode oligonucleotide bead as described elsewhere herein, e.g., beads 522 and 524, respectively. As with other examples described herein, the barcoded oligonucleotides are released from the beads and used to attach the barcode sequence the reporter molecules present within each partition with a barcode that is common to a given partition, but which varies widely among different partitions. For example, as shown in FIG. 5, the reporter molecules that associate with cell 502 in partition 514 are barcoded with barcode sequence 518, while the reporter molecules associated with cell 504 in partition 516 are barcoded with barcode 520. As a result, one is provided with a library of oligonucleotides that reflects the surface ligands of the cell, as reflected by the reporter molecule, but which is substantially attributable to an individual cell by virtue of a common barcode sequence, allowing a single cell level profiling of the surface characteristics of the cell. As will be appreciated, this process is not limited to cell surface receptors but may be used to identify the presence of a wide variety of specific cell structures, chemistries or other characteristics.

Single cell processing and analysis methods and systems described herein can be utilized for a wide variety of applications, including analysis of specific individual cells, analysis of different cell types within populations of differing cell types, analysis and characterization of large populations of cells for environmental, human health, epidemiological forensic, or any of a wide variety of different applications.

A particularly valuable application of the single cell analysis processes described herein is in the sequencing and characterization of a diseased cell. A diseased cell can have altered metabolic properties, gene expression, and/or morphologic features. Examples of diseases include inflammatory disorders, metabolic disorders, nervous system disorders, and cancer.

Of particular interest are cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences.

Non-limiting examples of cancer cells include cells of cancers such as Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

Where cancer cells are to be analyzed, primer sequences useful in any of the various operations for attaching barcode sequences and/or amplification reactions may comprise gene specific sequences which target genes or regions of genes associated with or suspected of being associated with cancer. For example, this can include genes or regions of genes where the presence of mutations (e.g., insertions, deletions, polymorphisms, copy number variations, and gene fusions) associated with a cancerous condition are suspected to be present in a cell population.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. As will be appreciated, such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome.

Also of interest are immune cells. Methods and compositions disclosed herein can be utilized for sequence analysis of the immune repertoire. Analysis of sequence information underlying the immune repertoire can provide a significant improvement in understanding the status and function of the immune system.

Non-limiting examples of immune cells which can be analyzed utilizing the methods described herein include B cells, T cells (e.g., cytotoxic T cells, natural killer T cells, regulatory T cells, and T helper cells), natural killer cells, cytokine induced killer (CIK) cells; myeloid cells, such as granulocytes (basophil granulocytes, eosinophil granulocytes, neutrophil granulocytes/hypersegmented neutrophils), monocytes/macrophages, mast cell, thrombocytes/megakaryocytes, and dendritic cells. In some embodiments, individual T cells are analyzed using the methods disclosed herein. In some embodiments, individual B cells are analyzed using the methods disclosed herein.

Immune cells express various adaptive immunological receptors relating to immune function, such as T cell receptors and B cell receptors. T cell receptors and B cells receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells the TCR consists of an alpha ($\alpha$) and beta ($\beta$) chain, whereas in 5% of T cells the TCR consists of gamma and delta ($\gamma/\delta$) chains. This ratio can change during ontogeny and in diseased states as well as in different species. When the TCR engages with antigenic peptide and MHC (peptide/MHC), the T lymphocyte is activated through signal transduction.

Each of the two chains of a TCR contains multiple copies of gene segments—a variable 'V' gene segment, a diversity 'D' gene segment, and a joining 'J' gene segment. The TCR alpha chain is generated by recombination of V and J segments, while the beta chain is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 'J' gene segment. Each light chain gene contains multiple copies of two different gene segments for the variable region of the protein—a variable 'V' gene segment and a joining 'J' gene segment. The recombination can generate a molecule with one of each of the V, D, and J segments. Furthermore, several bases may be deleted and others added (called N and P nucleotides) at each of the two junctions, thereby generating further diversity. After B cell activation, a process of affinity maturation through somatic hypermutation occurs. In this process progeny cells of the activated B cells accumulate distinct somatic mutations throughout the gene with higher mutation concentration in the CDR regions leading to the generation of antibodies with higher affinity to the antigens. In addition to somatic hypermutation activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

In some embodiments, the methods, compositions and systems disclosed herein are utilized to analyze the various sequences of TCRs and BCRs from immune cells, for example various clonotypes. In some embodiments, methods, compositions and systems disclosed herein are used to analyze the sequence of a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In some embodiments, methods, compositions and systems disclosed herein are used to analyze the sequence of a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions may comprise gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

The ability to characterize individual cells from larger diverse populations of cells is also of significant value in both environmental testing as well as in forensic analysis, where samples may, by their nature, be made up of diverse populations of cells and other material that "contaminate" the sample, relative to the cells for which the sample is being tested, e.g., environmental indicator organisms, toxic organisms, and the like for, e.g., environmental and food safety testing, victim and/or perpetrator cells in forensic analysis for sexual assault, and other violent crimes, and the like.

Additionally the methods and compositions disclosed herein, allow the determination of not only the immune repertoire and different clonotypes, but the functional characteristics (e.g., the transcriptome) of the cells associated with a clonotype or plurality of clonotypes that bind to the same or similar antigen. These functional characteristics can comprise transcription of cytokine, chemokine, or cell-surface associated molecules, such as, costimulatory molecules, checkpoint inhibitors, cell surface maturation markers, or cell-adhesion molecules. Such analysis allows a cell or cell population expressing a particular T cell receptor, B cell receptor, or immunoglobulin to be associated with certain functional characteristics. For example, for any given antigen there will be multiple clonotypes of T cell receptor, B cell receptor, or immunoglobulin that specifically bind to that antigen. Multiple clonotypes that bind to the same antigen are known as the idiotype.

Additional useful applications of the above described single cell sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. *Nature* 460, 1127-1131 (2009)). These differences have been postulated as being related to a person's susceptibility to neuro-logical disorders (see, e.g., Muotri, A. R. et al. *Nature* 468, 443-446 (2010)), or provide the brain with a diversity with which to respond to challenges. As such, the methods described herein may be used in the sequencing and characterization of individual neural cells.

The single cell analysis methods described herein are also useful in the analysis of gene expression, as noted above, both in terms of identification of RNA transcripts and their quantitation. In particular, using the single cell level analysis methods described herein, one can isolate and analyze the RNA transcripts present in individual cells, populations of cells, or subsets of populations of cells. In particular, in some cases, the barcode oligonucleotides may be configured to prime, replicate and consequently yield barcoded fragments of RNA from individual cells. For example, in some cases, the barcode oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcode oligonucleotides.

Figure 6:
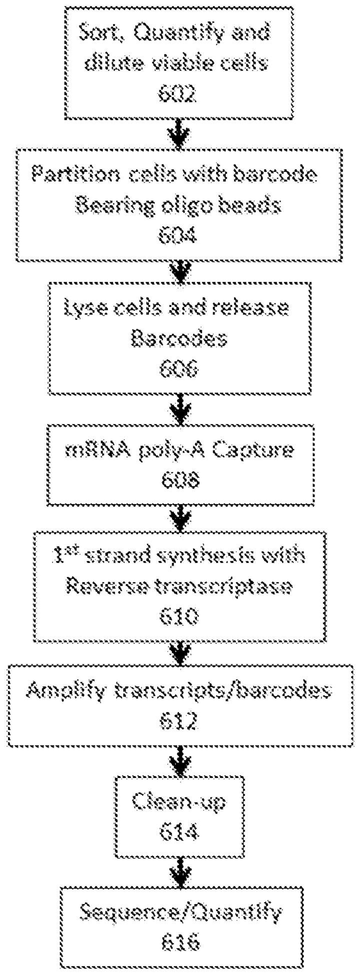
FIG. 6 provides a schematic illustration of an example workflow for performing RNA analysis using the methods described herein.

FIG. 6 provides a schematic of one example method for RNA expression analysis in individual cells using the methods described herein. As shown, at operation 602 a cell containing sample is sorted for viable cells, which are quantified and diluted for subsequent partitioning. At operation 604, the individual cells separately co-partitioned with gel beads bearing the barcoding oligonucleotides as described herein. The cells are lysed and the barcoded oligonucleotides released into the partitions at operation 606, where they interact with and hybridize to the mRNA at operation 608, e.g., by virtue of a poly-T primer sequence, which is complementary to the poly-A tail of the mRNA. Using the poly-T barcode oligonucleotide as a priming sequence, a reverse transcription reaction is carried out at operation 610 to synthesize a cDNA transcript of the mRNA that includes the barcode sequence. The barcoded cDNA transcripts are then subjected to additional amplification at operation 612, e.g., using a polymerase chain reaction (PCR) process, purification at operation 614, before they are placed on a nucleic acid sequencing system for determination of the cDNA sequence and its associated barcode sequence(s). In some cases, as shown, operations 602 through 608 can occur while the reagents remain in their original droplet or partition, while operations 612 through 616 can occur in bulk (e.g., outside of the partition). In the case where a partition is a droplet in an emulsion, the emulsion can be broken and the contents of the droplet pooled in order to complete operations 612 through 616. In some cases, barcode oligonucleotides may be digested with exonucleases after the emulsion is broken. Exonuclease activity can be inhibited by ethylenediaminetetraacetic acid (EDTA) following primer digestion. In some cases, operation 610 may be performed either within the partitions based upon co-partitioning of the reverse transcription mixture, e.g., reverse transcriptase and associated reagents, or it may be performed in bulk.

As noted elsewhere herein, the structure of the barcode oligonucleotides may include a number of sequence elements in addition to the oligonucleotide barcode sequence. One example of a barcode oligonucleotide for use in RNA analysis as described above is shown in FIG. 7. As shown, the overall oligonucleotide 702 is coupled to a bead 704 by a releasable linkage 706, such as a disulfide linker. The oligonucleotide may include functional sequences that are used in subsequent processing, such as functional sequence 708, which may include one or more of a sequencer specific flow cell attachment sequence, e.g., a P5 sequence for Illumina sequencing systems, as well as sequencing primer sequences, e.g., a R1 primer for Illumina sequencing systems. A barcode sequence 710 is included within the structure for use in barcoding the sample RNA. An mRNA specific priming sequence, such as poly-T sequence 712 is also included in the oligonucleotide structure. An anchoring sequence segment 714 may be included to ensure that the poly-T sequence hybridizes at the sequence end of the mRNA. This anchoring sequence can include a random short sequence of nucleotides, e.g., 1-mer, 2-mer, 3-mer or longer sequence, which will ensure that the poly-T segment is more likely to hybridize at the sequence end of the poly-A tail of the mRNA. An additional sequence segment 716 may be provided within the oligonucleotide sequence. In some cases, this additional sequence provides a unique molecular identifier (UMI) sequence segment, e.g., as a random sequence (e.g., such as a random N-mer sequence) that varies across individual oligonucleotides coupled to a single bead, whereas barcode sequence 710 can be constant among oligonucleotides tethered to an individual bead. This unique sequence serves to provide a unique identifier of the starting mRNA molecule that was captured, in order to allow quantitation of the number of original expressed RNA. As will be appreciated, although shown as a single oligonucleotide tethered to the surface of a bead, individual bead can include tens to hundreds of thousands or even millions of individual oligonucleotide molecules, where, as noted, the barcode segment can be constant or relatively constant for a given bead, but where the variable or unique sequence segment will vary across an individual bead. This unique molecular identifier (UMI) sequence segment may include from 5 to about 8 or more nucleotides within the sequence of the oligonucleotides. In some cases, the unique molecular identifier (UMI) sequence segment can be 2, 3, 4, 5, 6, 7, 8, 9, 10, 11, 12, 13, 14, 15, 16, 17, 18, 19 or 20 nucleotides in length or longer. In some cases, the unique molecular identifier (UMI) sequence segment can be at least 2, 3, 4, 5, 6, 7, 8, 9, 10, 11, 12, 13, 14, 15, 16, 17, 18, 19 or 20 nucleotides in length or longer. In some cases, the unique molecular identifier (UMI) sequence segment can be at most 2, 3, 4, 5, 6, 7, 8, 9, 10, 11, 12, 13, 14, 15, 16, 17, 18, 19 or 20 nucleotides in length or shorter.

Figure 7:
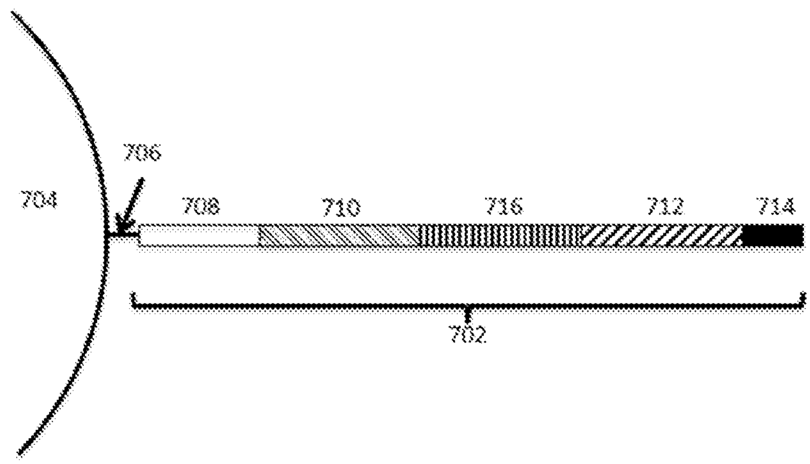
FIG. 7 provides a schematic illustration of an example barcoded oligonucleotide structure for use in analysis of ribonucleic (RNA) using the methods described herein.

In operation, and with reference to FIGS. 6 and 7, a cell is co-partitioned along with a barcode bearing bead and lysed while the barcoded oligonucleotides are released from the bead. The poly-T portion of the released barcode oligonucleotide then hybridizes to the poly-A tail of the mRNA. The poly-T segment then primes the reverse transcription of the mRNA to produce a cDNA transcript of the mRNA, but which includes each of the sequence segments 708-716 of the barcode oligonucleotide. Again, because the oligonucleotide 702 includes an anchoring sequence 714, it will more likely hybridize to and prime reverse transcription at the sequence end of the poly-A tail of the mRNA. Within any given partition, all of the cDNA transcripts of the individual mRNA molecules will include a common barcode sequence segment 710. However, by including the unique random N-mer sequence, the transcripts made from different mRNA molecules within a given partition will vary at this unique sequence. This provides a quantitation feature that can be identifiable even following any subsequent amplification of the contents of a given partition, e.g., the number of unique segments associated with a common barcode can be indicative of the quantity of mRNA originating from a single partition, and thus, a single cell. As noted above, the transcripts are then amplified, cleaned up and sequenced to identify the sequence of the cDNA transcript of the mRNA, as well as to sequence the barcode segment and the unique sequence segment.

As noted elsewhere herein, while a poly-T primer sequence is described, other targeted or random priming sequences may also be used in priming the reverse transcription reaction. In some cases, the primer sequence can be a gene specific primer sequence which targets specific genes for reverse transcription. In some examples, such target genes comprise T cell receptor genes, B cell receptor genes or immunoglobulin receptor genes. Likewise, although described as releasing the barcoded oligonucleotides into the partition along with the contents of the lysed cells, it will be appreciated that in some cases, the gel bead bound oligonucleotides may be used to hybridize and capture the mRNA on the solid phase of the gel beads, in order to facilitate the separation of the RNA from other cell contents.

Figure 9A:
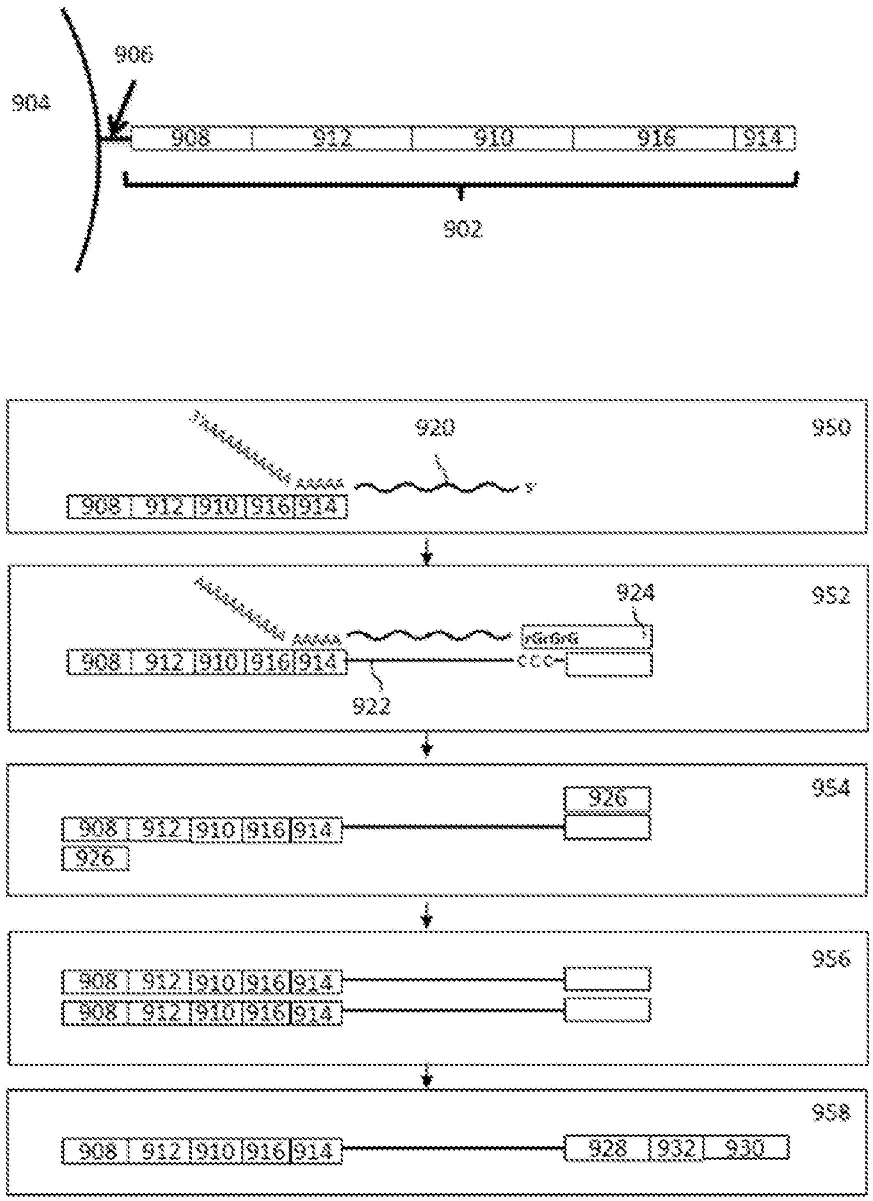
FIGS. 9A-9E provide schematic illustration of example barcoded oligonucleotide structures for use in analysis of RNA and example operations for performing RNA analysis.

An additional example of a barcode oligonucleotide for use in RNA analysis, including messenger RNA (mRNA, including mRNA obtained from a cell) analysis, is shown in FIG. 9A. As shown, the overall oligonucleotide 902 can be coupled to a bead 904 by a releasable linkage 906, such as a disulfide linker. The oligonucleotide may include functional sequences that are used in subsequent processing, such as functional sequence 908, which may include a sequencer specific flow cell attachment sequence, e.g., a P5 sequence for Illumina sequencing systems, as well as functional sequence 910, which may include sequencing primer sequences, e.g., a R1 primer binding site for Illumina sequencing systems. A barcode sequence 912 is included within the structure for use in barcoding the sample RNA. An RNA specific (e.g., mRNA specific) priming sequence, such as poly-T sequence 914 is also included in the oligonucleotide structure. An anchoring sequence segment (not shown) may be included to ensure that the poly-T sequence hybridizes at the sequence end of the mRNA. An additional sequence segment 916 may be provided within the oligonucleotide sequence. This additional sequence can provide a unique molecular identifier (UMI) sequence segment, e.g., as a random N-mer sequence that varies across individual oligonucleotides coupled to a single bead, whereas barcode sequence 912 can be constant among oligonucleotides tethered to an individual bead. As described elsewhere herein, this unique sequence can serve to provide a unique identifier of the starting mRNA molecule that was captured, in order to allow quantitation of the number of original expressed RNA, e.g., mRNA counting. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular RNA (e.g., mRNA) analysis and in reference to FIG. 9A, a cell is co-partitioned along with a barcode bearing bead, switch oligo 924, and other reagents such as reverse transcriptase, a reducing agent and dNTPs into a partition (e.g., a droplet in an emulsion). In operation 950, the cell is lysed while the barcoded oligonucleotides 902 are released from the bead (e.g., via the action of the reducing agent) and the poly-T segment 914 of the released barcode oligonucleotide then hybridizes to the poly-A tail of mRNA 920 that is released from the cell. Next, in operation 952 the poly-T segment 914 is extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the additional bases added to the cDNA transcript and facilitate template switching. A sequence complementary to the switch oligo sequence can then be incorporated into the cDNA transcript 922 via extension of the cDNA transcript 922 using the switch oligo 924 as a template. Within any given partition, all of the cDNA transcripts of the individual mRNA molecules will include a common barcode sequence segment 912. However, by including the unique random N-mer sequence 916, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. Following operation 952, the cDNA transcript 922 is then amplified with primers 926 (e.g., PCR primers) in operation 954. Next, the amplified product is then purified (e.g., via solid phase reversible immobilization (SPRI)) in operation 956. At operation 958, the amplified product is then sheared, ligated to additional functional sequences, and further amplified (e.g., via PCR). The functional sequences may include a sequencer specific flow cell attachment sequence 930, e.g., a P7 sequence for Illumina sequencing systems, as well as functional sequence 928, which may include a sequencing primer binding site, e.g., for a R2 primer for Illumina sequencing systems, as well as functional sequence 932, which may include a sample index, e.g., an i7 sample index sequence for Illumina sequencing systems. In some cases, operations 950 and 952 can occur in the partition, while operations 954, 956 and 958 can occur in bulk solution (e.g., in a pooled mixture outside of the partition). In the case where a partition is a droplet in an emulsion, the emulsion can be broken and the contents of the droplet pooled in order to complete operations 954, 956 and 958. In some cases, operation 954 may be completed in the partition. In some cases, barcode oligonucleotides may be digested with exonucleases after the emulsion is broken. Exonuclease activity can be inhibited by ethylenediaminetetraacetic acid (EDTA) following primer digestion. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

In an alternative example of a barcode oligonucleotide for use in RNA (e.g., cellular RNA) analysis as shown in FIG. 9A, functional sequence 908 may be a P7 sequence and functional sequence 910 may be a R2 primer binding site. Moreover, the functional sequence 930 may be a P5 sequence, functional sequence 928 may be a R1 primer binding site, and functional sequence 932 may be an i5 sample index sequence for Illumina sequencing systems. The configuration of the constructs generated by such a barcode oligonucleotide can help minimize (or avoid) sequencing of the poly-T sequence during sequencing.

Figure 9B:
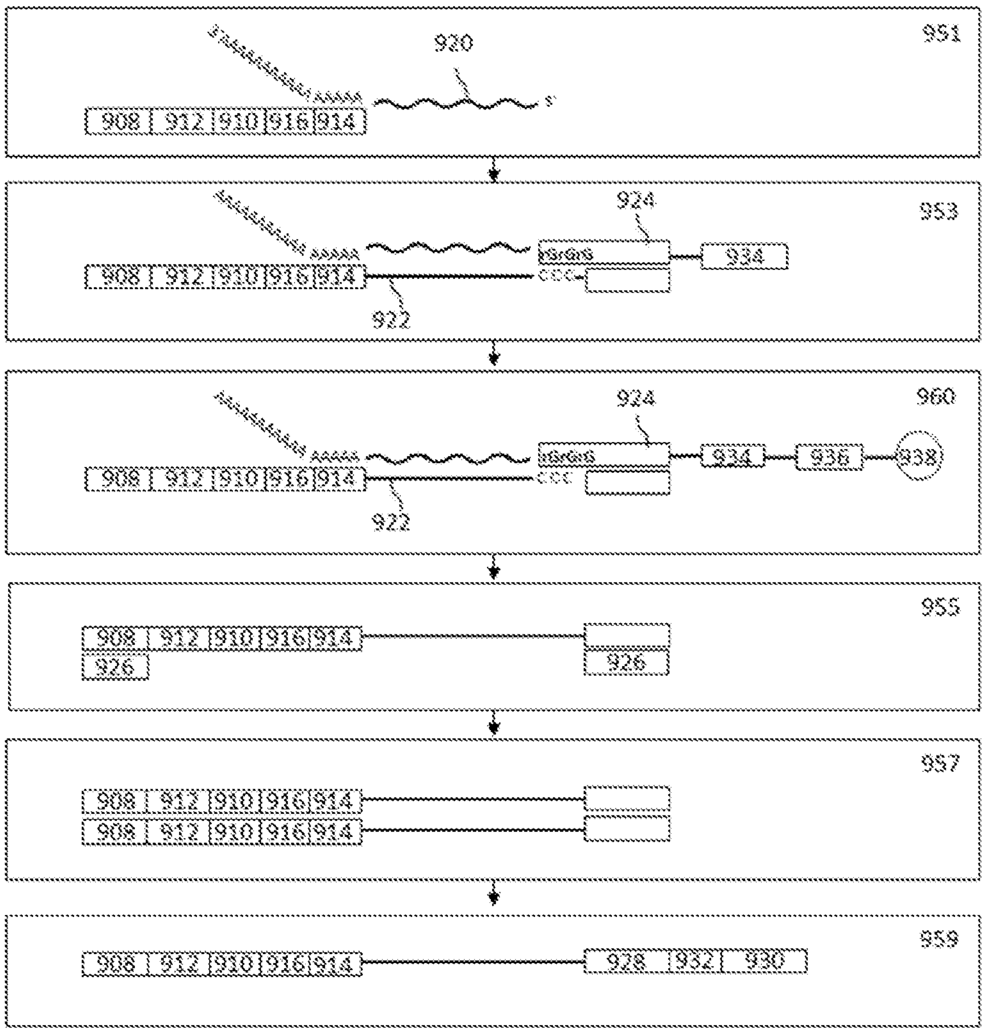

Shown in FIG. 9B is another example method for RNA analysis, including cellular mRNA analysis. In this method, the switch oligo 924 is co-partitioned with the individual cell and barcoded bead along with reagents such as reverse transcriptase, a reducing agent and dNTPs into a partition (e.g., a droplet in an emulsion). The switch oligo 924 may be labeled with an additional tag 934, e.g., biotin. In operation 951, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide hybridizes to the poly-A tail of mRNA 920 that is released from the cell. In operation 953, the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Next, an isolation operation 960 can be used to isolate the cDNA transcript 922 from the reagents and oligonucleotides in the partition. The additional tag 934, e.g., biotin, can be contacted with an interacting tag 936, e.g., streptavidin, which may be attached to a magnetic bead 938. At operation 960 the cDNA can be isolated with a pull-down operation (e.g., via magnetic separation, centrifugation) before amplification (e.g., via PCR) in operation 955, followed by purification (e.g., via solid phase reversible immobilization (SPRI)) in operation 957 and further processing (shearing, ligation of sequences 928, 932 and 930 and subsequent amplification (e.g., via PCR)) in operation 959. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, as shown, operations 951 and 953 can occur in the partition, while operations 960, 955, 957 and 959 can occur in bulk solution (e.g., in a pooled mixture outside of the partition). In the case where a partition is a droplet in an emulsion, the emulsion can be broken and the contents of the droplet pooled in order to complete operation 960. The operations 955, 957, and 959 can then be carried out following operation 960 after the transcripts are pooled for processing.

Figure 9C:
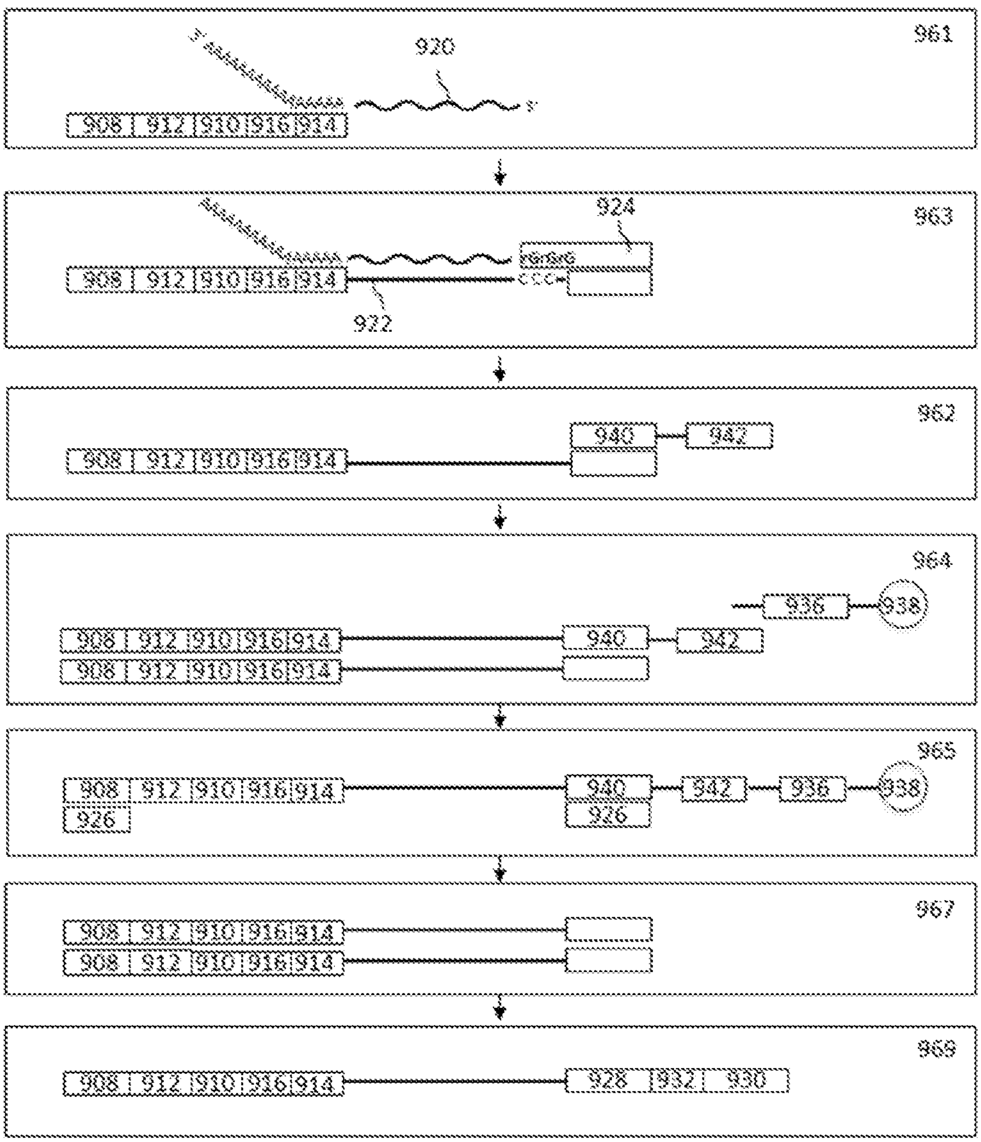

Shown in FIG. 9C is another example method for RNA analysis, including cellular mRNA analysis. In this method, the switch oligo 924 is co-partitioned with the individual cell and barcoded bead along with reagents such as reverse transcriptase, a reducing agent and dNTPs in a partition (e.g., a droplet in an emulsion). In operation 961, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment 914 of the released barcode oligonucleotide then hybridizes to the poly-A tail of mRNA 920 that is released from the cell. Next, in operation 963 the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Following operation 961 and operation 963, mRNA 920 and cDNA transcript 922 are denatured in operation 962. At operation 964, a second strand is extended from a primer 940 having an additional tag 942, e.g., biotin, and hybridized to the cDNA transcript 922. Also in operation 964, the biotin labeled second strand can be contacted with an interacting tag 936, e.g., streptavidin, which may be attached to a magnetic bead 938. The cDNA can be isolated with a pull-down operation (e.g., via magnetic separation, centrifugation) before amplification (e.g., via polymerase chain reaction (PCR)) in operation 965, followed by purification (e.g., via solid phase reversible immobilization (SPRI)) in operation 967 and further processing (shearing, ligation of sequences 928, 932 and 930 and subsequent amplification (e.g., via PCR)) in operation 969. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 961 and 963 can occur in the partition, while operations 962, 964, 965, 967, and 969 can occur in bulk (e.g., outside the partition). In the case where a partition is a droplet in an emulsion, the emulsion can be broken and the contents of the droplet pooled in order to complete operations 962, 964, 965, 967 and 969.

Figure 9D:
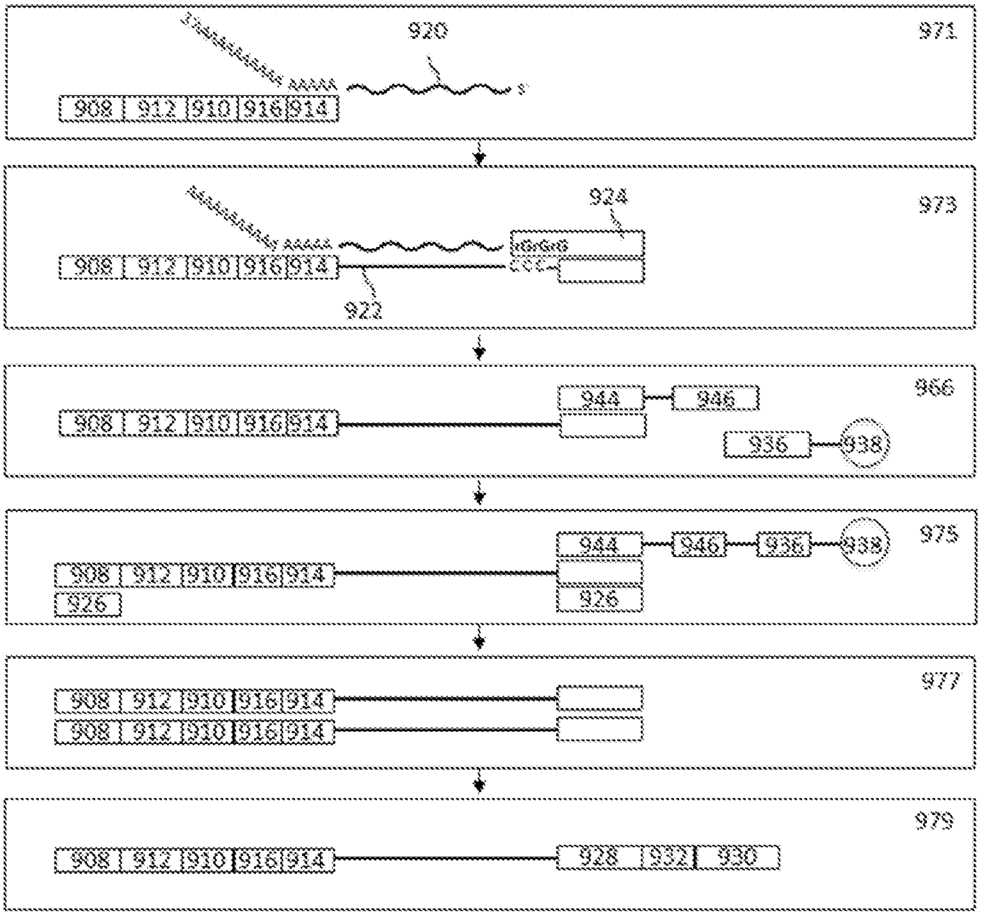

Shown in FIG. 9D is another example method for RNA analysis, including cellular mRNA analysis. In this method, the switch oligo 924 is co-partitioned with the individual cell and barcoded bead along with reagents such as reverse transcriptase, a reducing agent and dNTPs. In operation 971, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next the poly-T segment 914 of the released barcode oligonucleotide then hybridizes to the poly-A tail of mRNA 920 that is released from the cell. Next in operation 973, the poly-T segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. In operation 966, the mRNA 920, cDNA transcript 922 and switch oligo 924 can be denatured, and the cDNA transcript 922 can be hybridized with a capture oligonucleotide 944 labeled with an additional tag 946, e.g., biotin. In this operation, the biotin-labeled capture oligonucleotide 944, which is hybridized to the cDNA transcript, can be contacted with an interacting tag 936, e.g., streptavidin, which may be attached to a magnetic bead 938. Following separation from other species (e.g., excess barcoded oligonucleotides) using a pull-down operation (e.g., via magnetic separation, centrifugation), the cDNA transcript can be amplified (e.g., via PCR) with primers 926 at operation 975, followed by purification (e.g., via solid phase reversible immobilization (SPRI)) in operation 977 and further processing (shearing, ligation of sequences 928, 932 and 930 and subsequent amplification (e.g., via PCR)) in operation 979. In some cases where sequence 908 is a P7 sequence and sequence 910 is a R2 primer binding site, sequence 930 is a P5 sequence and sequence 928 is a R1 primer binding site and sequence 932 is an i5 sample index sequence. In other cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 971 and 973 can occur in the partition, while operations 966, 975, 977 (purification), and 979 can occur in bulk (e.g., outside the partition). In the case where a partition is a droplet in an emulsion, the emulsion can be broken and the contents of the droplet pooled in order to complete operations 966, 975, 977 and 979.

Figure 9E:
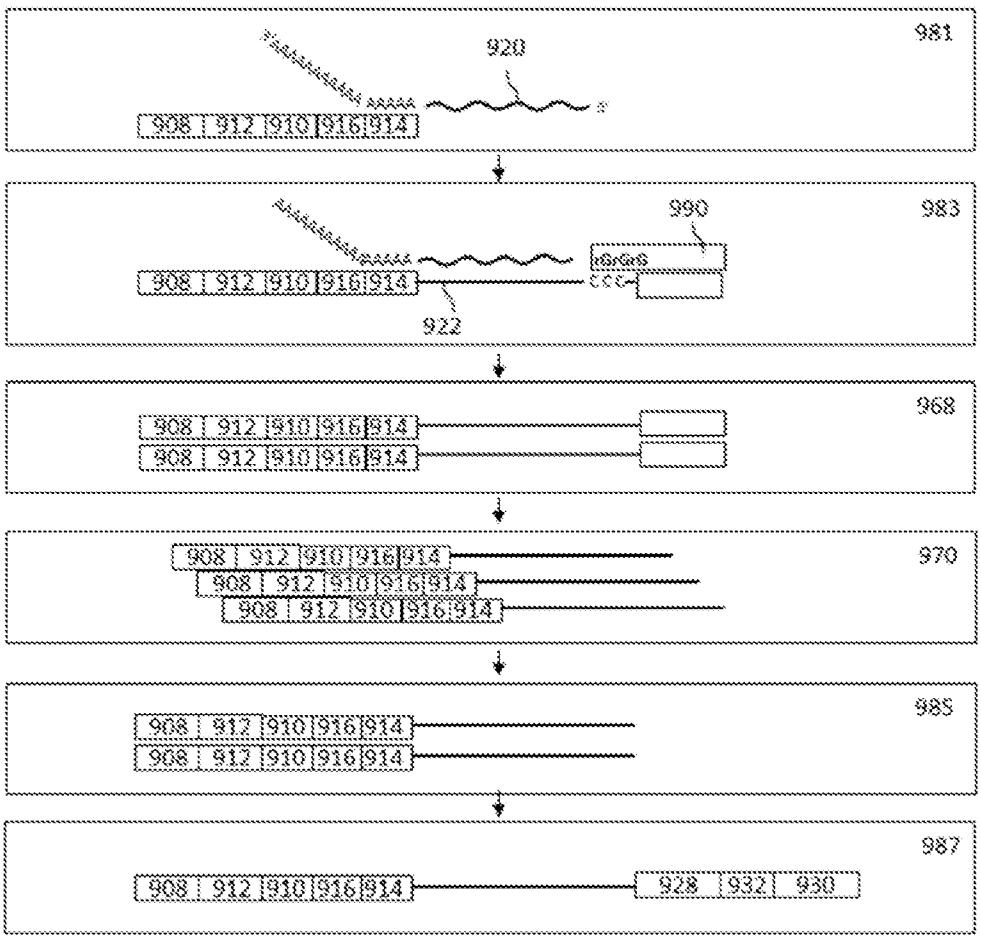

Shown in FIG. 9E is another example method for RNA analysis, including cellular RNA analysis. In this method, an individual cell is co-partitioned along with a barcode bearing bead, a switch oligo 990, and other reagents such as reverse transcriptase, a reducing agent and dNTPs into a partition (e.g., a droplet in an emulsion). In operation 981, the cell is lysed while the barcoded oligonucleotides (e.g., 902 as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-T segment of the released barcode oligonucleotide then hybridizes to the poly-A tail of mRNA 920 released from the cell. Next at operation 983, the poly-T segment is then extended in a reverse transcription reaction to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 990 may then hybridize with the cDNA transcript and facilitate template switching. A sequence complementary to the switch oligo sequence and including a T7 promoter sequence, can be incorporated into the cDNA transcript 922. At operation 968, a second strand is synthesized and at operation 970 the T7 promoter sequence can be used by T7 polymerase to produce RNA transcripts in in vitro transcription. At operation 985 the RNA transcripts can be purified (e.g., via solid phase reversible immobilization (SPRI)), reverse transcribed to form DNA transcripts, and a second strand can be synthesized for each of the DNA transcripts. In some cases, prior to purification, the RNA transcripts can be contacted with a DNase (e.g., DNAase I) to break down residual DNA. At operation 987 the DNA transcripts are then fragmented and ligated to additional functional sequences, such as sequences 928, 932 and 930 and, in some cases, further amplified (e.g., via PCR). In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, prior to removing a portion of the DNA transcripts, the DNA transcripts can be contacted with an RNase to break down residual RNA. In some cases, operations 981 and 983 can occur in the partition, while operations 968, 970, 985 and 987 can occur in bulk (e.g., outside the partition). In the case where a partition is a droplet in an emulsion, the emulsion can be broken and the contents of the droplet pooled in order to complete operations 968, 970, 985 and 987.

The approaches of FIGS. 9A-9E may be employed for use with various target regions. In some examples, such target regions are TCR, BCR, and/or immunoglobulin regions. In such examples, oligonucleotides coupled to beads may include primers with sequences that are targeted for such target regions (e.g., constant regions). For example, polyT primer regions can instead be gene specific primer sequences.

Figure 10:
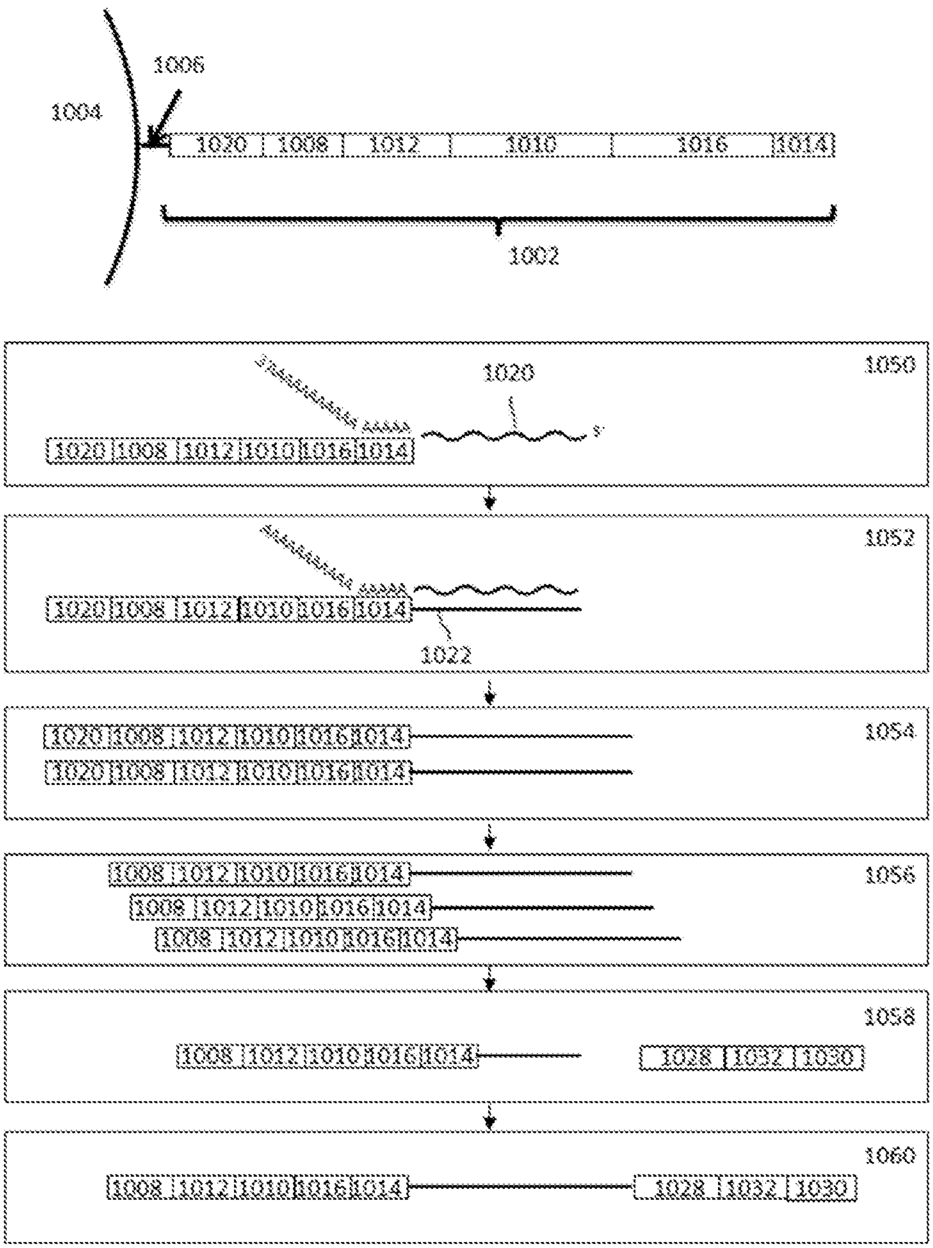
FIG. 10 provides schematic illustration of example barcoded oligonucleotide structure for use in example analysis of RNA and use of a sequence for in vitro transcription.

Another example of a barcode oligonucleotide for use in RNA analysis, including messenger RNA (mRNA, including mRNA obtained from a cell) analysis is shown in FIG. 10. As shown, the overall oligonucleotide 1002 is coupled to a bead 1004 by a releasable linkage 1006, such as a disulfide linker. The oligonucleotide may include functional sequences that are used in subsequent processing, such as functional sequence 1008, which may include a sequencer specific flow cell attachment sequence, e.g., a P7 sequence, as well as functional sequence 1010, which may include sequencing primer sequences, e.g., a R2 primer binding site. A barcode sequence 1012 is included within the structure for use in barcoding the sample RNA. An RNA specific (e.g., mRNA specific) priming sequence, such as poly-T sequence 1014 may be included in the oligonucleotide structure. An anchoring sequence segment (not shown) may be included to ensure that the poly-T sequence hybridizes at the sequence end of the mRNA. An additional sequence segment 1016 may be provided within the oligonucleotide sequence. This additional sequence can provide a unique molecular identifier (UMI) sequence segment, as described elsewhere herein. An additional functional sequence 1020 may be included for in vitro transcription, e.g., a T7 RNA polymerase promoter sequence. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular RNA analysis and in reference to FIG. 10, a cell is co-partitioned along with a barcode bearing bead, and other reagents such as reverse transcriptase, reducing agent and dNTPs into a partition (e.g., a droplet in an emulsion). In operation 1050, the cell is lysed while the barcoded oligonucleotides 1002 are released (e.g., via the action of the reducing agent) from the bead, and the poly-T segment 1014 of the released barcode oligonucleotide then hybridizes to the poly-A tail of mRNA 1020. Next at operation 1052, the poly-T segment is then extended in a reverse transcription reaction using the mRNA as template to produce a cDNA transcript 1022 of the mRNA and also includes each of the sequence segments 1020, 1008, 1012, 1010, 1016, and 1014 of the barcode oligonucleotide. Within any given partition, all of the cDNA transcripts of the individual mRNA molecules will include a common barcode sequence segment 1012. However, by including the unique random N-mer sequence, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. At operation 1054 a second strand is synthesized and at operation 1056 the T7 promoter sequence can be used by T7 polymerase to produce RNA transcripts in in vitro transcription. At operation 1058 the transcripts are fragmented (e.g., sheared), ligated to additional functional sequences, and reverse transcribed. The functional sequences may include a sequencer specific flow cell attachment sequence 1030, e.g., a P5 sequence, as well as functional sequence 1028, which may include sequencing primers, e.g., a R1 primer binding sequence, as well as functional sequence 1032, which may include a sample index, e.g., an i5 sample index sequence. At operation 1060 the RNA transcripts can be reverse transcribed to DNA, the DNA amplified (e.g., via PCR), and sequenced to identify the sequence of the cDNA transcript of the mRNA, as well as to sequence the barcode segment and the unique sequence segment. In some cases, operations 1050 and 1052 can occur in the partition, while operations 1054, 1056, 1058 and 1060 can occur in bulk (e.g., outside the partition). In the case where a partition is a droplet in an emulsion, the emulsion can be broken and the contents of the droplet pooled in order to complete operations 1054, 1056, 1058 and 1060.

In an alternative example of a barcode oligonucleotide for use in RNA (e.g., cellular RNA) analysis as shown in FIG. 10, functional sequence 1008 may be a P5 sequence and functional sequence 1010 may be a R1 primer binding site. Moreover, the functional sequence 1030 may be a P7 sequence, functional sequence 1028 may be a R2 primer binding site, and functional sequence 1032 may be an i7 sample index sequence.

Figure 11:
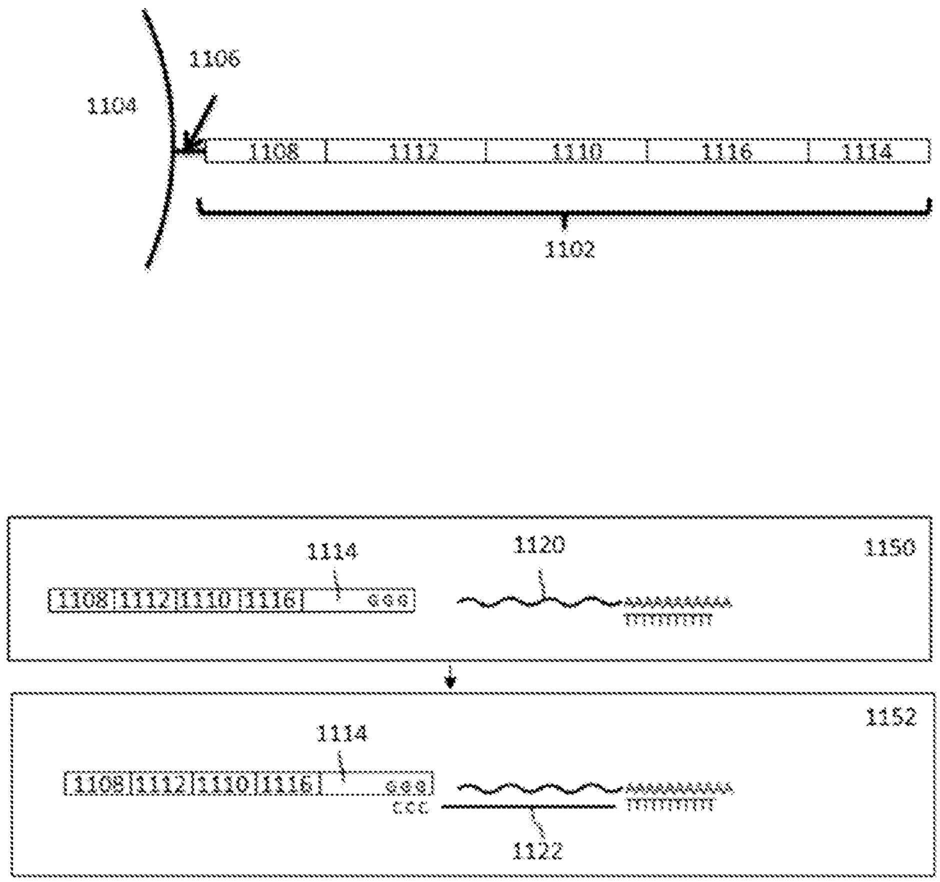
FIG. 11 provides schematic illustration of an example barcoded oligonucleotide structure for use in analysis of RNA and example operations for performing RNA analysis.

An additional example of a barcode oligonucleotide for use in RNA analysis, including messenger RNA (mRNA, including mRNA obtained from a cell) analysis is shown in FIG. 11. As shown, the overall oligonucleotide 1102 is coupled to a bead 1104 by a releasable linkage 1106, such as a disulfide linker. The oligonucleotide may include functional sequences that are used in subsequent processing, such as functional sequence 1108, which may include a sequencer specific flow cell attachment sequence, e.g., a P5 sequence, as well as functional sequence 1110, which may include sequencing primer sequences, e.g., a R1 primer binding site. In some cases, sequence 1108 is a P7 sequence and sequence 1110 is a R2 primer binding site. A barcode sequence 1112 is included within the structure for use in barcoding the sample RNA. An additional sequence segment 1116 may be provided within the oligonucleotide sequence. In some cases, this additional sequence can provide a unique molecular identifier (UMI) sequence segment, as described elsewhere herein. An additional sequence 1114 may be included to facilitate template switching, e.g., polyG. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular mRNA analysis and in reference to FIG. 11, a cell is co-partitioned along with a microcapsule (e.g., bead bearing a barcoded oligonucleotide), polyT sequence, and other reagents such as a DNA polymerase, a reverse transcriptase, oligonucleotide primers, dNTPs, and reducing agent into a partition (e.g., a droplet in an emulsion). The partition can serve as a reaction volume. As described elsewhere herein, the partition serving as the reaction volume can comprise a container or vessel such as a well, a microwell, vial, a tube, through ports in nanoarray substrates, or micro-vesicles having an outer barrier surrounding an inner fluid center or core, emulsion, or a droplet. In some embodiments, the partition comprises a droplet of aqueous fluid within a non-aqueous continuous phase, e.g., an oil phase. Within the partition, the cell can be lysed and the barcoded oligonucleotides can be released from the bead (e.g., via the action of the reducing agent or other stimulus). Cell lysis and release of the barcoded oligonucleotides from the microcapsule may occur simultaneously in the partition (e.g., a droplet in an emulsion) or the reaction volume. In some embodiments, cell lysis precedes release of the barcoded oligonucleotides from the microcapsule. In some embodiments, release of the barcoded oligonucleotides from the microcapsule precedes cell lysis.

Subsequent to cell lysis and the release of barcoded oligonucleotides from the microcapsule, the reaction volume can be subjected to an amplification reaction to generate an amplification product. In an example amplification reaction, the polyT sequence hybridizes to the polyA tail of mRNA 1120 released from the cell as illustrated in operation 1150. Next, in operation 1152, the polyT sequence is then extended in a reverse transcription reaction using the mRNA as a template to produce a cDNA transcript 1122 complementary to the mRNA. Terminal transferase activity of the reverse transcriptase can add additional bases to the cDNA transcript (e.g., polyC) in a template independent manner. The additional bases added to the cDNA transcript, e.g., polyC, can then hybridize with 1114 of the barcoded oligonucleotide. This can facilitate template switching and a sequence complementary to the barcoded oligonucleotide can be incorporated into the cDNA transcript. In various embodiments, the barcoded oligonucleotide does not hybridize to the template polynucleotide.

The barcoded oligonucleotide, upon release from the microcapsule, can be present in the reaction volume at any suitable concentration. In some embodiments, the barcoded oligonucleotide is present in the reaction volume at a concentration of about 0.2 μM, 0.3 μM, 0.4 μM, 0.5 μM, 1 μM, 5 μM, 10 μM, 15 μM, 20 μM, 25 μM, 30 μM, 35 μM, 40 μM, 50 μM, 100 μM, 150 μM, 200 μM, 250 μM, 300 μM, 400 μM, or 500 μM. In some embodiments, the barcoded oligonucleotide is present in the reaction volume at a concentration of at least about 0.2 μM, 0.3 μM, 0.4 μM, 0.5 μM, 1 μM, 5 μM, 10 μM, 15 μM, 20 μM, 25 μM, 30 μM, 35 μM, 40 μM, 50 μM, 100 μM, 150 μM, 200 μM, 250 μM, 300 μM, 400 μM, 500 μM or greater. In some embodiments, the barcoded oligonucleotide is present in the reaction volume at a concentration of at most about 0.2 μM, 0.3 μM, 0.4 μM, 0.5 μM, 1 μM, 5 μM, 10 μM, 15 μM, 20 μM, 25 μM, 30 μM, 35 μM, 40 μM, 50 μM, 100 μM, 150 μM, 200 μM, 250 μM, 300 μM, 400 μM, or 500 μM.

The transcripts can be further processed (e.g., amplified, portions removed, additional sequences added, etc.) and characterized as described elsewhere herein. In some embodiments, the transcripts are sequenced directly. In some embodiments, the transcripts are further processed (e.g., portions removed, additional sequences added, etc) and then sequenced. In some embodiments, the reaction volume is subjected to a second amplification reaction to generate an additional amplification product. The transcripts or first amplification products can be used as the template for the second amplification reaction. In some embodiments, primers for the second amplification reaction comprise the barcoded oligonucleotide and polyT sequence. In some embodiments, primers for the second amplification reaction comprise additional primers co-partitioned with the cell. In some embodiments, these additional amplification products are sequenced directly. In some embodiments, these additional amplification products are further processed (e.g., portions removed, additional sequences added, etc) and then sequenced. The configuration of the amplification products (e.g., first amplification products and second amplification products) generated by such a method can help minimize (or avoid) sequencing of the poly-T sequence during sequencing.

Figure 12A:
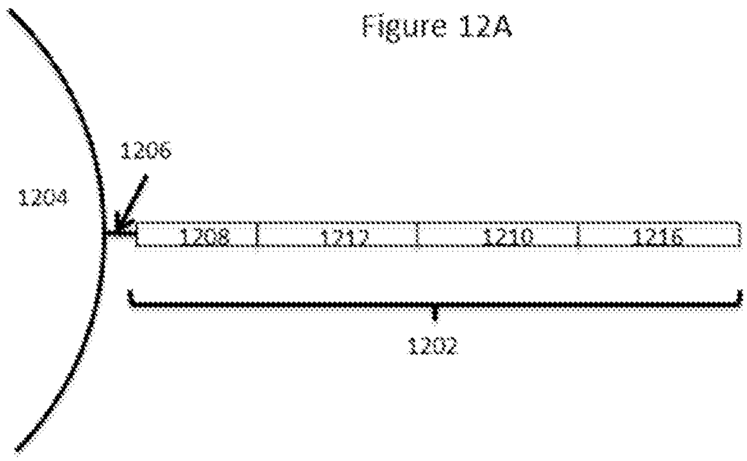
FIGS. 12A-12B provide schematic illustrations of example barcoded oligonucleotide structure for use in analysis of RNA.

An additional example of a barcode oligonucleotide for use in RNA analysis, including cellular RNA analysis is shown in FIG. 12A. As shown, the overall oligonucleotide 1202 is coupled to a bead 1204 by a releasable linkage 1206, such as a disulfide linker. The oligonucleotide may include functional sequences that are used in subsequent processing, such as functional sequence 1208, which may include a sequencer specific flow cell attachment sequence, e.g., a P5 sequence, as well as functional sequence 1210, which may include sequencing primer sequences, e.g., a R1 primer binding site. In some cases, sequence 1208 is a P7 sequence and sequence 1210 is a R2 primer binding site. A barcode sequence 1212 is included within the structure for use in barcoding the sample RNA. An additional sequence segment 1216 may be provided within the oligonucleotide sequence. In some cases, this additional sequence can provide a unique molecular identifier (UMI) sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular RNA analysis using this barcode, a cell is co-partitioned along with a barcode bearing bead and other reagents such as RNA ligase and a reducing agent into a partition (e.g., a droplet in an emulsion). The cell is lysed while the barcoded oligonucleotides are released (e.g., via the action of the reducing agent) from the bead. The barcoded oligonucleotides can then be ligated to the 5' end of mRNA transcripts while in the partitions by RNA ligase. Subsequent operations may include purification (e.g., via solid phase reversible immobilization (SPRI)) and further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for the additional operations.

Figure 12B:
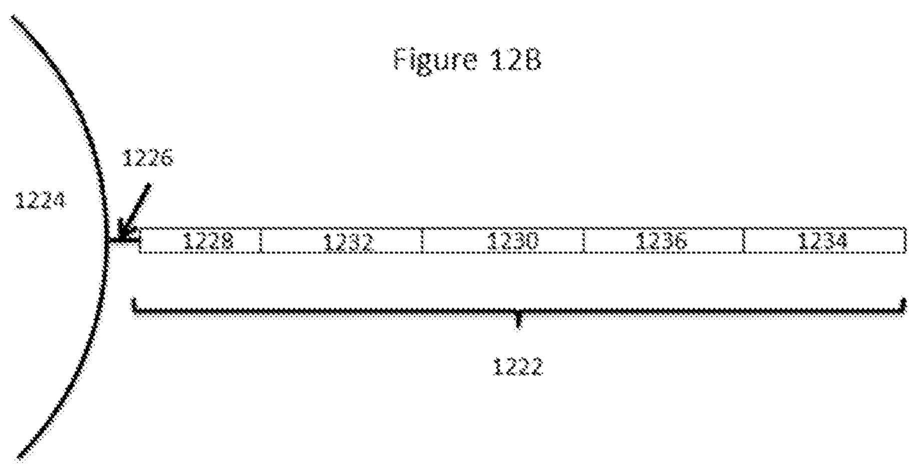

An additional example of a barcode oligonucleotide for use in RNA analysis, including cellular RNA analysis is shown in FIG. 12B. As shown, the overall oligonucleotide 1222 is coupled to a bead 1224 by a releasable linkage 1226, such as a disulfide linker. The oligonucleotide may include functional sequences that are used in subsequent processing, such as functional sequence 1228, which may include a sequencer specific flow cell attachment sequence, e.g., a P5 sequence, as well as functional sequence 1230, which may include sequencing primer sequences, e.g., a R1 primer binding site. In some cases, sequence 1228 is a P7 sequence and sequence 1230 is a R2 primer binding site. A barcode sequence 1232 is included within the structure for use in barcoding the sample RNA. A priming sequence 1234 (e.g., a random priming sequence) can also be included in the oligonucleotide structure, e.g., a random hexamer. An additional sequence segment 1236 may be provided within the oligonucleotide sequence. In some cases, this additional sequence provides a unique molecular identifier (UMI) sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular mRNA analysis using the barcode oligonucleotide of FIG. 12B, a cell is co-partitioned along with a barcode bearing bead and additional reagents such as reverse transcriptase, a reducing agent and dNTPs into a partition (e.g., a droplet in an emulsion). The cell is lysed while the barcoded oligonucleotides are released from the bead (e.g., via the action of the reducing agent). In some cases, sequence 1228 is a P7 sequence and sequence 1230 is a R2 primer binding site. In other cases, sequence 1228 is a P5 sequence and sequence 1230 is a R1 primer binding site. The priming sequence 1234 of random hexamers can randomly hybridize cellular mRNA. The random hexamer sequence can then be extended in a reverse transcription reaction using mRNA from the cell as a template to produce a cDNA transcript complementary to the mRNA and also includes each of the sequence segments 1228, 1232, 1230, 1236, and 1234 of the barcode oligonucleotide. Subsequent operations may include purification (e.g., via solid phase reversible immobilization (SPRI)), further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA and cDNA from cells. Alternatively, rRNA removal agents may be applied during additional processing operations. The configuration of the constructs generated by such a method can help minimize (or avoid) sequencing of the poly-T sequence during sequencing.

The single cell analysis methods described herein may also be useful in the analysis of the whole transcriptome. Referring back to the barcode of FIG. 12B, the priming sequence 1234 may be a random N-mer. In some cases, sequence 1228 is a P7 sequence and sequence 1230 is a R2 primer binding site. In other cases, sequence 1228 is a P5 sequence and sequence 1230 is a R1 primer binding site. In an example method of whole transcriptome analysis using this barcode, the individual cell is co-partitioned along with a barcode bearing bead, poly-T sequence, and other reagents such as reverse transcriptase, polymerase, a reducing agent and dNTPs into a partition (e.g., droplet in an emulsion). In an operation of this method, the cell is lysed while the barcoded oligonucleotides are released from the bead (e.g., via the action of the reducing agent) and the poly-T sequence hybridizes to the poly-A tail of cellular mRNA. In a reverse transcription reaction using the mRNA as template, cDNA transcripts of cellular mRNA can be produced. The RNA can then be degraded with an RNase. The priming sequence 1234 in the barcoded oligonucleotide can then randomly hybridize to the cDNA transcripts. The oligonucleotides can be extended using polymerase enzymes and other extension reagents co-partitioned with the bead and cell similar to as shown in FIG. 3 to generate amplification products (e.g., barcoded fragments), similar to the example amplification product shown in FIG. 3 (panel F). The barcoded nucleic acid fragments may, in some cases subjected to further processing (e.g., amplification, addition of additional sequences, clean up processes, etc. as described elsewhere herein) characterized, e.g., through sequence analysis. In this operation, sequencing signals can come from full length RNA.

In some embodiments, the barcode sequence can be appended to the 3' end of the template polynucleotide sequence (e.g., mRNA). Such configuration may be desired, for example, if the sequence at the 3' end of the template polynucleotide is desired to be analyzed.

In some embodiments, the barcode sequence can be appended to the 5' end of a template polynucleotide sequence (e.g., mRNA). Such configuration may be desired, for example, if the sequence at the 5' end of the template polynucleotide is desired to be analyzed.

In some embodiments, a barcode sequence can be appended to the 3' end of a first subset of the template polynucleotides, and a barcode sequence can be appended to the 5' end of a second subset of the template polynucleotides. In some embodiments, the first subset of template polynucleotides and the second subset of template polynucleotides are appended to barcode sequences in the same partition. In some cases, the barcodes appended to the 3' ends of template polynucleotides are different from the barcodes appended to the 5' ends of template polynucleotides. For example, the barcodes appended to the 3' ends may have a different barcode sequence compared to the barcodes appended to the 5' end. In some cases, the barcodes appended to the 3' ends of template polynucleotides have the same barcode sequence as the barcodes appended to the 5' ends of template polynucleotides. In some cases, beads are used to deliver the barcode oligonucleotides to partitions. The different barcodes can be attached to the same or different bead.

A barcode sequence can be appended to the 5' end of a template polynucleotide sequence by any suitable method. In some cases, the template polynucleotide is a messenger RNA, mRNA, molecule. The barcode sequence can be appended to the 5' end of a template polynucleotide sequence by use of a primer comprising the barcode sequence in a primer extension reaction. For example, the barcode may be present in a primer used for a primer extension reaction in which the template polynucleotide or a derivative thereof, for example an amplification product, is used as the template for primer extension. In some cases, the barcode may be present on a template switching oligonucleotide participating in a primer extension reaction. As an alternative, the barcode sequence can be appended to the 5' end of a template polynucleotide by ligating an oligonucleotide comprising the barcode sequence directly to the template polynucleotide.

In another aspect, the present disclosure provides a method of appending a barcode sequence to the 5' end of a template polynucleotide sequence by a primer extension reaction using a primer comprising a barcode sequence and the template polynucleotide or a derivative thereof as the template for primer extension. The primer extension reaction may occur in a partition. In some embodiments, a cell, or a nucleic acid derivative thereof, is co-partitioned with a primer capable of primer extension and a template switching oligo comprising a barcode sequence. The primer capable of primer extension may hybridize to a nucleic acid of the cell or to a nucleic acid derivative. In some cases, the template switching oligo comprising the barcode sequence is releasably attached to a bead, e.g., a gel bead. In some embodiments, a cell, or a nucleic acid derivative thereof, is co-partitioned with a primer having a sequence towards a 3' end that hybridizes to the template polynucleotide, a template switching oligonucleotide having a first predefined sequence towards a 5' end, and a microcapsule, such as a bead, having barcoded oligonucleotides releasably coupled thereto. In some embodiments, the oligonucleotides coupled to the bead include barcode sequences that are identical (e.g., all oligonucleotides sharing the same barcode sequence). In some aspects, the oligonucleotides coupled to the beads additionally include unique molecular identifier (UMI) sequence segments (e.g., all oligonucleotides having different unique molecular identifier sequences).

Figure 18:
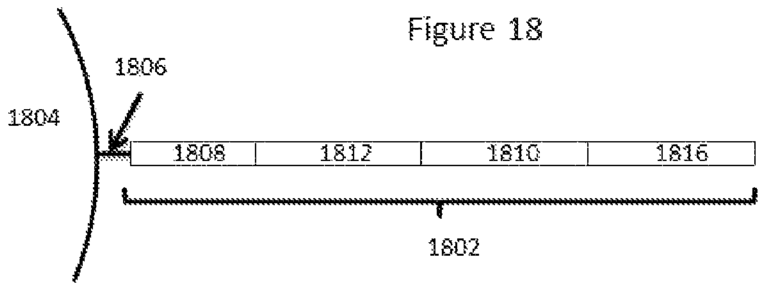
FIG. 18 provides a schematic illustration of an example barcoded oligonucleotide structure.

In an example, FIG. 18 shows a barcoded oligonucleotide coupled to a bead. As shown, the overall oligonucleotide 1802 is coupled to a bead 1804 by a releasable linkage 1806, such as a disulfide linker. The oligonucleotide may include functional sequences that are useful for subsequent processing, such as functional sequence 1808, which may include a sequencer specific flow cell attachment sequence, e.g., a P5 sequence, as well as functional sequence 1810, which may include sequencing primer sequences, e.g., a R1 primer binding site. In some cases, sequence 1808 is a P7 sequence and sequence 1810 is a R2 primer binding site. A barcode sequence 1812 can be included within the structure for use in barcoding the template polynucleotide. The functional sequences may be selected for compatibility with a variety of different sequencing systems, e.g., 454 Sequencing, Ion Torrent Proton or PGM, Illumina X10, etc., and the requirements thereof. In many cases, the barcode sequence 1812, functional sequences 1808 (e.g., flow cell attachment sequence) and 1810 (e.g., sequencing primer sequences) may be common to all of the oligonucleotides attached to a given bead. The barcoded oligonucleotide can also comprise a sequence 1816 to facilitate template switching (e.g., a polyG sequence). In some cases, the additional sequence provides a unique molecular identifier (UMI) sequence segment, as described elsewhere herein. The one or more functional sequences that may be present in an oligonucleotide can be arranged in any suitable order.

Although shown as a single oligonucleotide tethered to the surface of a bead, individual beads can include tens to hundreds of thousands or even millions of individual oligonucleotide molecules, where, as previously noted herein, the barcode sequence can be constant or relatively constant for a given bead.

In an example method of generating labeled polynucleotides using a barcode oligonucleotide, a cell or a nucleic acid derived therefrom is co-partitioned with a bead bearing a barcoded oligonucleotide and reagents such as reverse transcriptase, poly-T primers, dNTPs, and a chemical stimulus (e.g., reducing agent) into a partition. The barcoded oligonucleotide attached to the bead can comprise a sequence to facilitate template switching (e.g., polyG or riboG). The partition can be a droplet in an emulsion. In cases where a cell is provided in the partition, the partition can further comprise a lysis reagent to lyse the cell.

Where the bead is a degradable or disruptable bead, the barcoded oligonucleotide can be released from the bead when contacted with the chemical stimulus (e.g., reducing agent). Following release from the bead, the barcoded oligonucleotide can be present in the partition at any suitable concentration. In some embodiments, the barcoded oligonucleotide is present in the partition at a concentration that is suitable for generating a sufficient yield of amplification products for downstream processing and analysis, including, but not limited to, sequencing adaptor attachment and sequencing analysis.

Figure 19A:
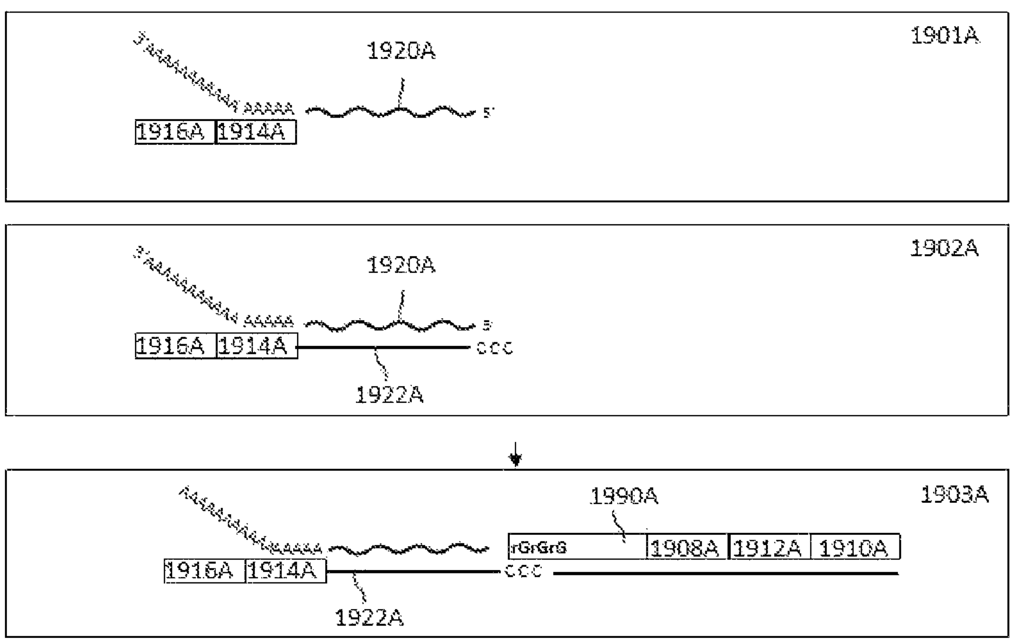
FIGS. 19A and 19B show example operations for performing RNA analysis.

With reference to FIG. 19A, in 1901A, an oligonucleotide with a poly-T sequence 1914A, and in some cases an additional sequence 1916A that binds to, for example, a sequencing or PCR primer, anneals to a target mRNA 1920A. In 1902A, the oligonucleotide is extended yielding an anti-sense strand 1922A which is appended by multiple cytidines on the 3' end. In 1903A, the template switching sequence 1990A (e.g., polyG or riboG) of the barcoded oligonucleotide pairs with the cytidines of the anti-sense strand 1922A and the anti-sense strand is extended using the barcoded oligonucleotide as template. In addition to the riboG sequence, the barcoded oligonucleotide can comprise additional functional sequences 1908A, 1912A, and 1910A. In some cases, the barcoded oligonucleotide comprises a unique molecular identifier (UMI, for example 1908A), a barcode sequence (for example 1912A), and a Read 1 sequence (R1, for example 1910A). Operations 1901A, 1902A, and 1903A may be performed in the partition (e.g., droplet or well). The extension in 1902A and 1903A can be facilitated by an enzyme comprising polymerase activity. For example, the extension can be facilitated by a DNA-dependent polymerase or a reverse-transcriptase (e.g., RNA dependent). In some embodiments, the extension comprises polymerase chain reaction. In some embodiments, the extension comprises reverse transcription. The enzyme can add nucleotides in a template independent manner. In some cases, at least three cytidines are appended to the 3' end of the cDNA transcript in a template independent manner.

Subsequent to 1903A, the nucleic acid product (e.g., cDNA product) may be released from the partition and subject to further processing reactions such as additional amplification. In some cases, the nucleic acid product is pooled with products from other partitions for subsequent processing in bulk. In some cases, a portion of the amplified product can be subjected to enrichment to obtain a subset of nucleic acids corresponding to genes of interest.

In some cases, enrichment to obtain a subset of nucleic acids corresponding to genes of interest comprises one or more amplification reactions. One or more gene specific primers can be used for primer extension using the cDNA molecule as a template. Any of a variety of polymerases can be used in embodiments herein for primer extension, non-limiting examples of which include exonuclease minus DNA Polymerase I large (Klenow) Fragment, Phi29 DNA polymerase, Taq DNA Polymerase, T4 DNA polymerase, T7 DNA polymerase, and the like. Further examples of polymerase enzymes that can be used in embodiments herein include thermostable polymerases, including but not limited to, *Thermus thermophilus* HB8; *Thermus oshimai; Thermus scotoductus; Thermus thermophilus* 1B21*; Thermus thermophilus* GK24*; Thermus aquaticus* polymerase AmpliTaq® FS or Taq (G46D; F667Y), Taq (G46D; F667Y; E6811), and Taq (G46D; F667Y; T664N; R660G); *Pyrococcus furiosus* polymerase; *Thermococcus* gorgonarius polymerase; *Pyrococcus* species GB-D polymerase; *Thermococcus* sp. (strain 9 deg. N-7) polymerase; *Bacillus* stearo *thermophilus* polymerase; Tsp polymerase; *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. In some embodiments, a hot start polymerase is used. A hot start polymerase is a modified form of a DNA polymerase that can be activated by incubation at elevated temperatures.

Additional functional sequences can be added to the nucleic acid product or an amplification product thereof. The additional functional sequences may allow for amplification or sample identification. This may occur in the partition or, alternatively, in bulk. In some cases, the amplification products can be sheared, ligated to adapters and amplified to add additional functional sequences. In some cases, both the enriched and unenriched amplification products are subject to analysis.

In an example method of cellular polynucleotide analysis using the barcode oligonucleotide of FIG. 18, a cell is co-partitioned along with a bead bearing a barcoded oligonucleotide and additional reagents such as reverse transcriptase, primers, oligonucleotides (e.g., template switching oligonucleotides), dNTPs, and reducing agent into a partition (e.g., a droplet in an emulsion). Within the partition, the cell can be lysed to yield a plurality of template polynucleotides (e.g., DNA such as genomic DNA, RNA such as mRNA, etc). In some cases, the cell is lysed using a lysis reagent that is co-partitioned with the cell.

Where the bead is a degradable or disruptable bead, the barcoded oligonucleotide can be released from the bead following the application of stimulus as previously described herein. Following release from the bead, the barcoded oligonucleotide can be present in the partition at any suitable concentration. In some embodiments, the barcoded oligonucleotide is present in the partition at a concentration that is suitable for generating a sufficient yield of amplification products for downstream processing and analysis, including, but not limited to, sequencing adaptor attachment and sequencing analysis. In some embodiments, the concentration of the barcoded oligonucleotide is limited by the loading capacity of the barcode bearing bead, or the amount of oligonucleotides deliverable by the bead.

The template switching oligonucleotide, which can be co-partitioned with the cell, bead bearing barcoded oligonucleotides, etc, can be present in the partition at any suitable concentration. In some embodiments, the template switching oligonucleotide is present in the partition at a concentration that is suitable for efficient template switching during an amplification reaction. The concentration of the template switching oligonucleotide can be dependent on the reagents used for droplet generation. In some embodiments, the template switching oligonucleotide is among a plurality of template switching oligonucleotides.

In some embodiments, the barcoded oligonucleotide and template switching oligonucleotide are present in the partition at similar concentrations. In some embodiments, the barcoded oligonucleotide and template switching oligonucleotides may be present in proportions reflective of the desired amount of amplification products to be generated using each oligonucleotide. In some embodiments, the template switching oligonucleotide is present in the partition at a greater concentration than the barcoded oligonucleotide. This difference in concentration can be due to limitations on the capacity of the barcode bearing bead. In some embodiments, the concentration of the template switching oligonucleotide in the reaction volume is at least 2, 5, 10, 20, 50, 100, 200 or more times that of the concentration of the barcoded oligonucleotide in the same reaction volume when the barcoded oligonucleotide is free in the partition (e.g., not attached to the bead).

Figure 19B:
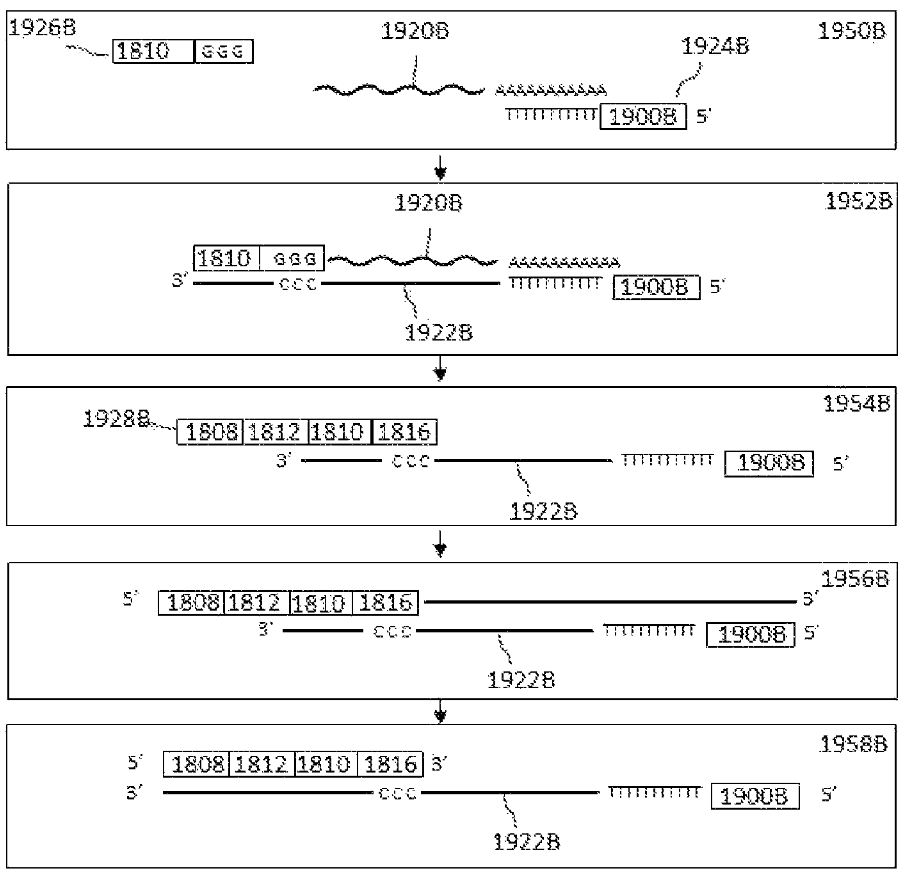

As illustrated in FIG. 19B, a reaction mixture comprising a template polynucleotide from a cell 1920B and (i) the primer 1924B having a sequence towards a 3' end that hybridizes to the template polynucleotide (e.g., polyT) and an additional sequence element 1900B and (ii) a template switching oligonucleotide 1926B that comprises a first predefined sequence 1810 towards a 5' end can be subjected to an amplification reaction to yield a first amplification product. In some cases, the template polynucleotide is an mRNA with a polyA tail and the primer that hybridizes to the template polynucleotide comprises a polyT sequence towards a 3' end, which is complementary to the polyA segment. The first predefined sequence can comprise at least one of an adaptor sequence, a barcode sequence, a unique molecular identifier (UMI) sequence, a primer binding site, and a sequencing primer binding site or any combination thereof. In some cases, the first predefined sequence 1810 is a sequence that can be common to all partitions of a plurality of partitions. For example, the first predefined sequence may comprise a flow cell attachment sequence, an amplification primer binding site, or a sequencing primer binding site and the first amplification reaction facilitates the attachment the predefined sequence to the template polynucleotide from the cell. In some embodiments, the first predefined sequence comprises a primer binding site. In some embodiments, the first predefined sequence comprises a sequencing primer binding site. In some embodiments, the first predefined sequence comprises a barcode sequence. As illustrated in operation 1950B, the sequence towards a 3' end (e.g., polyT) of the primer 1924B hybridizes to the template polynucleotide 1920B. In a first amplification reaction, extension reaction reagents, e.g., reverse transcriptase, nucleoside triphosphates, co-factors (e.g., Mg2+ or Mn2+), that are also co-partitioned, can extend the primer 1924B sequence using the cell's nucleic acid as a template, to produce a transcript, e.g., cDNA transcript, 1922B having a fragment complementary to the nucleic acid to which the primer annealed. In some cases, the reverse transcriptase has terminal transferase activity and the reverse transcriptase adds additional nucleotides, e.g., polyC, to the cDNA transcript in a template independent manner. As illustrated in operation 1952B, the template switching oligonucleotide 1926B, for example a template switching oligonucleotide which includes a polyG sequence, can hybridize to the cDNA transcript 1922B and facilitate template switching in the first amplification reaction. The transcript, therefore, may comprise the sequence of the primer 1924B, a sequence complementary to the template polynucleotide from the cell, and a sequence complementary to the template switching oligonucleotide.

Among a plurality of partitions, the primer and template switching oligonucleotide may be universal to all partitions. The partitions may individually contain more than one cell, one cell, no cells, or nucleic acids derived from a cell. Where analysis of mRNA is desired, for example, the primer may comprise at least a polyT segment capable of hybridizing and priming an extension reaction from the polyA segment of an mRNA. Where analysis of a variety of polynucleotides is desired, the primer may comprise a random sequence capable of hybridizing to and priming extension reactions randomly on various polynucleotide templates. As template switching can occur with the use of an enzyme having terminal transferase activity, a template switching oligonucleotide having a sequence capable of hybridizing to the appended bases can be used for template switching in manner that is independent of the sequence of the polynucleotide templates to be analyzed. In some embodiments, the template switching oligonucleotide can comprise a first predefined sequence towards a 5' end that does not specifically hybridize to the template. In some embodiments, analysis of particular genes is desired. In such cases, the primer may comprise a gene specific sequence capable of hybridizing to and priming extension reactions from templates comprising specific genes. In some embodiments, multiple genes are to be analyzed and a primer is among a plurality of primers. Individual primers of the plurality may target different genes. Each of the plurality of primers may have a sequence for a particular gene.

Subsequent to the first amplification reaction, the first amplification product or transcript can be subjected to a second amplification reaction to generate a second amplification product. In some cases, additional sequences (e.g., functional sequences such as flow cell attachment sequence, sequencing primer binding sequences, barcode sequences, etc) are to be attached. The first and second amplification reactions can be performed in the same volume, such as for example in a droplet or well. In some cases, the first amplification product is subjected to a second amplification reaction in the presence of a barcoded oligonucleotide to generate a second amplification product having a barcode sequence. The barcode sequence can be unique to a partition, that is, each partition has a unique barcode sequence. The barcoded oligonucleotide may comprise a sequence of at least a segment of the template switching oligonucleotide and at least a second predefined sequence. The segment of the template switching oligonucleotide on the barcoded oligonucleotide can facilitate hybridization of the barcoded oligonucleotide to the transcript, e.g., cDNA transcript, to facilitate the generation of a second amplification product. In addition to a barcode sequence, the barcoded oligonucleotide may comprise a second defined sequence such as at least one of an adaptor sequence, a unique molecular identifier (UMI) sequence, a primer binding site, and a sequencing primer binding site or any combination thereof.

In some embodiments, the second amplification reaction uses the first amplification product as a template and the barcoded oligonucleotide as a primer. As illustrated in operation 1954B, the segment of the template switching oligonucleotide on the barcoded oligonucleotide 1928B can hybridize to the portion of the cDNA transcript or complementary fragment 1922B having a sequence complementary to the template switching oligonucleotide or that which was copied from the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence using the first amplification product as template as illustrated in operation 1956B. The second amplification product can comprise a second predefined sequence (e.g., 1808, 1812, and 1810), a sequence of a segment of the template polynucleotide (e.g., mRNA), and a sequence complementary to the primer (e.g., 1924B). In cases where the template polynucleotide is an mRNA molecule, amplification products derived therefrom can comprise the corresponding DNA sequence, for example thymine instead of uracil bases.

In some embodiments, the second amplification product uses the barcoded oligonucleotide as a template and at least a portion of the first amplification product as a primer. As illustrated in operation 1954B, the segment of the first amplification product (e.g., cDNA transcript) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence (e.g., first amplification product) using the barcoded oligonucleotide as template as illustrated in operation 1958B. The second amplification product may comprise the sequence of the primer (e.g., 1924B), a sequence which is complementary to the sequence of the template polynucleotide (e.g., mRNA), and a sequence complementary to the second predefined sequence (e.g., 1808, 1812, and 1810).

In some embodiments, the second amplification reaction is performed subsequent to the first amplification reaction in the presence of an intervening purification step. An intervening purification step can be used, for example, to purify the template (e.g., first amplification product) from excess reagents, including excess primers such as template switching oligonucleotides. In some embodiments, the amplification reaction is performed in the absence of an intervening purification step. In certain embodiments, an intervening purification step is not performed so that all sample preparation is performed in a same reaction volume. In the absence of an intervening purification step, the template switching oligonucleotide may compete with barcoded oligonucleotide in the second amplification reaction as the barcoded oligonucleotide comprises at least a segment of the template switching oligonucleotide. Competition between the template switching oligonucleotide and barcoded oligonucleotide in the second amplification reaction to generate additional amplification product may result in a second amplification product lacking a barcode sequence. Such amplification products lacking a barcode sequence may be undesirable as they lack a barcode sequence which can provide unique identifying information of the template. In some embodiments, the template switching oligonucleotide may out-compete the barcoded oligonucleotide in the second amplification reaction if the template switching oligonucleotide is present at a higher concentration in the reaction volume than the barcoded oligonucleotide. Various approaches can be utilized to favor the use of the barcoded oligonucleotide in the second amplification reaction to generate amplification products having a barcode sequence in situations where the barcoded oligonucleotide is present at a lower concentration than the template switching oligonucleotide in the reaction volume.

In some embodiments, the template switching oligonucleotide is not available for primer extension during the second amplification reaction. In some embodiments, the template switching oligonucleotide is degraded prior to the second amplification reaction. In some embodiments, the template switching oligonucleotide is degraded during the second amplification reaction. The template switching oligonucleotide may comprise ribonucleic acids (RNA). A template switching oligonucleotide comprising RNA can be degraded, for example, by elevated temperatures or alkaline conditions. In some embodiments, the template switching oligonucleotide comprises at least 10%, 15%, 20%, 25%, 30%, 35%, 40%, 45%, 50%, 55%, 60%, 65%, 70%, 75%, 80%, 85%, 90%, or 95% RNA. In some embodiments, the template switching oligonucleotide comprises 100% RNA. In some embodiments, a first reaction rate of the second amplification reaction using the barcoded oligonucleotide is greater than a second reaction rate of the second amplification using the template switching oligonucleotide.

In some embodiments, the barcoded oligonucleotide can hybridize to the first amplification product at a higher annealing temperature as compared to the template switching oligonucleotide. For example, the first amplification product and the barcoded oligonucleotide can have a higher melting temperature as compared to a melting temperature of the first amplification product and the template switching oligonucleotide. In such cases, the second amplification reaction may be performed with an annealing temperature at which the barcoded oligonucleotide is able to hybridize to the first amplification product and initiation primer extension and at which the template switching oligonucleotide is unable to hybridize to the first amplification product and initiate primer extension. In some embodiments, the primer annealing temperature of the second amplification reaction is at least about 0.5° C., 1° C., 2° C., 3° C., 4° C., 5° C., 6° C., 7° C., 8° C., 9° C., 10° C. or greater than a primer annealing temperature of the first amplification reaction. The difference in melting temperatures can result from the presence of modified nucleotides in the template switching oligonucleotide. In some embodiment, the template switching oligonucleotide comprises at least 10%, 15%, 20%, 25%, 30%, 35%, 40%, 45%, 50%, 55%, 60%, 65%, 70%, 75%, 80%, 85%, 90%, or 95% modified nucleotides. In some embodiments, the template switching oligonucleotide comprises 100% modified oligonucleotides. In some embodiments, the difference in melting temperature can be the result of the presence of modified nucleotides in the barcoded oligonucleotide. In some embodiment, the barcoded oligonucleotide comprises at least 10%, 15%, 20%, 25%, 30%, 35%, 40%, 45%, 50%, 55%, 60%, 65%, 70%, 75%, 80%, 85%, 90%, or 95% modified nucleotides. In some embodiments, the barcoded oligonucleotide comprises 100% modified oligonucleotides. Modified nucleotides include, but are not limited to, 2-Aminopurine, 2,6-Diaminopurine (2-Amino-dA), inverted dT, 5-Methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, and 2' Fluoro bases (e.g., Fluoro C, Fluoro U, Fluoro A, and Fluoro G).

In various embodiments, the first amplification reaction is facilitated using an enzyme comprising polymerase activity.

For example, the first amplification reaction can be facilitated by a DNA-dependent polymerase or a reverse-transcriptase (e.g., RNA dependent). In some embodiments, the first amplification reaction comprises polymerase chain reaction. In some embodiments, the first amplification reaction comprises reverse transcription. In various embodiments, the second amplification reaction is facilitated using an enzyme comprising polymerase activity. For example, the second amplification reaction can be facilitated by a DNA-dependent polymerase. In some embodiments, the second amplification reaction comprises polymerase chain reaction.

In another aspect, a template polynucleotide comprising mRNA may first be reverse transcribed to cDNA (e.g., an amplification product of the template polynucleotide). The mRNA molecule can be reverse transcribed to cDNA using a reverse transcriptase enzyme and a primer, such as a poly-T primer. Non-limiting examples of enzymes that can be used for reverse transcription in embodiments herein include HIV-1 reverse transcriptase, M-MLV reverse transcriptase, AMV reverse transcriptase, telomerase reverse transcriptase, and variants, modified products and derivatives thereof.

A gene specific primer having a barcode sequence can then be used for primer extension using the cDNA molecule (e.g., amplification product of the template polynucleotide) as a template. A primer comprising a barcode can hybridize to the cDNA molecule via sequence complementarity. Extension of the primer using the cDNA molecule as template may result in a polynucleotide product comprising the template polynucleotide sequence and the barcode sequence located at the 5' end of the template polynucleotide sequence. Any of a variety of polymerases can be used in embodiments herein for primer extension, non-limiting examples of which include exonuclease minus DNA Polymerase I large (Klenow) Fragment, Phi29 DNA polymerase, Taq DNA Polymerase, T4 DNA polymerase, T7 DNA polymerase, and the like. Further examples of polymerase enzymes that can be used in embodiments herein include thermostable polymerases, including but not limited to, *Thermus thermophilus* HB8; *Thermus oshimai; Thermus scotoductus; Thermus thermophilus* 1B21*; Thermus thermophilus* GK24*; Thermus aquaticus* polymerase AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9 deg. N-7) polymerase; *Bacillus* stearo *thermophilus* polymerase; Tsp polymerase; *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. In some embodiments, a hot start polymerase is used. A hot start polymerase is a modified form of a DNA polymerase that can be activated by incubation at elevated temperatures. Such a polymerase can be used, for example, to further increase sensitivity, specificity, and yield; and/or to further improve low copy target amplification.

In another aspect, a barcode sequence is appended to the 5' end of a template polynucleotide sequence by ligating an oligonucleotide comprising a barcode sequence directly to the 5' end of the template polynucleotide. Ligating an oligonucleotide comprising a barcode sequence to a template polynucleotide can be implemented by various methods. In some embodiments herein, ligating an oligonucleotide comprising a barcode sequence to a template polynucleotide involves an enzyme, such as a ligase (e.g., an RNA ligase or a DNA ligase). Non-limiting examples of enzymes that can be used for ligation in embodiments herein include ATP-dependent double-stranded polynucleotide ligases, NAD+ dependent DNA or RNA ligases, and single-strand polynucleotide ligases. Non-limiting examples of ligases which can be used in embodiments herein include CircLigase I and CircLigase II (Epicentre; Madison, WI), *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre® Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants.

In some embodiments where a barcode oligonucleotide is ligated to a template polynucleotide comprising mRNA, the mRNA molecule can be treated to yield a 5' monophosphate group prior to ligating. Any suitable reaction may be employed to yield a 5' monophosphate group. For example, the mRNA molecule can be treated with an enzyme such as a pyrophosphohydrolase. An example of a pyrophosphohydrolase that can be used in embodiments herein is RNA 5' phyrophosphohydrolase (RppH). In some cases, all of the phosphate groups at the 5' end of the molecule are removed and a single phosphate groups is added back to the 5' end. In some cases, two phosphate groups are removed from a triphosphate group to yield a monophosphate. In some cases, a single enzyme both removes the phosphate groups present on the mRNA molecule and adds the monophosphate group. In some cases, a first enzyme removes the phosphate groups present on the mRNA molecule and a second enzyme adds the monophosphate group. In some cases, the phosphate groups are removed from the 5' end of the mRNA molecule and the 5' end is adenylated. An enzyme which can be used for 5' adenylation in embodiments herein includes Mth RNA ligase.

In some cases, the oligonucleotide comprising the barcode sequence is ligated to the template polynucleotide within a partition (e.g., droplet or well). A partition, in some cases, comprises a polynucleotide sample comprising the template polynucleotide, an oligonucleotide having the barcode sequence, a ligase enzyme, and any other suitable reagents for ligation. The ligase can implement the attachment of the oligonucleotide comprising the barcode sequence to the template polynucleotide within the partition. In some cases, the template polynucleotide is an mRNA molecule and the oligonucleotide ligated to it is a DNA molecule. In some cases, the oligonucleotide comprising the barcode sequence is ligated to the template polynucleotide outside of a partition.

Following the attachment of an oligonucleotide comprising a barcode sequence to the 5' end of a template polynucleotide, for example an mRNA polynucleotide, the barcoded template can be subjected to further amplification. In some cases, one or more further amplification reactions are performed within the partition. In some cases, one or more further amplification reactions are performed outside of a partition. In some cases, a plurality of barcoded mRNA polynucleotides, for example from a plurality of partitions, is pooled and subjected to further processing in bulk. In some embodiments, the barcoded template polynucleotide is subjected to polymerase chain reaction. In some embodiments, the template polynucleotide comprises mRNA and the barcoded template polynucleotide is subjected to reverse transcription, yielding a cDNA transcript. In embodiments where reverse transcription is performed in a partition, the partitions can comprise primers having a poly-T region capable of hybridizing to the poly-A region of the barcoded mRNA. Within the partition, the primer having a poly-T region can hybridize to the barcoded template and initiate primer extension in reverse transcription. Non-limiting examples of enzymes that can be used for reverse transcription in embodiments herein include HIV-1 reverse transcriptase, M-MLV reverse transcriptase, AMV reverse transcriptase, telomerase reverse transcriptase, and variants, modified products and derivatives thereof. A partition can contain a reverse transcriptase enzyme capable of reverse transcribing a template polynucleotide that is attached at its 5' end to a barcoded oligonucleotide. In embodiments where reverse transcription is performed in bulk, a plurality of barcoded mRNA polynucleotides from a plurality of partitions can be pooled for bulk processing. The reaction volume for performing reverse transcription can comprise primers having a poly-T region capable of hybridizing to the poly-A region of a barcoded mRNA. In some cases, the primers for reverse transcription further comprise additional elements, such as tags, which can be used, for example, for isolating cDNA transcripts. For example, cDNA transcripts comprising biotin tags can be isolated from components of the reaction volume (e.g., excess primers, reverse transcriptase enzyme, barcoded mRNA molecules) by performing a purification reaction with streptavidin or other molecule capable of binding biotin.

Following the generation of barcoded template polynucleotides or derivatives (e.g., amplification products) thereof, subsequent operations may be performed, including purification (e.g., via solid phase reversible immobilization (SPRI)) or further processing (e.g., shearing, addition of functional sequences, and subsequent amplification (e.g., via PCR)). Functional sequences, such as flow cell sequences, may be added by ligation. These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example first amplification products and/or second amplification products, may be subject to sequencing for sequence analysis.

Although operations with various barcode designs have been discussed individually, individual beads can include barcode oligonucleotides of various designs for simultaneous use.

In addition to characterizing individual cells or cell subpopulations from larger populations, the processes and systems described herein may also be used to characterize individual cells as a way to provide an overall profile of a cellular, or other organismal population. A variety of applications require the evaluation of the presence and quantification of different cell or organism types within a population of cells, including, for example, microbiome analysis and characterization, environmental testing, food safety testing, epidemiological analysis, e.g., in tracing contamination or the like. In particular, the analysis processes described above may be used to individually characterize, sequence and/or identify large numbers of individual cells within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the single cell analysis methods and systems described herein, one can again, characterize, sequence and identify individual cells in an overall population, and identify shifts within that population that may be indicative of diagnostic ally relevant factors. By way of example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is incorporated herein by reference in its entirety for all purposes. Likewise, identification and diagnosis of infection or potential infection may also benefit from the single cell analyses described herein, e.g., to identify microbial species present in large mixes of other cells or other biological material, cells and/or nucleic acids, including the environments described above, as well as any other diagnostically relevant environments, e.g., cerebrospinal fluid, blood, fecal or intestinal samples, or the like.

The foregoing analyses may also be particularly useful in the characterization of potential drug resistance of different cells or pathogens, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Although described in terms of cells, it will be appreciated that any of a variety of individual biological organisms, or components of organisms are encompassed within this description, including, for example, cells, viruses, organelles, cellular inclusions, vesicles, or the like. Additionally, where referring to cells, it will be appreciated that such reference includes any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms.

Similarly, analysis of different environmental samples to profile the microbial organisms, viruses, or other biological contaminants that are present within such samples, can provide important information about disease epidemiology, and potentially aid in forecasting disease outbreaks, epidemics an pandemics.

As described above, the methods, systems and compositions described herein may also be used for analysis and characterization of other aspects of individual cells or populations of cells. In one example process, a sample is provided that contains cells that are to be analyzed and characterized as to their cell surface proteins. Also provided is a library of antibodies, antibody fragments, or other molecules having a binding affinity to the cell surface proteins or antigens (or other cell features) for which the cell is to be characterized (also referred to herein as cell surface feature binding groups). For ease of discussion, these affinity groups are referred to herein as binding groups. The binding groups can include a reporter molecule that is indicative of the cell surface feature to which the binding group binds. In particular, a binding group type that is specific to one type of cell surface feature will comprise a first reporter molecule, while a binding group type that is specific to a different cell surface feature will have a different reporter molecule associated with it. In some aspects, these reporter molecules will comprise oligonucleotide sequences. Oligonucleotide based reporter molecules provide advantages of being able to generate significant diversity in terms of sequence, while also being readily attachable to most biomolecules, e.g., antibodies, etc., as well as being readily detected, e.g., using sequencing or array technologies. In the example process, the binding groups include oligonucleotides attached to them. Thus, a first binding group type, e.g., antibodies to a first type of cell surface feature, will have associated with it a reporter oligonucleotide that has a first nucleotide sequence. Different binding group types, e.g., antibodies having binding affinity for other, different cell surface features, will have associated therewith reporter oligonucleotides that comprise different nucleotide sequences, e.g., having a partially or completely different nucleotide sequence. In some cases, for each type of cell surface feature binding group, e.g., antibody or antibody fragment, the reporter oligonucleotide sequence may be known and readily identifiable as being associated with the known cell surface feature binding group. These oligonucleotides may be directly coupled to the binding group, or they may be attached to a bead, molecular lattice, e.g., a linear, globular, cross-slinked, or other polymer, or other framework that is attached or otherwise associated with the binding group, which allows attachment of multiple reporter oligonucleotides to a single binding group.

In the case of multiple reporter molecules coupled to a single binding group, such reporter molecules can comprise the same sequence, or a particular binding group will include a known set of reporter oligonucleotide sequences. As between different binding groups, e.g., specific for different cell surface features, the reporter molecules can be different and attributable to the particular binding group.

Attachment of the reporter groups to the binding groups may be achieved through any of a variety of direct or indirect, covalent or non-covalent associations or attachments. For example, in the case of oligonucleotide reporter groups associated with antibody based binding groups, such oligonucleotides may be covalently attached to a portion of an antibody or antibody fragment using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available (See, e.g., Fang, et al., *Fluoride-Cleavable Biotinylation Phosphoramidite for 5'-end-Labeling and Affinity Purification of Synthetic Oligonucleotides*, Nucleic Acids Res. Jan. 15, 2003; 31(2):708-715, DNA 3' End Biotinylation Kit, available from Thermo Scientific, the full disclosures of which are incorporated herein by reference in their entirety for all purposes). Likewise, protein and peptide biotinylation techniques have been developed and are readily available (See, e.g., U.S. Pat. No. 6,265,552, the full disclosures of which are incorporated herein by reference in their entirety for all purposes).

The reporter oligonucleotides may be provided having any of a range of different lengths, depending upon the diversity of reporter molecules desired or a given analysis, the sequence detection scheme employed, and the like. In some cases, these reporter sequences can be greater than about 5 nucleotides in length, greater than about 10 nucleotides in length, greater than about 20, 30, 40, 50, 60, 70, 80, 90, 100, 120, 150 or even 200 nucleotides in length. In some cases, these reporter nucleotides may be less than about 250 nucleotides in length, less than about 200, 180, 150, 120 100, 90, 80, 70, 60, 50, 40, or even 30 nucleotides in length. In many cases, the reporter oligonucleotides may be selected to provide barcoded products that are already sized, and otherwise configured to be analyzed on a sequencing system. For example, these sequences may be provided at a length that ideally creates sequenceable products of a desired length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample is incubated with the binding molecules and their associated reporter oligonucleotides, for any of the cell surface features desired to be analyzed. Following incubation, the cells are washed to remove unbound binding groups. Following washing, the cells are partitioned into separate partitions, e.g., droplets, along with the barcode carrying beads described above, where each partition includes a limited number of cells, e.g., in some cases, a single cell. Upon releasing the barcodes from the beads, they will prime the amplification and barcoding of the reporter oligonucleotides. As noted above, the barcoded replicates of the reporter molecules may additionally include functional sequences, such as primer sequences, attachment sequences or the like.

The barcoded reporter oligonucleotides are then subjected to sequence analysis to identify which reporter oligonucleotides bound to the cells within the partitions. Further, by also sequencing the associated barcode sequence, one can identify that a given cell surface feature likely came from the same cell as other, different cell surface features, whose reporter sequences include the same barcode sequence, i.e., they were derived from the same partition.

Based upon the reporter molecules that emanate from an individual partition based upon the presence of the barcode sequence, one may then create a cell surface profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

The present disclosure also provides methods for reducing nonspecific priming in a single-cell 5' gene expression assay. In generating an assay that allows measurement of 1) a cell barcode sequence (barcode), 2) a unique molecular identifier sequence (UMI) and 3) the 5' sequence of an mRNA transcript simultaneously, one strategy is to place these sequences on a sequence that attaches to the 5' end of an mRNA transcript—in the present disclosure, this may be accomplished by placing the barcode and UMI on a template switching oligonucleotide (TSO). This oligonucleotide may be attached to the first strand cDNA via a template switching reaction where the reverse transcription (RT) enzyme 1) reverse transcribes a messenger RNA (mRNA) sequence into first-strand complementary DNA (cDNA) from a primer targeting the 3' end of the mRNA, 2) adds nontemplated cytidines to the 5' end of the first-strand cDNA, 3) switches template to the TSO, which may contain 3' guanidines or guanidine-derivatives that hybridize to the added cytidines. The result is a first-strand cDNA molecule that is complementary to the TSO sequence: cell-barcode, UMI, guanidines, and the 5' end of the mRNA.

In some cases, the TSO may co-exist in solution with the RT enzyme and the total RNA contents of a cell. If the TSO is a single stranded DNA (ssDNA) molecule, it can participate as an RT primer rather than as a template-switching substrate. Given, for example, that the over 90% of the total RNA contents of a cell include noncoding ribosomal RNA (rRNA), this may produce barcoded off products that do not contribute to the 5' gene expression or V(D)J sequencing assay but do consume sequencing reads, increasing the cost required to achieve the same sequencing depth. In addition, if the UMI is implemented as a randomer, the presence of this randomer at the 3' end of the TSO greatly increases its ability to serve as a primer on rRNA template.

In some cases, a TSO that is less likely to serve as an RT primer via the introduction of a particular spacer sequence between the UMI and terminal riboGs may be used. Another approach is to design and include a set of auxiliary blocking oligonucleotides that may hybridize to rRNA and prevent binding of the TSO.

The spacer sequence can be optimized by selecting a sequence that minimizes the predicted melting temperature of the (spacer-GGG):rRNA duplex against all human ribosomal RNA molecules.

The blocker sequences can be optimized by selecting sequences that maximize the predicted melting temperature of the (blocker):rRNA duplex against all human ribosomal RNA molecules.

Provided herein are TSO that are less likely to serve as an RT primer via the introduction of a particular spacer sequence between the UMI and terminal riboGs. Additionally, described herein are auxiliary blocking oligonucleotides that hybridize to rRNA and prevent binding of the TSO.

Table 1 provides examples of spacer sequences that are optimized by selecting a sequence that minimizes the predicted melting temperature of the (spacer-GGG):rRNA duplex against all human ribosomal RNA molecules.

TABLE 1

| Spacer sequences | | SEQ ID NO |
|---|---|---|
| GG_S1_6 | TTATATGGG | |
| GG_S1_10 | TTTCTTATATGGG | 1 |
| GG_S1_20 | AAATCAAATCTTTCTTATATGGG | 2 |
| GG_S1_30 | ACAAACAAATAAATCAAATCTTTCTTATATGGG | 3 |
| GG_S2_6 | TTTAAAGGG | |
| GG_S2_10 | GAAATTTAAAGGG | 4 |

TABLE 1-continued

| Spacer sequences | | SEQ ID NO |
|---|---|---|
| GG_S2_20 | CACTCTACATGAAATTTAAAGGG | 5 |
| GG_S2_30 | CCAAAGTTGTCACTCTACATGAAATTTAAAGGG | 6 |
| GL6_S3_6 | ATATAAGGG | |
| GL6_S3_10 | ATATATATAAGGG | 7 |
| GL6_S3_20 | ATATATATATATATATATAAGGG | 8 |
| GL6_S3_30 | ATATATATATATATATATATATATATAAGGG | 9 |

Table 2 provides examples of blocker sequences that are optimized by selecting sequences that maximize the predicted melting temperature of the (blocker):rRNA duplex against all human ribosomal RNA molecules.

TABLE 2

| Blocker sequences | | SEQ ID NO |
|---|---|---|
| 28S_30_3130 | GCCGGCCGCCCCGGCGGCCGCCGCGCGGCC | 10 |
| 18S_30_254 | GCCGCCGGCGCCCGCCCCCCGGCCGGGGCC | 11 |
| 28S_30_2088 | GCGCGCGCGCGCCGCCCCCGCCGCTCCC | 12 |
| 28S_30_3284 | GGGGCGCGCCGCGCCGCCGCCGGGCTCCCC | 13 |
| 28S_30_834 | GCCGCCGCCACCGCCGCCGCCGCCGCCGCC | 14 |
| 28S_30_3373 | GCCCCGCCCCGCCGCCCGCCGACCGCCGCC | 15 |
| 28S_30_3473 | GCGGCCCCTCCGCCGCCTGCCGCCGCCGCC | 16 |
| 28S_30_4105 | GGAGCGGGTCGCGCCCGGCCGGGCGGGCGC | 17 |
| 28S_30_1129 | GCCCCGCCCCCCGACCCGCGCGCGGCACCC | 18 |
| 28S_30_3989 | GGCGGCCCGCAGGGCCGCGGACCCCGCCCC | 19 |
| 28S_30_4781 | GGCGGGGCACGCGCCCTCCCGCGGCGGGGC | 20 |
| 18S_30_1750 | GCCAGGGCCGTGGGCCGACCCCGGCGGGGC | 21 |
| 28S_30_611 | GTCCCCCGCCGACCCCACCCCCGGCCCCGC | 22 |
| 18S_30_693 | GGCTCGCCTCGCGGCGGACCGCCCGCCCGC | 23 |
| 28S_30_232 | GACCCGGGCGCGCGCCGGCCGCTACCGGCC | 24 |
| 28S_30_2919 | GCGCGCCTCGTCCAGCCGCGGCGCGCGCCC | 25 |
| 28S_30_1050 | GCGCCGTGGGAGGGGTGGCCCGGCCCCCCC | 26 |
| 28S_30_725 | GGGCCCCCCGAGCCACCTTCCCCGCCGGGC | 27 |
| 28S_30_2295 | GGCGGCTCCACCCGGGCCCGCGCCCTAGGC | 28 |
| 28S_30_3004 | GGCGCGGGGTGGGGAGGGAGCGAGCGGCGC | 29 |
| 28S_30_3547 | GCTAGGCGCCGGCCGAGGCGAGGCGCGCGC | 30 |
| 28S_30_115 | GTCCCGCGCCCCGCGGGGCGGGGATTCGGC | 31 |
| 28S_30_4858 | GGGGCGGCCGCCTTTCCGGCCGCGCCCCGT | 32 |

TABLE 2-continued

Blocker sequences

| | | SEQ ID NO |
|---|---|---|
| 28S_30_1451 | ACCTCCCCGGCGCGGCGGGCGAGACGGGCC | 33 |
| 28S_30_472 | GATCCGCCGGGCCGCCGACACGGCCGGACC | 34 |
| 28S_30_1246 | GCCGACCCCGTGCGCTCGCTCCGCCGTCCC | 35 |
| 28S_30_936 | GCGCGGCGACGGGTCTCGCTCCCTCGGCCC | 36 |
| 28S_30_3207 | GCCCGGCTCGCGTCCAGAGTCCGCGCCGCC | 37 |
| 28S_30_2578 | TCCCCGGGGCTCCCGCCGGCTTCTCCGGGA | 38 |
| 28S_30_1380 | ACCTCGGCCGGCGAGCGCGCCGGCCTTCAC | 39 |
| 28S_30_1791 | ACGCCCGGCTCCACGCCAGCGAGCCGGGCT | 40 |
| 28S_30_2684 | GCTCACCGGACGCCGCCGGAACCGCGACGC | 41 |
| 28S_30_2441 | TCGCCCGTCCCTTCGGAACGGCGCTCGCCC | 42 |
| 28S_30_1671 | GGGGTGCGTCGGGTCTGCGAGAGCGCCAGC | 43 |
| 28S_30_4696 | GGCCAACCGAGGCTCCGCGGCGCTGCCGTA | 44 |
| 18S_30_1551 | GTTACCCGCGCCTGCCGGCGTAGGGTAGGC | 45 |
| 28S_30_3634 | GCGTCAACACCCGCCGCGGGCCTTCGCGAT | 46 |
| 18S_30_827 | AGCTGCGGTATCCAGGCGGCTCGGGCCTGC | 47 |
| 28S_30_1883 | GCGTCGGCATCGGGCGCCTTAACCCGGCGT | 48 |
| 18S_30_1088 | GGGAATAACGCCGCCGCATCGCCGGTCGGC | 49 |
| 18S_30_923 | GCGGCGCAATACGAATGCCCCCGGCCGTCC | 50 |
| 28S_30_2755 | TGCTGCGGATATGGGTACGGCCCGGCGCGA | 51 |
| 18S_30_328 | GGGCAGACGTTCGAATGGGTCGTCGCCGCC | 52 |
| 18S_30_1207 | GCCGCAGGCTCCACTCCTGGTGGTGCCCTT | 53 |
| 18S_30_597 | ACCGCGGCTGCTGGCACCAGACTTGCCCTC | 54 |
| 18S_30_473 | GGGTCGGGAGTGGGTAATTTGCGCGCCTGC | 55 |
| 28S_30_1 | AGCGGGTCGCCACGTCTGATCTGAGGTCGC | 56 |
| 28S_30_3851 | TTCCCCGCTGATTCCGCCAAGCCCGTTCCC | 57 |
| 28S_30_1556 | TGCACGTCAGGACCGCTACGGACCTCCACC | 58 |
| 28S_30_1954 | AGCGGATTCCGACTTCCATGGCCACCGTCC | 59 |
| 28S_30_4608 | AGCTTCGCCCCATTGGCTCCTCAGCCAAGC | 60 |
| 28S_30_4971 | GATCGCAGCGAGGGAGCTGCTCTGCTACGT | 61 |
| 18S_30_1311 | GAACGGCCATGCACCACCACCCACGGAATC | 62 |
| 18S_30_1446 | TCTCGGGTGGCTGAACGCCACTTGTCCCTC | 63 |
| 18S_30_164 | GGGTCAGCGCCCGTCGGCATGTATTAGCTC | 64 |
| 28S_30_4191 | TCCTCCCTGAGCTCGCCTTAGGACACCTGC | 65 |
| 18S_30_400 | GGAATCGAACCCTGATTCCCCGTCACCCGT | 66 |
| 18S_30_1679 | ACGGGCGGTGTGTACAAAGGGCAGGGACTT | 67 |
| 28S_30_2827 | TACGGATCCGGCTTGCCGACTTCCCTTACC | 68 |
| 18S_30_46 | ACCGGCCGTGCGTACTTAGACATGCATGGC | 69 |

TABLE 2-continued

Blocker sequences

| | | SEQ ID NO |
|---|---|---|
| 28S_30_3716 | GTCATAGTTACTCCCGCCGTTTACCCGCGC | 70 |
| 18S_30_1837 | GATCCTTCCGCAGGTTCACCTACGGAAACC | 71 |
| 28S_30_4484 | TCACGACGGTCTAAACCCAGCTCACGTTCC | 72 |
| 28S_30_4273 | GGCCCCGCTTTCACGGTCTGTATTCGTACT | 73 |
| 28S_30_328 | GTACTTGTTGACTATCGGTCTCGTGCCGGT | 74 |
| 28S_30_2368 | GGAACCCTTCTCCACTTCGGCCTTCAAAGT | 75 |
| 28S_30_401 | ACCCGTTTACCTCTTAACGGTTTCACGCCC | 76 |
| 18S_30_1017 | GAACCTCCGACTTTCGTTCTTGATTAATGA | 77 |
| 28S_50_3116 | GCCCCCGCCGGCCGCCCCGGCGGCCGCCGCGCG GCCCCTGCCGCCCCGAC | 78 |
| 28S_50_823 | GCCCCCGCCGCCGCCGCCACCGCCGCCGCCGCC GCCGCCCCGACCCGCGC | 79 |
| 28S_50_3463 | GGACCGGCCCGCGGCCCCTCCGCCGCCTGCCGC CGCCGCCGCCGCGCGCC | 80 |
| 28S_50_3353 | GCCCCGCCCCGCCGCCCGCCGACCGCCGCCGCC CGACCGCTCCCGCCCCC | 81 |
| 28S_50_1113 | GTCCGCCCCGCCCCCCGACCCGCGCGCGGCACC CCCCCCGTCGCCGGGGC | 82 |
| 28S_50_4779 | ACCCCGGTCCCGGCGCGCGGCGGGGCACGCGCC CTCCCGCGGCGGGGCGC | 83 |
| 28S_50_569 | GGCCCCGCCCGCCCACCCCCGCACCCGCCGGAG CCCGCCCCCTCCGGGGA | 84 |
| 28S_50_3969 | GGCGGCCCGCAGGGCCGCGGACCCCGCCCCGGG CCCCTCGCGGGGACACC | 85 |
| 28S_50_2094 | GCCGCCCTCCGACGCACACCACACGCGCGCGCG CGCGCGCCGCCCCCGCC | 86 |
| 28S_50_2904 | GGGGCGCGCGCCTCGTCCAGCCGCGGCGCGCGC CCAGCCCCGCTTCGCGC | 87 |
| 18S_50_235 | AGCCGCCGGCGCCCGCCCCCCGGCCGGGGCCGG AGAGGGGCTGACCGGGT | 88 |
| 18S_50_690 | GGGCGGGGACGGGCGGTGGCTCGCCTCGCGGCG GACCGCCCGCCCGCTCC | 89 |
| 28S_50_3189 | GGGCCCGGCTCGCGTCCAGAGTCCGCGCCGCCG CCGGCCCCCCGGGTCCC | 90 |
| 28S_50_4097 | GGCACTGTCCCCGGAGCGGGTCGCGCCCGGCCG GGCGGGCGCTTGGCGCC | 91 |
| 28S_50_1030 | GCGCCGTGGGAGGGGTGGCCCGGCCCCCCCACG AGGAGACGCCGGCGCGC | 92 |
| 28S_50_1434 | TCCACCTCCCCGGCGCGGCGGGCGAGACGGGCC GGTGGTGCGCCCTCGGC | 93 |
| 28S_50_687 | TCCCCGCCGGGCCTTCCCAGCCGTCCCGGAGCC GGTCGCGGCGCACCGCC | 94 |
| 28S_50_3534 | GTCGGCTGCTAGGCGCCGGCCGAGGCGAGGCGC GCGCGGAACCGCGGCCC | 95 |
| 28S_50_207 | GGGCGCGCGCCGGCCGCTACCGGCCTCACACCG TCCACGGGCTGGGCCTC | 96 |

TABLE 2-continued

| Blocker sequences | | SEQ ID NO |
|---|---|---|
| 28S_50_1187 | GGGACGCGCGCGTGGCCCCGAGAGAACCTCCCCCGGGCCCGACGGCGCGA | 97 |
| 28S_50_461 | GGCGGGAAAGATCCGCCGGGCCGCCGACACGGCCGGACCCGCCGCCGGGT | 98 |
| 18S_50_1750 | GACCGTCTTCTCAGCGCTCCGCCAGGGCCGTGGGCCGACCCCGGCGGGGC | 99 |
| 28S_50_131 | AGCGGCGCCGGGGAGCGGGTCTTCCGTACGCCACATGTCCCGCGCCCCGC | 100 |
| 28S_50_2240 | GGCTCACCGCAGCGGCCCTCCTACTCGTCGCGGCGTAGCGTCCGCGGGGC | 101 |
| 28S_50_916 | GCGCGGCGACGGGTCTCGCTCCCTCGGCCCCGGGATTCGGCGAGTGCTGC | 102 |
| 28S_50_1360 | ACCTCGGCCGGCGAGCGCGCCGGCCTTCACCTTCATTGCGCCACGGCGGC | 103 |
| 28S_50_2442 | GGCCGAGGGCAACGGAGGCCATCGCCCGTCCCTTCGGAACGGCGCTCGCC | 104 |
| 28S_50_4678 | GAGGCCAACCGAGGCTCCGCGGCGCTGCCGTATCGTTCGCCTGGGCGGGA | 105 |
| 28S_50_2665 | AGCTCACCGGACGCCGCCGGAACCGCGACGCTTTCCAAGGCACGGGCCCC | 106 |
| 28S_50_1259 | TCAAGACGGGTCGGGTGGGTAGCCGACGTCGCCGCCGACCCCGTGCGCTC | 107 |
| 28S_50_2560 | TCTCCCCGGGGCTCCCGCCGGCTTCTCCGGGATCGGTCGCGTTACCGCAC | 108 |
| 18S_50_1085 | GCTGCCCGGCGGGTCATGGGAATAACGCCGCCGCATCGCCGGTCGGCATC | 109 |
| 28S_50_1796 | GTGGCCCACTAGGCACTCGCATTCCACGCCCGGCTCCACGCCAGCGAGCC | 110 |
| 28S_50_2020 | GCGACGGCCGGGTATGGGCCCGACGCTCCAGCGCCATCCATTTTCAGGGC | 111 |
| 18S_50_1509 | GGGTAGGCACACGCTGAGCCAGTCAGTGTAGCGCGCGTGCAGCCCCGGAC | 112 |
| 28S_50_1875 | GGGGTCTGATGAGCGTCGGCATCGGGCGCCTTAACCCGGCGTTCGGTTCA | 113 |
| 28S_50_3635 | GCACTGGGCAGAAATCACATCGCGTCAACACCCGCCGCGGGCCTTCGCGA | 114 |
| 28S_50_2757 | GAGGCTGTTCACCTTGGAGACCTGCTGCGGATATGGGTACGGCCCGGCGC | 115 |
| 18S_50_469 | TCGTCACTACCTCCCCGGGTCGGGAGTGGGTAATTTGCGCGCCTGCTGCC | 116 |
| 28S_50_4889 | GAATGGTTTAGCGCCAGGTTCCCCACGAACGTGCGGTGCGTGACGGGCGA | 117 |
| 28S_50_1646 | GCGTCGGGTCTGCGAGAGCGCCAGCTATCCTGAGGGAAACTTCGGAGGGA | 118 |
| 28S_50_1557 | ACCCAGGTCGGACGACCGATTTGCACGTCAGGACCGCTACGGACCTCCAC | 119 |
| 18S_50_376 | TCGAACCCTGATTCCCCGTCACCCGTGGTCACCATGGTAGGCACGGCGAC | 120 |
| 28S_50_3831 | TTCCCCGCTGATTCCGCCAAGCCCGTTCCCTTGGCTGTGGTTTCGCTGGA | 121 |

TABLE 2-continued

| Blocker sequences | | SEQ ID NO |
|---|---|---|
| 18S_50_903 | GCGGCGCAATACGAATGCCCCCGGCCGTCCCTCTTAATCATGGCCTCAGT | 122 |
| 18S_50_1223 | GGGCCGGGTGAGGTTTCCCGTGTTGAGTCAAATTAAGCCGCAGGCTCCAC | 123 |
| 18S_50_827 | GGTCCTATTCCATTATTCCTAGCTGCGGTATCCAGGCGGCTCGGGCCTGC | 124 |
| 18S_50_595 | GCTATTGGAGCTGGAATTACCGCGGCTGCTGGCACCAGACTTGCCCTCCA | 125 |
| 28S_50_4172 | GTCCTCCCTGAGCTCGCCTTAGGACACCTGCGTTACCGTTTGACAGGTGT | 126 |
| 18S_50_1307 | TCGCTCCACCAACTAAGAACGGCCATGCACCACCACCCACGGAATCGAGA | 127 |
| 28S_50_4967 | GGGCTGACTTTCAATAGATCGCAGCGAGGGAGCTGCTCTGCTACGTACGA | 128 |
| 28S_50_1948 | GTTACACACTCCTTAGCGGATTCCGACTTCCATGGCCACCGTCCTGCTGT | 129 |
| 28S_50_4602 | ATCCCACAGATGGTAGCTTCGCCCCATTGGCTCCTCAGCCAAGCACATAC | 130 |
| 18S_50_46 | GCCATTCGCAGTTTCACTGTACCGGCCGTGCGTACTTAGACATGCATGGC | 131 |
| 18S_50_1669 | GGTAGTAGCGACGGGCGGTGTGTACAAAGGGCAGGGACTTAATCAACGCA | 132 |
| 28S_50_390 | GCGGACCCCACCCGTTTACCTCTTAACGGTTTCACGCCCTCTTGAACTCT | 133 |
| 28S_50_2312 | TTGAATATTTGCTACTACCACCAAGATCTGCACCTGCGGCGGCTCCACCC | 134 |
| 28S_50_2832 | TTAGAGCCAATCCTTATCCCGAAGTTACGGATCCGGCTTGCCGACTTCCC | 135 |
| 28S_50_288 | TCGTGCCGGTATTTAGCCTTAGATGGAGTTTACCACCCGCTTTGGGCTGC | 136 |
| 28S_50_3718 | GGCATTTGGCTACCTTAAGAGAGTCATAGTTACTCCCGCCGTTTACCCGC | 137 |
| 28S_50_4472 | AACCTGTCTCACGACGGTCTAAACCCAGCTCACGTTCCCTATTAGTGGGT | 138 |
| 18S_50_144 | GGGTCAGCGCCCGTCGGCATGTATTAGCTCTAGAATTACCACAGTTATCC | 139 |
| 28S_50_4252 | GCCCCGCTTTCACGGTCTGTATTCGTACTGAAAATCAAGATCAAGCGAGC | 140 |
| 28S_50_9 | TCCTCCGCTGACTAATATGCTTAAATTCAGCGGGTCGCCACGTCTGATCT | 141 |
| 18S_50_1438 | GTTATTGCTCAATCTCGGGTGGCTGAACGCCACTTGTCCCTCTAAGAAGT | 142 |
| 28S_50_1723 | TGAGAATAGGTTGAGATCGTTTCGGCCCCAAGACCTCTAATCATTCGCTT | 143 |
| 18S_50_1003 | GTCTTCGAACCTCCGACTTTCGTTCTTGATTAATGAAAACATTCTTGGCA | 144 |

Table 3 provides examples of full construct barcodes.

TABLE 3

| Full construct barcodes | | |
|---|---|---|
| | | SEQ ID NO |
| P7 no UMI | CAAGCAGAAGACGGCATACGAGATXXXXXXGTXXXXXXGTGACTGGAGTTCAGACGTGTGCTCTTCCGATCTrGrGrG | 145 |
| P7 early UMI | CAAGCAGAAGACGGCATACGAGATNNNNNNNNNNXXXXXXGTXXXXXXGTGACTGGAGTTCAGACGTGTGCTCTTCCGATCTrGrGrG | 146 |
| P5 no UMI | AATGATACGGCGACCACCGAGATCTACACXXXXXXGTXXXXXXACACTCTTTCCCTACACGACGCTCTTCCGATCTrGrGrG | 147 |
| P5 early UMI | AATGATACGGCGACCACCGAGATCTACACNNNNNNNNNNXXXXXXGTXXXXXXACACTCTTTCCCTACACGACGCTCTTCCGATCTrGrGrG | 148 |
| R1 inline no UMI | CTACACGACGCTCTTCCGATCTXXXXXXGTXXXXXXrGrGrG | 149 |
| R1 inline late UMI | CTACACGACGCTCTTCCGATCTXXXXXXGTXXXXXXNNNNNNNNNNrGrGrG | 150 |
| R1 late UMI AT rich | CTACACGACGCTCTTCCGATCTXXXXXXGTXXXXXX(N1:25252525)N1N1N1N1(N2:40101040)N2N2WWrGrGrG | 151 |
| R1 inline early UMI | CTACACGACGCTCTTCCGATCTNNNNNNNNNNXXXXXXGTXXXXXXrGrGrG | 152 |
| R1 inline late UMI Spacer 2 | CTACACGACGCTCTTCCGATCTXXXXXXGTXXXXXXNNNNNNNNNNATrGrGrG | 153 |
| R1 inline late UMI Spacer 4 | CTACACGACGCTCTTCCGATCTXXXXXXGTXXXXXXNNNNNNNNNNACATrGrGrG | 154 |
| R1 inline late UMI Spacer 6 | CTACACGACGCTCTTCCGATCTXXXXXXGTXXXXXXNNNNNNNNNNTAACATrGrGrG | 155 |
| R1 inline late UMI Spacer 8 | CTACACGACGCTCTTCCGATCTXXXXXXGTXXXXXXNNNNNNNNNNCGTAACATrGrGrG | 156 |
| R1 inline late UMI Spacer 10 | CTACACGACGCTCTTCCGATCTXXXXXXGTXXXXXXNNNNNNNNNNACCGTAACATrGrGrG | 157 |
| R1 inline late UMI Full Spacer | CTACACGACGCTCTTCCGATCTXXXXXXGTXXXXXXNNNNNNNNNNACACAAGAGGCACGCGTAACATrGrGrG | 158 |

X represents nucleotides that make up the barcode sequence. All oligos on one bead can have the same barcode sequence, oligos on different beads may have different barcode sequences.
N and W represent any of {A,C,G,T} and any of {A,T} respectively that make up the UMI sequence. UMIs may be different across different oligos on the same bead.
N1 is any one of {A,C,G,T}; N1 positions with ratios of 25%, 25%, 25% and 25% for the four nucleotides.
N2 is any one of {A,C,G,T}; N2 positions with ratios of 40%, 10%, 10% and 40% for the four nucleotides.

In some examples, a cell barcode may be a 16 base sequence that is a random choice from about 737,000 sequences. The length of the barcode (16) can be altered. The diversity of potential barcode sequences (737 k) can be alterable. The defined nature of the barcode can be altered, for example, it may also be completely random (16 Ns) or semi-random (16 bases that come from a biased distribution of nucleotides).

The canonical UMI sequence may be a 10 nucleotide randomer. The length of the UMI can be altered. The random nature of the UMI can be altered, for example, it may be semi-random (bases that come from a biased distribution of nucleotides.) In a certain case, the distribution of UMI nucleotide(s) may be biased; for example, UMI sequences that do not contain Gs or Cs may be less likely to serve as primers.

The spacer may alterable within given or predetermined parameters. For example one method may give an optimal sequence of TTTCTTATAT (SEQ ID NO: 159), but using a slightly different optimization strategy results in a sequence that is likely just as or nearly as good.

The selected template switching region can comprise 3 consecutive riboGs or more. The selected template switching region can comprise 4, 5, 6, 7, 8, 9, 10, 11, 12, 13, 14, 15, 16, 17, 18, 19, 20 consecutive riboGs or more. Alternative nucleotide may be used such as deoxyribo Gs, LNA G's, and potentially any combination thereof.

The present disclosure also provides methods of enriching cDNA sequences. Enrichment may be useful for TCR, BCR, and immunoglobulin gene analysis since these genes may possess similar yet polymorphic variable region sequences. These sequences can be responsible for antigen binding and peptide-MHC interactions. For example, due to gene recombination events in individual developing T cells, a single human or mouse will naturally express many thousands of different TCR genes. This T cell repertoire can exceed 100,000 or more different TCR rearrangements occurring during T cell development, yielding a total T cell population that is highly polymorphic with respect to its TCR gene sequences especially for the variable region. For immunoglobulin genes, the same may apply, except even greater diversity may be present. As previously noted, each distinct sequence may correspond to a clonotype. In certain embodiments, enrichment increases accuracy and sensitivity of methods for sequencing TCR, BCR and immunoglobulin genes at a single cell level. In certain embodiments, enrichment increases the number of sequencing reads that map to a TCR, BCR, or immunoglobulin gene. In some embodiments, enrichment leads to greater than or equal to 25%, 30%, 35%, 40%, 45%, 50%, 55%, 60%, 65%, 70%, 75%, 80%, 85%, 90%, 95% or more of total sequencing reads mapping to a TCR, BCR or immunoglobulin gene. In some embodiments, enrichment leads to greater than or equal to 25%, 30%, 35%, 40%, 45%, 50%, 55%, 60%, 65%, 70%, 75%, 80%, 85%, 90%, 95% or more of total sequencing reads mapping to a variable region of a TCR, BCR or immunoglobulin gene.

In order to aide in sequencing, detection, and analysis of sequences of interest, an enrichment step can be employed. Enrichment may be useful for the sequencing and analysis of genes that may be related yet highly polymorphic. In some embodiments, an enriched gene comprises a TCR sequence, a BCR sequence, or an immunoglobulin sequence. In some embodiments, an enriched gene comprises a mitochondrial gene or a cytochrome family gene. In some embodiments, enrichment is employed after an initial round of reverse transcription (e.g., cDNA production). In some embodiments, enrichment is employed after an initial round of reverse transcription and cDNA amplification for at least 5, 10, 15, 20, 25, 30, 40 or more cycles. In some embodiments, enrichment is employed after a cDNA amplification. In some embodiments, the amplified cDNA can be subjected to a clean up step before the enrichment step using a column, gel extraction, or beads in order to remove unincorporated primers, unincorporated nucleotides, very short or very long nucleic acid fragments and enzymes. In some embodiments, enrichment is followed by a clean-up step before sequencing library preparation.

Enrichment of gene or cDNA sequences can be facilitated by a primer that anneals within a known sequence of the target gene. In some embodiments, for enrichment of a TCR, BCR, or immunoglobulin gene, a primer that anneals to a constant region of the gene or cDNA can be paired with a sequencing primer that anneals to a TSO functional sequence. In some embodiments, the enriched cDNA falls into a length range that approximately corresponds to that genes variable region. In some embodiments, greater than about 50%, 60%, 70%, 80%, 85%, 90%, 95% or more cDNA or cDNA fragments fall within a range of about 300 base pairs to about 900 base pairs, of about 400 base pairs to about 800 base pairs, of about 500 base pairs to about 700 base pairs, or of about 500 base pairs to about 600 base pairs.

Figure 20:
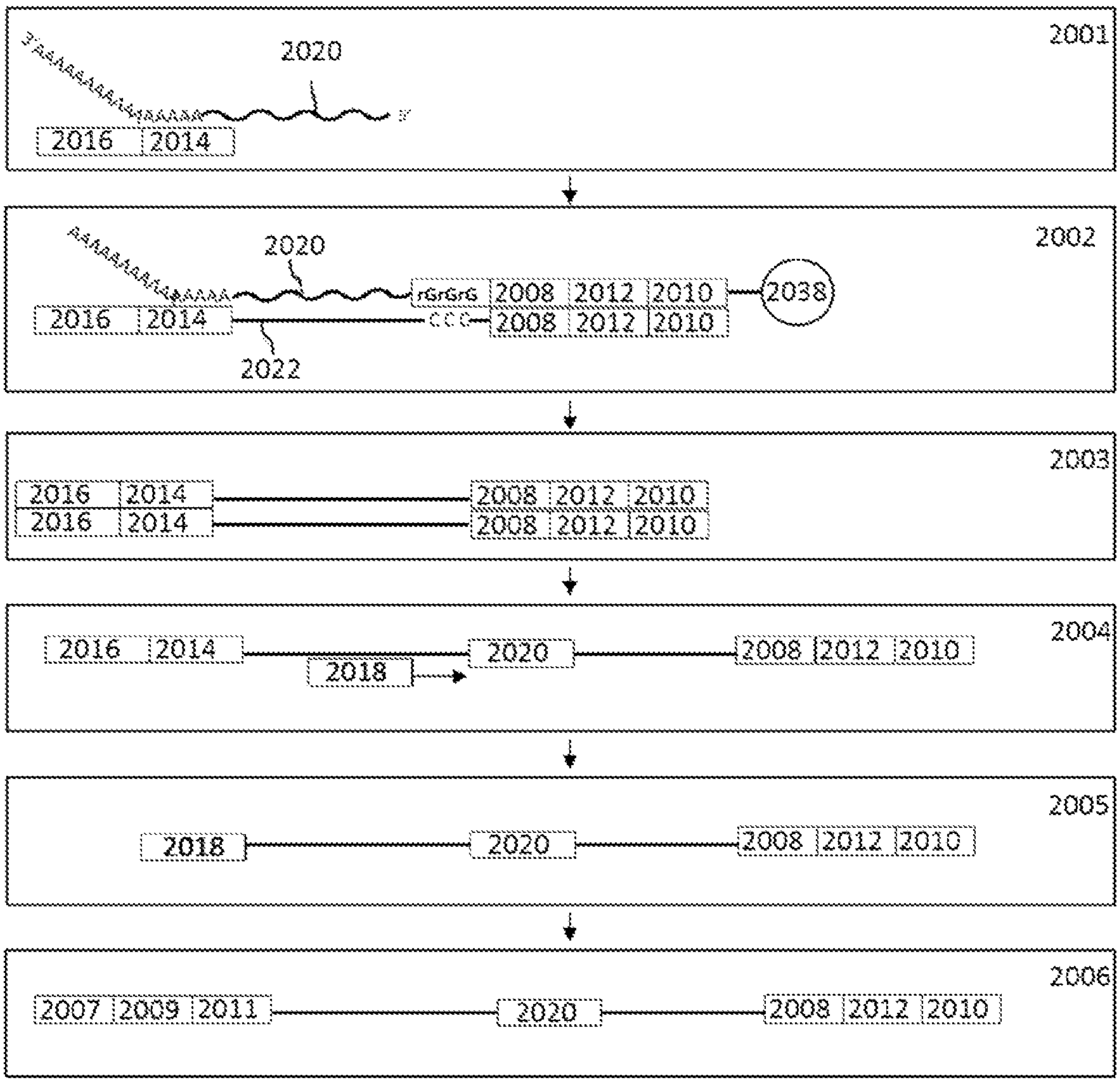
FIG. 20 shows a schematic for enriching VDJ sequences from immune molecules such as TCRs, BCRs, and immunoglobulins.

FIG. 20 shows an example enrichment scheme. In operation 2001, an oligonucleotide with a poly-T sequence 2014, and in some cases an additional sequence 2016 that binds to, for example, a sequencing or PCR primer, anneals to a target RNA 2020. In operation 2002 the oligonucleotide is extended yielding an anti-sense strand 2022 which is appended by multiple cytidines on the 3' end. A template switching oligonucleotide attached to a gel bead 2038 is provided and a riboG of the TSO pairs with the cytidines of the sense strand and is extended to create a sense and an antisense strand. In some cases, the template switching oligonucleotide is released from the gel bead during extension. In some cases, the template switching oligonucleotide is released from the gel bead prior to extension. In some cases, the template switching oligonucleotide is released from the gel bead after extension. In addition to the riboG sequence, the TSO comprises a barcode 2012 and one or two additional functional sequences 2008 and 2012. The additional functional sequences can comprise a P7 or R2 sequence for attachment to an Illumina sequencing flow cell, for example. Operations 2001 and 2002 may be performed in a partition (e.g., droplet or well). Subsequent to operation 2002, the nucleic acid product from operations 2001 and 2002 may be removed from the partition and in some cases pooled with other products from other partitions for subsequent processing.

Next, additional functional sequences can be added that allow for amplification or sample identification. This may occur in a partition or in bulk. This reaction yields amplified cDNA molecules as in 2003 which are mixed templates comprising a barcode and sequencing primers. In some cases, not all of these cDNA molecules will comprise a target variable region sequence. In one enrichment scheme, shown in operation 2004, a primer 2018 that anneals to a sequence 3' of a TCR, BCR or immunoglobulin variable region 2020 specifically amplifies the variable region comprising cDNAs yielding products as shown in operation 2005. Such enrichment may be performed for various approaches described herein, such as, e.g., the approaches described above in the context of FIGS. 19A and 19B.

Figure 21A:
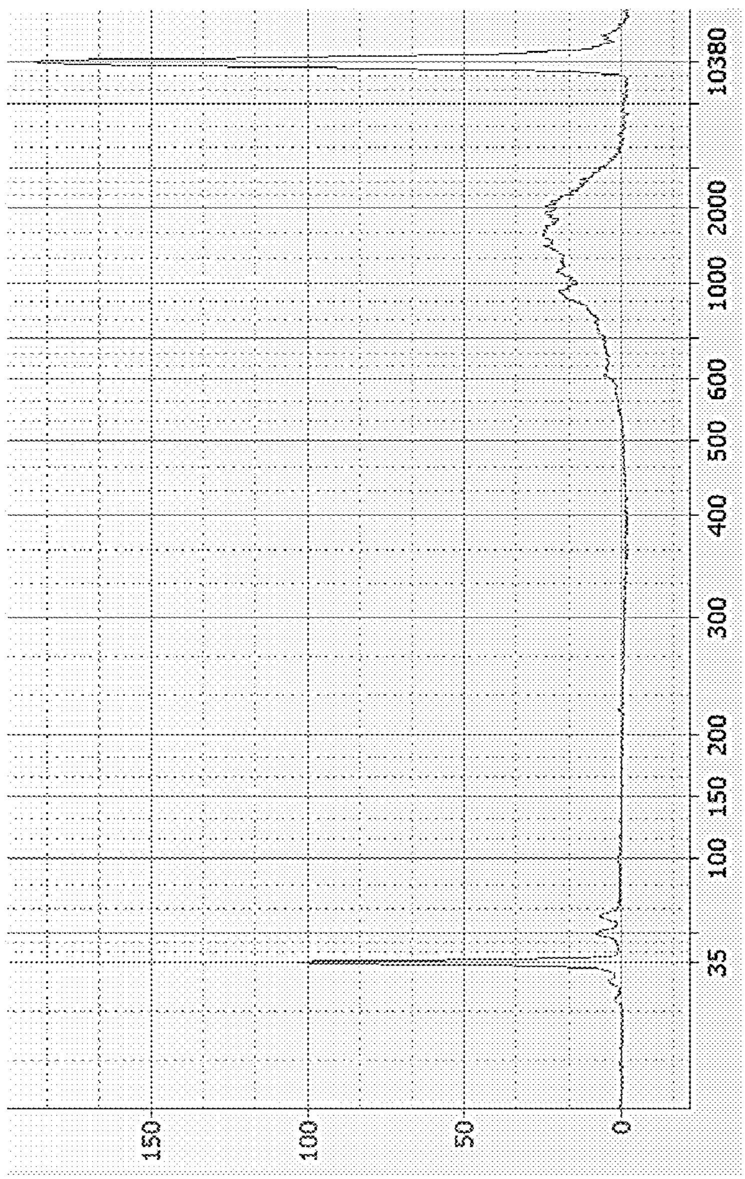
FIGS. 21A-21C show enrichment of target sequences (FIG. 21A) after cDNA amplification, (FIG. 21B) after enrichment, and (FIG. 21C) after sequencing library preparation.
Figure 21B:
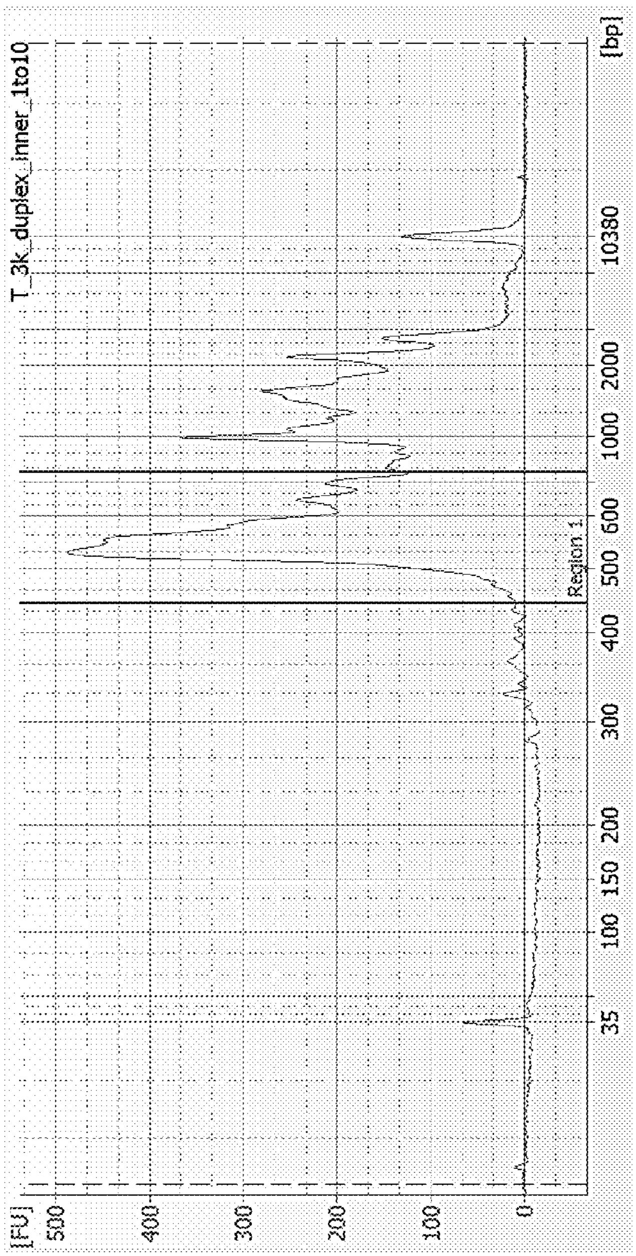
Figure 21C:
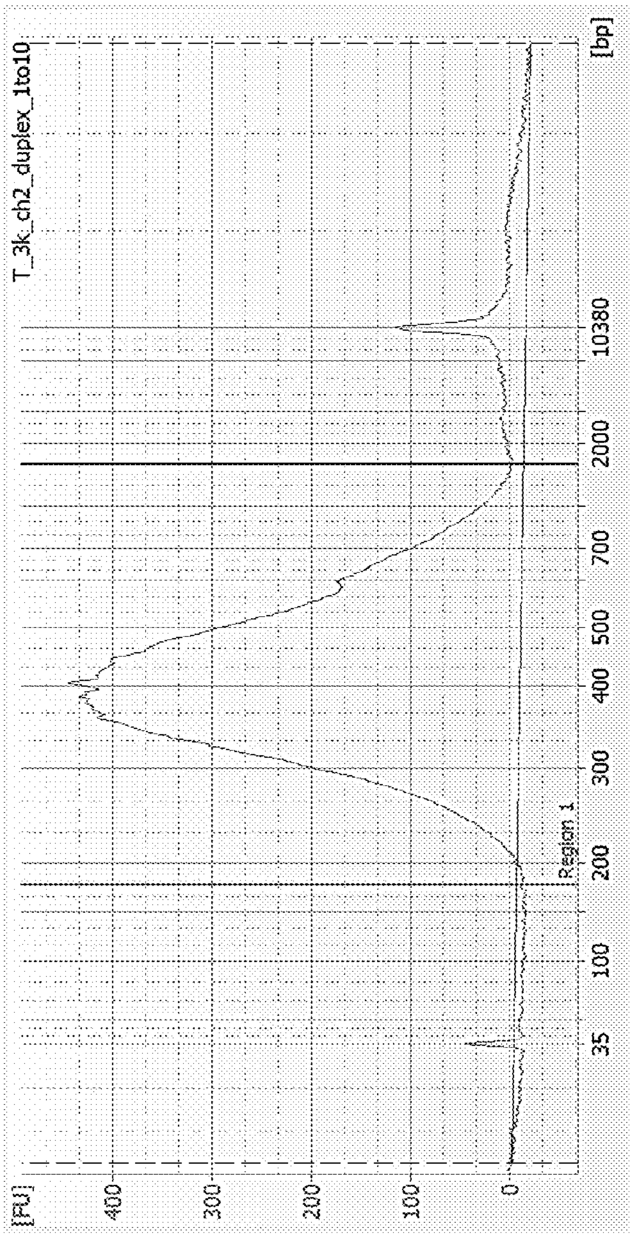

In certain aspects, primer 2018 anneals in a constant region of a TCR (e.g., TCR-alpha or TCR-beta), BCR or immunoglobulin gene. After amplification the products are sheared, adaptors ligated and amplified a second time to add additional functional sequences 2007 and 2011 and a sample index 2009 as shown in operation 2006. The additional functional sequences can functionally complement the first pair 2008 and 2010 and comprise for example a P5 or R1 sequence. FIG. 21 shows example size distributions after cDNA amplification but before enrichment (A), after enrichment but before sequencing library prep (B), and after sequencing library preparation (C). In some embodiments, the initial poly-T primer, comprising sequences 2016 and 2014 can be attached to a gel bead as opposed to the TSO. In some embodiments, the poly-T comprising primer comprises functional sequences and barcode sequences 2008, 2010, 2012, and the TSO comprises sequence 2016. Operations 2003-2006 may be performed in bulk.

In some embodiments, clonotype information derived from next-generation sequencing data of cDNA prepped from cellular RNA is combined with other targeted on non targeted cDNA enrichment to illuminate functional and ontological aspects of B-cell and T cells that express a given TCR, BCR, or immunoglobulin. In some embodiments, clonotype information is combined with analysis of expression of an immunologically relevant cDNA. In some embodiments, the cDNA encodes a cell lineage marker, a cell surface functional marker, immunoglobulin isotype, a cytokine and/or chemokine, an intracellular signaling polypeptide, a cell metabolism polypeptide, a cell-cycle polypeptide, an apoptosis polypeptide, a transcriptional activator/inhibitor, an miRNA or lncRNA.

Also disclosed herein are methods and systems for reference-free clonotype identification. Such methods may be implemented by way of software executing algorithms. Tools for assembling T-cell Receptor (TCR) sequences may use known sequences of V and C regions to "anchor" assemblies. This may make such tools only applicable to organisms with well characterized references (human and mouse). However, most mammalian T cell receptors have similar amino acid motifs and similar structure. In the absence of a reference, a method can scan assembled transcripts for regions that are diverse or semi-diverse, find the junction region which should be highly diverse, then scan for known amino acid motifs. In some cases, it may not be critical that the complementary CDRs, such as the CDR1, CDR2, or CDR3, region be accurately delimited, only that a diverse sequence is found that can uniquely identify the clonotype. One advantage of this method is that the software may not require a set of reference sequences and can operate fully de novo, thus this method can enable immune research in eukaryotes with poorly characterized genomes/transcriptomes.

The methods described herein allow simultaneously obtaining single-cell gene expression information with single-cell immune receptor sequences (TCRs/BCRs). This can be achieved using the methods described herein, such as by amplifying genes relevant to lymphocyte function and state (either in a targeted or unbiased way) while simultaneously amplifying the TCR/BCR sequences for clonotyping. This can allow such applications as 1) interrogating changes in lymphocyte activation/response to an antigen, at the single clonotype or single cell level; or 2) classifying lymphocytes into subtypes based on gene expression while simultaneously sequencing their TCR/BCRs. UMIs are typically ignored during TCR (or generally transcriptome) assembly.

Key analytical operations involved in clonotype sequencing according to the methods described herein include: 1) Assemble each UMI separately, then merge highly similar assembled sequences. High depth per molecule in TCR sequencing makes this feasible. This may result in a reduced chance of "chimeric" assemblies; 2) Assemble all UMIs from each cell together but use UMI information to choose paths in the assembly graph. This is analogous to using barcode and read-pair information to resolve "bubbles" in WGS assemblies; 3) Base quality estimation. UMI information and alignment of short reads may be used to assemble contigs to compute per-base quality scores. Base quality scoring may be important as a few base differences in a CDR sequence may differentiate one clonotype from another. This may be in contrast to other methods that rely on using long-read sequencing.

Thus, base quality estimates for assembled contigs can inform clonotype inference. Errors can make cells with the same (real) clonotype have mismatching assembled sequences. Further, combining base-quality estimates and clonotype abundances to correct clonotype assignments. For example, if 10 cells have clonotype X and one cell has a clonotype that differs by X in only a few bases and these bases have low quality, then this cell may be assigned to clonotype X. In some embodiments, clonotypes that differ by a single amino acid or nucleic acid may be discriminated. In some embodiments, clonotypes that differ by less than 50, 40, 30, 20, 15, 10, 9, 8, 7, 6, 5, 4, 3, or 2 amino acids or nucleic acids may be discriminated. An example, non limiting, base error calculation scheme is shown below in Example VII.

Also provided herein are the microfluidic devices used for partitioning the cells as described above. Such microfluidic devices can comprise channel networks for carrying out the partitioning process like those set forth in FIGS. 1 and 2. Briefly, these microfluidic devices can comprise channel networks, such as those described herein, for partitioning cells into separate partitions, and co-partitioning such cells with oligonucleotide barcode library members, e.g., disposed on beads. These channel networks can be disposed within a solid body, e.g., a glass, semiconductor or polymer body structure in which the channels are defined, where those channels communicate at their termini with reservoirs for receiving the various input fluids, and for the ultimate deposition of the partitioned cells, etc., from the output of the channel networks. By way of example, and with reference to FIG. 2, a reservoir fluidly coupled to channel 202 may be provided with an aqueous suspension of cells 214, while a reservoir coupled to channel 204 may be provided with an aqueous suspension of beads 216 carrying the oligonucleotides. Channel segments 206 and 208 may be provided with a non-aqueous solution, e.g., an oil, into which the aqueous fluids are partitioned as droplets at the channel junction 212. Finally, an outlet reservoir may be fluidly coupled to channel 210 into which the partitioned cells and beads can be delivered and from which they may be harvested. As will be appreciated, while described as reservoirs, it will be appreciated that the channel segments may be coupled to any of a variety of different fluid sources or receiving components, including tubing, manifolds, or fluidic components of other systems.

Also provided are systems that control flow of these fluids through the channel networks e.g., through applied pressure differentials, centrifugal force, electrokinetic pumping, capillary or gravity flow, or the like.

Also provided herein are kits for analyzing individual cells or small populations of cells. The kits may include one, two, three, four, five or more, up to all of partitioning fluids, including both aqueous buffers and non-aqueous partitioning fluids or oils, nucleic acid barcode libraries that are releasably associated with beads, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

Figure 17:
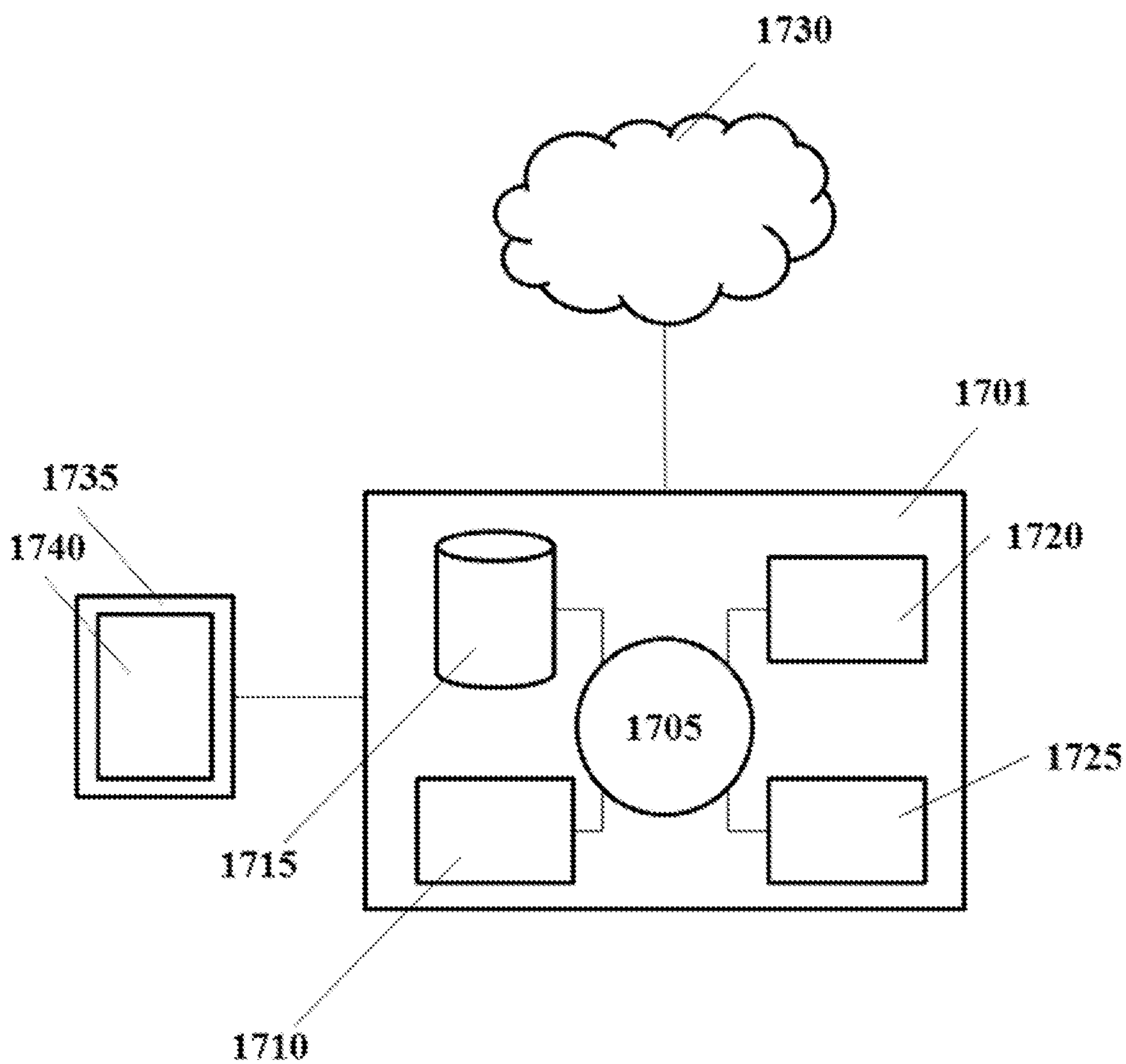
FIG. 17 shows an example computer control system that is programmed or otherwise configured to implement methods provided herein.

The present disclosure provides computer control systems that are programmed to implement methods of the disclosure. FIG. 17 shows a computer system 1701 that is programmed or otherwise configured to implement methods of the disclosure including nucleic acid sequencing methods, interpretation of nucleic acid sequencing data and analysis of cellular nucleic acids, such as RNA (e.g., mRNA), and characterization of cells from sequencing data. The computer system 1701 can be an electronic device of a user or a computer system that is remotely located with respect to the electronic device. The electronic device can be a mobile electronic device.

The computer system 1701 includes a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are external to the computer system 1701, such as located on a remote server that is in communication with the computer system 1701 through an intranet or the Internet.

The computer system 1701 can communicate with one or more remote computer systems through the network 1730. For instance, the computer system 1701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, results of nucleic acid sequencing, analysis of nucleic acid sequencing data, characterization of nucleic acid sequencing samples, cell characterizations, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705. The algorithm can, for example, initiate nucleic acid sequencing, process nucleic acid sequencing data, interpret nucleic acid sequencing results, characterize nucleic acid samples, characterize cells, etc.

EXAMPLES

The following non-limiting examples are given for the purpose of illustrating various embodiments of present disclosure.

Example I. Cellular RNA Analysis Using Emulsions

In an example, reverse transcription with template switching and cDNA amplification (via PCR) is performed in emulsion droplets with operations as shown in FIG. 9A. The reaction mixture that is partitioned for reverse transcription and cDNA amplification (via PCR) includes 1,000 cells or 10,000 cells or 10 ng of RNA, beads bearing barcoded oligonucleotides/0.2% Tx-100/5× Kapa buffer, 2× Kapa HS HiFi Ready Mix, 4 μM switch oligo, and Smartscribe. Where cells are present, the mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are purified with Dynabeads and 0.6×SPRI as in operation 956.

Figure 13A:
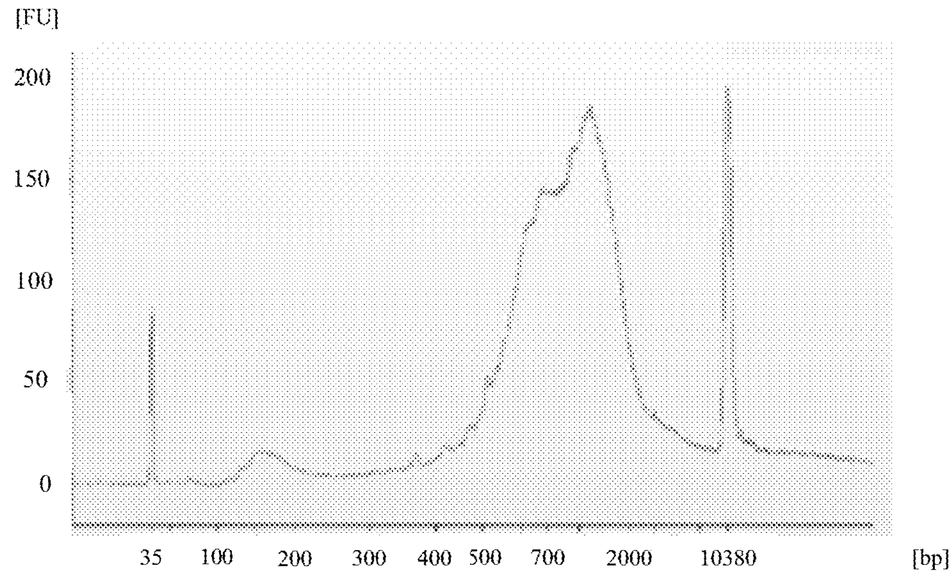
FIGS. 13A-13C provide illustrations of example yields from template switch reverse transcription and PCR in partitions.
Figure 13B:
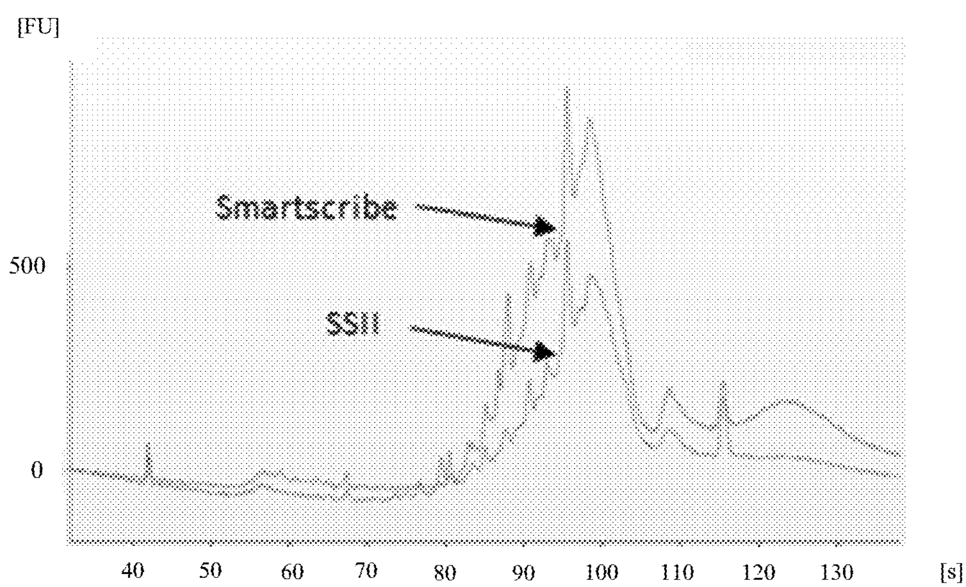
Figure 13C:
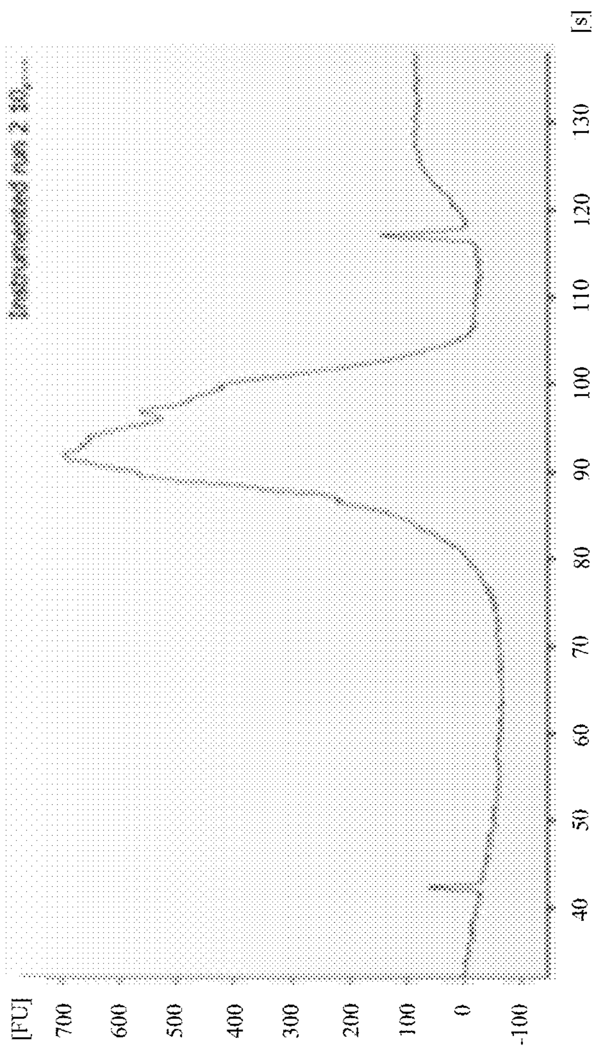

The yield from template switch reverse transcription and PCR in emulsions is shown for 1,000 cells in FIG. 13A and 10,000 cells in FIG. 13C and 10 ng of RNA in FIG. 13B (Smartscribe line). The cDNA transcripts from RT and PCR performed in emulsions for 10 ng RNA is sheared and ligated to functional sequences, cleaned up with 0.8×SPRI, and is further amplified by PCR as in operation 958. The amplification product is cleaned up with 0.8×SPRI. The yield from this processing is shown in FIG. 13B (SSII line).

Example II: Cellular RNA Analysis Using Emulsions

Figure 14A:
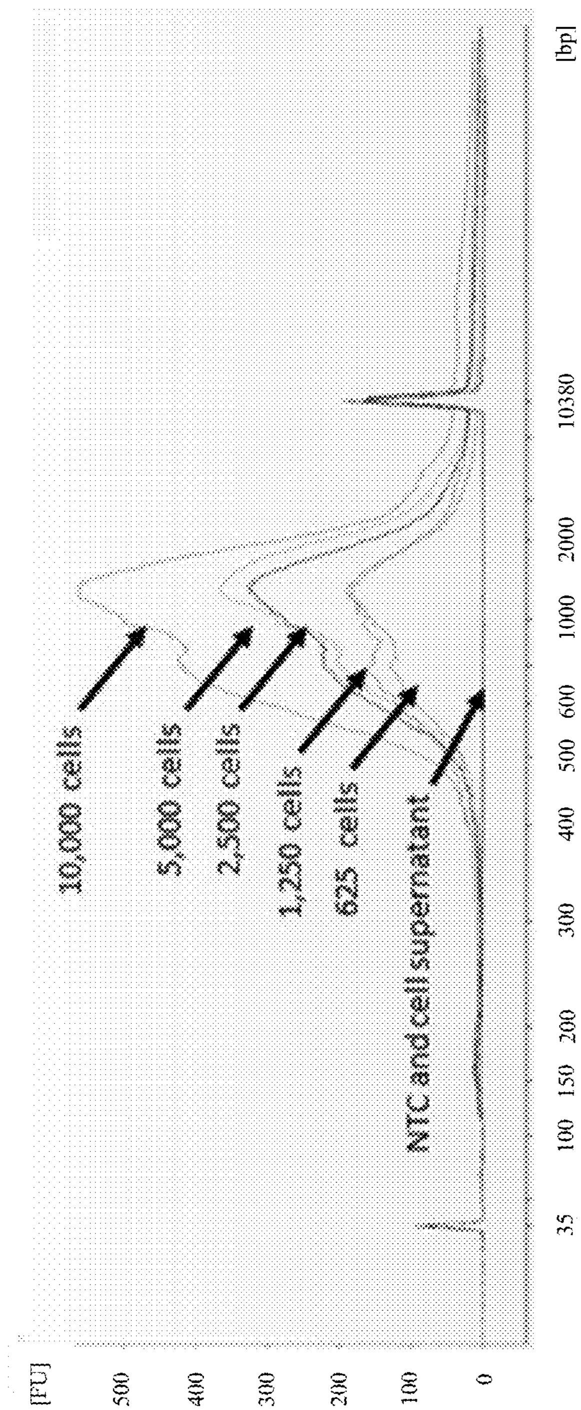
FIGS. 14A-14B provide illustrations of example yields from reverse transcription and complementary deoxyribonucleic acid (cDNA) amplification in partitions with various cell numbers.
Figure 14B:
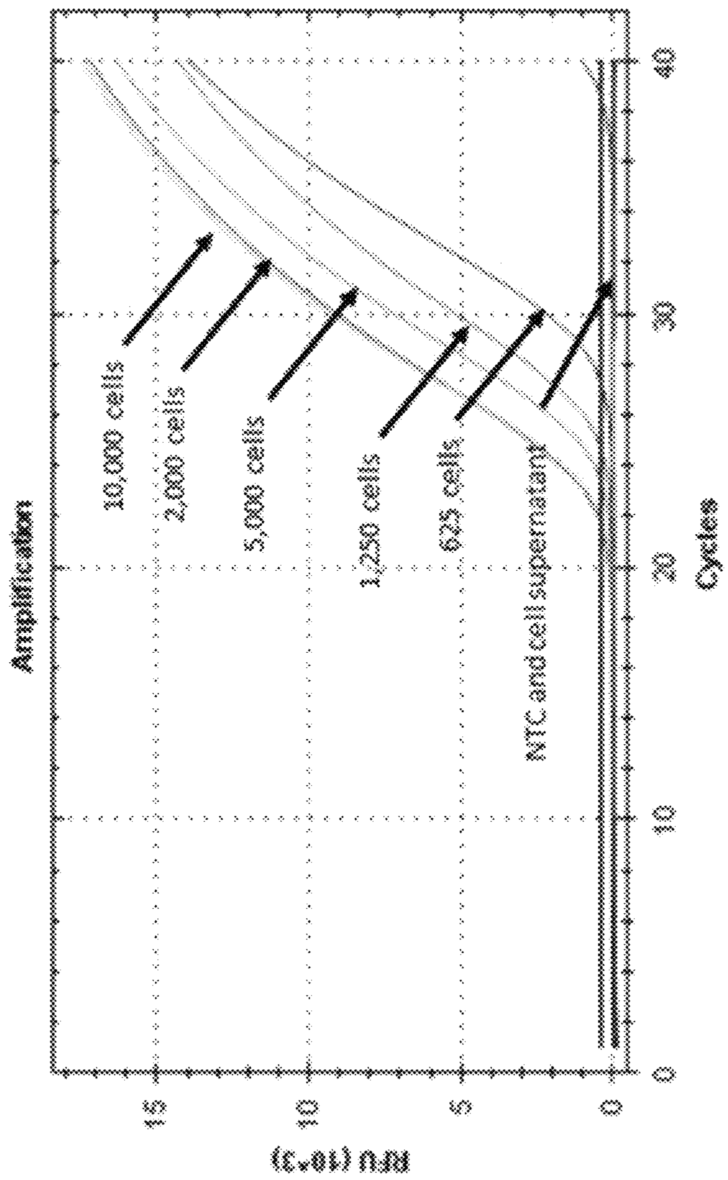

In another example, reverse transcription with template switching and cDNA amplification (via PCR) is performed in emulsion droplets with operations as shown in FIG. 9A. The reaction mixture that is partitioned for reverse transcription and cDNA amplification (via PCR) includes Jurkat cells, beads bearing barcoded oligonucleotides/0.2% TritonX-100/5× Kapa buffer, 2× Kapa HS HiFi Ready Mix, 4 μM switch oligo, and Smartscribe. The mixture is partitioned such that a majority or all of the droplets comprise a single cell and single bead. The cells are lysed while the barcoded oligonucleotides are released from the bead, and the poly-T segment of the barcoded oligonucleotide hybridizes to the poly-A tail of mRNA that is released from the cell as in operation 950. The poly-T segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are cleaned-up with Dynabeads and 0.6×SPRI as in operation 956. The yield from reactions with various cell numbers (625 cells, 1,250 cells, 2,500 cells, 5,000 cells, and 10,000 cells) is shown in FIG. 14A. These yields are confirmed with GADPH qPCR assay results shown in FIG. 14B.

Example III: RNA Analysis Using Emulsions

Figure 15:
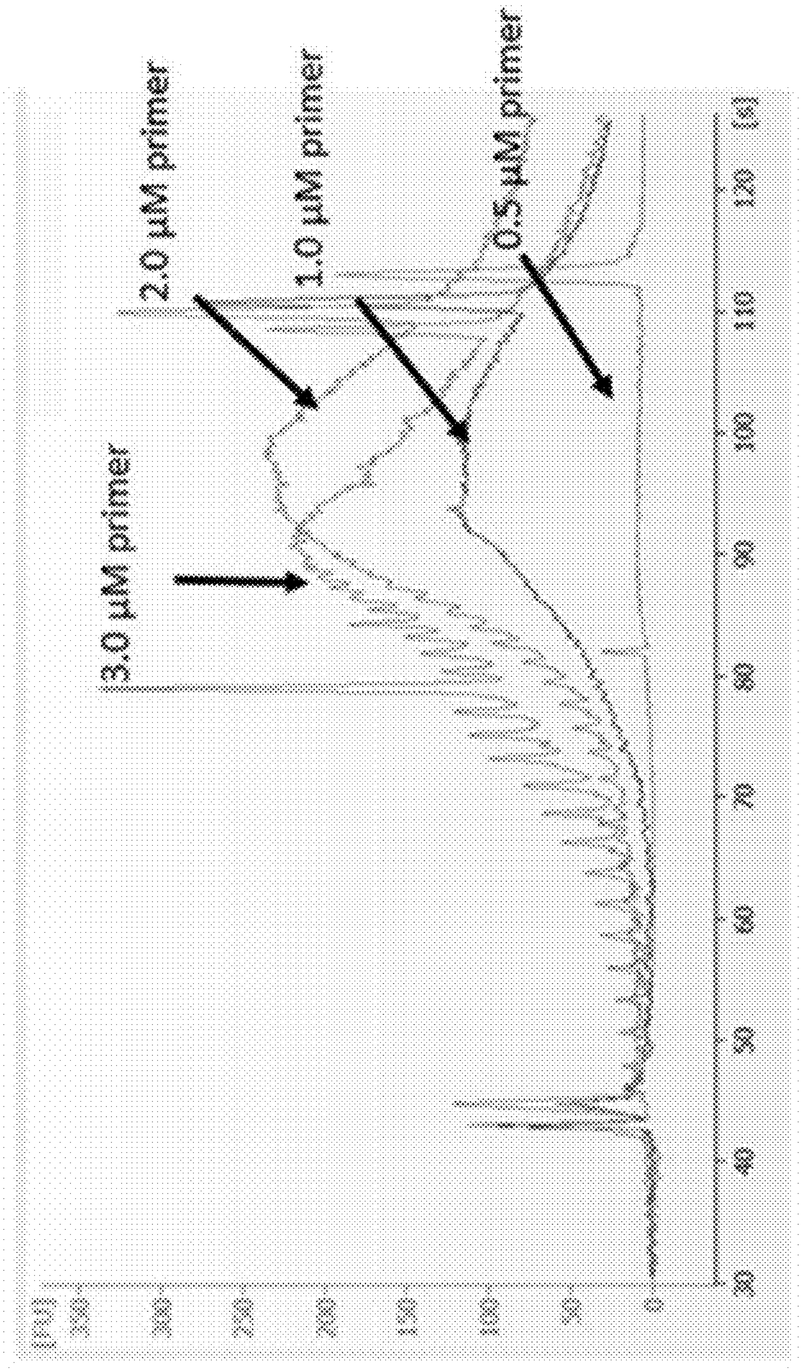
FIG. 15 provides an illustration of example yields from cDNA synthesis and real-time quantitative PCR at various input cell concentrations and also the effect of varying primer concentration on yield at a fixed cell input concentration.

In another example, reverse transcription is performed in emulsion droplets and cDNA amplification is performed in bulk in a manner similar to that as shown in FIG. 9C. The reaction mixture that is partitioned for reverse transcription includes beads bearing barcoded oligonucleotides, 10 ng Jurkat RNA (e.g., Jurkat mRNA), 5× First-Strand buffer, and Smartscribe. The barcoded oligonucleotides are released from the bead, and the poly-T segment of the barcoded oligonucleotide hybridizes to the poly-A tail of the RNA as in operation 961. The poly-T segment is extended in a reverse transcription reaction as in operation 963. The thermal cycling conditions for reverse transcription are one cycle at 42° C. for 2 hours and one cycle at 70° C. for 10 min. Following thermal cycling, the emulsion is broken and RNA and cDNA transcripts are denatured as in operation 962. A second strand is then synthesized by primer extension with a primer having a biotin tag as in operation 964. The reaction conditions for this primer extension include cDNA transcript as the first strand and biotinylated extension primer ranging in concentration from 0.5-3.0 μM. The thermal cycling conditions are one cycle at 98° C. for 3 min and one cycle of 98° C. for 15 sec, 60° C. for 20 sec, and 72° C. for 30 min. Following primer extension, the second strand is pulled down with Dynabeads MyOne Streptavidin C1 and T1, and cleaned-up with Agilent SureSelect XT buffers. The second strand is pre-amplified via PCR as in operation 965 with the following cycling conditions—one cycle at 98° C. for 3 min and one cycle of 98° C. for 15 sec, 60° C. for 20 sec, and 72° C. for 30 min. The yield for various concentrations of biotinylated primer (0.5 μM, 1.0 μM, 2.0 μM, and 3.0 μM) is shown in FIG. 15.

Example IV: RNA Analysis Using Emulsions

Figure 16:
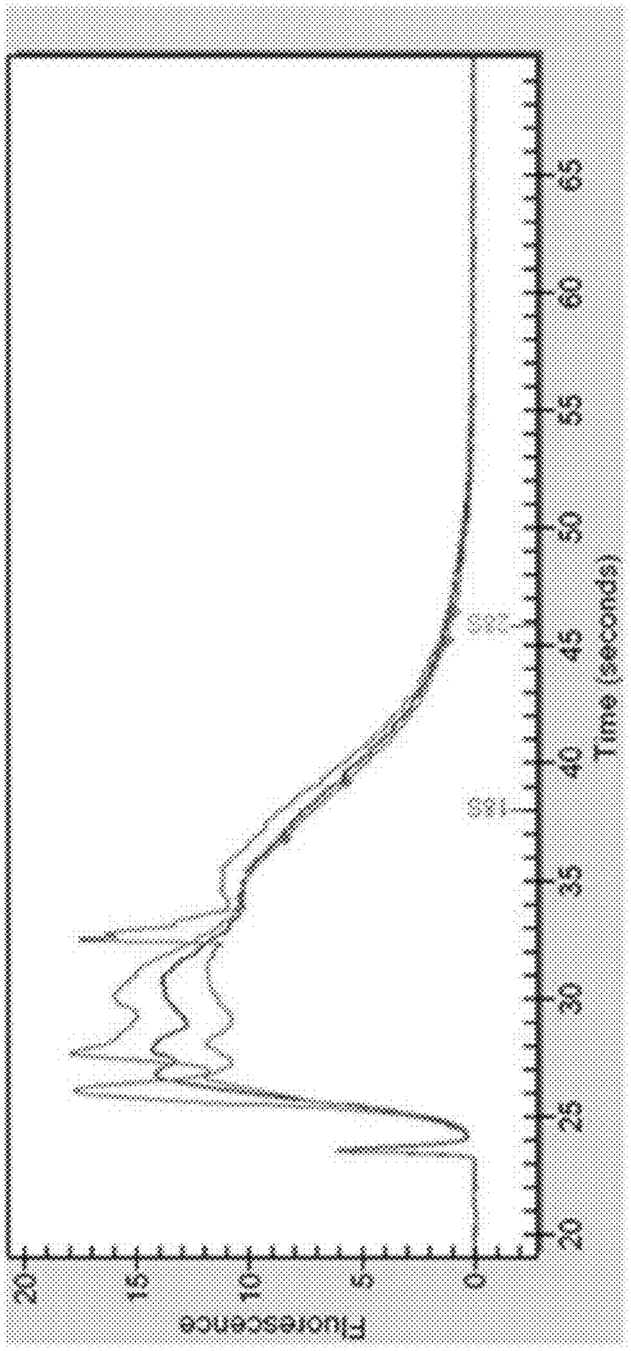
FIG. 16 provides an illustration of example yields from in vitro transcription.

In another example, in vitro transcription by T7 polymerase is used to produce RNA transcripts as shown in FIG. 10. The mixture that is partitioned for reverse transcription includes beads bearing barcoded oligonucleotides which also include a T7 RNA polymerase promoter sequence, 10 ng human RNA (e.g., human mRNA), 5× First-Strand buffer, and Smartscribe. The mixture is partitioned such that a majority or all of the droplets comprise a single bead. The barcoded oligonucleotides are released from the bead, and the poly-T segment of the barcoded oligonucleotide hybridizes to the poly-A tail of the RNA as in operation 1050. The poly-T segment is extended in a reverse transcription reaction as in operation 1052. The thermal cycling conditions are one cycle at 42° C. for 2 hours and one cycle at 70° C. for 10 min. Following thermal cycling, the emulsion is broken and the remaining operations are performed in bulk. A second strand is then synthesized by primer extension as in operation 1054. The reaction conditions for this primer extension include cDNA transcript as template and extension primer. The thermal cycling conditions are one cycle at 98° C. for 3 min and one cycle of 98° C. for 15 sec, 60° C. for 20 sec, and 72° C. for 30 min. Following this primer extension, the second strand is purified with 0.6×SPRI. As in operation 1056, in vitro transcription is then performed to produce RNA transcripts. In vitro transcription is performed overnight, and the transcripts are purified with 0.6×SPRI. The RNA yields from in vitro transcription are shown in FIG. 16.

Example V: Analysis of T-Cell Receptors (TCRs)

In this example, methods disclosed herein are used to assay T-cell receptors. To generate labeled polynucleotides comprising T-cell receptor gene sequences, T-cells are co-partitioned with gel beads comprising barcoded template switching oligonucleotides. Prior to partitioning, T-cells are optionally enriched from a cell sample, for example by fluorescence activated cell sorting (FACS) or other sorting technique. Additional reagents for generating labeled polynucleotides including, but not limited to, reverse transcriptase enzyme, poly(dT) primer, and dNTPs, are delivered to partitions as part of a master mix. Within partitions, cells are lysed, thereby yielding template polynucleotides comprising nucleic acids from T-cells. As illustrated schematically in FIG. 19, a T-cell derived template polynucleotide comprising mRNA (e.g., 1920), poly(dT) primer (e.g., 1924), and a template switching oligonucleotide (e.g., 1926) are subjected to an amplification reaction to yield a first amplification product. The poly(dT) primer hybridizes to the polyA tail of the mRNA template polynucleotide and acts as a primer for reverse transcription by the reverse transcriptase enzyme that is co-partitioned with the T-cell (e.g., 1950). The reverse transcriptase enzyme has terminal transferase activity and adds additional nucleotides, e.g., polyC, to the cDNA transcript in a template independent manner. The template switching oligonucleotide (e.g., 1926) hybridizes to the cDNA transcript and facilitates template switching in the first amplification reaction (e.g., 1952).

Using methods disclosed herein, reverse transcription performed within partitions generates unbiased cDNA comprising a sequencing adapter, a cell barcode and a unique molecular identifier (UMI) on the 5' end of the transcript. To enrich for transcripts comprising TCR gene sequences, the first amplification reaction product or cDNA transcript is subjected to a second amplification reaction to generate a second amplification product. Polymerase chain reaction (PCR) is performed with one primer for the 5' end of the transcript and one or more primers for the desired TCR/Ig constant region(s) (e.g., primers targeting TCR alpha (α) and/or beta (β) chain, and in some cases gamma and/or delta (γ/δ) chains). The contents of multiple partitions can be combined such that the second amplification reaction is performed in bulk.

Next, amplification products are subjected to enzymatic fragmentation and further processed to attach sequencing adaptors to generate a sequencing library. Additional sequences include functional sequences such as flow cell attachment sequences and sequencing primer binding sequences. The labeled polynucleotides are sequenced to yield sequencing reads, and sequencing reads are used to assemble full or partial TCR receptor gene sequences. Additional analysis includes transcript counting for which an analysis pipeline may include, for example, (i) barcode processing, (ii) read filtering, (iii) cell-by-cell consensus assembly, (iv) V(D)J annotation, and (v) clonotype inference and clustering.

Other receptors (e.g., B-cell receptors (BCRs) and Ig receptors) can be similarly analyzed using the methods described herein by partitioning the appropriate immune cell type for generating labeled polynucleotides and using receptor specific primers to generate amplification products.

Example VI: Enrichment of T-Cell Receptor (TCR) Transcripts

Figure 22:
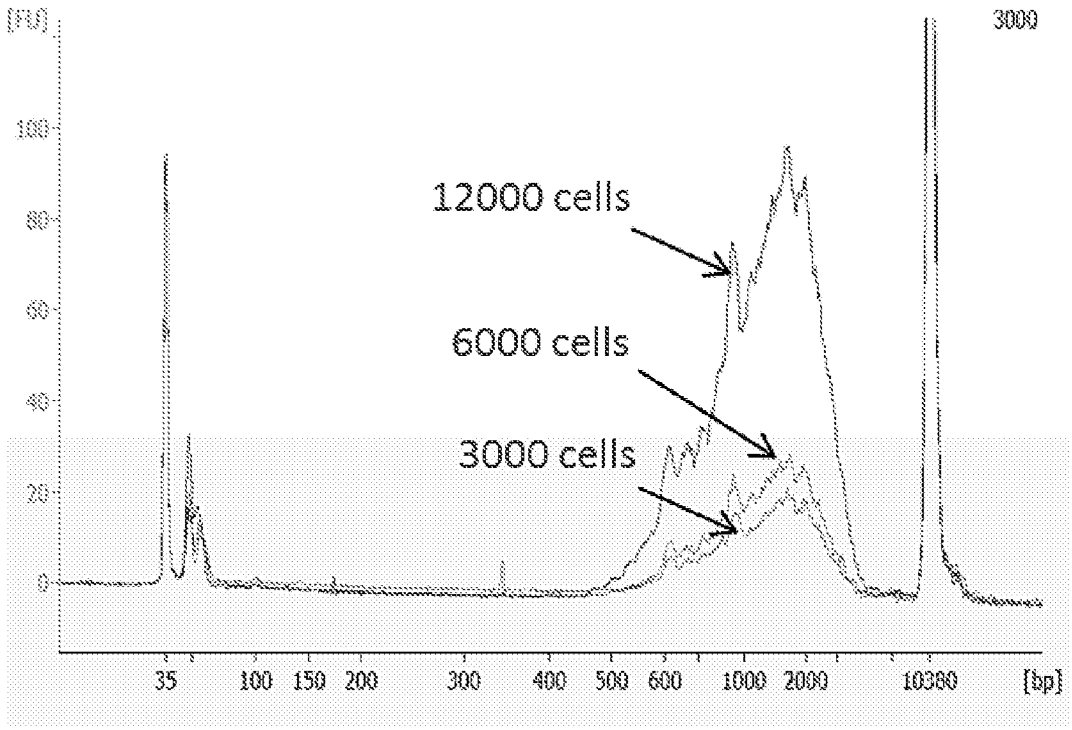
FIG. 22 shows cDNA yields from 12,000; 6,000; or 3,000 cells using gel-beads in an emulsion-reverse transcription reaction (GEM-RT).

In this example, cellular suspensions of 3,000; 6,000; or 12,000 primary human T cells were loaded on a GemCode Single Cell Instrument (10× Genomics, Pleasanton, CA) to generate single cell-gel bead emulsions (SC-GEMs). The gel beads were modified to carry a template switching oligonucleotide (TSO) as shown in FIG. 18 or FIG. 20 at 8 μM, yielding a final concentration of 0.32 μM in GEM. After creation of SC-GEMs, reverse transcription was performed on the cells in emulsion using a poly-T primer and reverse transcriptase for 5 minutes at 55° C., followed by 1 hour and 55 minutes at 52° C. After RT, GEMs were broken and the single-stranded cDNA was cleaned up with DynaBeads® MyOne™ Silane Beads and SPRIselect Reagent Kit (0.6× SPRI). cDNA was amplified for 15 cycles with 1 minute extensions and amplified cDNA product was cleaned up with the SPRIselect Reagent Kit (0.6×SPRI). FIG. 22 shows the cDNA yields from all three cellular suspensions. cDNA yields from 12,000 cells was greater than either 6,000 or 3,000 cells, which yielded similar amounts.

Indexed sequencing libraries were constructed using the GemCode Single Cell 3' Library Kit, following these steps: 1) end repair and A-tailing; 2) adapter ligation; 3) post-ligation cleanup with SPRIselect; 4) sample index PCR and cleanup. These sequencing libraries were sequenced using an Illumina MiSeq sequencer. Sequencing performance of poly-T primed libraries was compared to libraries constructed from enriched cDNA libraries created by using an enriched priming method which substituted the poly-T primer with primers that bound the constant region of TCRα, TCRβ, or both. FIG. 23 shows that enrichment led to reduced mapping of sequencing reads to the transcriptome (8.9% unmappable reads with poly-T priming versus 49.3% for TCRα priming, 45.7% for TCRβ priming, or 39% for both). However, more reads mapped to the VDJ regions of TCR transcripts, indicating that enrichment is important for targeted VDJ sequencing (0.3% VDJ mappable fragments with poly T priming versus 15.5% for TCRα priming, 19.7% for TCRβ priming, or 29.50% for both). See FIG. 23, Fraction fragments mapped to VDJ column.

Figure 24A:
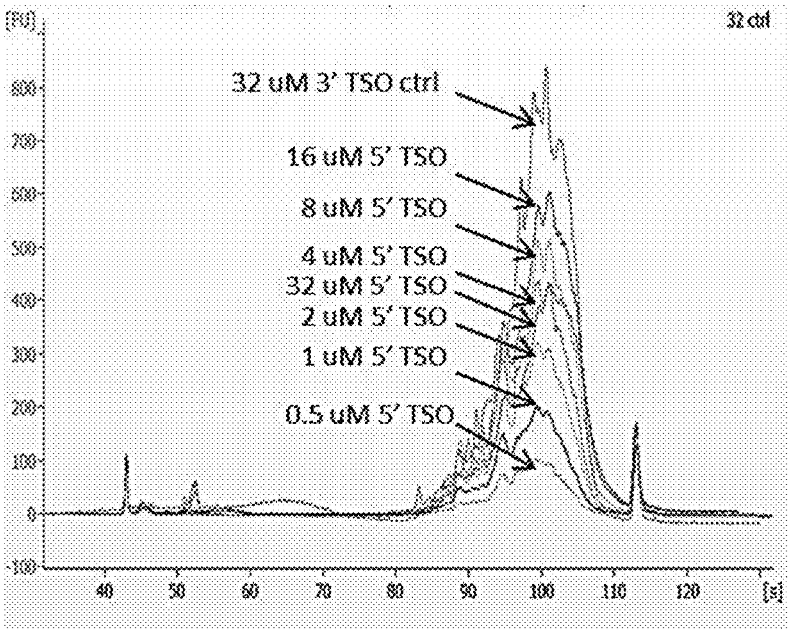
FIG. 24A-24B shows cDNA yields using differing concentrations of a template switch oligo (TSO) were tested.
Figure 24B:
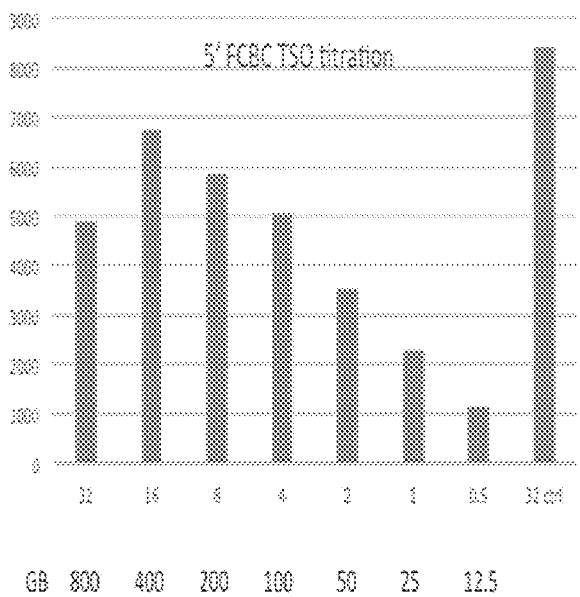
Figure 25A:
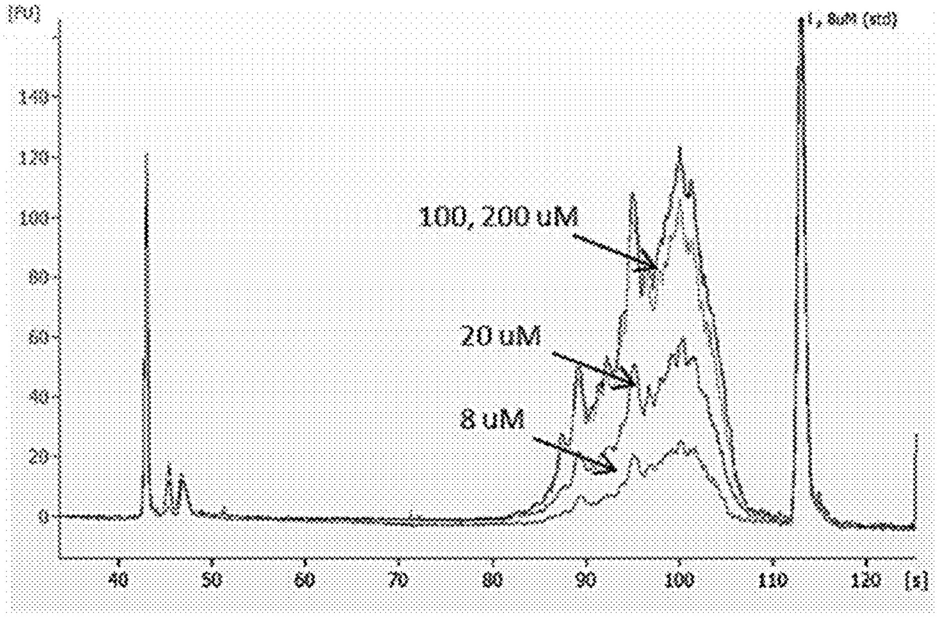
FIGS. 25A-25D show cDNA yields from TSO immobilized to gel beads (GB-TSO) using either 6,000 primary T cells (FIG. 25A-25B) or 2,200 Jurkat cells (FIG. 25C-25D).
Figure 25B:
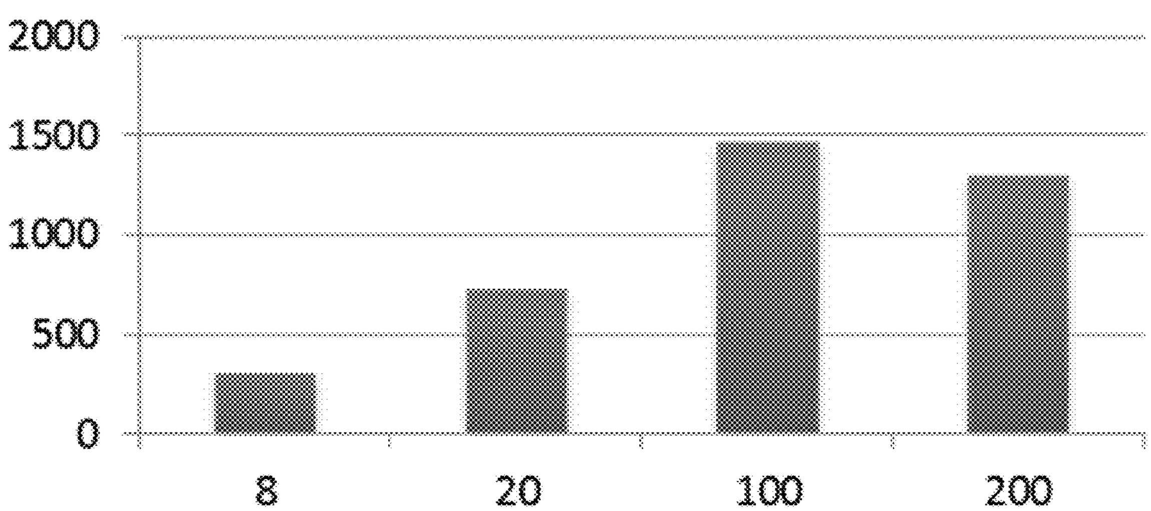
Figure 25C:
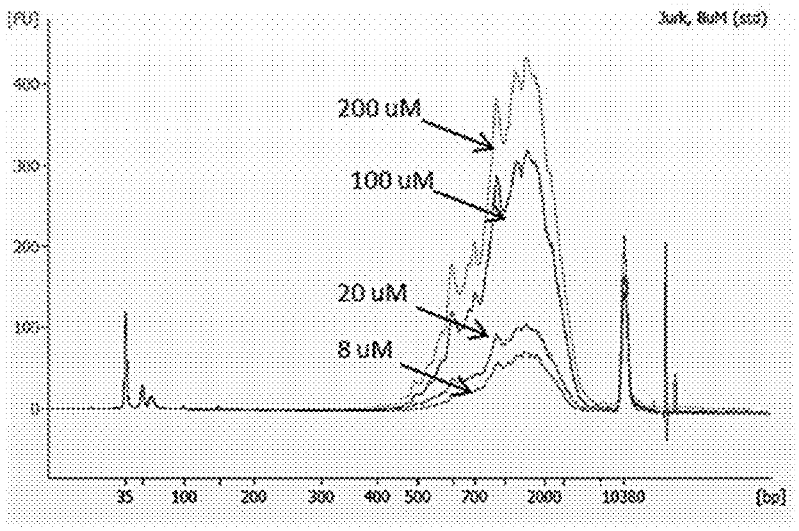
Figure 25D:
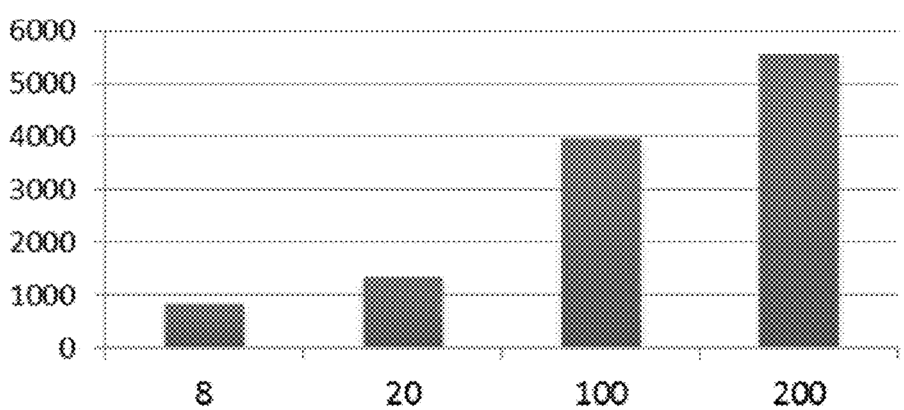

In order to increase cDNA yields prior to sequencing library preparation, differing concentrations of TSO were tested. TSO were tested at concentrations of 32, 16, 8, 4, 2, 1, and 0.5 μM (which may correspond to 800, 400, 200, 100, 50, 25, and 12.5 μM immobilized to gel beads). Jurkat T cells were used for this experiment, and results are shown in FIG. 24 with cDNA yields directly correlating with TSO concentration and plateauing at about a concentration of 16 μM. These experiments were repeated with TSO immobilized to gel beads (GB-TSTO) using either 6,000 primary T cells as shown in FIG. 25A, or 2,200 Jurkat cells as shown in FIG. 25B. GB-TSO concentrations of 8, 20, 100, and 200 μM were tested and concentrations of 100 and 200 μM showed a significant increase over the lower concentrations of 8 and 20 μM.

Figure 26A:
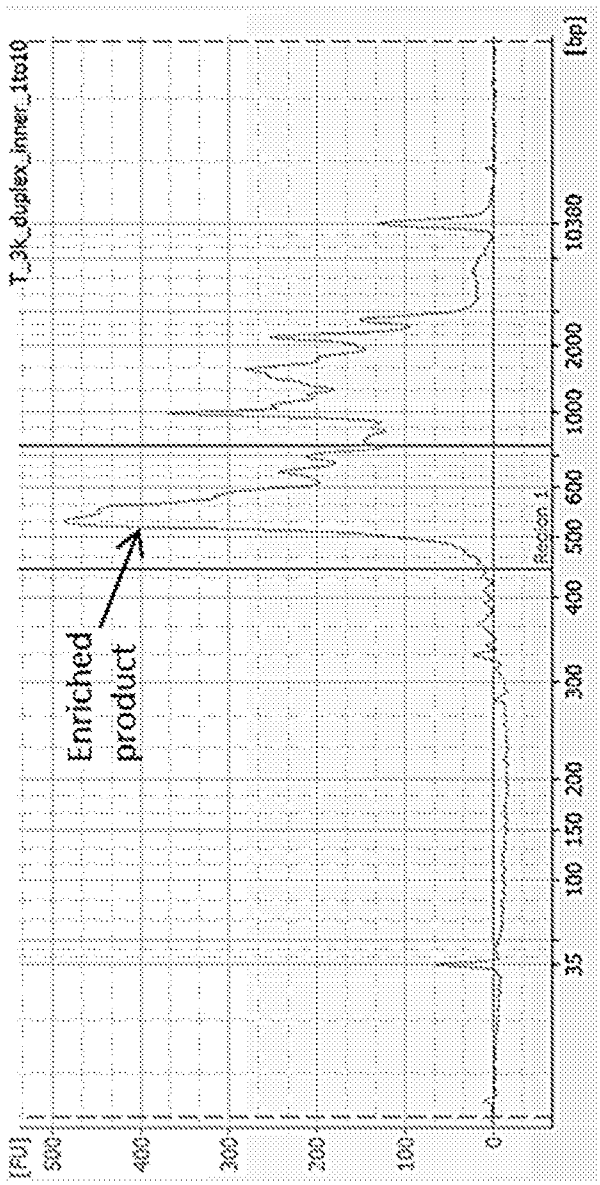
FIGS. 26A and 26B show cDNA yields from an enrichment using an in solution RT reaction (FIG. 26A) or a GEM RT reaction (FIG. 26B) using nested enrichment primers.
Figure 26B:
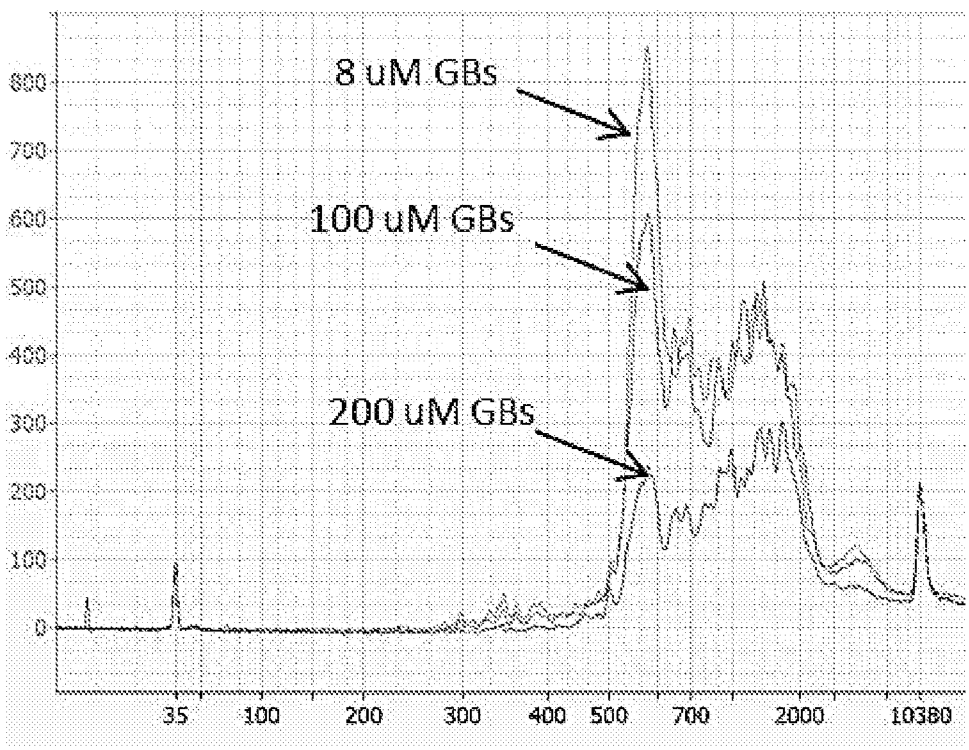

Differing enrichment schemes were tested to determine optimal enrichment methods. Using a non-GEM protocol, cDNA from 3,000 primary T cells was prepared using poly-T priming followed by enrichment using primers that anneal to TCR constant regions, yielding 38.5% VDJ mappable reads, quantitation of this enrichment is shown in FIG. 26A. Using a gel-beads in emulsion-reverse transcription reaction (GEM-RT) protocol, cDNA from 6,000 primary T cells was prepared using Poly-T priming and gel beads with a TSO at 8, 100 or 200 M concentration followed by enrichment using a two stage nested approach. This nested enrichment comprised PCR using outer primers annealing to the TCR alpha and beta paired with a P7 primer for 10 cycles using 60° C. extensions, followed by PCR using inner primers annealing to the TCR alpha and beta paired with a P7 primer for 10 cycles using 60' C extensions. Results of this are shown in FIG. 26B with the largest amount of enrichment exhibited using a lower concentration of gel beads (8 μM).

To further optimize enrichment, a comparison was conducted between using P7 primers and variable region specific primers in combination with the constant region primers for cDNA amplification. Primer sequences used are shown in Table 4.

TABLE 4

Enrichment primer sequences and predicted products

| | Primer | Sequence |
|---|---|---|
| V region primers | TRA-V1 | ACTTGTCCAGCCTAACCTGC (SEQ ID NO: 160) |
| | TRA-V2 | TTACCCTGGGAGGAACCAGA (SEQ ID NO: 161) |
| | TRB-V1 | TTTCAGGCCACAACTCCCTT (SEQ ID NO: 162) |
| | TRB-V2 | CAGACAGACCATGATGCGGG (SEQ ID NO: 163) |
| | TRB-V3 | GCCACAACTCCCTTTTCTGG (SEQ ID NO: 164) |
| Constant region primers | TRAC-inner | AGTCTCTCAGCTGGTACACG (SEQ ID NO: 165) |
| | TRBC-inner | TCTGATGGCTCAAACACAGC (SEQ ID NO: 166) |

TABLE 4-continued

Enrichment primer sequences and predicted products

| | Primer | Sequence |
|---|---|---|
| Predicted amplicon size | TRA-V1/TRAC-inner | 554 |
| | TRA-V2/TRAC-inner | 413 |
| | TRB-V1/TRBC-inner | 324 |
| | TRB-V2/TRBC-inner | 296 |
| | TRB-V3/TRBC-inner | 318 |

Figure 27A:
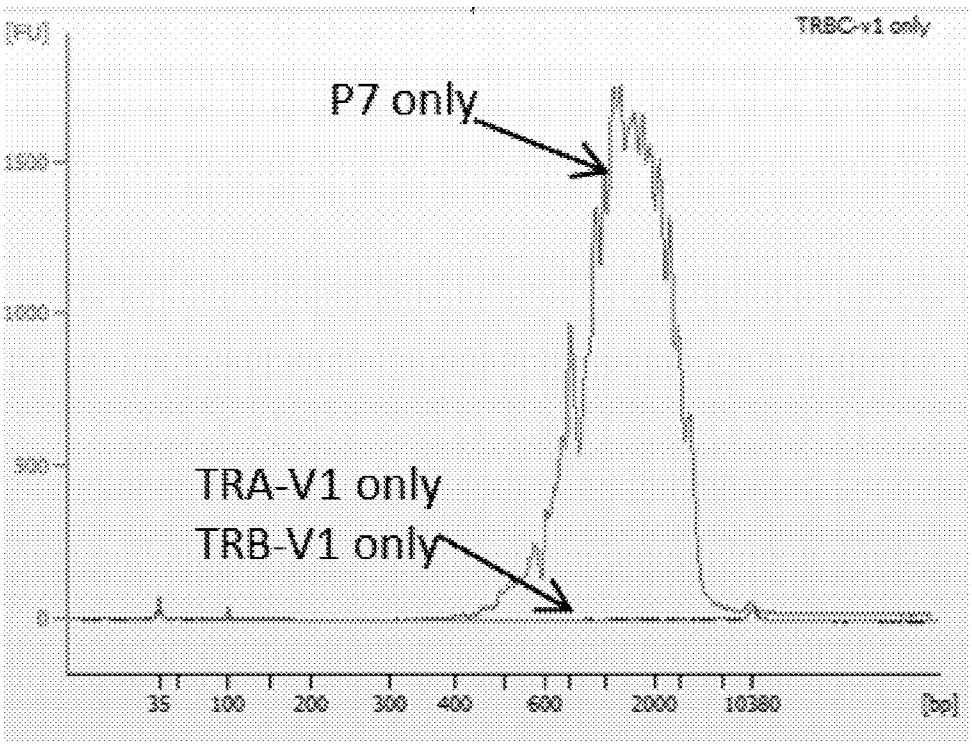
FIGS. 27A-27C show enrichment of TCR cDNA using p7 primers only (FIG. 27A), variable region primers with TCR beta chain constant region primers (FIG. 27B), and variable region primers with TCR alpha chain constant region primers (FIG. 27C).
Figure 27B:
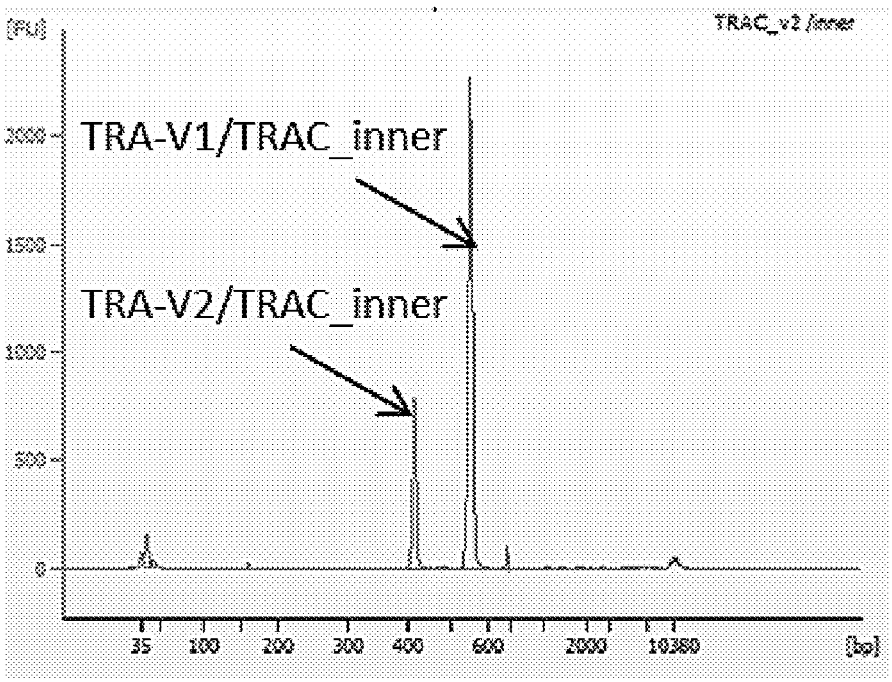
Figure 27C:
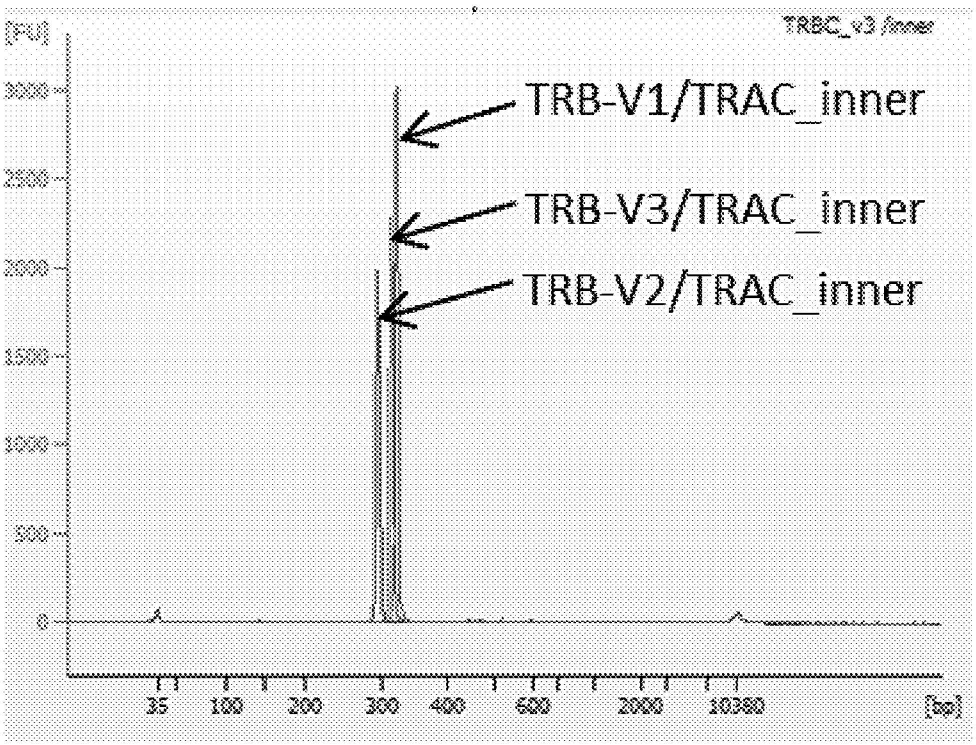
Figure 28A:
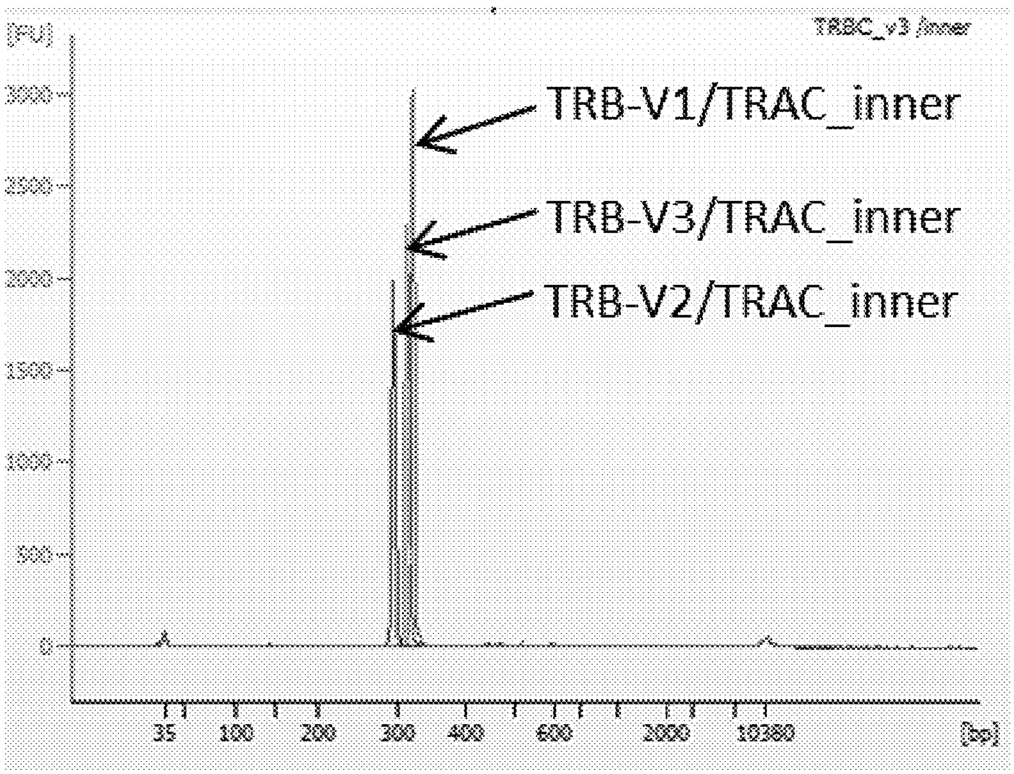
FIGS. 28A-28D show a comparison of enriched product generated with either 8 μM or 200 μM TSO gel beads using P7 primers with TCR alpha chain constant region primers (FIG. 28A), variable region primers with TCR beta chain constant region primers (FIG. 28B), variable region primers with TCR alpha chain constant region primers (FIG. 28C), and variable region primers with TCR beta chain constant region primers (FIG. 28D).
Figure 28B:
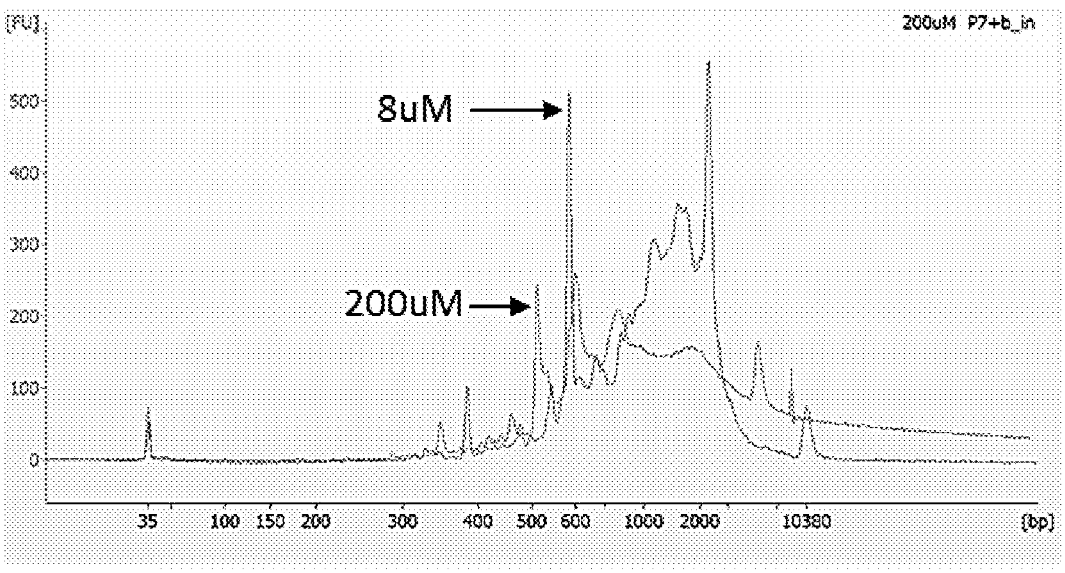
Figure 28C:
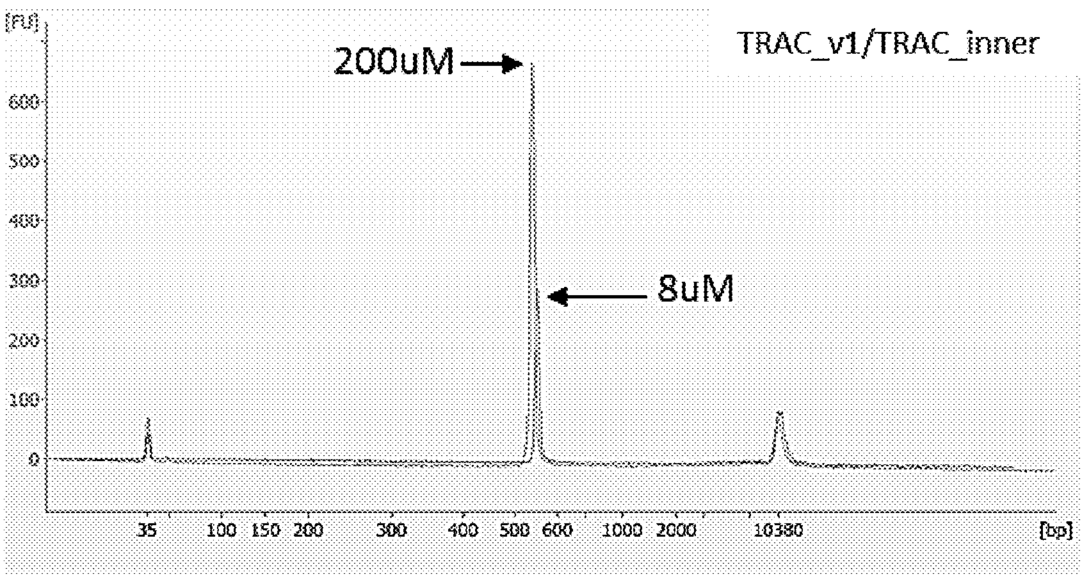
Figure 28D:
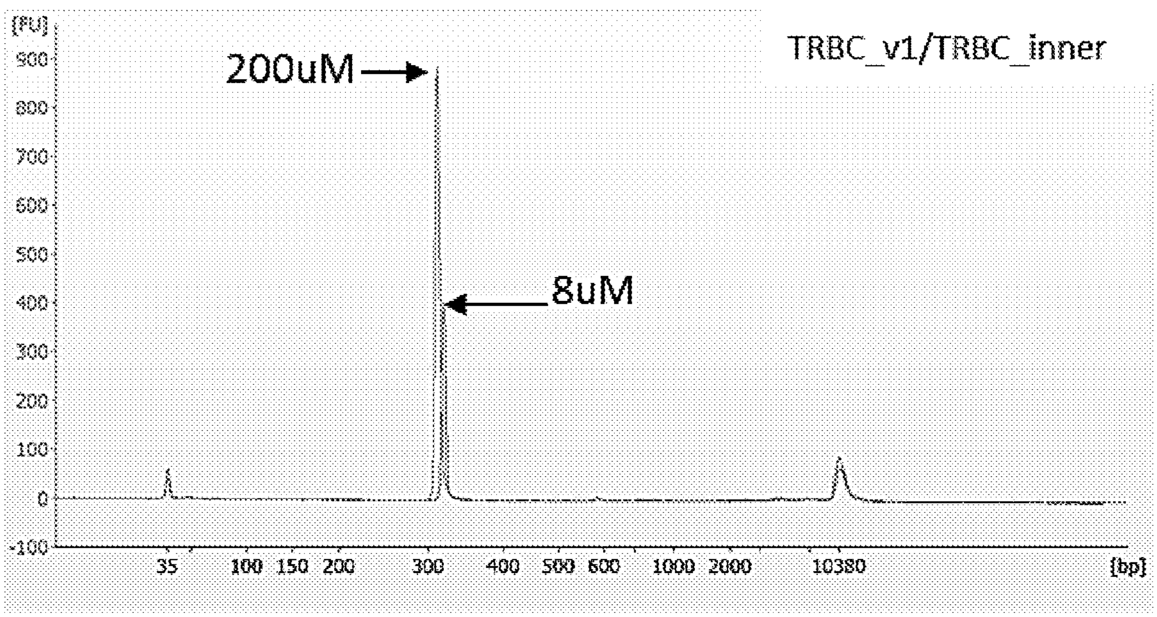

GEM-RT was carried out using poly-T priming followed by a template switch using 8 μM TSO-GB, followed by clean up, 15 cycles of cDNA amplification and enrichment for 20 cycles. Results shown in FIGS. 27A-27C show that using V region primers in conjunction with constant region primers specifically enrich TCR alpha (FIG. 27B) and TCR beta sequences (FIG. 27C) compared to P7 primers paired with constant region primers. FIG. 28 further shows that by using specific enrichment (28C and D; V region+C region primers) compared to general enrichment (28A and B; P7 primer+C region primer) yields of specifically enriched product were increased by increasing the amount of TSO-GB (from 8 μM to 200 μm). This is in contrast to what was observed using P7-constant region primer enrichment which required using less TSO-GB (8 μM) in the GEM-RT reaction to produce more enriched product. Overall using the P7-constant region enrichment allows preservation of barcode information in the subsequent sequencing reaction. This configuration yields at least 30% reads mappable to VDJ genes.

Example VII: Generating Labeled Polynucleotides

Figure 29A:
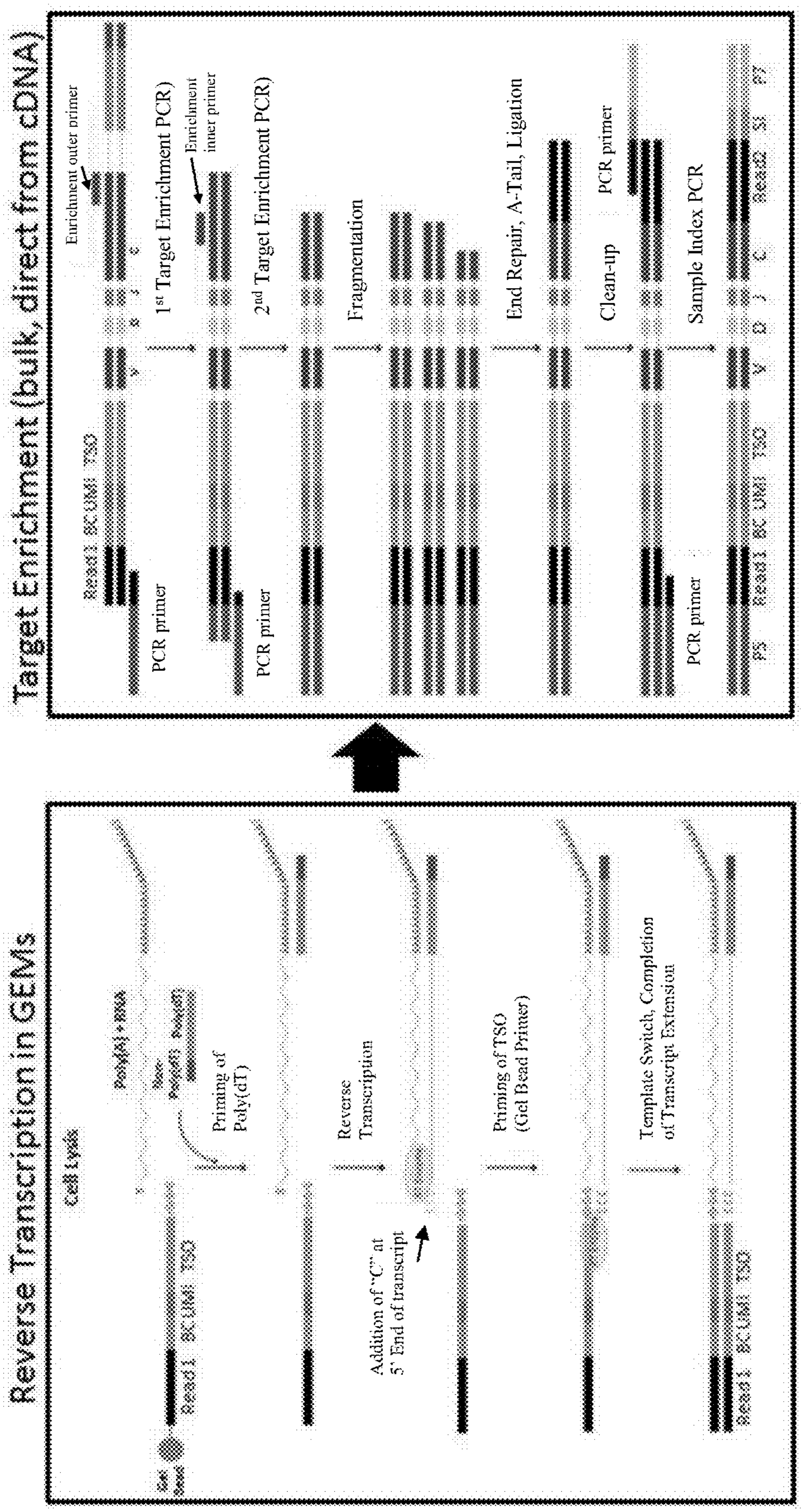
FIGS. 29A and 29B show variations of a schematic for generating labeled polynucleotides.
Figure 29B:
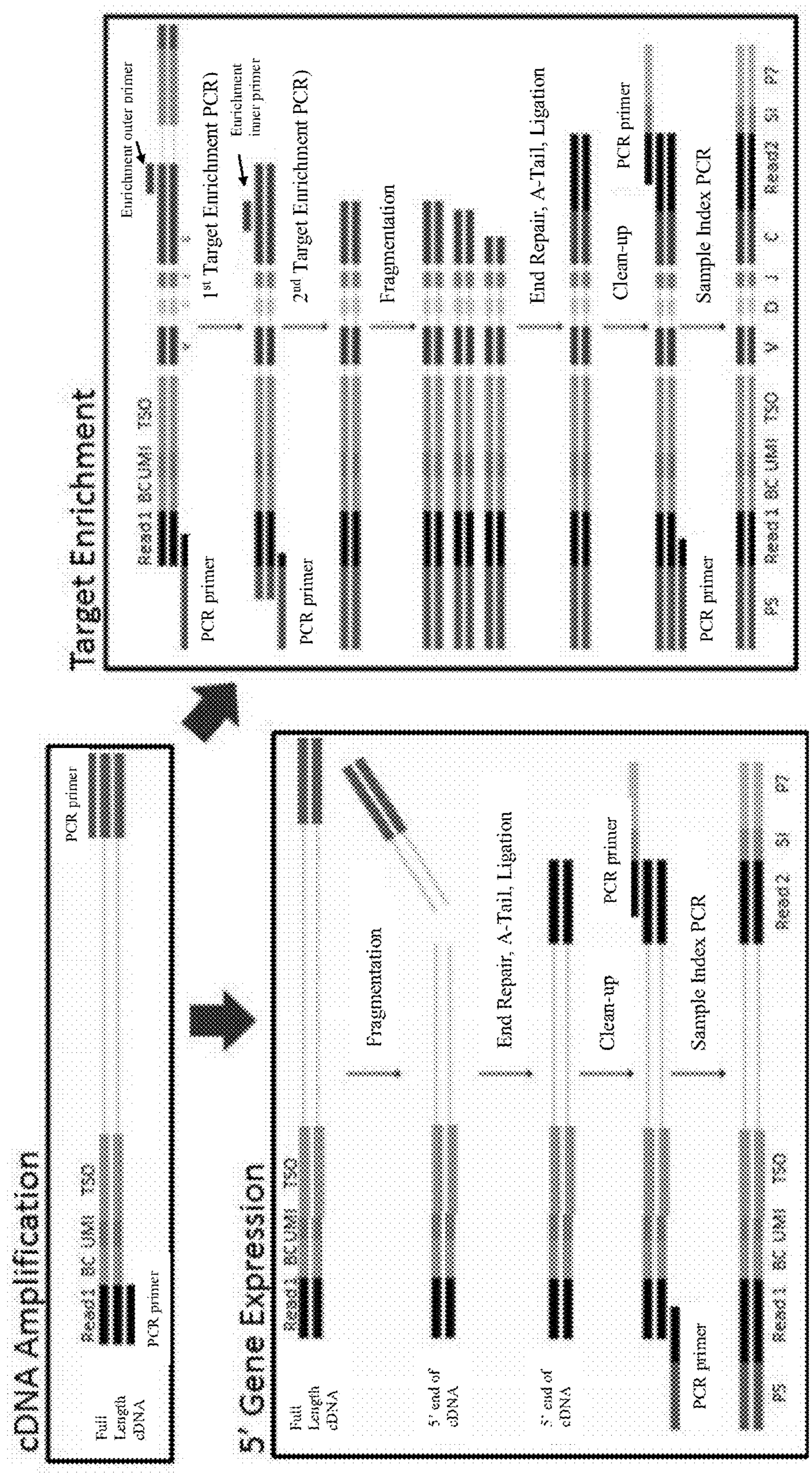

In this example, and with reference to FIGS. 29A and 29B, individual cells are lysed in partitions comprising gel bead emulsions (GEMs). GEMs, for example, can be aqueous droplets comprising gel beads. Within GEMs, a template polynucleotide comprising an mRNA molecule can be reverse transcribed by a reverse transcriptase and a primer comprising a poly(dT) region. A template switching oligo (TSO) present in the GEM, for example a TSO delivered by the gel bead, can facilitate template switching so that a resulting polynucleotide product or cDNA transcript from reverse transcription comprises the primer sequence, a reverse complement of the mRNA molecule sequence, and a sequence complementary to the template switching oligo. The template switching oligo can comprise additional sequence elements, such as a unique molecular identifier (UMI), a barcode sequence (BC), and a Read1 sequence. See FIG. 29A. In some cases, a plurality of mRNA molecules from the cell is reverse transcribed within the GEM, yielding a plurality of polynucleotide products having various nucleic acid sequences. Following reverse transcription, the polynucleotide product can be subjected to target enrichment in bulk. Prior to target enrichment, the polynucleotide product can be optionally subjected to additional reaction(s) to yield double-stranded polynucleotides. The target may comprise VDJ sequences of a T cell and/or B cell receptor gene sequence. As shown at the top of the right panel of FIG. 29A, the polynucleotide product (shown as a double-stranded molecule, but can optionally be a single-stranded transcript) can be subjected to a first target enrichment polymerase chain reaction (PCR) using a primer that hybridizes to the Read 1 region and a second primer that hybridizes to a first region of the constant region (C) of the receptor sequence (e.g., TCR or BCR). The product of the first target enrichment PCR can be subjected to a second, optional target enrichment PCR. In the second target enrichment PCR, a second primer that hybridizes to a second region of the constant region (C) of the receptor can be used. This second primer can, in some cases, hybridize to a region of the constant region that is closer to the VDJ region that the primer used in the first target enrichment PCR. Following the first and second (optional) target enrichment PCR, the resulting polynucleotide product can be further processed to add additional sequences useful for downstream analysis, for example sequencing. The polynucleotide products can be subjected to fragmentation, end repair, A-tailing, adapter ligation, and one or more clean-up/purification operations.

In some cases, a first subset of the polynucleotide products from cDNA amplification can be subjected to target enrichment (FIG. 29B, right panel) and a second subset of the polynucleotide products from cDNA amplification is not subjected to target enrichment (FIG. 29B, bottom left panel). The second subset can be subjected to further processing without enrichment to yield an unenriched, sequencing ready population of polynucleotides. For example, the second subset can be subjected to fragmentation, end repair, A-tailing, adapter ligation, and one or more clean-up/purification operations.

The labeled polynucleotides can then be subjected to sequencing analysis. Sequencing reads of the enriched polynucleotides can yield sequence information about a particular population of the mRNA molecules in the cell whereas the enriched polynucleotides can yield sequence information about various mRNA molecules in the cell.

Example VIII: Base Error Calculations

All calculations of this example are for a single base. The terms transcript and UMI will be used inter-changeably, assuming that there is a 1-1 relationship between transcripts and UMIs. Let D be all observed data (reads, qualities, UMIs) at a given base and $D_u$, u=1, . . . , m be the data from UMI u. Let R be the real template base at the given position and $T_u$ be the (unobserved) base at the given position on transcript/UMI u. Let $_{Rui}$ and $_{Rui}$ be the real (pre-sequencing errors) and observed (post-sequencing errors) bases on the $i^{th}$ read of UMI u and $_{Qui}$ be the corresponding base quality. Let $_{prt}$ be probability of an RT error, and $p_{per}$ be the probability of a PCR error. Let also $p_s(Q)=10-Q/10$ be the probability of a sequencing error given a base quality of Q. Finally, let L={A, C, G, T}. Transcripts are conditionally independent given the real template base and reads from a transcript are conditionally independent given the base of the transcript (i.e. errors occur completely independently of one another). Below, Equation I can be derived by summing over the unobserved value c of transcript u at the given position and the (also unobserved) real value d of each read at this position.

Equation I $$P(D|R) = \prod_{u} P(D_u|R) = \prod_{u}\sum_{c\in L} P(D_u|T_u = c)P(T_u = c|R) = \prod_{u}\sum_{c\in L}\prod_{i} P(R_{u_i}|T_u = c)P(T_u = c|R) =$$

$$\prod_{u}\sum_{c\in L}\prod_{i}\sum_{d\in L} P(R_{u_i}|\bar{R}_{u_i} = d)P(\bar{R}_{u_i} = d|T_u = c)P(T_u = c|R) =$$

$$\prod_{u}\sum_{c\in L}\left[\prod_{i}\sum_{d\in L}\left[\left(\frac{p_s(Q_{u_i})}{3}\right)^{\bar{R}_{u_i}\neq d}(1-p_s(Q_{u_i}))^{\bar{R}_{u_i}=d}\left(\frac{p_{pcr}}{3}\right)^{d\neq c}(1-p_{pcr})^{d=c}\right]\left(\frac{p_{rt}}{3}\right)^{R\neq c}(1-p_{rt})^{R=c}\right]$$

If it is assumed that $p_{per}$ is negligible (compared to sequencing and RT errors), that is the sequenced base $R_{ui}$ always equals the transcript base $T_u$, the simplified form of Equation II can be derived below.

Equation II $$\prod_{u}\sum_{c\in L}\left[\left(\frac{p_{rt}}{3}\right)^{R\neq c}(1-p_{rt})^{R=c}\prod_{i}\left(\frac{p_s(Q_{u_i})}{3}\right)^{\bar{R}_{u_i}\neq c}(1-p_s(Q_{u_i}))^{\bar{R}_{u_i}=c}\right]$$

Let X be the called base at that position (i.e. the base in the assembled sequence). The probability of an error is:

$$P(R\neq X|D) = 1 - P(R = X|D) = 1 - \frac{P(D|R = X)P(R = X)}{P(D)} = 1 - \frac{0.25 * P(D|c)}{\Sigma_{c\in L}0.25 * P(D|c)}$$

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method for nucleic acid sequencing, comprising:

(a) providing a plurality of partitions, wherein a partition of the plurality of partitions comprises:

(i) a plurality of ribonucleic acid (RNA) molecules from a single cell; and (ii) a particle comprising nucleic acid barcode molecules coupled thereto, wherein the nucleic acid barcode molecules coupled to the particle comprise a first subset and a second subset, wherein the first subset comprises a partition-specific barcode sequence and a first primer region comprising a poly-T sequence, and wherein the second subset comprises the partition-specific barcode sequence and a second primer region comprising a sequence that is complementary to a sequence encoding a T cell receptor (TCR) or B cell receptor (BCR) constant region;

(b) using the plurality of RNA molecules and the first subset of nucleic acid barcode molecules to generate a first plurality of barcoded nucleic acid molecules, each comprising: 1) the partition-specific barcode sequence or a complement thereof, and 2) a sequence of a messenger RNA (mRNA) molecule of the plurality of RNA molecules or a complement thereof; and using the plurality of RNA molecules and the second subset of nucleic acid barcode molecules to generate a second plurality of barcoded nucleic acid molecules, each comprising: 1) the partition-specific barcode sequence or a complement thereof, and 2) a TCR or BCR variable region-encoding sequence or a complement thereof; wherein the generating the first plurality of barcoded nucleic acid molecules and the second plurality of barcoded nucleic acid molecules comprises:

(i) hybridizing the first subset of nucleic acid barcode molecules to poly-A sequences in mRNA molecules of the plurality of RNA molecules in the partition, and hybridizing the second subset of nucleic acid barcode molecules to sequences encoding TCR or BCR constant regions in mRNA molecules of the plurality of RNA molecules in the partition;

(ii) extending the first and second subsets of the nucleic acid barcode molecules using the hybridized mRNA molecules as template with a reverse transcriptase having terminal transferase activity to generate first and second barcoded cDNA molecules comprising 3' terminal sequences added by the reverse transcriptase;

(iii) hybridizing the 3' terminal sequences of the first and second barcoded cDNA molecules to hybridization regions of template switching oligonucleotides (TSOs), and (iv) extending the first and second barcoded cDNA molecules using the TSOs as templates, thereby generating the first plurality of barcoded nucleic acid molecules and the second plurality of barcoded nucleic acid molecules;

(c) amplifying barcoded nucleic acid molecules of the first plurality of barcoded nucleic acid molecules or derivatives thereof to generate an unenriched sequencing library; and (d) amplifying barcoded nucleic acid molecules of the second plurality of barcoded nucleic acid molecules or derivatives thereof to generate an immune receptor-enriched sequencing library.

2. The method of claim 1, wherein the particle is a bead.

3. The method of claim 1, wherein the particle is a gel bead and/or a magnetic bead.

4. The method of claim 3, wherein the partition initially comprises the single cell, and the method comprises lysing the single cell to release the RNA molecules.

5. The method of claim 1, wherein the nucleic acid barcode molecules are released from the particle upon application of a stimulus.

6. The method of claim 5, wherein the stimulus comprises a biological stimulus, a chemical stimulus, a thermal stimulus, an electrical stimulus, a magnetic stimulus, or a photo stimulus.

7. The method of claim 1, wherein the nucleic acid barcode molecules are released from the particle prior to step (b), and/or upon formation of the partition.

8. The method of claim 1, 2, or 3, wherein the nucleic acid barcode molecules further comprise unique molecule identifier (UMI) sequences.

9. The method of claim 8, wherein the method further comprises sequencing the unenriched sequencing library, sequencing the immune receptor-enriched sequencing library, and associating sequenced molecules from the unenriched sequencing library and sequenced molecules from the immune receptor-enriched sequencing library with individual partitions of the plurality of partitions and/or single cells.

10. The method of claim 9, wherein the immune receptor-enriched sequencing library comprises sequences corresponding to an immune receptor variable region of a TCR or BCR.

11. The method of claim 1, wherein the nucleic acid barcode molecules further comprise a sequencing primer sequence.

12. The method of claim 1, wherein the partition initially comprises the single cell, and the method comprises lysing the single cell to release the RNA molecules.

13. The method of claim 1, wherein the partition is a droplet, a microwell, or a well.

14. The method of claim 1, 2, or 3, wherein amplifying the barcoded nucleic acid molecules of the second plurality of barcoded nucleic acid molecules or derivatives thereof comprises using a target-specific primer to amplify TCR or BCR variable region-encoding sequences.

15. The method of claim 1 or 2, wherein the hybridization regions of the TSOs comprise a polyG sequence, and the 3' terminal sequence added by the reverse transcriptase comprises a polyC sequence.

16. The method of claim 1, wherein (c) comprises adding a functional sequence to the barcoded nucleic acid molecules of the first plurality of barcoded nucleic acid molecules, and (d) comprises adding a functional sequence to the barcoded nucleic acid molecules of the second plurality of barcoded nucleic acid molecules or derivatives thereof.

17. The method of claim 16, wherein the functional sequence in (c) or (d) comprises a flow cell attachment sequence and/or a sequencing primer binding sequence.

18. The method of claim 1, wherein the first and second primer regions are at the 3' ends of the first and second subsets of nucleic acid barcode molecules, respectively.

19. The method of claim 1, 2, or 3, wherein the method further comprises sequencing the unenriched sequencing library, sequencing the immune receptor-enriched sequencing library, and associating sequenced molecules from the unenriched sequencing library and sequenced molecules from the immune receptor-enriched sequencing library with individual partitions of the plurality of partitions and/or single cells.

20. The method of claim 19, wherein the immune receptor-enriched sequencing library comprises sequences corresponding to an immune receptor variable region of a TCR or BCR.

21. The method of claim 1, wherein step (b) is carried out in the partition after lysis of the single cell.

22. The method of claim 1, wherein the method comprises analyzing both immune receptor expression and non-immune receptor gene expression in the same single cell for one or more single cells.

* * * * *

SEQUENCE LISTING

```
<160> NUMBER OF SEQ ID NOS: 170

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tttcttatat ggg                                                          13


<210> SEQ ID NO 2
<211> LENGTH: 23
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 2
aaatcaaatc tttcttatat ggg 23

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acaaacaaat aaatcaaatc tttcttatat ggg 33

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaaatttaaa ggg 13

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cactctacat gaaatttaaa ggg 23

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccaaagttgt cactctacat gaaatttaaa ggg 33

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atatatataa ggg 13

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
atatatatat atatatataa ggg 23

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
atatatatat atatatatat atatatataa ggg 33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
gccggccgcc ccggcggccg ccgcgcggcc 30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
gccgccggcg cccgcccccc ggccggggcc 30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
gcgcgcgcgc gcgccgcccc cgccgctccc 30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
ggggcgcgcc gcgccgccgc cgggctcccc 30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
gccgccgcca ccgccgccgc cgccgccgcc 30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
gccccgcccc gccgcccgcc gaccgccgcc 30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
gcggcccctc cgccgcctgc cgccgccgcc 30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
ggagcgggtc gcgcccggcc gggcgggcgc 30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
gccccgcccc ccgacccgcg cgcggcaccc 30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ggcggcccgc agggccgcgg accccgcccc 30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ggcggggcac gcgccctccc gcggcggggc 30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
gccagggccg tgggccgacc ccggcggggc 30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gtcccccgcc gaccccaccc ccggccccgc 30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ggctcgcctc gcggcggacc gcccgcccgc 30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
gacccgggcg cgcgccggcc gctaccggcc 30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gcgcgcctcg tccagccgcg gcgcgcgccc 30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gcgccgtggg aggggtggcc cggccccccc 30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gggccccccg agccaccttc cccgccgggc 30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ggcggctcca cccgggcccg cgccctaggc 30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
ggcgcggggt ggggagggag cgagcggcgc 30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gctaggcgcc ggccgaggcg aggcgcgcgc 30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
gtcccgcgcc ccgcggggcg gggattcggc 30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32

-continued

```
ggggcggccg cctttccggc cgcgccccgt                                        30


<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

acctccccgg cgcggcgggc gagacgggcc                                        30


<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

gatccgccgg gccgccgaca cggccggacc                                        30


<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

gccgaccccg tgcgctcgct ccgccgtccc                                        30


<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

gcgcggcgac gggtctcgct ccctcggccc                                        30


<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

gcccggctcg cgtccagagt ccgcgccgcc                                        30


<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

tccccggggc tcccgccggc ttctccggga                                        30
```

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
acctcggccg gcgagcgcgc cggccttcac 30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
acgcccggct ccacgccagc gagccgggct 30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
gctcaccgga cgccgccgga accgcgacgc 30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
tcgcccgtcc cttcggaacg gcgctcgccc 30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
ggggtgcgtc gggtctgcga gagcgccagc 30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ggccaaccga ggctccgcgg cgctgccgta 30

-continued

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
gttacccgcg cctgccggcg tagggtaggc 30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
gcgtcaacac ccgccgcggg ccttcgcgat 30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
agctgcggta tccaggcggc tcgggcctgc 30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
gcgtcggcat cgggcgcctt aacccggcgt 30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
gggaataacg ccgccgcatc gccggtcggc 30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
gcggcgcaat acgaatgccc ccggccgtcc 30

```
<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

tgctgcggat atgggtacgg cccggcgcga                                        30


<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

gggcagacgt tcgaatgggt cgtcgccgcc                                        30


<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

gccgcaggct ccactcctgg tggtgccctt                                        30


<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

accgcggctg ctggcaccag acttgccctc                                        30


<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

gggtcgggag tgggtaattt gcgcgcctgc                                        30


<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

agcgggtcgc cacgtctgat ctgaggtcgc                                        30


<210> SEQ ID NO 57
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

ttccccgctg attccgccaa gcccgttccc                                     30


<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

tgcacgtcag gaccgctacg gacctccacc                                     30


<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

agcggattcc gacttccatg gccaccgtcc                                     30


<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

agcttcgccc cattggctcc tcagccaagc                                     30


<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

gatcgcagcg agggagctgc tctgctacgt                                     30


<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

gaacggccat gcaccaccac ccacggaatc                                     30


<210> SEQ ID NO 63
<211> LENGTH: 30
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
tctcgggtgg ctgaacgcca cttgtccctc 30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
gggtcagcgc ccgtcggcat gtattagctc 30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
tcctccctga gctcgcctta ggacacctgc 30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
ggaatcgaac cctgattccc cgtcacccgt 30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
acgggcggtg tgtacaaagg gcagggactt 30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
tacggatccg gcttgccgac ttcccttacc 30

<210> SEQ ID NO 69
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 69
accggccgtg cgtacttaga catgcatggc 30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
gtcatagtta ctcccgccgt ttacccgcgc 30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
gatccttccg caggttcacc tacggaaacc 30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
tcacgacggt ctaaacccag ctcacgttcc 30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
ggccccgctt tcacggtctg tattcgtact 30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
gtacttgttg actatcggtc tcgtgccggt 30

<210> SEQ ID NO 75
<211> LENGTH: 30
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 75
ggaacccttc tccacttcgg ccttcaaagt 30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acccgtttac ctcttaacgg tttcacgccc 30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gaacctccga ctttcgttct tgattaatga 30

<210> SEQ ID NO 78
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcccccgccg gccgccccgg cggccgccgc gcggcccctg ccgccccgac 50

<210> SEQ ID NO 79
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcccccgccg ccgccgccac cgccgccgcc gccgccgccc cgacccgcgc 50

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggaccggccc gcggcccctc cgccgcctgc cgccgccgcc gccgcgcgcc 50

<210> SEQ ID NO 81
<211> LENGTH: 50
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 81
gccccgcccc gccgcccgcc gaccgccgcc gcccgaccgc tcccgccccc 50

<210> SEQ ID NO 82
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gtccgccccg ccccccgacc cgcgcgcggc acccccccg tcgccggggc 50

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
accccggtcc cggcgcgcgg cggggcacgc gccctcccgc ggcggggcgc 50

<210> SEQ ID NO 84
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggccccgccc gcccaccccc gcacccgccg gagcccgccc cctccgggga 50

<210> SEQ ID NO 85
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggcggcccgc agggccgcgg accccgcccc gggcccctcg cggggacacc 50

<210> SEQ ID NO 86
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gccgccctcc gacgcacacc acacgcgcgc gcgcgcgcgc cgcccccgcc 50

<210> SEQ ID NO 87
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ggggcgcgcg cctcgtccag ccgcggcgcg cgcccagccc cgcttcgcgc 50

<210> SEQ ID NO 88
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
agccgccggc gcccgccccc cggccggggc cggagagggg ctgaccgggt 50

<210> SEQ ID NO 89
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
gggcggggac gggcggtggc tcgcctcgcg gcggaccgcc cgcccgctcc 50

<210> SEQ ID NO 90
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
gggcccggct cgcgtccaga gtccgcgccg ccgccggccc cccgggtccc 50

<210> SEQ ID NO 91
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
ggcactgtcc ccggagcggg tcgcgcccgg ccgggcgggc gcttggcgcc 50

<210> SEQ ID NO 92
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
gcgccgtggg aggggtggcc cggccccccc acgaggagac gccggcgcgc 50

<210> SEQ ID NO 93
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
tccacctccc cggcgcggcg ggcgagacgg gccggtggtg cgccctcggc 50

<210> SEQ ID NO 94
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
tccccgccgg gccttcccag ccgtcccgga gccggtcgcg gcgcaccgcc 50

<210> SEQ ID NO 95
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
gtcggctgct aggcgccggc cgaggcgagg cgcgcgcgga accgcggccc 50

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
gggcgcgcgc cggccgctac cggcctcaca ccgtccacgg gctgggcctc 50

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gggacgcgcg cgtggccccg agagaacctc ccccgggccc gacggcgcga 50

<210> SEQ ID NO 98
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
ggcgggaaag atccgccggg ccgccgacac ggccggaccc gccgccgggt 50

<210> SEQ ID NO 99
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
gaccgtcttc tcagcgctcc gccagggccg tgggccgacc ccggcggggc 50

<210> SEQ ID NO 100
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
agcggcgccg gggagcgggt cttccgtacg ccacatgtcc cgcgccccgc 50

<210> SEQ ID NO 101
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
ggctcaccgc agcggccctc ctactcgtcg cggcgtagcg tccgcggggc 50

<210> SEQ ID NO 102
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gcgcggcgac gggtctcgct ccctcggccc cgggattcgg cgagtgctgc 50

<210> SEQ ID NO 103
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
acctcggccg gcgagcgcgc cggccttcac cttcattgcg ccacggcggc 50

<210> SEQ ID NO 104
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
ggccgagggc aacggaggcc atcgcccgtc ccttcggaac ggcgctcgcc 50

<210> SEQ ID NO 105
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
gaggccaacc gaggctccgc ggcgctgccg tatcgttcgc ctgggcggga 50

<210> SEQ ID NO 106
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
agctcaccgg acgccgccgg aaccgcgacg ctttccaagg cacgggcccc 50

<210> SEQ ID NO 107
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
tcaagacggg tcgggtgggt agccgacgtc gccgccgacc ccgtgcgctc 50

<210> SEQ ID NO 108
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
tctccccggg gctcccgccg gcttctccgg gatcggtcgc gttaccgcac 50

<210> SEQ ID NO 109
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
gctgcccggc gggtcatggg aataacgccg ccgcatcgcc ggtcggcatc 50

<210> SEQ ID NO 110
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
gtggcccact aggcactcgc attccacgcc cggctccacg ccagcgagcc 50

<210> SEQ ID NO 111
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
gcgacggccg ggtatgggcc cgacgctcca gcgccatcca ttttcagggc 50

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
gggtaggcac acgctgagcc agtcagtgta gcgcgcgtgc agccccggac 50

<210> SEQ ID NO 113
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
ggggtctgat gagcgtcggc atcgggcgcc ttaacccggc gttcggttca 50

<210> SEQ ID NO 114
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
gcactgggca gaaatcacat cgcgtcaaca cccgccgcgg gccttcgcga 50

<210> SEQ ID NO 115
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
gaggctgttc accttggaga cctgctgcgg atatgggtac ggcccggcgc 50

<210> SEQ ID NO 116
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
tcgtcactac ctccccgggt cgggagtggg taatttgcgc gcctgctgcc 50

<210> SEQ ID NO 117
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
gaatggttta gcgccaggtt ccccacgaac gtgcggtgcg tgacgggcga 50

<210> SEQ ID NO 118
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gcgtcgggtc tgcgagagcg ccagctatcc tgagggaaac ttcggaggga 50

<210> SEQ ID NO 119
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
acccaggtcg gacgaccgat ttgcacgtca ggaccgctac ggacctccac 50

<210> SEQ ID NO 120
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
tcgaaccctg attccccgtc acccgtggtc accatggtag gcacggcgac 50

<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
ttccccgctg attccgccaa gcccgttccc ttggctgtgg tttcgctgga 50

<210> SEQ ID NO 122
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
gcggcgcaat acgaatgccc ccggccgtcc ctcttaatca tggcctcagt 50

<210> SEQ ID NO 123
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
gggccgggtg aggtttcccg tgttgagtca aattaagccg caggctccac 50

<210> SEQ ID NO 124
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
ggtcctattc cattattcct agctgcggta tccaggcggc tcgggcctgc 50

<210> SEQ ID NO 125
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
gctattggag ctggaattac cgcggctgct ggcaccagac ttgccctcca 50

<210> SEQ ID NO 126
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
gtcctccctg agctcgcctt aggacacctg cgttaccgtt tgacaggtgt 50

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
tcgctccacc aactaagaac ggccatgcac caccacccac ggaatcgaga 50

<210> SEQ ID NO 128
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
gggctgactt tcaatagatc gcagcgaggg agctgctctg ctacgtacga 50

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
gttacacact ccttagcgga ttccgacttc catggccacc gtcctgctgt 50

<210> SEQ ID NO 130
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
atcccacaga tggtagcttc gccccattgg ctcctcagcc aagcacatac 50

<210> SEQ ID NO 131
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
gccattcgca gtttcactgt accggccgtg cgtacttaga catgcatggc 50

<210> SEQ ID NO 132
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
ggtagtagcg acgggcggtg tgtacaaagg gcagggactt aatcaacgca 50

<210> SEQ ID NO 133
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
gcggacccca cccgtttacc tcttaacggt ttcacgccct cttgaactct 50

<210> SEQ ID NO 134
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
ttgaatattt gctactacca ccaagatctg cacctgcggc ggctccaccc 50

<210> SEQ ID NO 135
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
ttagagccaa tccttatccc gaagttacgg atccggcttg ccgacttccc 50

<210> SEQ ID NO 136

-continued

<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
tcgtgccggt atttagcctt agatggagtt taccacccgc tttgggctgc 50

<210> SEQ ID NO 137
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
ggcatttggc taccttaaga gagtcatagt tactcccgcc gtttacccgc 50

<210> SEQ ID NO 138
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
aacctgtctc acgacggtct aaacccagct cacgttccct attagtgggt 50

<210> SEQ ID NO 139
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
gggtcagcgc ccgtcggcat gtattagctc tagaattacc acagttatcc 50

<210> SEQ ID NO 140
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
gccccgcttt cacggtctgt attcgtactg aaaatcaaga tcaagcgagc 50

<210> SEQ ID NO 141
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tcctccgctg actaatatgc ttaaattcag cgggtcgcca cgtctgatct 50

<210> SEQ ID NO 142
<211> LENGTH: 50

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
gttattgctc aatctcgggt ggctgaacgc cacttgtccc tctaagaagt 50

<210> SEQ ID NO 143
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
tgagaatagg ttgagatcgt ttcggcccca agacctctaa tcattcgctt 50

<210> SEQ ID NO 144
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
gtcttcgaac ctccgacttt cgttcttgat taatgaaaac attcttggca 50

<210> SEQ ID NO 145
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (25)..(30)
<223> OTHER INFORMATION: a, c, t or g
<220> FEATURE:
<221> NAME/KEY: modified_base
<222> LOCATION: (33)..(38)
<223> OTHER INFORMATION: a, c, t or g

<400> SEQUENCE: 145
caagcagaag acggcatacg agatnnnnnn gtnnnnnngt gactggagtt cagacgtgtg 60
ctcttccgat ctggg 75

<210> SEQ ID NO 146
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (25)..(40)
<223> OTHER INFORMATION: a, c, t or g
<220> FEATURE:
<221> NAME/KEY: modified_base
<222> LOCATION: (43)..(48)
<223> OTHER INFORMATION: a, c, t or g

<400> SEQUENCE: 146
caagcagaag acggcatacg agatnnnnnn nnnnnnnnnn gtnnnnnngt gactggagtt 60
cagacgtgtg ctcttccgat ctggg 85

<210> SEQ ID NO 147
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (30)..(35)
<223> OTHER INFORMATION: a, c, t or g
<220> FEATURE:
<221> NAME/KEY: modified_base
<222> LOCATION: (38)..(43)
<223> OTHER INFORMATION: a, c, t or g

<400> SEQUENCE: 147
aatgatacgg cgaccaccga gatctacacn nnnnngtnnn nnnacactct ttccctacac 60
gacgctcttc cgatctggg 79

<210> SEQ ID NO 148
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (30)..(45)
<223> OTHER INFORMATION: a, c, t or g
<220> FEATURE:
<221> NAME/KEY: modified_base
<222> LOCATION: (48)..(53)
<223> OTHER INFORMATION: a, c, t or g

<400> SEQUENCE: 148
aatgatacgg cgaccaccga gatctacacn nnnnnnnnnn nnnnngtnnn nnnacactct 60
ttccctacac gacgctcttc cgatctggg 89

<210> SEQ ID NO 149
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(36)

<223> OTHER INFORMATION: a, c, t or g

<400> SEQUENCE: 149
ctacacgacg ctcttccgat ctnnnnnngt nnnnnnggg 39

<210> SEQ ID NO 150
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 150
ctacacgacg ctcttccgat ctnnnnnngt nnnnnnnnnn nnnnnnggg 49

<210> SEQ ID NO 151
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(42)
<223> OTHER INFORMATION: a, c, t or g
<220> FEATURE:
<223> OTHER INFORMATION: See specification as filed for detailed description of substitutions and preferred embodiments

<400> SEQUENCE: 151
ctacacgacg ctcttccgat ctnnnnnngt nnnnnnnnnn nnwwggg 47

<210> SEQ ID NO 152
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(38)
<223> OTHER INFORMATION: a, c, t or g
<220> FEATURE:
<221> NAME/KEY: modified_base
<222> LOCATION: (41)..(46)
<223> OTHER INFORMATION: a, c, t or g

<400> SEQUENCE: 152
ctacacgacg ctcttccgat ctnnnnnnnn nnnnnnnngt nnnnnnggg 49

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 153
ctacacgacg ctcttccgat ctnnnnnngt nnnnnnnnnn nnnnnnatgg g 51

<210> SEQ ID NO 154
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 154
ctacacgacg ctcttccgat ctnnnnnngt nnnnnnnnnn nnnnnnacat ggg 53

<210> SEQ ID NO 155
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 155
ctacacgacg ctcttccgat ctnnnnnngt nnnnnnnnnn nnnnnntaac atggg 55

<210> SEQ ID NO 156
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 156
ctacacgacg ctcttccgat ctnnnnnngt nnnnnnnnnn nnnnnncgta acatggg 57

<210> SEQ ID NO 157
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 157
ctacacgacg ctcttccgat ctnnnnnngt nnnnnnnnnn nnnnnnaccg taacatggg 59

<210> SEQ ID NO 158
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(28)
<223> OTHER INFORMATION: a, c, t or g
<220> FEATURE:
<221> NAME/KEY: modified_base
<222> LOCATION: (31)..(46)
<223> OTHER INFORMATION: a, c, t or g

<400> SEQUENCE: 158
ctacacgacg ctcttccgat ctnnnnnngt nnnnnnnnnn nnnnnnacac aagaggcacg 60
cgtaacatgg g 71

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159

-continued tttcttatat 10

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
acttgtccag cctaacctgc 20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
ttaccctggg aggaaccaga 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
tttcaggcca caactccctt 20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
cagacagacc atgatgcggg 20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
gccacaactc cctttctgg 20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165

-continued

```
agtctctcag ctggtacacg                                                  20


<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166

tctgatggct caaacacagc                                                  20


<210> SEQ ID NO 167
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

aaaaaaaaaa aaaaaa                                                      16


<210> SEQ ID NO 168
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

aaaaaaaaaa a                                                           11


<210> SEQ ID NO 169
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

tttttttttt t                                                           11


<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

aaaaaaaaaa aaaaaaaaaa a                                                21
```